(12) United States Patent
Batrakova et al.

(10) Patent No.: US 11,458,097 B2
(45) Date of Patent: Oct. 4, 2022

(54) BIOLOGICAL AGENT-EXOSOME COMPOSITIONS AND USES THEREOF

(71) Applicant: The University of North Carolina at Chapel Hill, Chapel Hill, NC (US)

(72) Inventors: Elena V. Batrakova, Durham, NC (US); Alexander V. Kabanov, Chapel Hill, NC (US); Marina Sokolsky, Chapel Hill, NC (US); Matthew J. Haney, Chapel Hill, NC (US); Dongfen Yuan, Chapel Hill, NC (US); Myung Soo Kim, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 678 days.

(21) Appl. No.: 16/089,833

(22) PCT Filed: Mar. 30, 2017

(86) PCT No.: PCT/US2017/024931
§ 371 (c)(1),
(2) Date: Sep. 28, 2018

(87) PCT Pub. No.: WO2017/173034
PCT Pub. Date: Oct. 5, 2017

(65) Prior Publication Data
US 2020/0297631 A1  Sep. 24, 2020

Related U.S. Application Data

(60) Provisional application No. 62/315,389, filed on Mar. 30, 2016.

(51) Int. Cl.
| | | |
|---|---|---|
| A61K 9/127 | (2006.01) | |
| A61K 31/7088 | (2006.01) | |
| A61K 47/65 | (2017.01) | |
| A61K 45/06 | (2006.01) | |
| A61K 31/337 | (2006.01) | |
| A61P 35/04 | (2006.01) | |

(52) U.S. Cl.
CPC .......... *A61K 9/127* (2013.01); *A61K 31/337* (2013.01); *A61K 31/7088* (2013.01); *A61K 45/06* (2013.01); *A61K 47/65* (2017.08); *A61P 35/04* (2018.01)

(58) Field of Classification Search
CPC ........ A61K 9/127; A61K 38/18; C12N 15/08; C12N 15/88; C07K 14/475
See application file for complete search history.

(56) References Cited

PUBLICATIONS

Batrakova et al (J. Control Release, Dec. 10, 2015, 219; 396-405). (Year: 2015).*
Nakase (Scientific Reports 5:10112; WWW.Nature.com/scientificreports; 1-13; Published May 26, 2015) (Year: 2015).*
Kooijmans et al. (Journal of Controlled Release 224 (2016) 77-85, Available online Jan. 7, 2016) (Year: 2016).*
Lai et al. (Biotechnology Advances 31 (2013) 543-551) (Year: 2013).*
International Preliminary Report on Patentability corresponding to International Application No. PCT/US2017/024931 dated Oct. 11, 2018.
Batrakova et al. "Using exosomes, naturally-equipped nanocarriers, for drug delivery", J Control Release 219:396-405 (2015).
Haney et al. "Exosomes as Drug Delivery Vehicles for Parkinson's Disease Therapy", J Control Release 207:18-30 (2015).
Zhao et al. "Polyelectrolyte Complex Optimization for Macrophage Delivery of Redox Enzyme Nanoparticles", Nanomedicine (Lond) 6(1):25-42 (2011).
International Search Report corresponding to International Application No. PCT/US2017/024931 dated Aug. 14, 2017.
Written Opinion of the International Searching Authority corresponding to International Application No. PCT/US2017/024931 dated Aug. 14, 2017.

* cited by examiner

*Primary Examiner* — Anna R Falkowitz
(74) *Attorney, Agent, or Firm* — Myers Bigel, P.A.

(57) ABSTRACT

The present invention relates to compositions comprising exosomes and biological agents and methods of using the compositions for the delivery of biological agents to cells and to subjects.

14 Claims, 52 Drawing Sheets

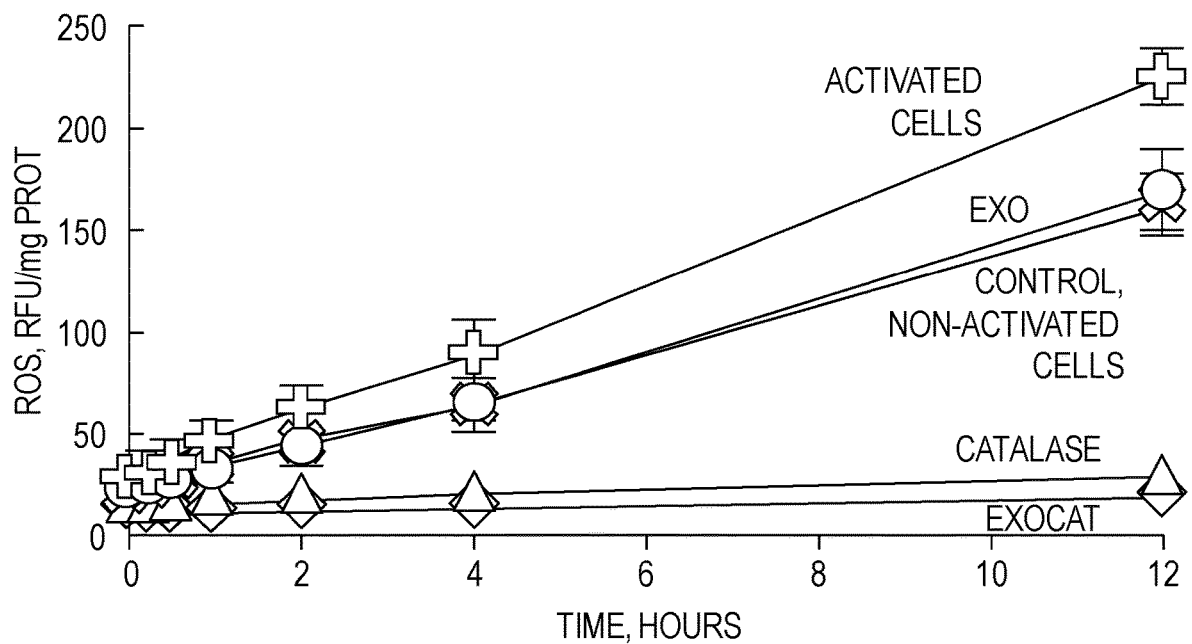
FIG. 4D
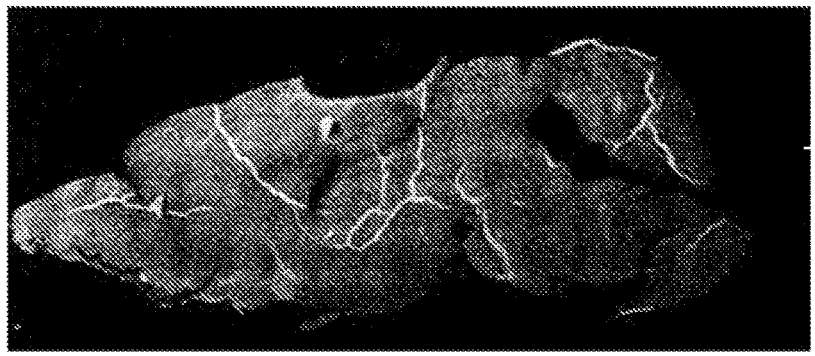
FIG. 5A
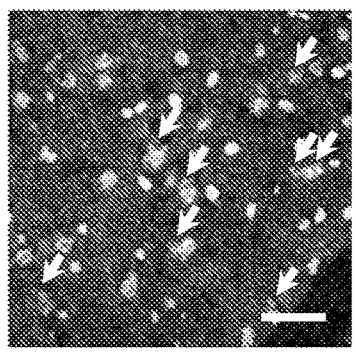 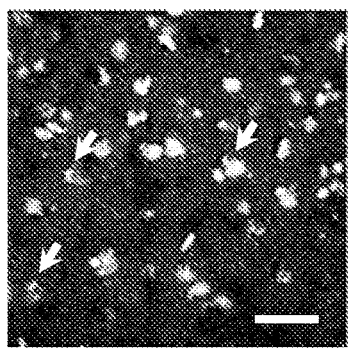 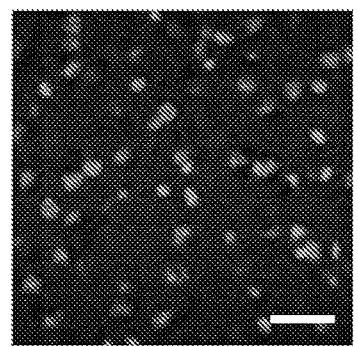
FIG. 5B　　　FIG. 5C　　　FIG. 5D

HEALTHY CONTROLS

PBS

EMPTY EXOSOMES

6-OHDA-INTOXICATED MICE

PBS

6-OHDA-INTOXICATED MICE

EXOCAT/SONIC

EXOCAT/SAPONIN

CATALASE

HEALTHY CONTROLS | 6-OHDA-INTOXICATED MICE
PBS/PBS | PBS/EMPTY EXOSOMES | PBS
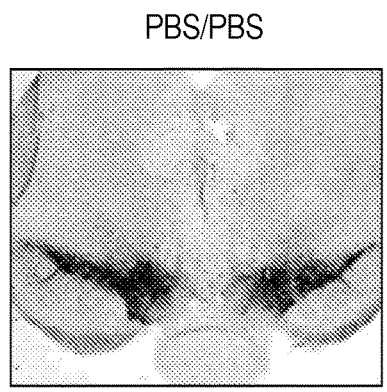 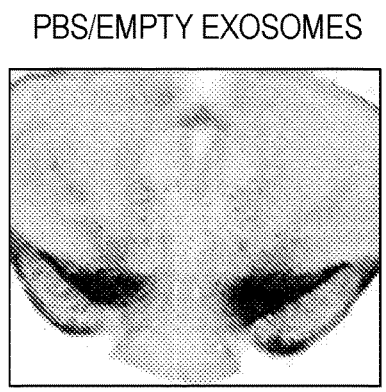 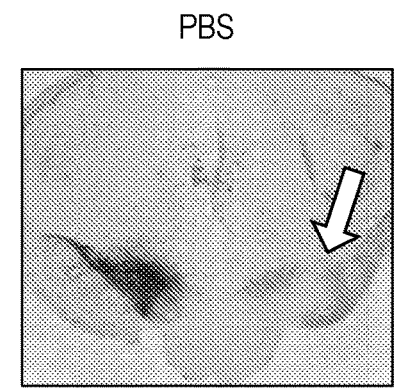
FIG. 8A | FIG. 8B | FIG. 8C
6-OHDA-INTOXICATED MICE
EXOCAT/SONIC | EXOCAT/SAPONIN | CATALASE
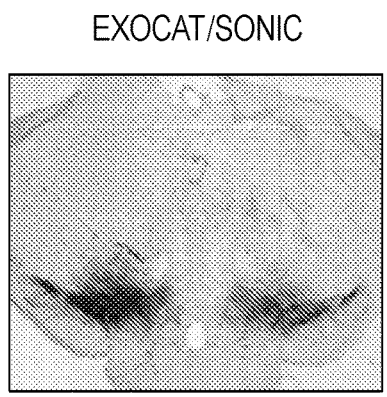 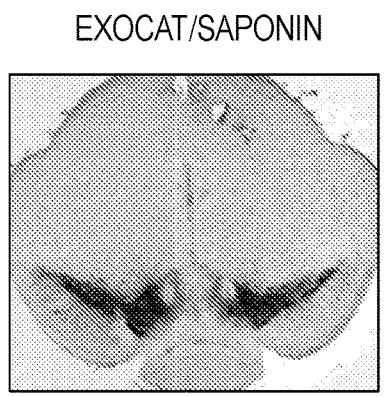 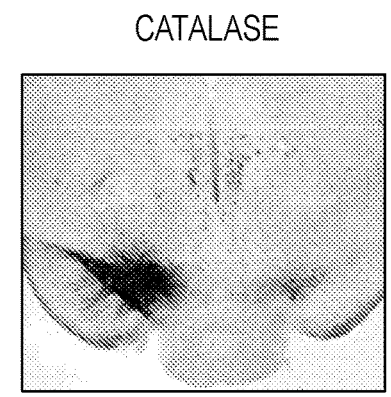
FIG. 8D | FIG. 8E | FIG. 8F

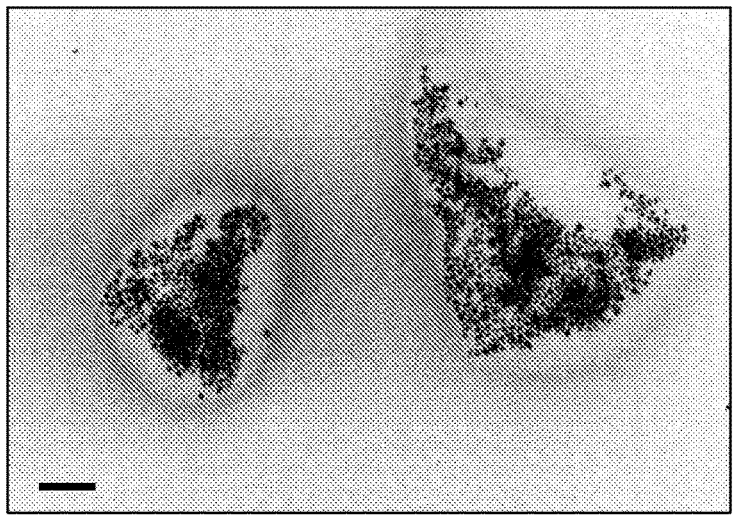
FIG. 11
| SAMPLE/<br>METHOD | SIZE BY<br>NTA (nm) | Z-AVERAGE<br>SIZE (nm) | ZETA<br>POTENTIAL (mV) | LOADING<br>CAPACITY (%) |
|---|---|---|---|---|
| NAÏVE | 110.2±3.3 | 70.8±2.8 | -10.74±1.13 | N/A |
| INCUBATION | 178.7±5.8(*) | 132.2±2.3(*) | -9.33±0.44 | 1.44±0.38 |
| ELECTROPORATION | 159.0±3.6(*) | 145.3±1.0(*) | -8.47±0.55 | 5.3±0.48 |
| SONICATION | 217.9±10.1(*) | 287.7±0.7(*) | -14.07±0.94 | 28.29±1.38 |
| EMPTY SONICATED | 326.0±23.5(*) | 356.1±3.5(*) | -12.33±0.24 | N/A |
FIG. 12A
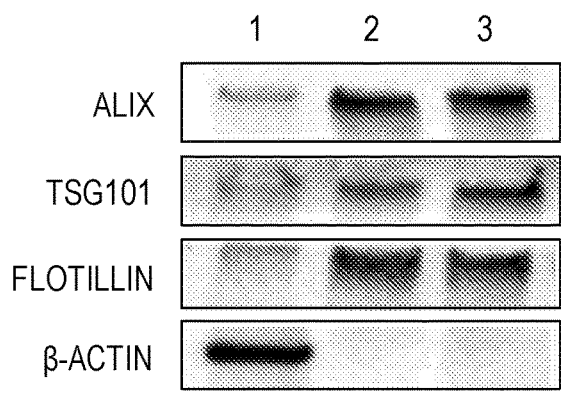
FIG. 12B

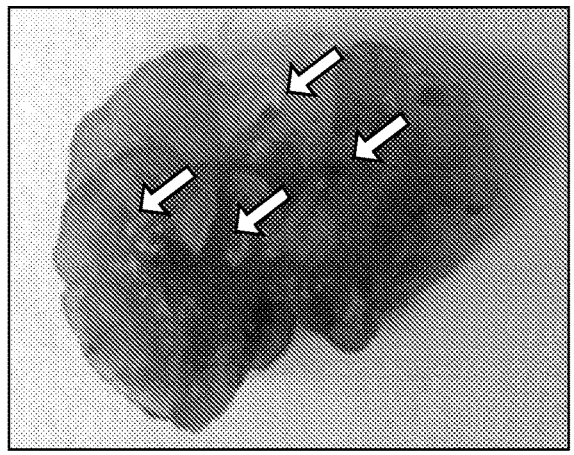
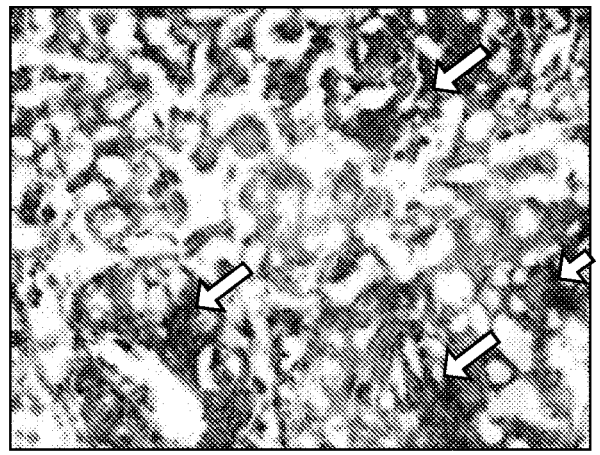
FIG. 19A  FIG. 19B
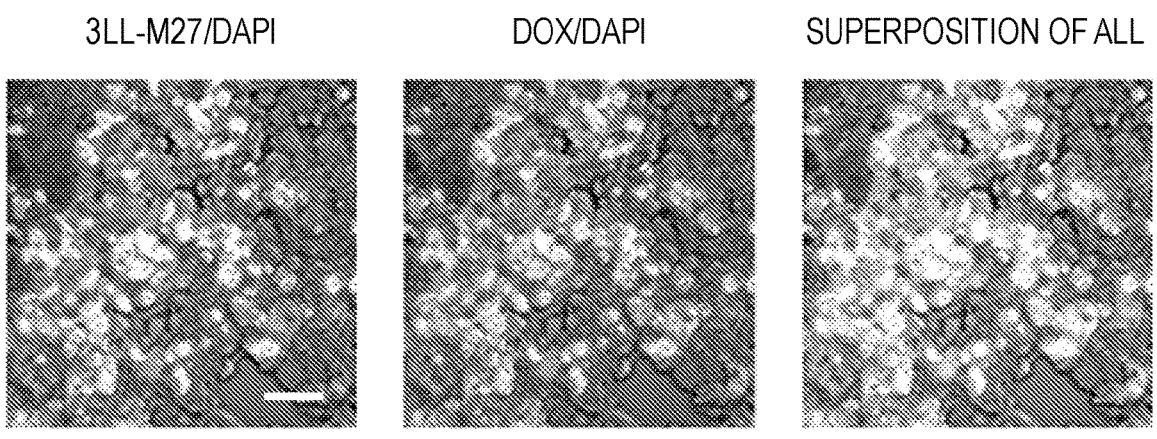
FIG. 20A  FIG. 20B  FIG. 20C

EXO+TRANSFERRIN    EXO+CTB

EXO+CLATHRIN Ab    EXO+CAVEOLIN Ab

| FORMULATION | SIZE BY NTA (nm) | SIZE BY DLS (nm) | ZETA POTENTIAL (mV) |
|---|---|---|---|
| NAÏVE EXOSOMES | 110.8±4.1 | 75.9±2.6 | -15.3±1.1 |
| SONICATED EXOSOMES | 232.0±9.5 | 291.1±3.5 | -12.3±0.3 |
| EXOPTX | 216.1±1.2 | 287.7±0.7 | -14.1±1.0 |
| AA-PEG-EXOPTX | 280.8±3.1 | 304.5±3.9 | -4.4±0.1 |

BIOLOGICAL AGENT-EXOSOME COMPOSITIONS AND USES THEREOF

STATEMENT OF PRIORITY

This application is a 35 U.S.C. § 371 notional phase application of PCT Application PCT/US2017/024931 filed Mar. 30, 2017, which claims the benefit of U.S. Provisional Application Ser. No. 62/315,389, filed Mar. 30, 2016, the entire contents of each of which are incorporated by reference herein in its entirety.

STATEMENT OF GOVERNMENT SUPPORT

This invention was made with government support under Grant No. NS057748 awarded by National Institutes of Health. The government has certain rights to this invention.

FIELD OF THE INVENTION

The present invention relates to compositions comprising exosomes and biological agents and methods of using the compositions for the delivery of biological agents to cells and to subjects.

BACKGROUND OF THE INVENTION

The delivery of biological agents to cells and tissues is hindered by a number of factors, including the instability of administered macromolecule agents in vivo, sequestration by tissues, the presence of the blood-brain barrier (BBB), and brain-to-blood efflux systems. Different drug nanoformulations have been developed to overcome the BBB. Unfortunately, the opsonization of drug-loaded nanoparticles in the bloodstream caused two main problems of drug nanoformulations: nanotoxicity and rapid drug clearance by the mononuclear phagocyte system (MPS).

Exosomes are nanosized vesicles secreted by a variety of cells, in particular cells of the immune system (Vlassov et al., *Biochem. Biophys. Acta* 1820:940 (2012)). Exosomes may have an immune-privileged status that can efficiently decrease drug clearance. Exosomes were initially thought to be a mechanism for removing unneeded proteins. Recent studies revealed that they are actually specialized in long-distance intercellular communications facilitating transfer of proteins (Johnstone, *Biochem. Cell Biol.* 70:179 (1992)), functional mRNAs and microRNAs for subsequent protein expression in target cells (Zomer et al., *Commun Integr. Biol.* 3:447 (2010); Valadi et al., *Nature Cell Biol.* 9:654 (2007)). To shuttle their cargo, exosomes can attach by a range of surface adhesion proteins and specific vector ligands (tetraspanins, integrins, CD11b and CD18 receptors), and deliver their payload to target cells (Thery et al., *Curr. Protoc. Cell Biol.* Chapter 3, Unit 3 22 (2006); Thery et al., *Nature Rev. Immunol.* 9:581 (2009)). Exosomes possess an intrinsic ability to cross biological barriers. Thus, tumor-derived exosomes and microvesicles originated in the brain of glioma-bearing mice, and human glioblastoma patients were detected in the blood circulation indicating their ability to cross the BBB (Skog et al., *Nature Cell Biol.* 10:1470 (2008)).

There is a need in the art for new compositions and methods for the delivery of biological agents to cells and to subjects.

SUMMARY OF THE INVENTION

The present invention is based on the development of compositions useful for delivering biological agents, e.g., therapeutic or protective agents such as small molecules, polypeptides, and polynucleotides, to cells in vitro and in vivo. The compositions provide improved delivery of biological agents, including crossing the BBB to the brain, and targeting inflamed tissues and tumors, thereby improving therapeutic effects while limiting immune response to the agents. The incorporation of biological agents into exosomes increases the circulation time, preserves therapeutic activity, and improves delivery to the central nervous system, the tumor microenvironment, and inflamed tissue. The exosomes enable intracellular delivery of the loaded biological agents to target cells such as cancer cells, muscle cells, brain cells, cells of the immune system, and the like. The exosomes can optionally be modified to increase loading of biological agents in these exosomes, and/or to enable targeting of the exosomes to the specific receptor at the surface of a target cell.

Thus, one aspect of the invention relates to a composition for delivery of a biological agent to a cell, the composition comprising an exosome comprising the biological agent, wherein the biological agent is not naturally present in the exosome. The exosomes may be isolated from donor cells such as cancer cells, immune cells, such as macrophages/monocytes or dendritic cells, or stem cells. The biological agent may be incorporated in the exosomes prior to or after isolation of the exosomes from the cells.

Another aspect of the invention relates to a method of delivering a biological agent to a cell, comprising contacting the cell with the composition of the invention, thereby delivering the biological agent to the cell.

A further aspect of the invention relates to a method of enhancing delivery of a biological agent to a cell in a tumor microenvironment, comprising contacting the cell with the composition of the invention, thereby enhancing delivery of the biological agent to the cell relative to the delivery of the biological agent in the absence of an exosome.

An additional aspect of the invention relates to a method of enhancing delivery of a biological agent to a cell in a tumor microenvironment, comprising contacting the cell with the composition of the invention, thereby enhancing delivery of the biological agent to the cell relative to the delivery of the biological agent in the absence of an exosome.

Another aspect of the invention relates to a method of enhancing delivery of a biological agent to a cancer cell, comprising contacting the cell with the composition of the invention, thereby enhancing delivery of the biological agent to the cell relative to the delivery of the biological agent in the absence of an exosome.

A further aspect of the invention relates to a method of enhancing delivery of a biological agent to a central nervous system cell, comprising contacting the cell with the composition of the invention, thereby enhancing delivery of the biological agent to the cell relative to the delivery of the biological agent in the absence of an exosome.

An additional aspect of the invention relates to a method of delivering a biological agent to a subject, comprising delivering the composition of the invention to the subject, thereby delivering the biological agent to the subject.

Another aspect of the invention relates to a method of delivering a biological agent across the BBB of a subject, comprising delivering the composition of the invention to the subject, thereby delivering the biological agent across the BBB of the subject.

A further aspect of the invention relates to a method of delivering a biological agent to inflamed tissue of a subject, comprising delivering the composition of the invention to the subject, thereby delivering the biological agent to inflamed tissue of the subject.

A further aspect of the invention relates to a method and compositions of exosomes for delivering polypeptides not naturally present in the exosomes.

A further aspect of the invention relates to a method and compositions of exosomes for delivering functional polynucleotides not naturally present in the exosomes.

A further aspect of the invention relates to a method and compositions of exosomes for delivering small molecules not naturally present in the exosomes.

Another aspect of this invention relates to a method of increasing the delivery of the exosomes to the target cells and organs such as cancer cells or tumor microenvironment and compositions in which the exosomes optionally carrying a biological agent are modified with the targeting groups. These targeting groups can be attached to the surface of exosomes using a polymeric linker that can be connected to a lipid group.

An additional aspect of the invention relates to a method of treating a disorder in a subject in need thereof, comprising delivering a therapeutically effective amount of the composition of the invention to the subject, wherein the biological agent is effective for treating the disorder, thereby treating the disorder in the subject.

Another aspect of the invention relates to a method of transfecting a cell with a polynucleotide, comprising contacting the cell with composition comprising an exosome comprising the polynucleotide, wherein the polynucleotide is not naturally present in the exosome. The exosomes may be isolated from donor mammalian cells, in particular, cancer cells, immune system cells, such as macrophages/monocytes or dendritic cells, or stem cells.

Another aspect of the invention relates to a method of increasing production of exosomes, comprising treating the donor cells with amphiphilic block copolymers that may be applied before and/or during isolation of the exosomes.

A further aspect of the invention relates to a method of loading a biological agent into an exosome, comprising a step selected from the group consisting of:
  a) incubating the biological agent with the exosome, optionally in the presence of a saponin;
  b) combining the biological agent and the exosome and subjecting them to a freeze-thaw cycle;
  c) combining the biological agent and the exosome and subjecting them to sonication;
  d) combining the biological agent and the exosome and subjecting them to extrusion; and
  e) modifying exosomes with a molecule containing multiple charges and optionally purifying the exosomes before adding the biological agent.

Another aspect of the invention relates to compositions of exosomes in which exosomes are modified with molecules containing multiple charges to increase incorporation of a biological agent into exosomes, and/or stability of the exosomes with the biological agent. The exosomes may be modified with a polyion or a lipid that can contain multiple charges that can be either positive or negative charges. The exosomes modified with a polyion or a lipid that can contain multiple charges may be purified after modification. The modified exosomes may be then loaded with a biological agent.

In another aspect this invention relates to a method of loading a biological agent into an exosome, comprising:
  a) loading a donor cell with a biological agent that optionally can be incorporated into a nanoparticle comprising a polymer or a lipid, such as polymeric micelle or a polyion complex;
  b) culturing the cells to allow for formation of exosomes;
  c) isolating exosomes loaded with the biological agent from these cells.

The cells may be optionally treated with a block copolymer to increase the yield (amount) of exosomes loaded with a biological agent.

In another aspect this invention relates to a method of loading a biological agent into an exosome, comprising:
  a) transfecting a donor cell with a polynucleotide that optionally can be incorporated into a nanoparticle comprising a polymer or a lipid, such as a cationic polymer or a cationic lipid;
  b) culturing the cells to allow for formation of exosomes;
  c) isolating exosomes from these cells.

The cells may be optionally treated with a block copolymer to increase the yield (amount) of exosomes. The isolated exosomes may carry the DNA, RNA and/or protein produced as a result of the transfection of the cells with this polynucleotide.

These and other aspects of the invention are set forth in more detail in the description of the invention below.

BRIEF DESCRIPTION OF THE DRAWINGS

FIGS. 1A-1D show characterization of exoCAT. Exosomes released from Raw 264.7 macrophages were loaded with catalase by different techniques and examined by: (FIG. 1A) western blot, (FIG. 1B) catalase enzymatic activity; and (FIG. 1C) catalase release. ExoCAT morphology was examined by AFM (FIG. 1D).

FIGS. 4A-4D show accumulation of exoCAT in PC12 cells, and therapeutic effects of exoCAT in in vitro models of oxidative stress. The exoCAT uptake in PC12 cells was examined by spectrofluorimetry (FIG. 4A), and confocal microscopy (FIG. 4B). The bar: 20 µm. The neuroprotection by exoCAT formulations was evaluated in the cell pre-incubated with 6-OHDA (FIG. 4C); (1) catalase, (2) empty exosomes, catalase loaded into exosomes by: (3) incubation at RT, (4) saponin permeabilization, (5) freeze/thaw cycles, (6) sonication, (7) extrusion. The ability to decrease levels of ROS produced in activated macrophages (pre-incubated with LPS and TNF-α) by exoCAT was evaluated by Ampex Red assay in vitro (FIG. 4D).

FIGS. 5A-5D show biodistribution of DIL-labeled exosomes in mouse brain. Exosomes were administered to mice with 6-OHDA-induced brain inflammation through: intra-nasal (FIG. 5A, FIG. 5B), or intravenous (FIG. 5C) routes; and compared to PBS-injected controls (FIG. 5D). The bar: 40 µm.

FIGS. 8A-8G show neuroprotective effects of exoCAT in PD mouse model. The i.n. administration of exoCAT protected DA neurons (FIG. 8D, FIG. 8E) in 6-OHDA-intoxicated mice compared to those intoxicated with 6-OHDA and then treated with PBS (FIG. 8C). Catalase alone was not efficient in this model (FIG. 8F). Empty exosomes did not affect the number of DA neurons in healthy animals (FIG. 8B) compared to healthy controls (FIG. 8A) indicating the absence of cytotoxic effects of the exosomal carriers. The neuroprotective effects of the described exosomal formulations were quantified by the amount of DA neurons in the SNpc (FIG. 8G).

FIG. 11 shows incorporation of gold nanoparticles into exosomes by sonication. Naïve exosomes isolated from macrophages concomitant media were sonicated in the presence of gold nanoparticles as described in methods section and visualized by TEM. The bar: 100 nm.

FIGS. 12A-12E show characterization of PTX exosomal formulations. Exosomes were collected from conditioned media of RAW 264.7 macrophages, and loaded with PTX by various methods: co-incubation at RT; electroporation, and sonication. The size of exoPTX was measured by NTA and DLS (FIG. 12A). The loading with PTX increased the size of exosomes, but did not significantly altered their surface charge. The loading efficiency of exosomes with PTX increased in a row: incubation at RT<electroporation <<sonication. The exosome protein content was confirmed by western blot (FIG. 12B). Significant amount of exosome-associated proteins, Alix, TSG101, and Flotillin was detected in naïve (2) and sonicated exosomes (3), but not in the cells (1). Effect of sonication on fluidity of exosomal membranes labeled with BODIPY-PC was examined by fluorescence polarization measurements (FIG. 12C). The microviscosity of exosomal membranes was significantly decreased by six cycles of ultrasound treatment (3) compared to naïve exosomes (1), or exosomes subjected to one sonication cycle (2). The microviscosity of sonicated exosomes was completely restored following one hour incubation period at 37 (5), but not after 30 min incubation (4). The morphology of drug-loaded exosomes was examined by AFM. (FIG. 12D). Images revealed small spherical naïve exosomes as well as PTX-loaded exosomes. The bar: 200 nm. A release PTX profile from pre-loaded exosomes was evaluated for the exoPTX formulation obtained by sonication (FIG. 12E). Values are means±SEM (n=4). Symbols indicate the relative level of significance compared with naïve exosomes ($p<0.05$).

FIGS. 19A-19B show a lung metastasis model of Lewis Lung Carcinoma (3LL-M27). C57BL/6 mice were i.v. injected with 3LL/M27 cells. 21 days following the injection, multiple metastases (arrows) were detected on gross images of tumor-bearing lungs (FIG. 19A), and lung sections (FIG. 19B).

FIGS. 20A-20C show co-localization of airway-delivered exoDOX with pulmonary metastases. Exosomes were isolated from macrophages conditioned media, and loaded with DOX. C57BL/6 mice were i.v. injected with 3LL-M27 cells transduced with lentiviral vectors encoding the optical reporter mCherry (8FlmC) fluorescent protein (FIG. 20A). 21 days later, the mice with established pulmonary metastases were i.n. injected with DID-labeled exosomes (FIG. 20B). 4 hours later, mice were euthanized, perfused, lungs were sectioned, and stained with DAPI. The confocal images revealed a significant co-localization of exosome-delivered DOX with metastases (FIG. 20C). Bar: 20 µm.

(FIG. 23A) Intensity-weighted size distribution of exosomes by DLS. (FIG. 23B) Number-weighted size distribution of exosomes by NTA. (FIG. 23C) Morphology of Mφ exosomes by TEM. Scale bar=200 nm, magnification×50,000. Insets show the aggregation and artificial cup-shape. (FIG. 23D) SDS-PAGE of lysates of RAW Mφs and exosomes for protein composition. (FIG. 23E) Western blot of lysates of RAW Mφs and exosomes at equal protein amount for exosomal markers and conserved proteins.

(FIG. 25A) Cell viability of hCMEC/D3 cells after 24 h incubation with exosomes and another 72 h in fresh culture medium was determined by MTT assay. Data are means±SD, n=6. Cell viability of exosomes-treated cells was comparable to untreated cells. (FIG. 25B) Time-dependent uptake of CM-DiI labeled exosomes at $0.6×10^{10}$ exosomes/ml. *** $p<0.001$ vs untreated cells. (FIG. 25C) Concentration-dependent uptake of CM-DiI labeled exosomes at 4 h. * $p<0.05$ and * $p<0.001$ vs untreated cells. (FIG. 25D) Concentration-dependent inhibition of non-labeled exosomes on uptake of CM-DiI labeled exosomes at $0.6×10^{10}$ exosomes/ml at 4 h. * $p<0.001$ vs indicated group. Cell uptake was determined by flow cytometry. Data are mean fluorescence of 5000-10000 live singlets±SD, n=3. Statistical comparisons are made by one-way ANOVA and post Newman-Keuls multiple comparison test.

(FIG. 28A) hCMEC/D3 cells were treated with CM-DiI labeled exosomes at $1×10^{11}$ exosomes/ml and Alexa Fluor 488-transferrin at 25 µg/ml or Alexa Fluor 488-CTB at 5 µg/ml for 0.5 h, and then fixed before imaging. (FIG. 28B) hCMEC/D3 cells were treated with CM-DiI labeled exosomes at $1×10^{11}$ exosomes/ml for 0.5 h, fixed and then immunostained with anti-clathrin heavy chain/-caveolin-1 antibody. Mean±SD of Mander's colocalization coefficients calculated by Image J JACoP plugin (Schneider et al., *Nature Methods* 9:671 (2012); Bolte et al., *J. Microsc.-Oxford* 224:213 (2006)) from 7-30 different fields of view are shown in percentage.

(FIG. 29A) Expression of LFA-1 in Raw Mφs and Mφ exosomes by western blot at equal protein loading. (FIG. 29B) Expression of ICAM-1 in hCMEC/D3 cells with or without 3 or 6 h stimulation with LPS (100 ng/ml). (FIG. 29C) Cell uptake of exosomes in hCMEC/D3 cells with or without 3 or 6 h pre-stimulation with LPS. (FIG. 29D) Effect of co-incubation with anti-ICAM-1 or anti-LFA-1 antibodies (100 µg/ml) on cell uptake of exosomes in hCMEC/D3 cells. Cell uptake was determined by flow cytometry after 4 h incubation with CM-DiI labeled exosomes at $0.6×10^{10}$ exosomes/ml. Data are mean fluorescence of 5000-10000 live singlets±SD, n=3.

p<0.01 and *p<0.001 vs indicated group by one-way ANOVA and post Newman-Keuls multiple comparison test.

Figure 30A:
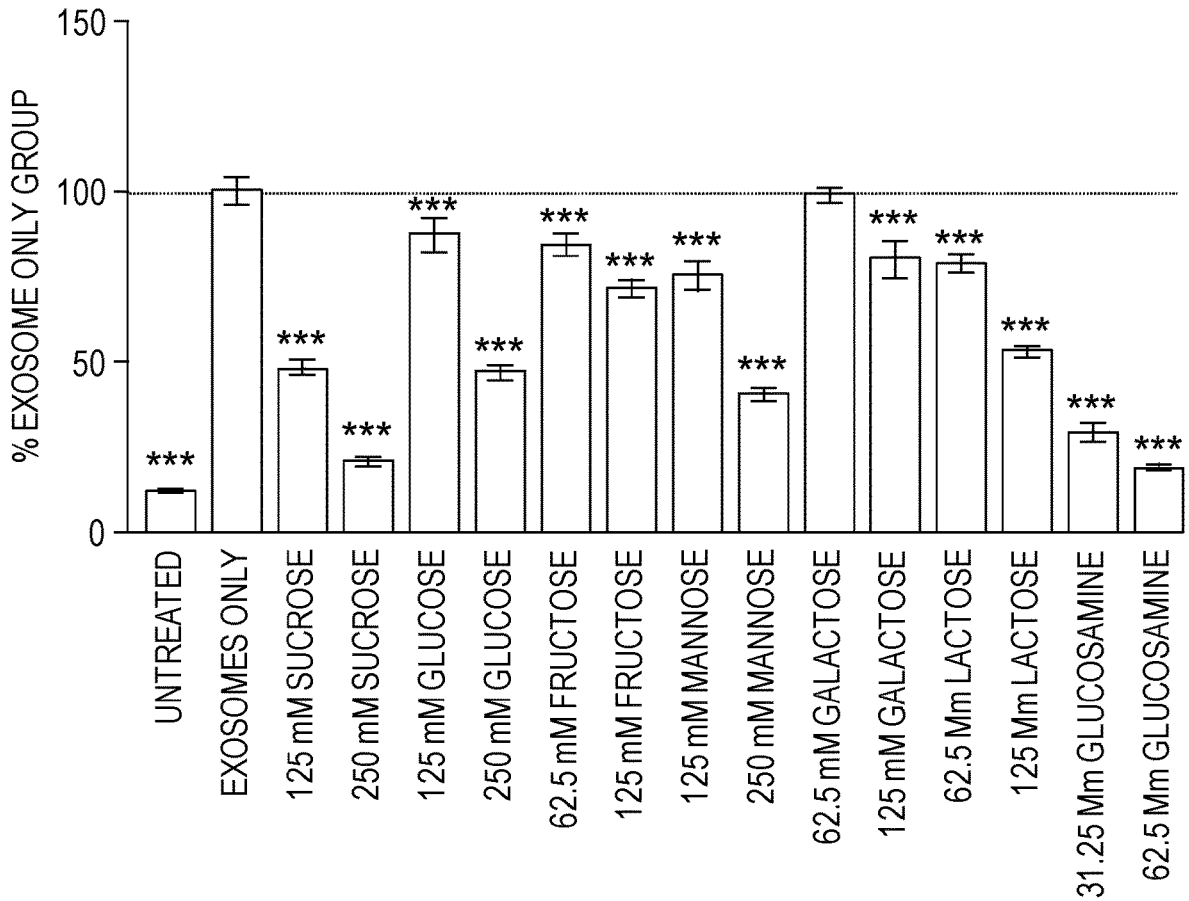
Figure 30B:
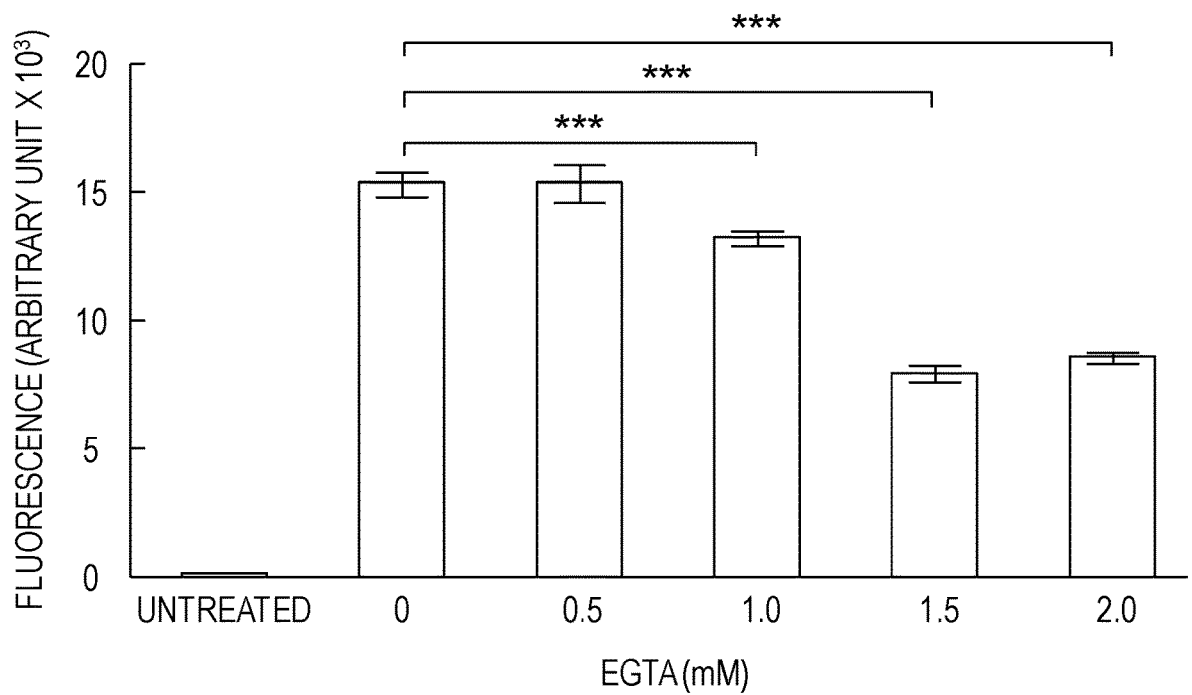
Figure 30C:
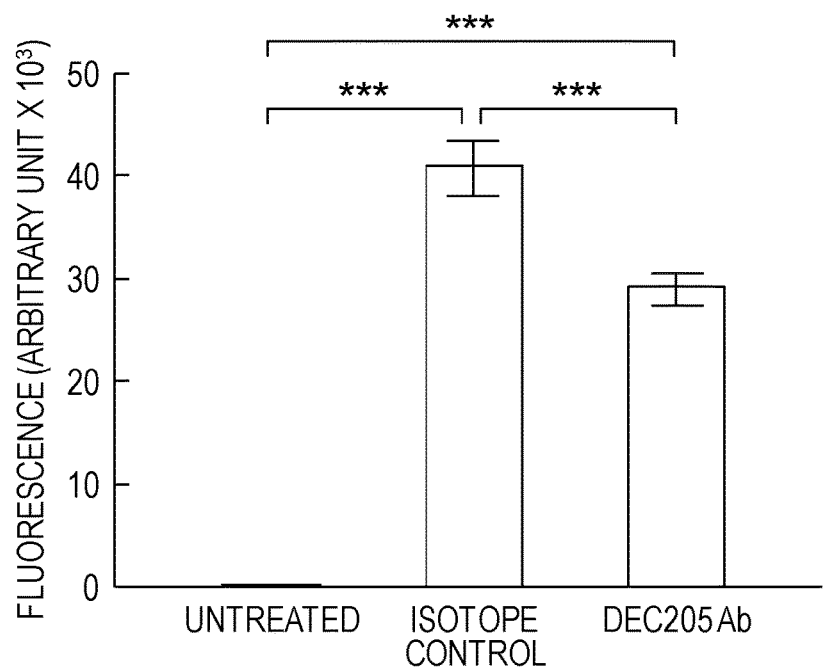

FIGS. 30A-30C show C-type lectin receptors mediated the uptake of MO exosomes in hCMEC/D3 cells. (FIG. 30A) hCMEC/D3 cells were pre-incubated with carbohydrates for 0.5 h, and then co-incubated with exosomes for 4 h. (FIG. 30B) hCMEC/D3 cells were co-incubated with EGTA and exosomes for 4 h. (FIG. 30C) hCMEC/D3 cells were co-incubated with exosomes and DEC205 antibody at 100 µg/ml for 4 h. In all experiments, exosomes were labeled with CM-DiI and used at $0.6 \times 10^{10}$ exosomes/ml. The selected concentrations for carbohydrates and EGTA ensured at least 80% cell viability. Cell uptake of CM-DiI labeled exosomes was determined by flow cytometry. Data are mean fluorescence of 5000-10000 live singlets±SD, n=3. (FIG. 30A) The data was collected in two flow cytometry assays, and each was normalized to cells treated with exosomes only. ***p<0.001 vs exosome only group (FIG. 30A) or indicated group (FIG. 30B, FIG. 30C) by one-way ANOVA and post Newman-Keuls multiple comparison test.

Figure 31:
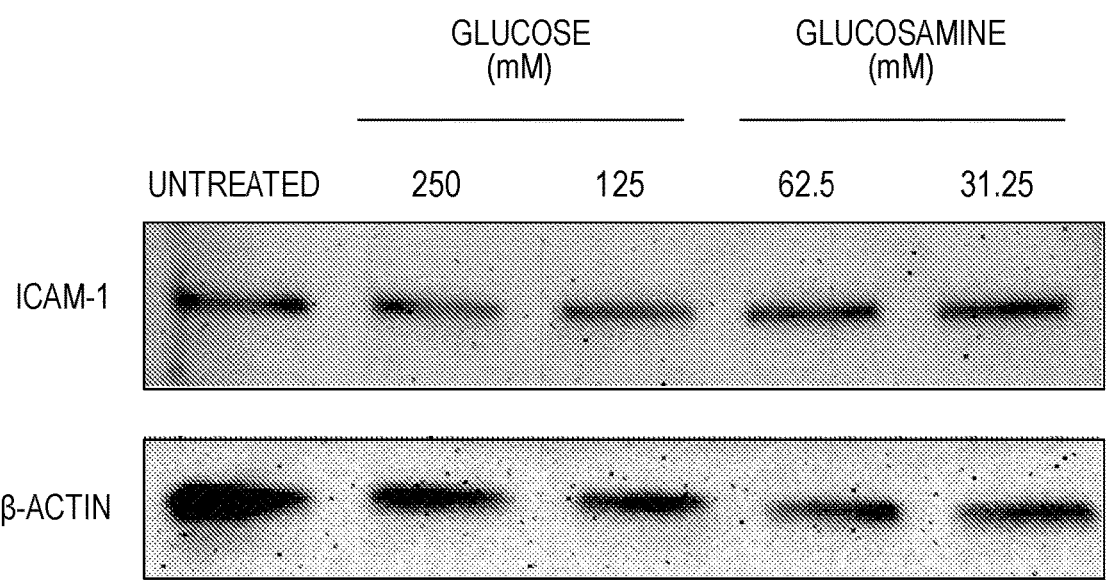

FIG. 31 shows the effect of glucose and glucosamine on ICAM-1 expression in hCMEC/D3 cells. hCMEC/D3 cells were treated with glucose and glucosamine at indicated concentrations for 5 h. Protein expression was determined by western blot using β-actin as loading control.

FIGS. 32A-32D show PK and biodistribution of Mϕ exosomes in healthy and brain-inflamed CD-1 mice. The brain inflammation in CD-1 mice was induced by intracranial injection of 10 µg of LPS a day before study. The mice were injected with $^{125}$I-labeled exosomes and $^{131}$I-labeled BSA via jugular vein. (FIG. 32A) Serum clearance of exosomes and BSA in healthy mice. n=1 per time point. (FIG. 32B) Biodistribution of exosome in healthy mice. (FIG. 32C) Multiple-time regression analysis of exosomes for brain influx rate in healthy and brain-inflamed mice. Delta brain/serum ratio was calculated by subtracting the brain/serum ratio of BSA from that of exosomes to correct for vascular space (Banks et al., Brain Behav. Immun. 24:102 (2010)). n=1 per time point. (FIG. 32D) Biodistribution of exosomes at 10 min. Tissue accumulation was corrected for vascular space using BSA data. Data are means±SEM, n=3-6. # p<0.05, ## p<0.01, and ### p<0.001 vs indicated group by unpaired two-tailed t-test.

Figure 33A:
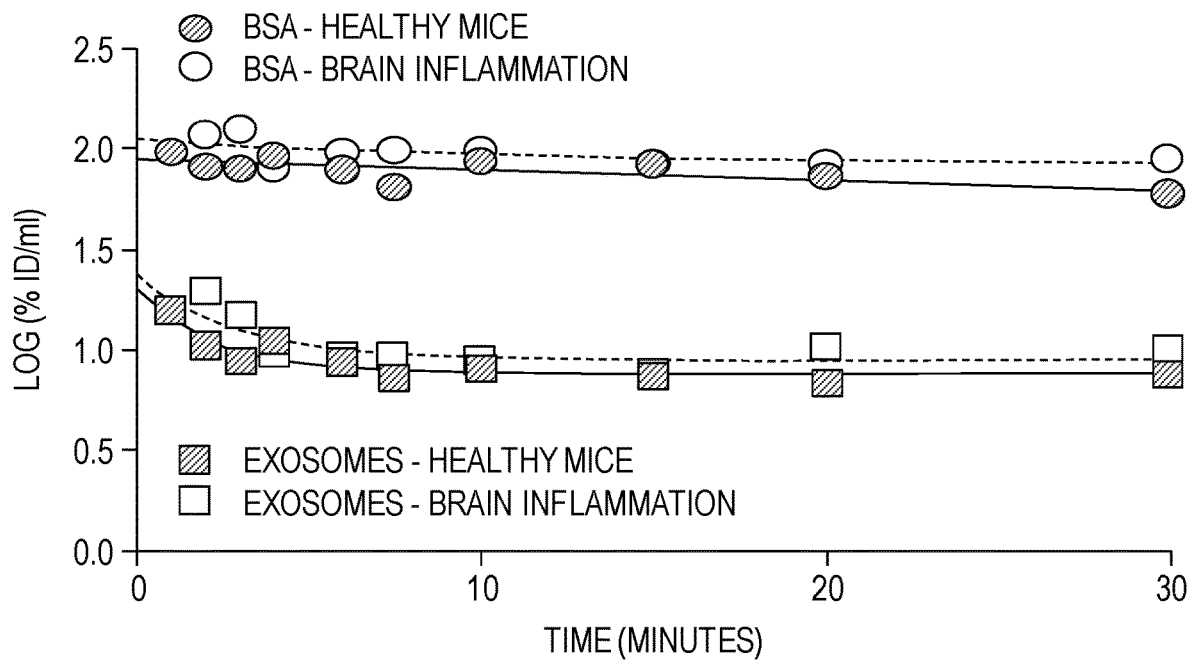
Figure 33B:
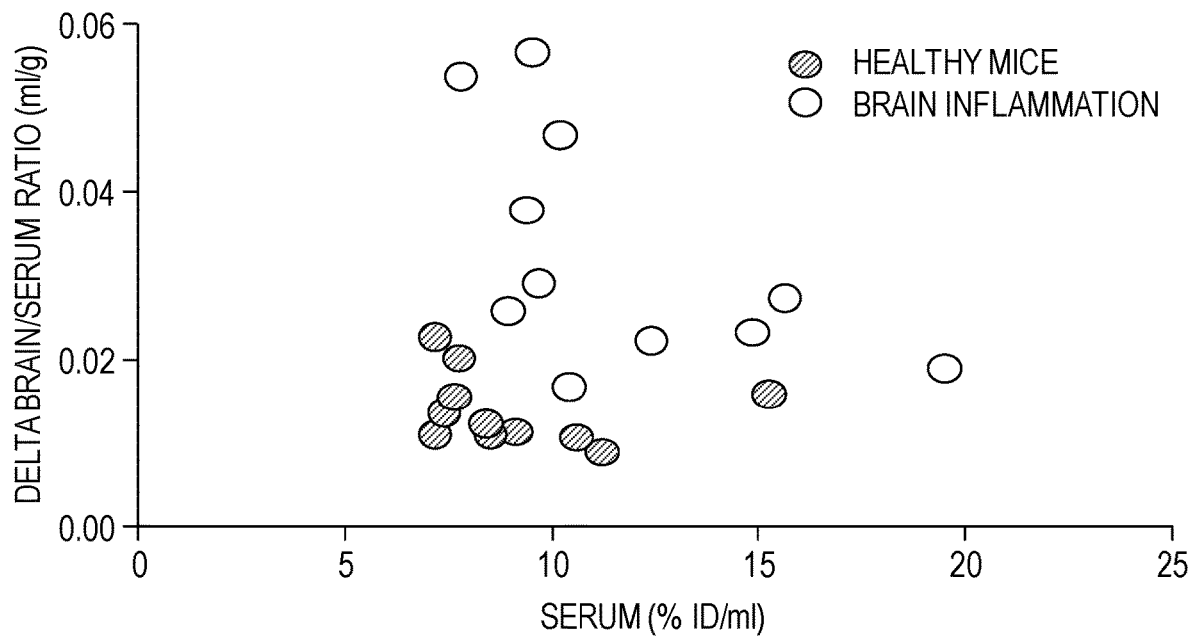
Figure 33C:
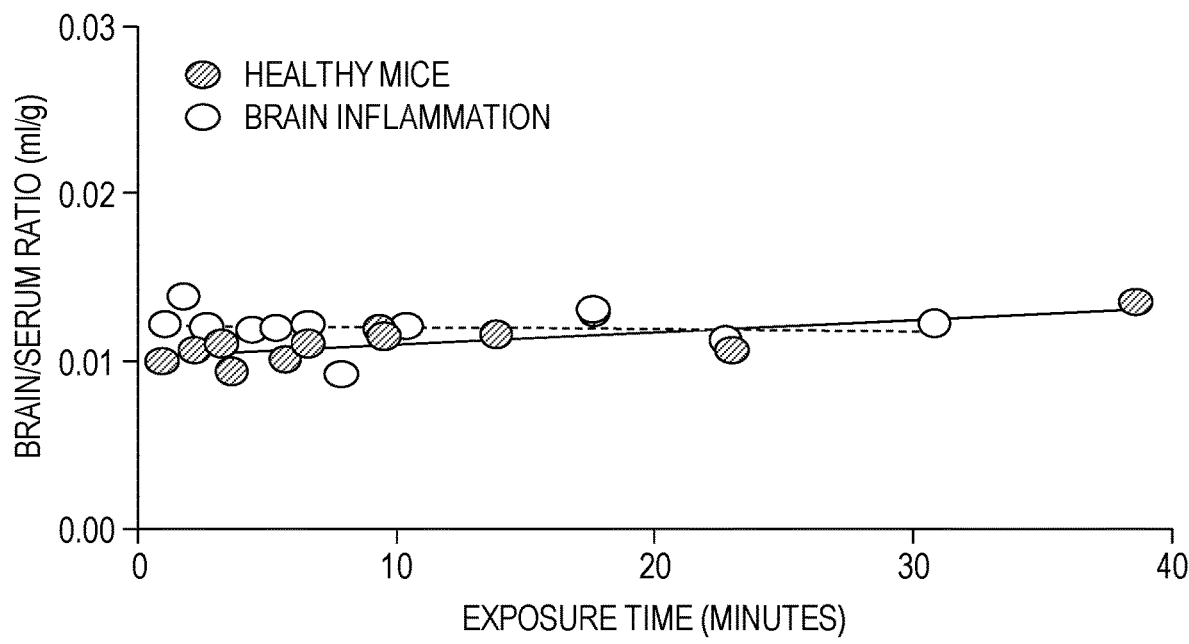

FIGS. 33A-33C show the PK of Mϕ exosomes and BSA in healthy and brain-inflamed CD-1 mice. The brain inflammation was induced by intracranial injection of 10 jpg of LPS a day before study. The mice were injected with $^{125}$I-labeled Mϕ exosomes and $^{131}$I-labeled BSA via jugular vein. (FIG. 33A) Serum clearance of Mϕ exosomes and co-injected BSA. n=1 per time point. (FIG. 33B) Plot of delta brain/serum ratio of Mϕ exosomes against serum concentration of Mϕ exosomes. Delta brain/serum ratio was calculated by subtracting the brain/serum ratio of BSA from that of exosomes to correct for vascular space (Banks et al., Brain Behav. Immun. 24:102 (2010)). (FIG. 33C) Multiple-time regression analysis of co-injected BSA for brain influx rate in healthy and brain inflamed mice. n=1 per time point. Both slopes are comparable to zero.

Figure 34A:
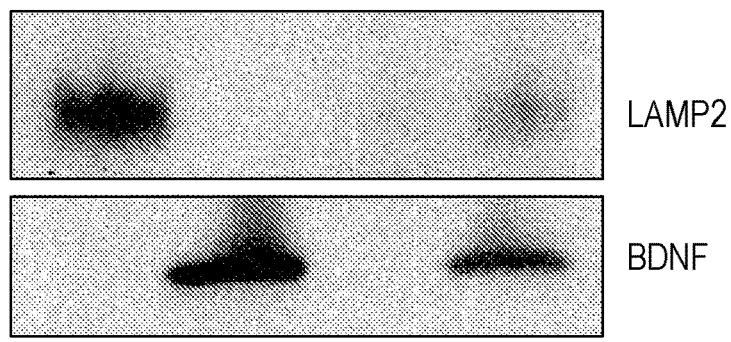
Figure 34B:
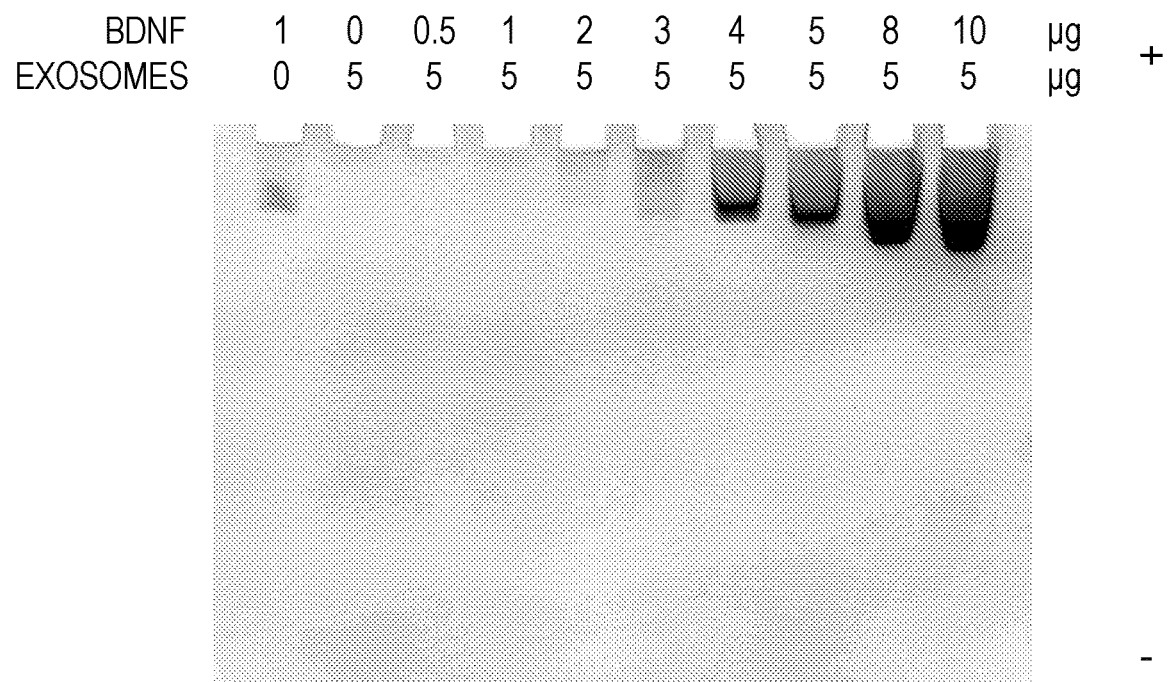

FIGS. 34A-34B show the interaction between Mϕ exosomes and BDNF. (FIG. 34A) BDNF loaded exosomes were isolated using protein G magnetic beads modified with BDNF-specific antibodies. (FIG. 34B) Native gel electrophoresis of mixture of MO exosomes and BDNF at different protein ratios.

Figure 35A:
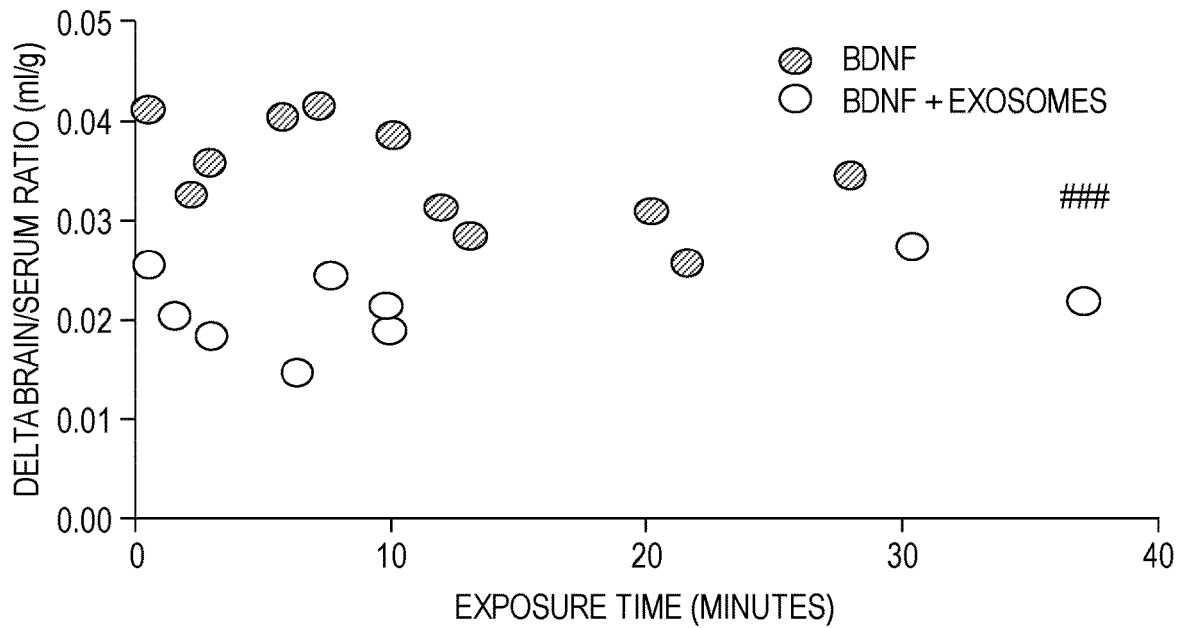
Figure 35B:
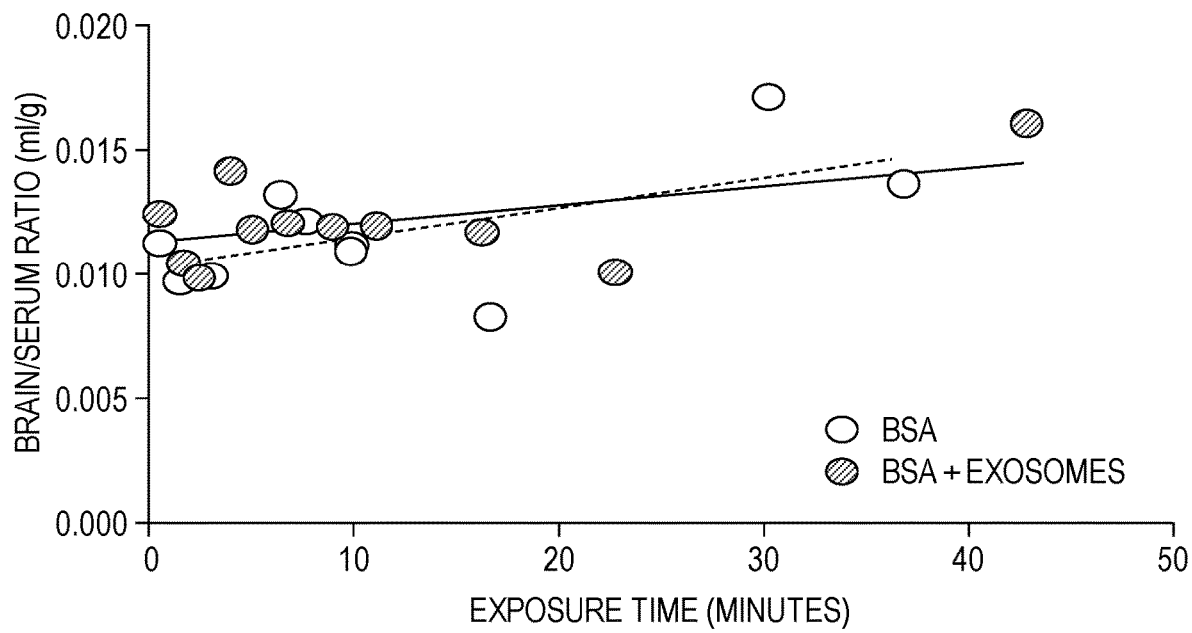
Figure 35C:
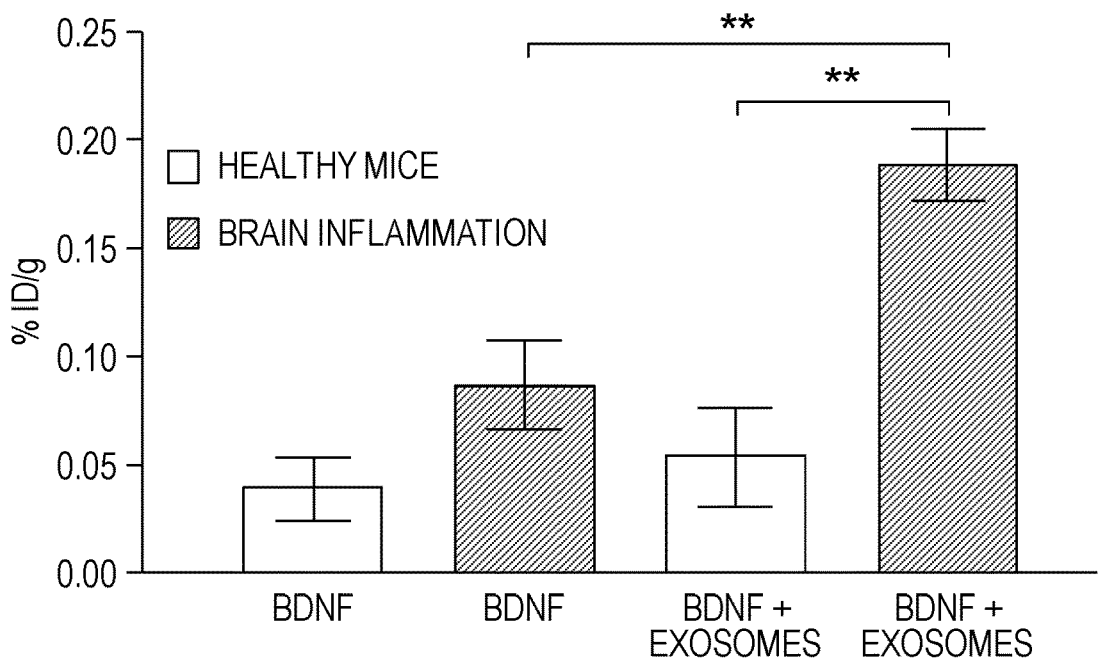

FIGS. 35A-35C show brain delivery of BDNF and Mϕ exosomes complex. Healthy or brain-inflamed mice were co-injected with $^{131}$I-labeled BSA and $^{125}$I-labeled BDNF with or without Mϕ exosomes via jugular vein. (FIG. 35A) Plot of delta brain/serum ratio of BDNF vs exposure time in healthy mice. Delta brain/serum ratio was calculated by subtracting the brain/serum ratio of BSA from that of BDNF to correct for vascular space (Banks et al., Brain Behav. Immun. 24:102 (2010)), n=1 per time point. The two groups were compared by unpaired two-tailed t-test, ### p<0.001. (FIG. 35B) Multiple-time regression analysis of co-injected BSA in healthy mice. Both slopes are comparable to 0 (p=0.064, 0.09 for BSA and BSA+Exosomes by unpaired two-tailed t-test, respectively). (FIG. 35C) Brain accumulation of naked or Mϕ exosomes formulated BDNF in healthy or brain-inflamed mice at 10 min. The brain accumulation was corrected for vascular space using co-injected BSA data. Data are means±SEM, n=3, ** p<0.01 indicated group by one-way ANOVA and post Newman-Keuls multiple comparison test.

Figure 36:
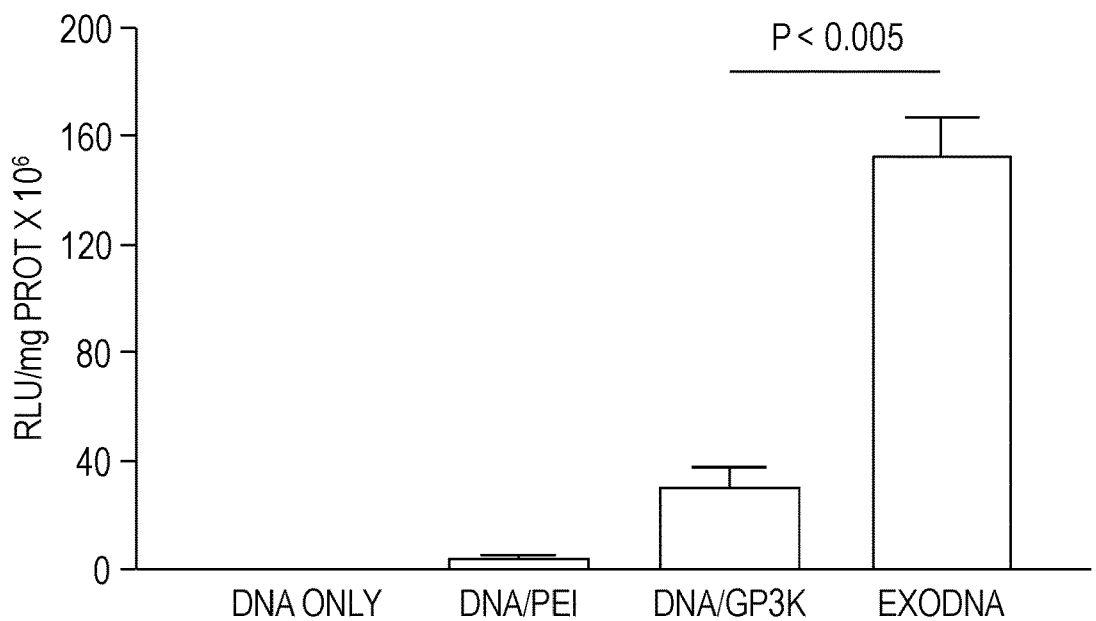

FIG. 36 shows transfection of RAW 264.7 macrophages with pDNA incorporated into exosomes. Various formulations of luciferase-encoding pDNA (2 µg/ml) were added to cell medium for 4 hours. Then, the cells were cultured for additional 20 hours, and the expression of luciferase in cell lysates were assessed by luminescence.

Figure 37:
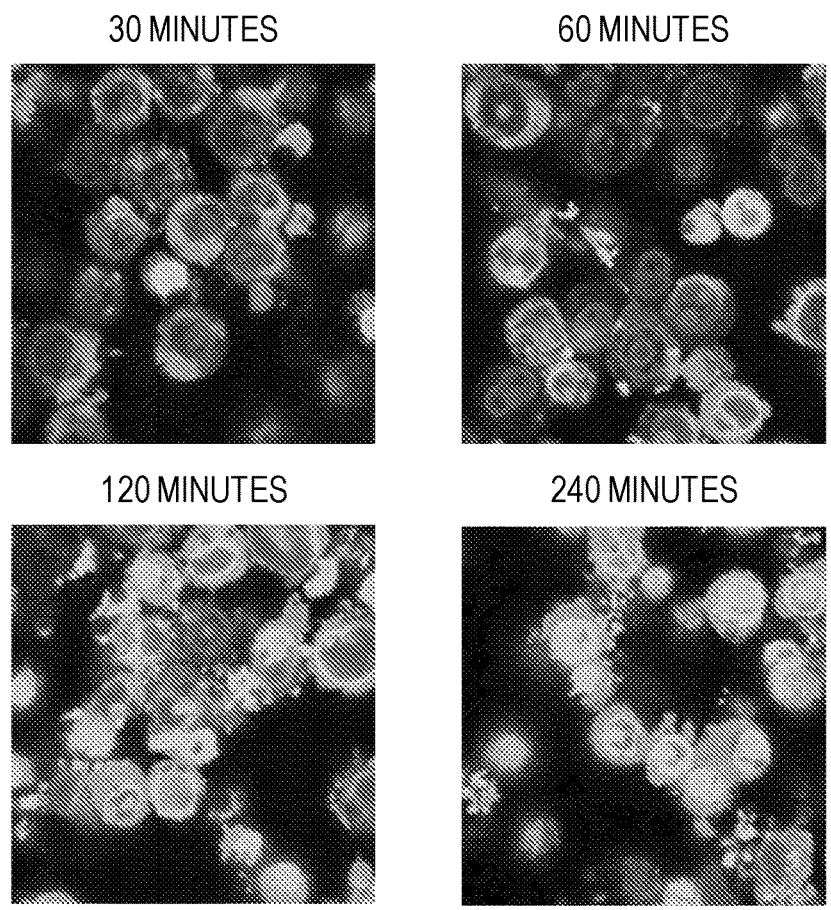

FIG. 37 shows exosome-mediated delivery of pDNA into nuclei of target cells. Model pDNA was labeled with fluorescent dye, YOYO, and formulated into exosomes. RAW 264.7 macrophages were incubated with exoDNA for 4 hours, then cells were washed, permeabilized, nuclei—labeled with DAPI. Co-localization of pDNA and nuclei is evident in the images.

Figure 38:
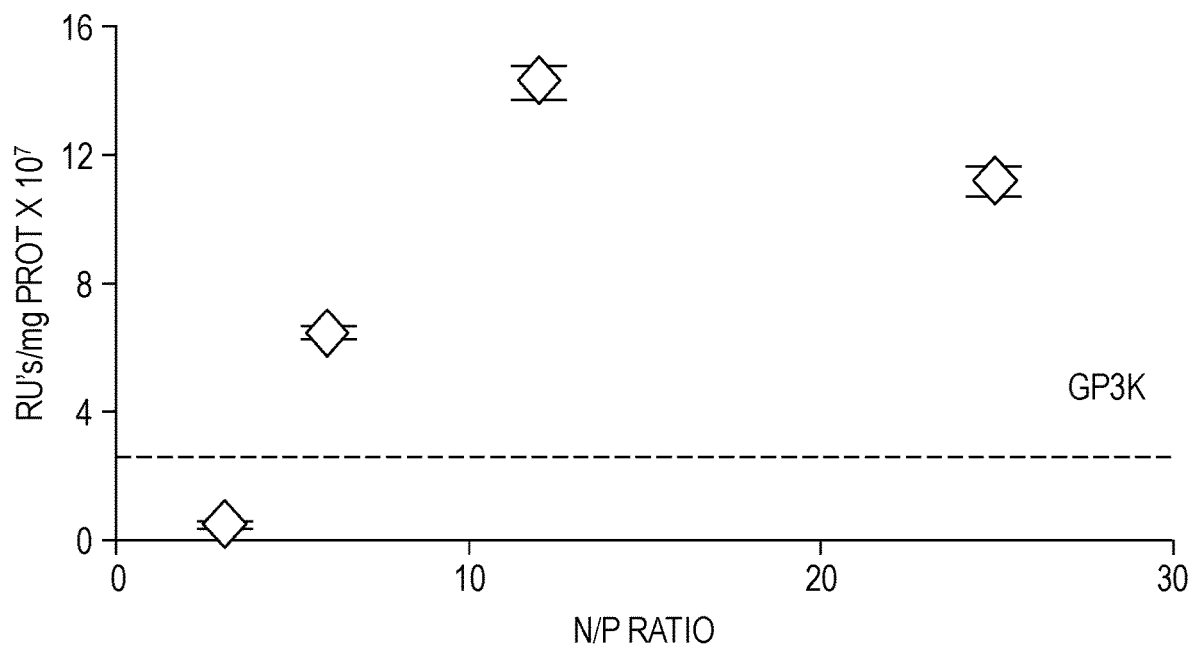

FIG. 38 shows optimization of exoDNA formulations. Various compositions of exoDNA with different N/P ratio were prepared and examined for their Transfection Efficacy in RAW 264.7 cells. The compositions with optimal N/P ratio (12) provided the best transfection efficacy.

Figure 39:
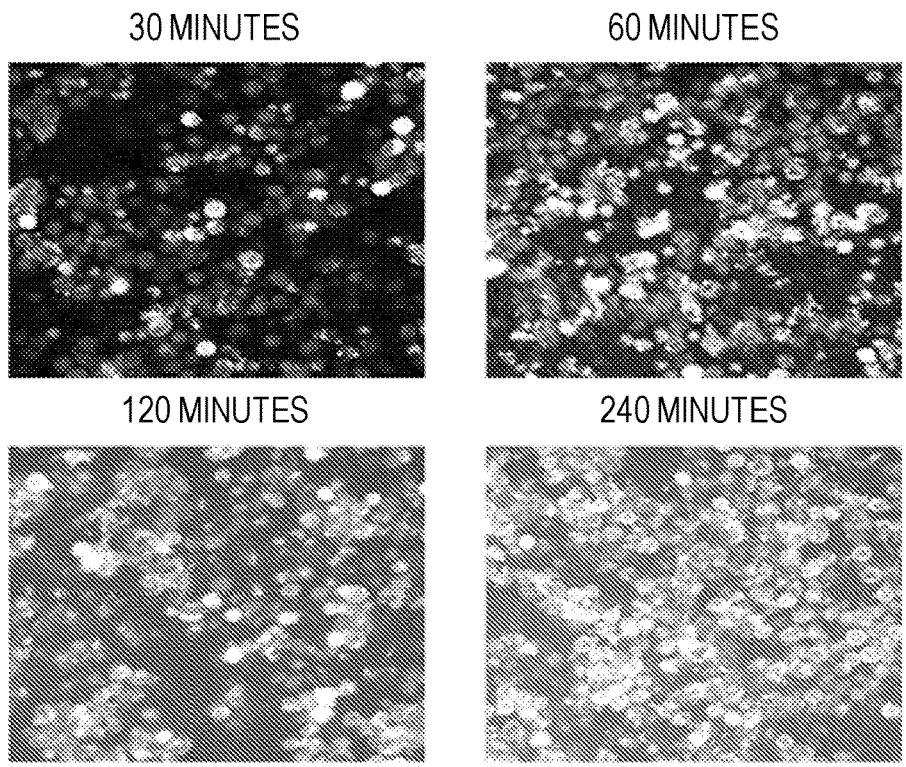

FIG. 39 shows intracellular distribution of exosomes and GFP in target cells. IC21 cells were transfected with optimal formulation GFP-encoding exoDNA formulation for 4 hours. Exosomes were labeled with DIL. Then, cells were permeabilized and nuclei—stained with DAPI. Expression of the encoded protein co-localized with exosomes was evident in the images.

Figure 40:
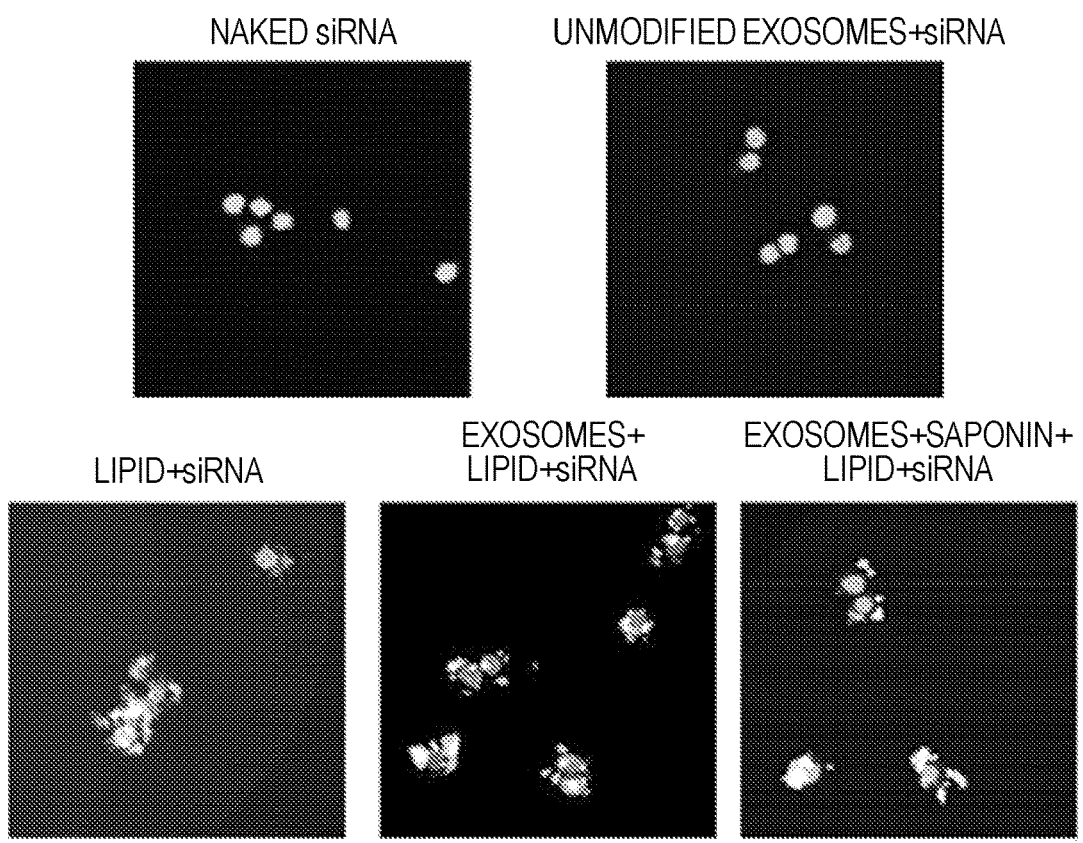

FIG. 40 shows exosome-mediated delivery of siRNA into nuclei of target triple negative breast cancer cells MDA-MB-468. The fluorescently-labeled siRNA was formulated into the cationic lipid-modified exosomes. MDA-MB-468 cancer cells were incubated with exo-siRNA for 4 hours, then cells were washed with PBS, permeabilized with PFA, and nuclei were labeled with Hoechst nucleic acid counterstain.

Figure 41:
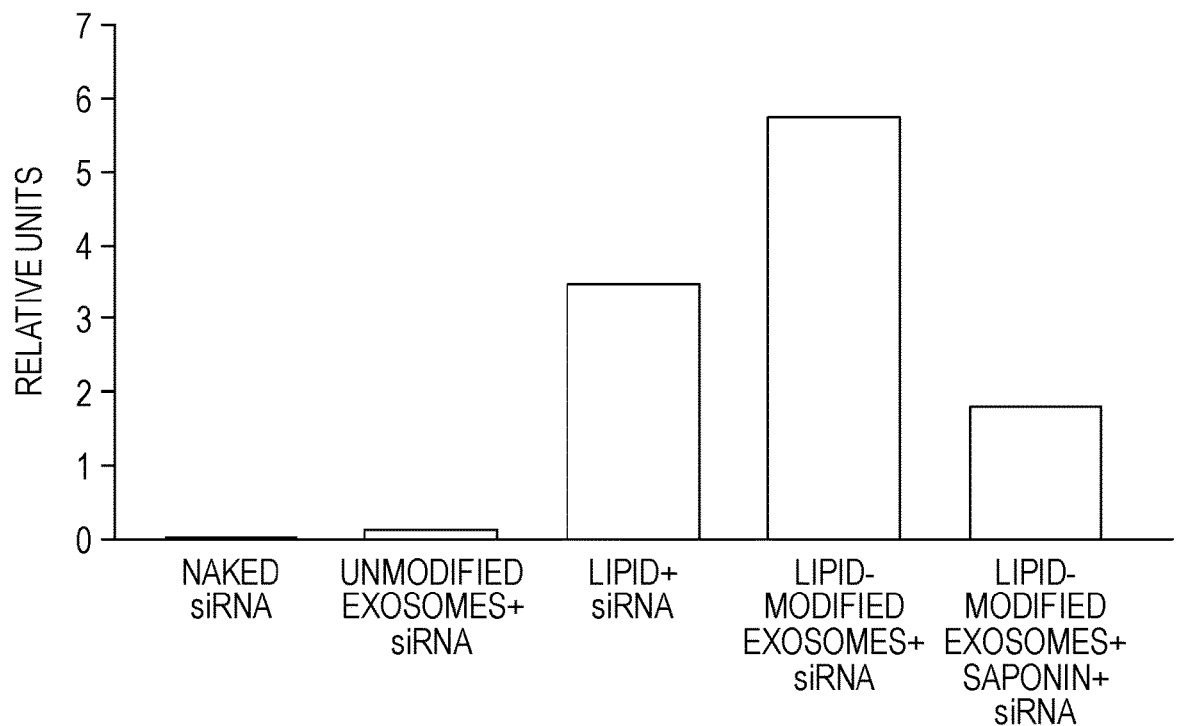

FIG. 41 shows the mean intensity of siRNA accumulation in MDA-MB-468 cancer cells. The fluorescently-labeled siRNA was formulated into the cationic lipid-modified exosomes. MDA-MB-468 cancer cells were incubated with exo-siRNA for 4 hours, then cells were washed with PBS, and permeabilized with PFA. The levels of siRNA accumulation in the cells were analyzed by Image J software.

Figure 42:
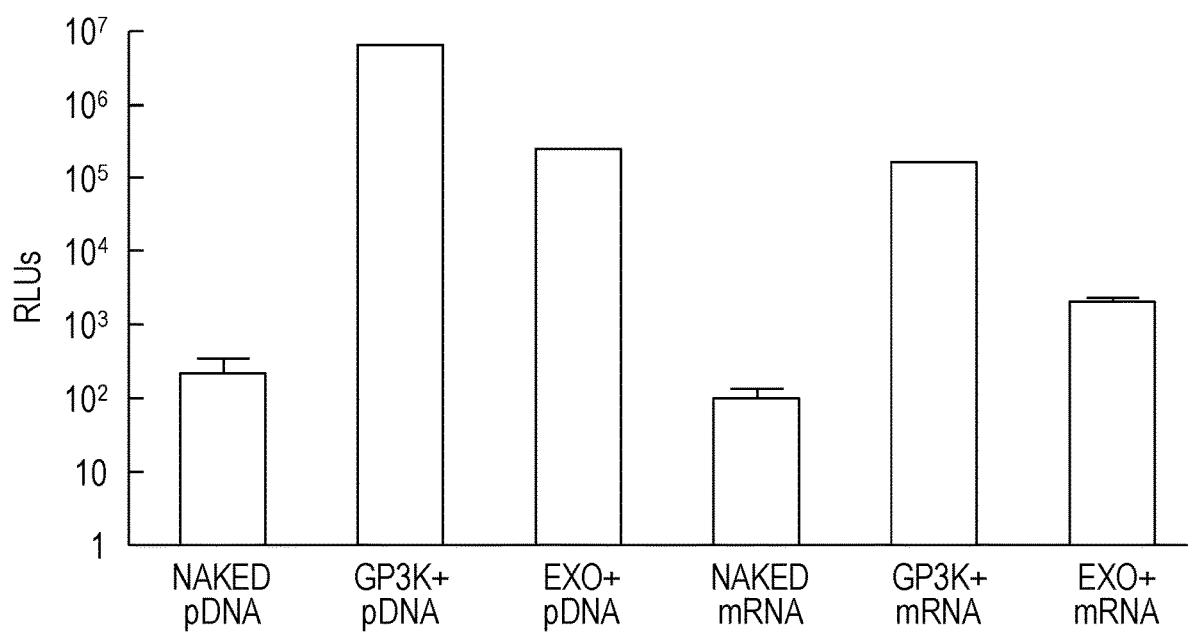

FIG. 42 shows transfection of Raw 264.7 macrophages with exosome-incorporated mRNA and pDNA. Luciferase-encoding mRNA or pDNA were formulated into the cationic lipid-modified exosomes. The cells were incubated with exo-mRNA or exo-pDNA, or control solutions (mRNA or pDNA formulated with GP3K; or naked mRNA or pDNA) for 4 hours, then cells were washed with PBS, and supplemented with full media for another 24 hours. Following the incubation, the cells were lysed and the luciferase levels were determined using a luminometer.

Figure 43A:
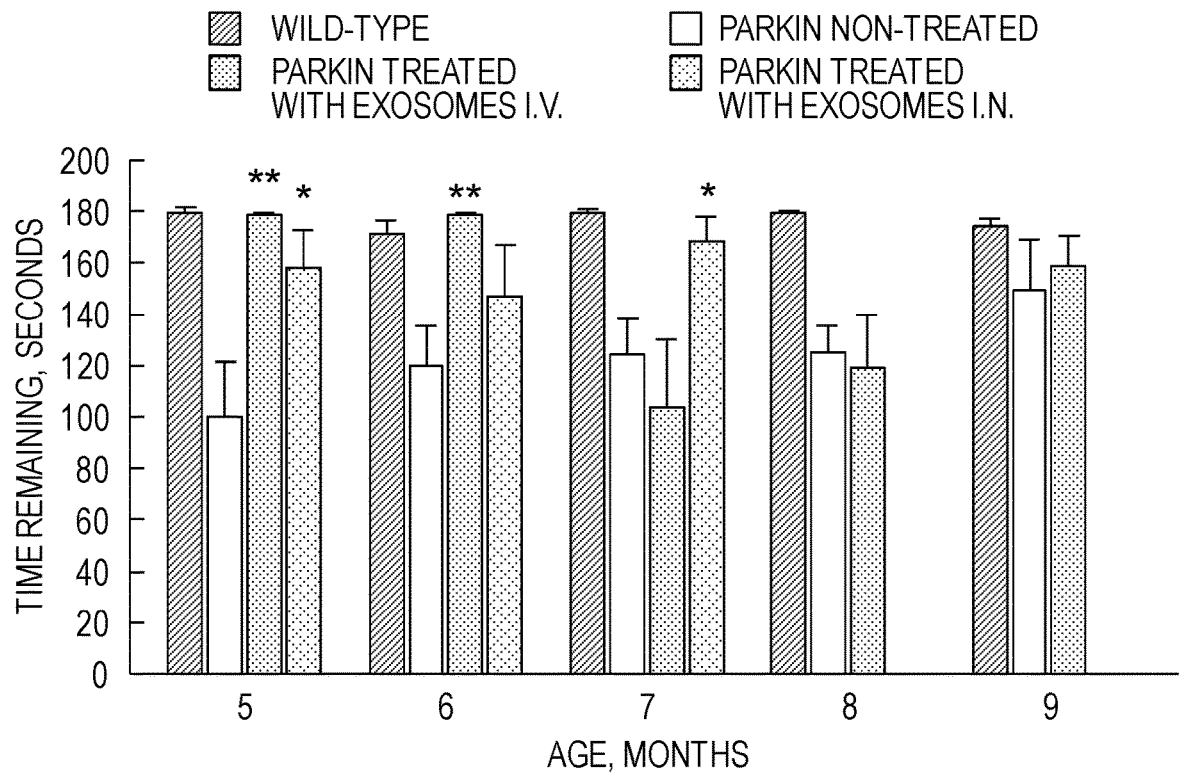
Figure 43B:
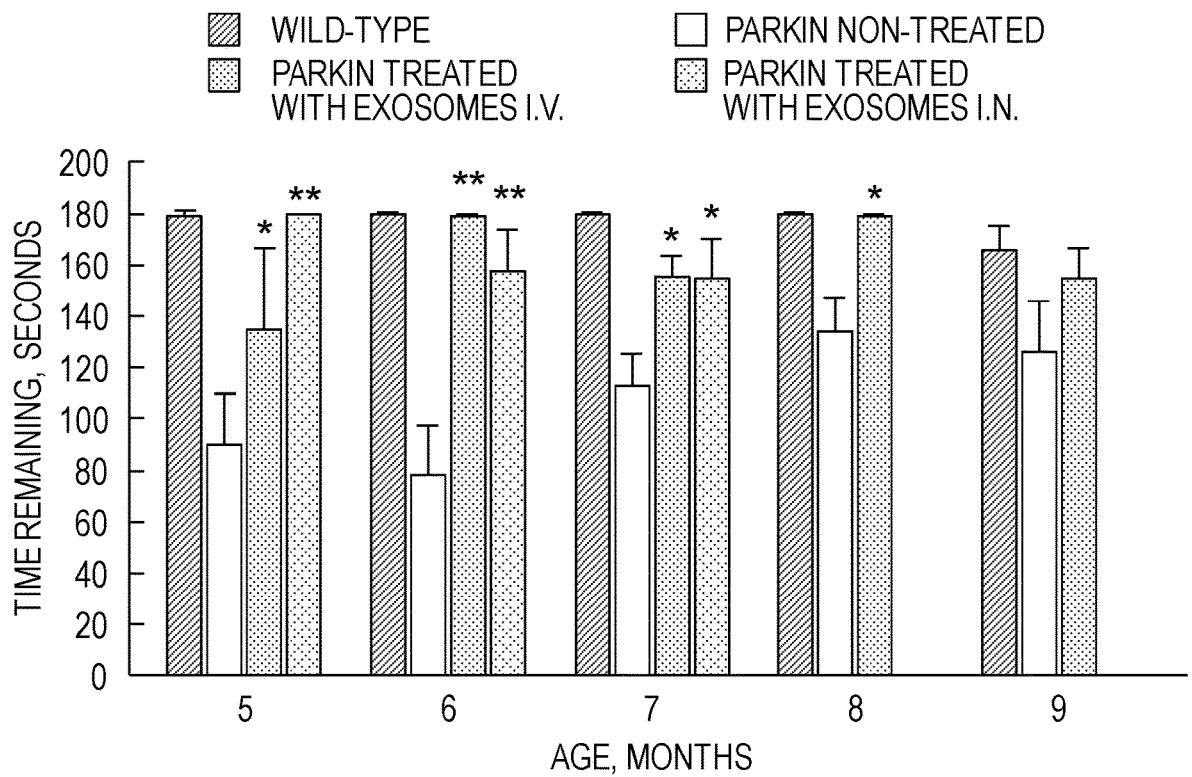
Figure 43C:
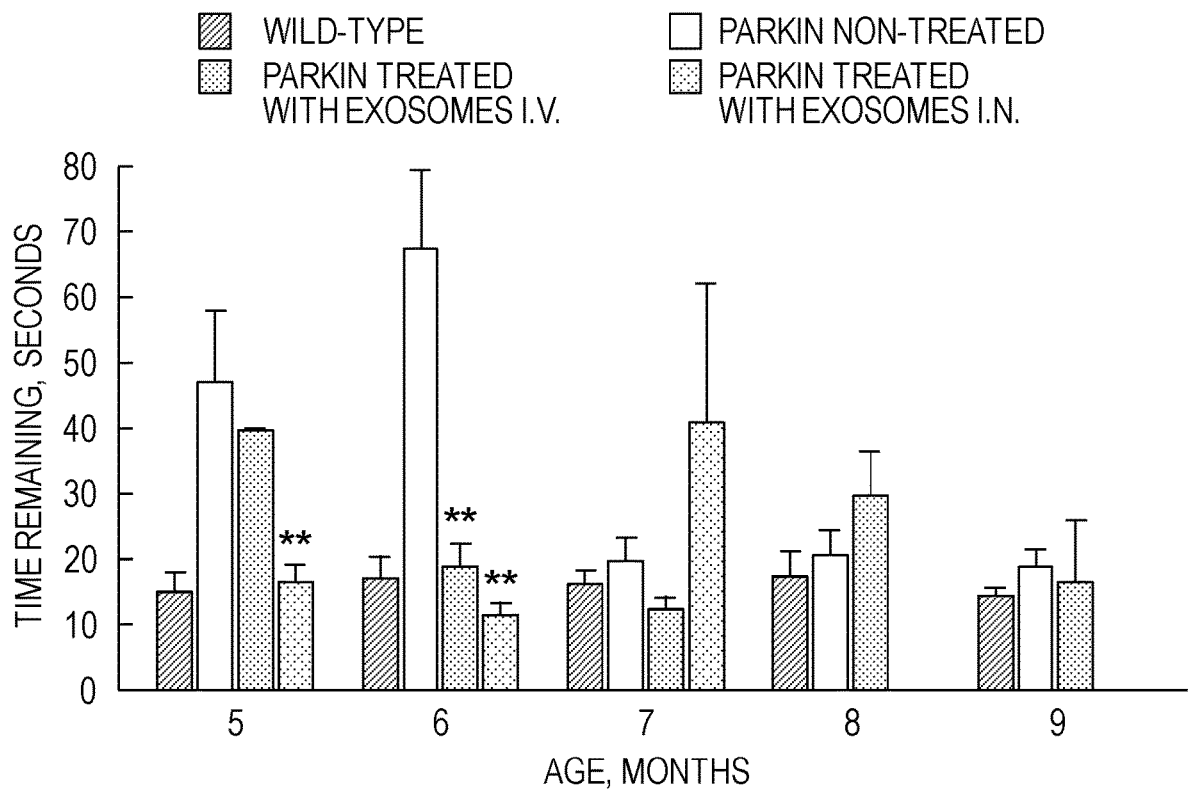

FIGS. 43A-43C shows the effect of exosomes released from GDNF-transfected macrophages on motor functions in ParkinQ311X(A) transgenic mice. IC21 macrophages were transfected with the GDNF-encoding pDNA, and exosomes released from GDNF-macrophages over 24 hours to exosome-depleted serum media were harvested. Parkin Q311X (A) 4-month-old mice were injected with exosomes collected from GDNF-macrophages, or PBS as a control PD mice three times every week. Healthy wild type mice were injected with PBS in the same manner. Behavioral studies, hanging wire (FIG. 43A), rotarod (FIG. 43B) and escaping activity (FIG. 43C) tests, were performed every month to examine effect of exosomal formulation on motor activity in PD mice. * $p<0.05$; ** $p<0.005$ compared to Parkin non-treated mice.

Figure 44:
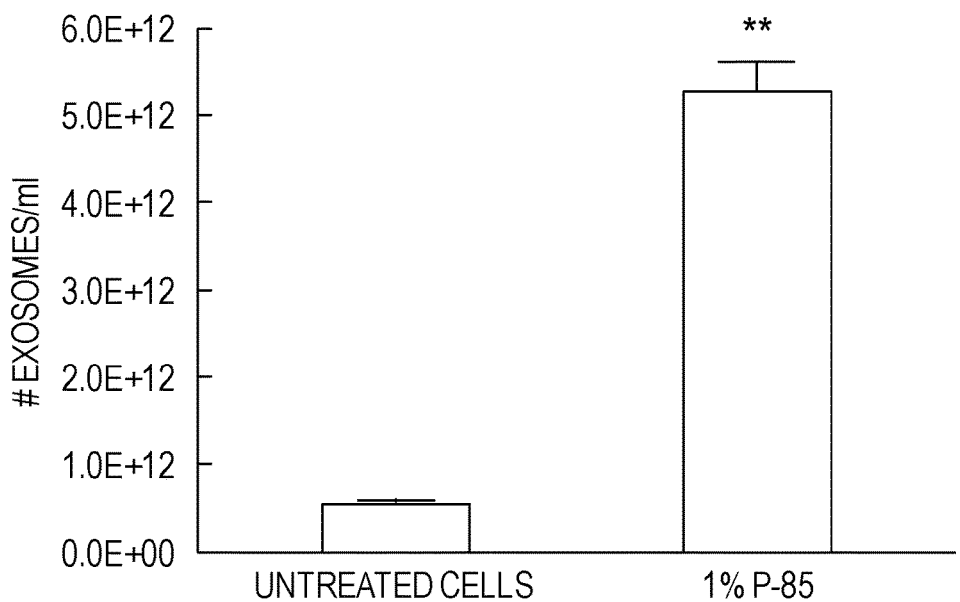

FIG. 44 shows the effect of Pluronic® P85 (P85) treatment on the number of exosomes released by IC21 macrophages. The cells were incubated with 1% Pluronic® P85, or Pluronic®-free media as a control for 4 hours, washed, and supplemented with serum-free media for another 20 hours. Following the incubation, exosomes were isolated from concomitant media and accounted by NTA. The treatment with Pluronic® increased production of exosomes more than an order of magnitude. ** $p<0.005$.

Figure 45:
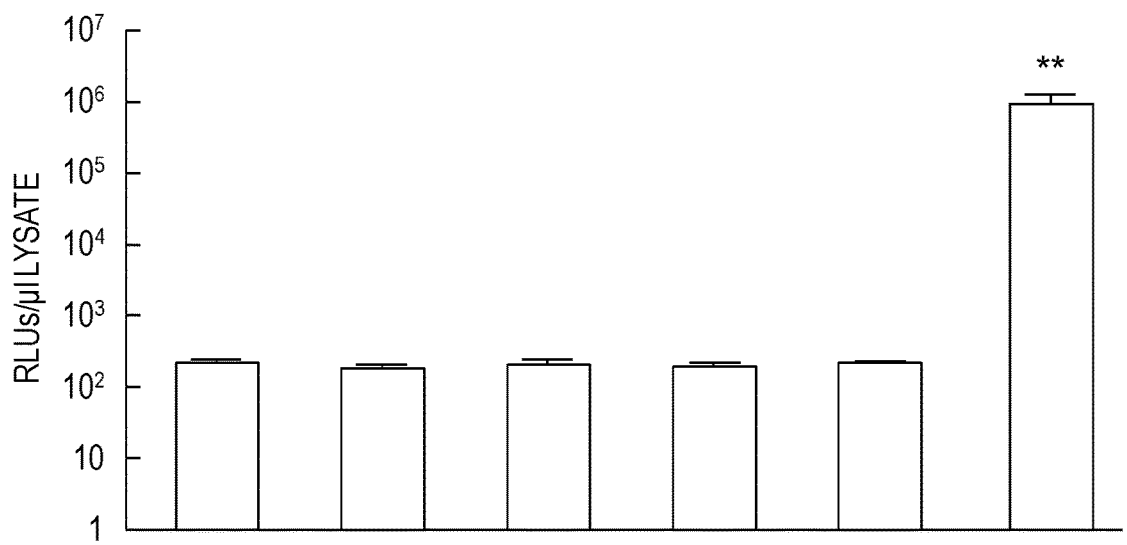

FIG. 45 shows efficient transfection of IC21 cells by exosomes released from Raw264.7 macrophages pre-transfected with luciferase-encoding pDNA. Raw264.7 macrophages were treated with GP3K and mRNA, or GP3K and pDNA. Control cells were treated with GP3K only, or media. Following the transfection, the cells were supplemented with 0.5% Pluronic® P85 (P85) solution for 18 hours at 37° C., or media as a control. Then, exosomes were isolated from each macrophage treatment group and added to IC21 macrophages for another 18 hours. Following the incubation, cells were lysed and accounted for luciferase. Only exosomes released from Raw 264.7 macrophages pre-transfected with pDNA were able to transfect IC21 macrophages. ** $p<0.0005$.

Figure 46:
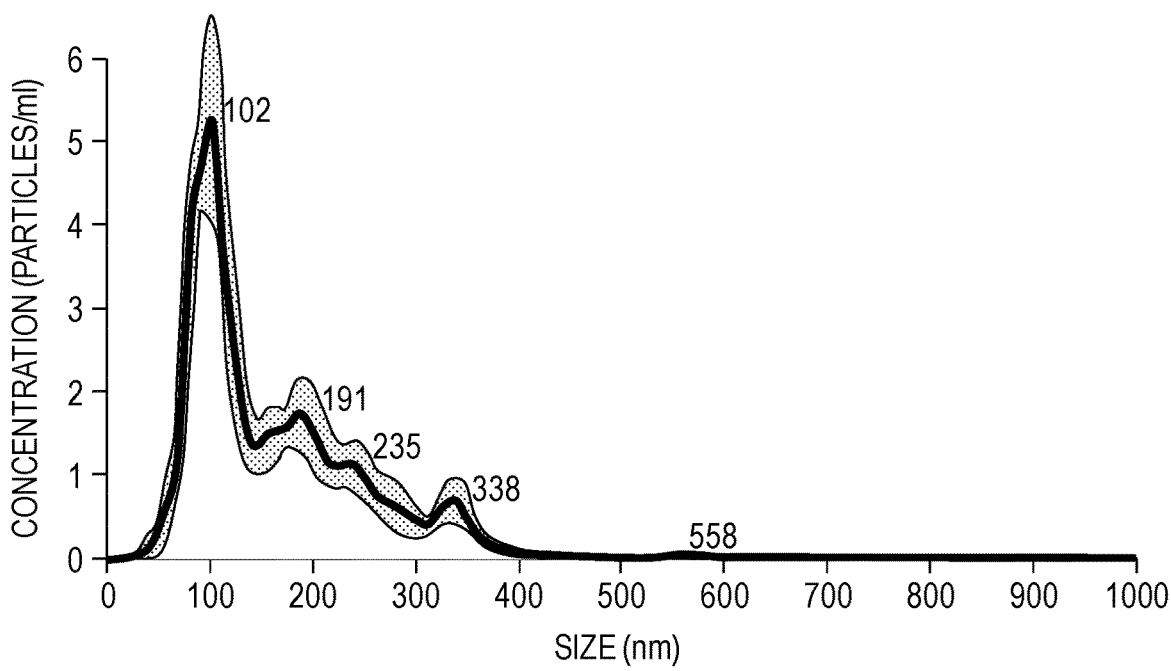

FIG. 46 shows characterization of exosomes isolated from human pluripotent stem cells (hiPSC) by NTA. Exosomes released from hiPSC were collected over 24 hours from concomitant media and washed with PBS. NTA shows particle size distribution with a major fraction at about 100 nm.

Figure 47:
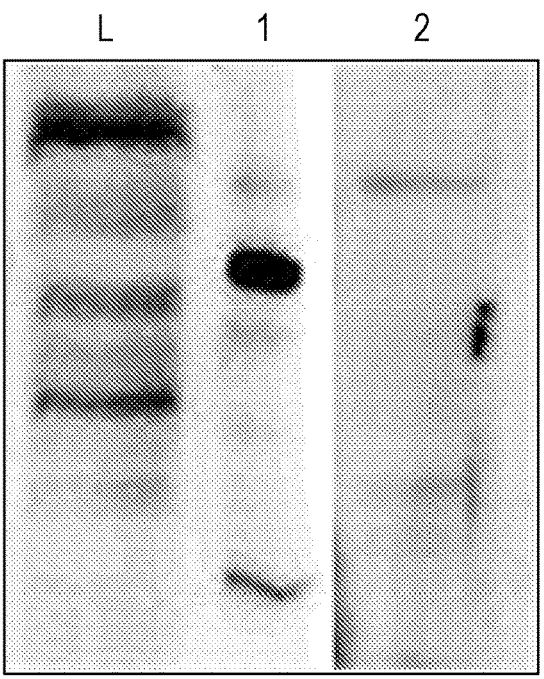
Figure 48A:
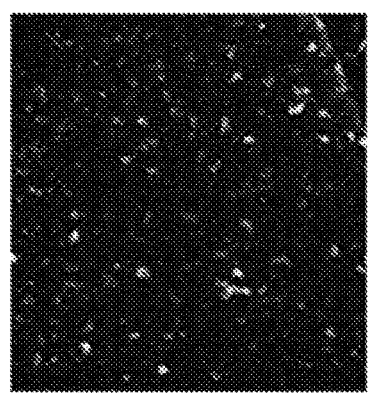
Figure 48B:
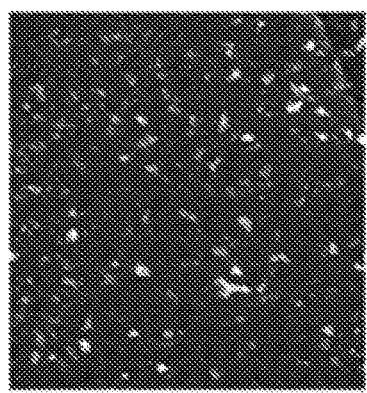
Figure 48C:
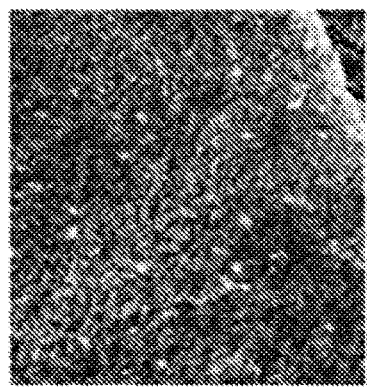
Figure 48D:
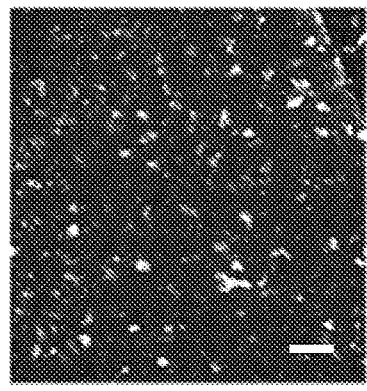

FIG. 47 shows characterization of exosomes isolated from human pluripotent stem cells (hiPSC) by western blot. Exosomes released from hiPSC were collected over 24 hours from concomitant media and washed with PBS. Western blot shows significant amount of exosome-associated protein flotilin (lane 1), as well as LFA-1 (lane 2) in the isolated exosomes. Protein ladder is shown for comparison (lane L).

FIGS. 48A-48D show delivery in vivo of exosomes released by hiPSC to cancer cells in a mouse model of pulmonary metastases. Exosomes released from hiPSC were collected over 24 hours from concomitant media and labeled with hydrophobic fluorescent dye DID. Fluorescently-labeled exosomes were administered i.n. to C57B/U6 mice with metastases produced by intravenous 8FlmC-FLuc-3LL-M27 LLC cells. Four hours after administration of the exosomes the animals were sacrificed, the lungs extracted and sectioned and analyzed by confocal microscopy. The microscopy reveals (FIG. 48A) cancer cells, (FIG. 48B) DID-labeled exosomes, (FIG. 48C) nuclei labeled with DAPI, and (FIG. 48D) colocalization of the exosomes and cancer cells. The bar: 50 µm.

Figure 49A:
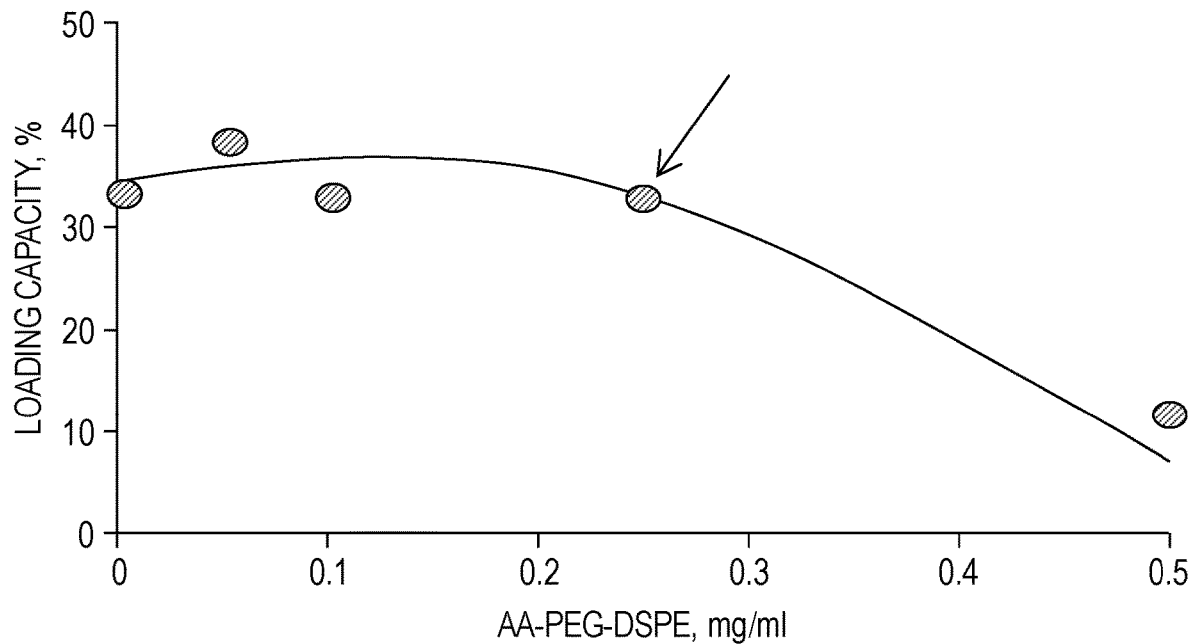
Figure 49B:
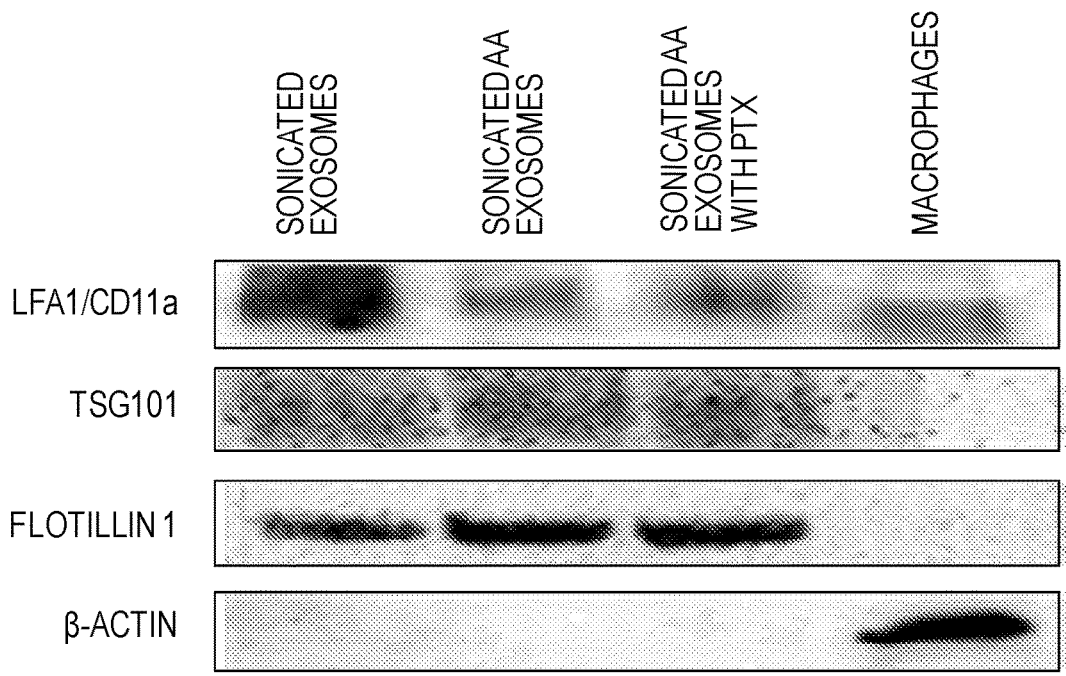
Figures 49C, 50:
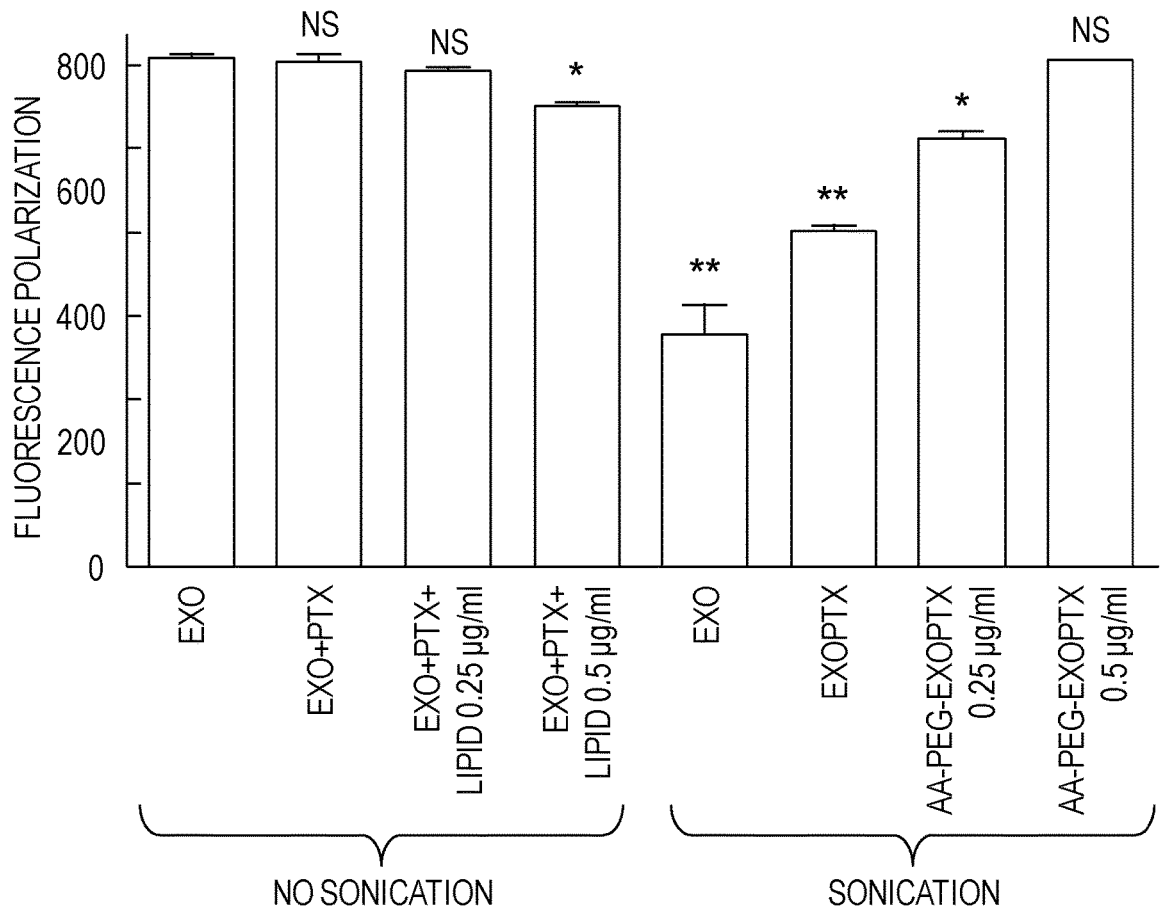

FIGS. 49A-49C show characterization exosomal formulations exoPTX and AA-PEG-exoPTX. PTX and vector moiety AA-PEG-DSPE was incorporated in exosomes by sonication procedure. (FIG. 49A) Loading Capacity (LC) for PTX in vectorized exosomes was measured by HPLC. Increasing amounts of vector moiety resulted in LC decrease. The highest concentration of AA-PEG-DSPE that did not lower the LC for PTX in exosomes was chosen for subsequent experiment (shown by arrow). (FIG. 49B) Western blot data indicated that formulations retained the exosome markers TSG101, flotillin, and LFA-1, a specific marker for lymphocytes. (FIG. 49C) Particle size was measured by NTA and DLS, the zeta potential was measured by DLS.

FIG. 50 shows the effect of AA-PEG-DSPE incorporation and PTX loading on fluidity of exosomal membranes. Exosomes were labeled with BODIPY-PC, and examined by fluorescence polarization measurements. The ultrasound treatment significantly decreased microviscosity of exosomal membranes compared to naïve exosomes. The microviscosity of sonicated exosomes was increased with PTX loading and then further increased with incorporation of the lipid upon sonication. Values are means±SEM (n=4). Symbols indicate the relative level of significance compared with naïve exosomes ($p<0.05$).

Figure 51A:
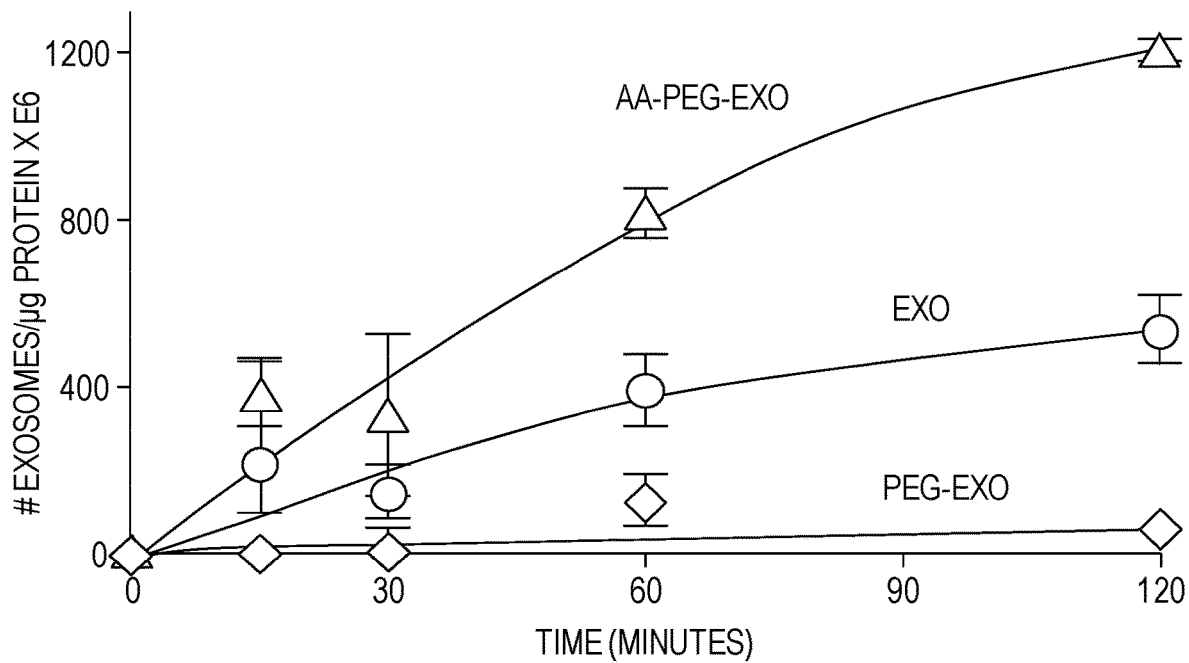
Figure 51B:
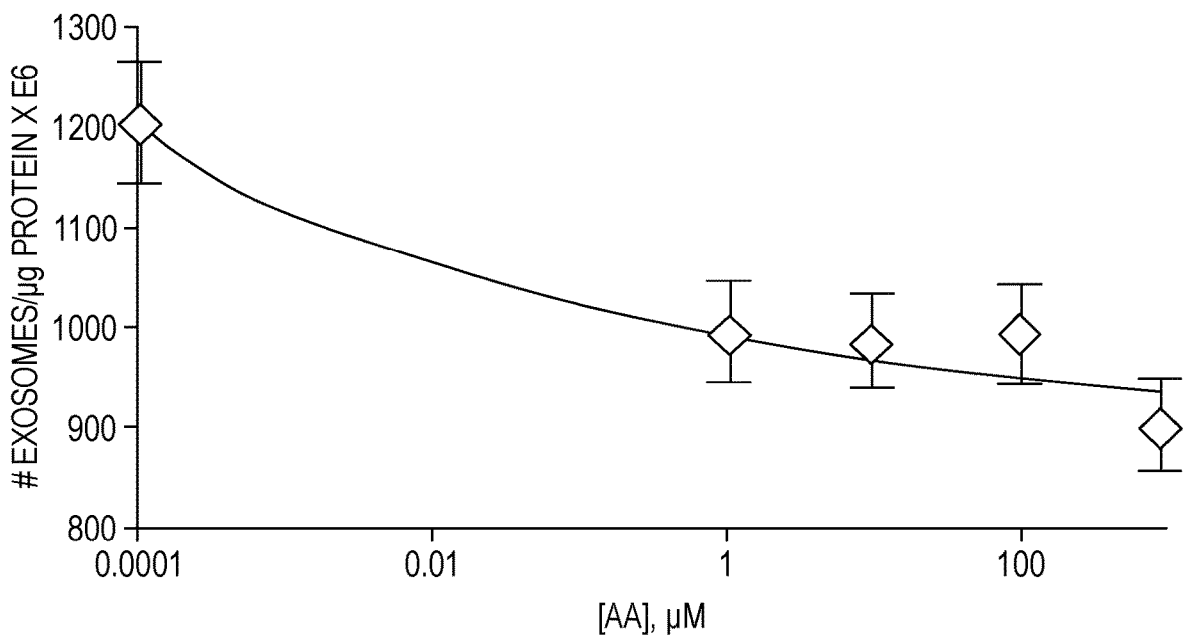

FIGS. 51A-51B shows accumulation of AA-vectorized exosomes in target cancer cells. (FIG. 51A) 3LL-M27 cells were incubated with fluorescently-labeled AA-PEG-exo, or PEG-exo, or exo for various times, and accumulation levels were recorded. AA-PEG-exo were more readily taken up by 3LL-M27 as compared to exo and PEG-exo. (FIG. 51B) AA-PEG-exo formulation showed a dose-dependent response to competitive inhibition by AA, indicating that this formulation was targeted to the sigma receptor and enters cells by receptor mediated endocytosis. Results are expressed as number of exosomes/g protein vs. concentration of AA.

Figure 52:
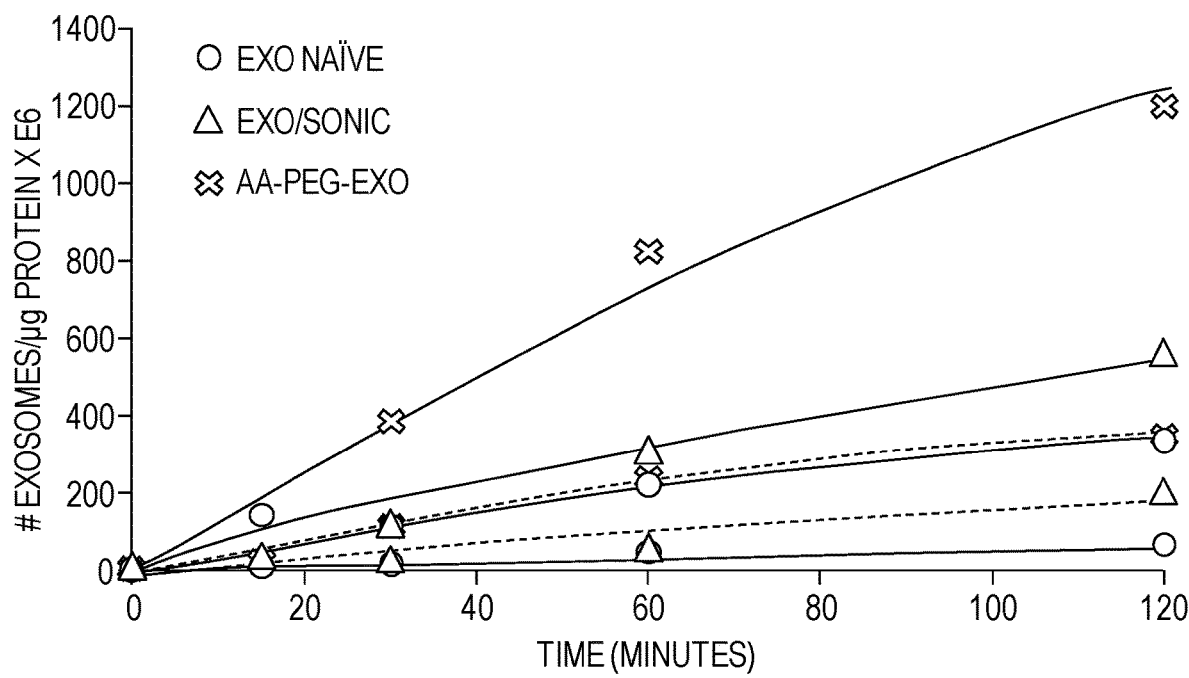

FIG. 52 shows importance of surface proteins on exosome accumulation in 3LL-M27 cancer cells. Naïve (circle), sonicated (triangle), and AA-vectorized (cross) exosomes were incubated with proteinase K to strip surface proteins, labeled with fluorescent dye (DIL), and accumulation of Proteinase K-treated exosomes (dashed line) or control exosomes (solid line) was examined in target cancer cells. Stripping the exosomal surface proteins resulted in significant decreases in accumulation levels in target cells for all formulations.

Figure 53A:
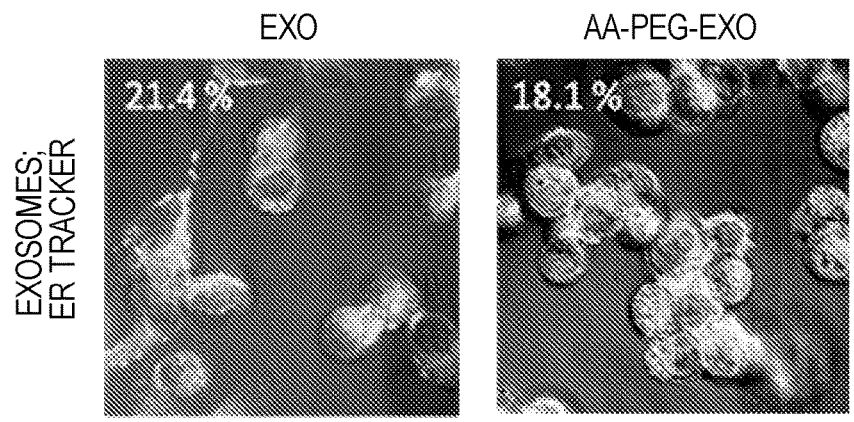
Figure 53B:
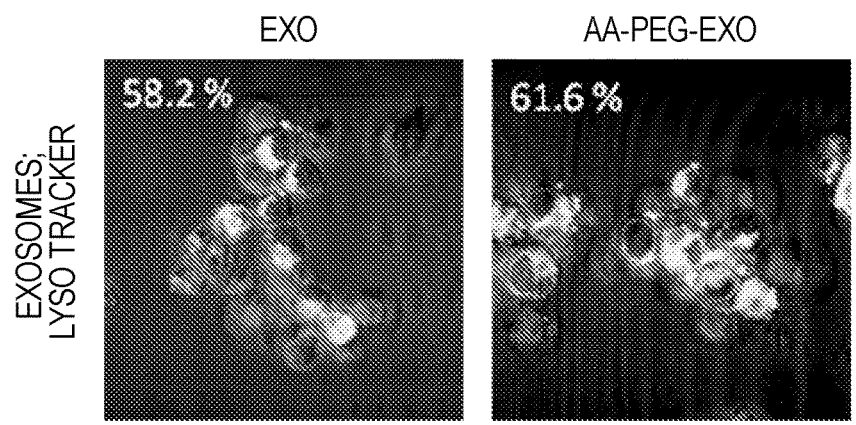
Figure 53C:
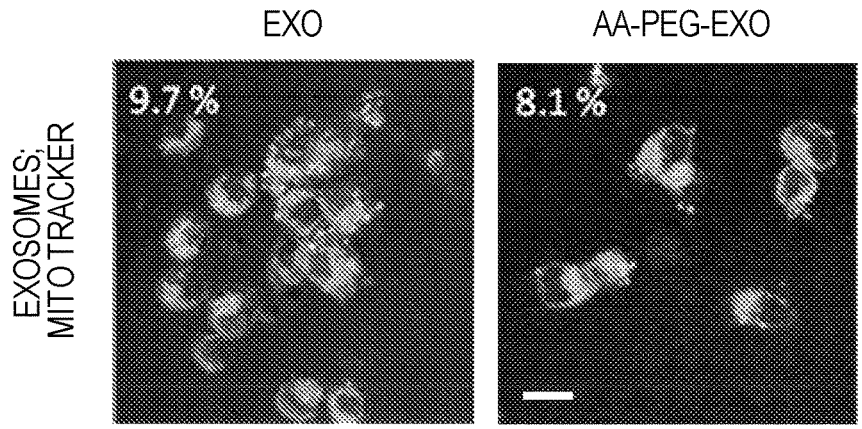

FIGS. 53A-53C show intracellular trafficking of AA-vectorized exosomes in cancer cells. Fluorescently labeled (DiL) exosomes were incubated with 3LL-M27 cells for one hour. Afterwards, cells were washed and stained with ER Tracker (FIG. 53A) or LysoTracker (FIG. 53B), or Mitotracker (FIG. 53C). Areas of co-localization were evident in the images. The bar: 20 µm.

Figures 54A, 54B, 54C:
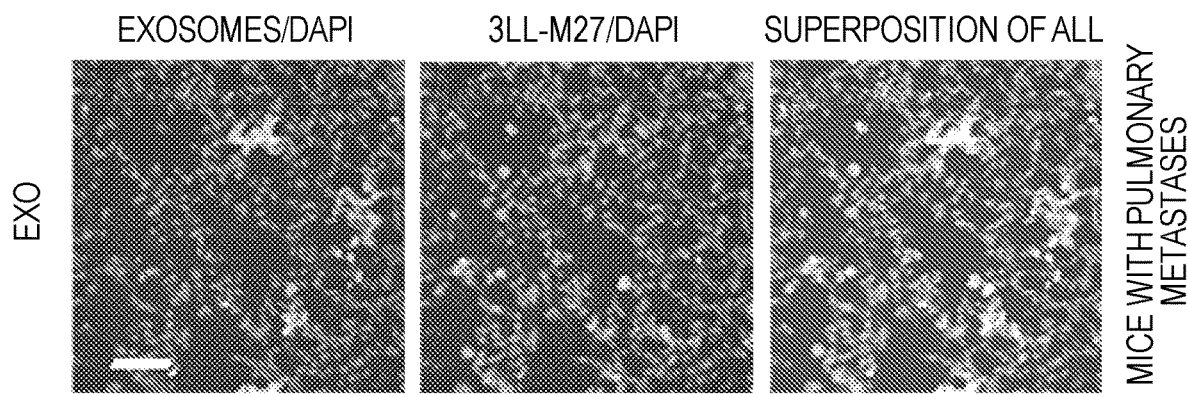
Figures 54D, 54E, 54F:
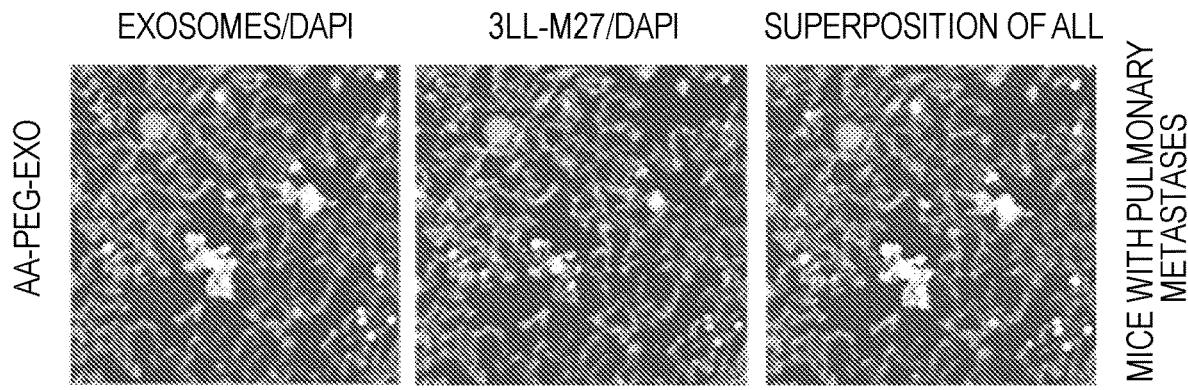
Figures 54G, 54H, 54I:
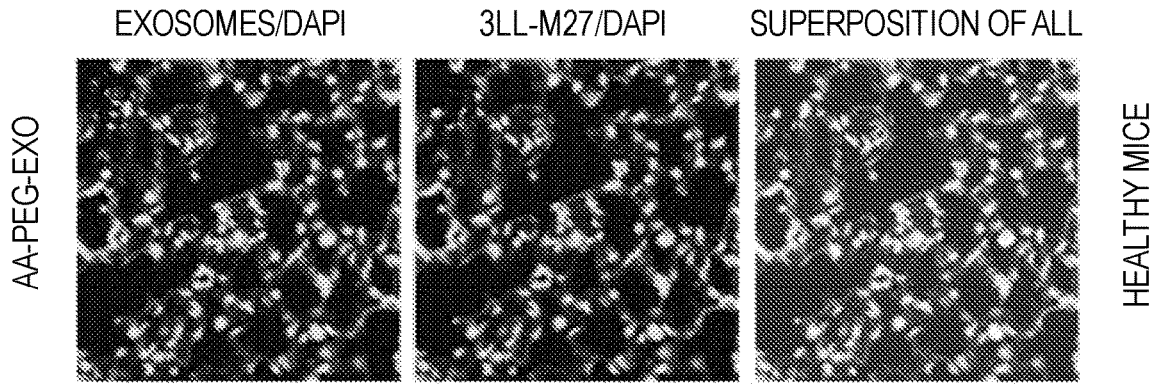

FIGS. 54A-54I show co-localization of intravenously-delivered AA-vectorized exosomes with pulmonary metastases. Exosomes were isolated from macrophages conditioned media, and labelled with DiL dye (FIG. 54A, FIG. 54D). C57BL/6 mice were i.v. injected with 3LL-M27 cells transduced with lentiviral vectors encoding the optical reporter GFP fluorescent protein (FIG. 54B, FIG. 54 E). 7 days later, the mice with established pulmonary metastases (green) were i.v. injected with DiL-labeled non-vectorized exosomes (FIG. 54A), or AA-vectorized exosomes (FIG. 54D). 4 hours later, mice were euthanized, perfused, lungs were sectioned, and stained with DAPI. The confocal images revealed a significant co-localization of vectorized exosomes with metastases (94.4+0.8%), that was greater than those of non-vectorized exosomes (21.8+0.2%) (FIG. 54F). No exosomes were found in lungs of healthy animals without metastases (FIGS. 54G-54I). The bar: 20 µm.

Figure 55A:
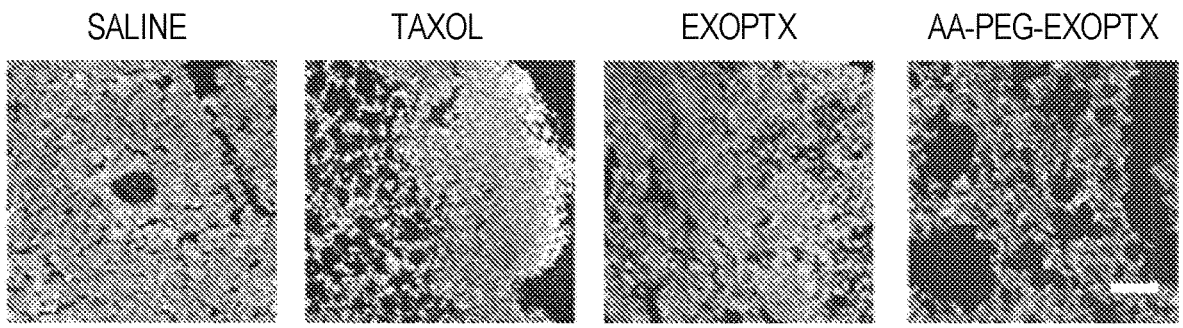
Figure 55B:
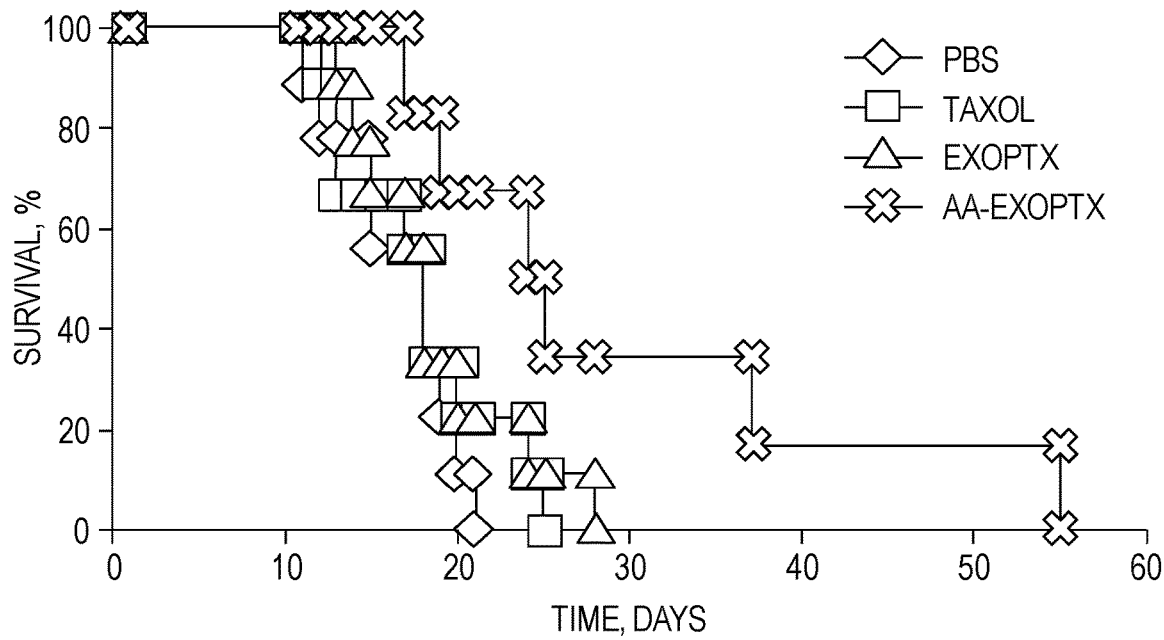

FIGS. 55A-55B show AA-PEG-ExoPTX induced potent anticancer effect against lung metastases in LLC mouse model. (FIG. 55A) C57BU6 mice with established Luc/mCherry-3LL-M27 lung metastases were i.v. treated with i) saline, or ii) Taxol, or iii) exoPTX, or iv) AA-PEG-exoPTX. 18 days later, mice were sacrificed, perfused, and lungs slides were examined by confocal microscopy. AA-PEG-exoPTX treatment resulted in a potent inhibition of metastases that was more effective than treatment with Taxol or exoPTX. The bar: 50 µm. (FIG. 55B) A survival curve of C57BL/6 mice with established metastases was recorded for four treatment groups: 1) saline (diamonds), or 2) Taxol (squares), or 3) exoPTX (triangles), or 4) AA-PEG-exoPTX (crosses). A superior effect on mice survival was recorded in AA-PEG-exoPTX treatment group (n=6).

DETAILED DESCRIPTION OF THE INVENTION

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Except as otherwise indicated, standard methods known to those skilled in the art may be used for production of recombinant and synthetic polypeptides, antibodies or antigen-binding fragments thereof, manipulation of nucleic acid sequences, and production of transformed cells. Such techniques are known to those skilled in the art. See, e.g., SAMBROOK et al., MOLECULAR CLONING: A LABORATORY MANUAL 2nd Ed (Cold Spring Harbor, N.Y., 1989); F. M. AUSUBEL et al. CURRENT PROTOCOLS IN MOLECULAR BIOLOGY (Green Publishing Associates, Inc. and John Wiley & Sons, Inc., New York).

All publications, patent applications, patents, nucleotide sequences, amino acid sequences and other references mentioned herein are incorporated by reference in their entirety.

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

Moreover, the present invention also contemplates that in some embodiments of the invention, any feature or combination of features set forth herein can be excluded or omitted.

Furthermore, the term "about," as used herein when referring to a measurable value such as an amount of a compound or agent of this invention, dose, time, temperature, and the like, is meant to encompass variations of 20%, ±10%, ±5%, ±1%, ±0.5%, or even ±0.1% of the specified amount.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

The transitional phrase "consisting essentially of" means that the scope of a claim is to be interpreted to encompass the specified materials or steps recited in the claim, "and those that do not materially affect the basic and novel characteristic(s)" of the claimed invention. See, *In re Herz*, 537 F.2d 549, 551-52, 190 USPQ 461, 463 (CCPA 1976) (emphasis in the original).

As used herein, the term "polypeptide" encompasses both peptides and proteins, unless indicated otherwise. The term also includes post-expression modifications of the polypeptide, for example, glycosylations, acetylations, phosphorylations and the like. In addition, protein fragments, analogs, mutated or variant proteins, fusion proteins and the like are included within the meaning of polypeptide.

A "polynucleotide," "nucleic acid," or "nucleotide sequence" is a sequence of nucleotide bases, and may be RNA, DNA or DNA-RNA hybrid sequences (including both naturally occurring and non-naturally occurring nucleotide), but is preferably either single or double stranded DNA sequences.

By the terms "treat," "treating," or "treatment of" (or grammatically equivalent terms) it is meant that the severity of the subject's condition is reduced or at least partially improved or ameliorated and/or that some alleviation, mitigation or decrease in at least one clinical symptom is achieved and/or there is a delay in the progression of the condition.

As used herein, the terms "prevent," "prevents," or "prevention" and "inhibit," "inhibits," or "inhibition" (and grammatical equivalents thereof) are not meant to imply complete abolition of disease and encompasses any type of prophylactic treatment that reduces the incidence of the condition, delays the onset of the condition, and/or reduces the symptoms associated with the condition after onset.

An "effective," "prophylactically effective," or "therapeutically effective" amount as used herein is an amount that is sufficient to provide some improvement or benefit to the subject. Alternatively stated, an "effective," "prophylactically effective," or "therapeutically effective" amount is an amount that will provide some delay, alleviation, mitigation, or decrease in at least one clinical symptom in the subject. Those skilled in the art will appreciate that the effects need not be complete or curative, as long as some benefit is provided to the subject.

The term "isolated" may refer to protein, nucleic acid, compound, or cell that has been sufficiently separated from the environment with which it would naturally be associated, so as to exist in "substantially pure" form. "Isolated" does not necessarily mean the exclusion of artificial or synthetic mixtures with other compounds or materials, or the presence of impurities that do not interfere with the fundamental activity, and that may be present, for example, due to incomplete purification.

The term "biological agent," as used herein, refers to any compound or molecule that exerts a biological effect when delivered to a cell or a subject. This includes therapeutic, prophylactic, neutral, or toxic effects as well as detectable effects (e.g., a reporter molecule).

The term "small molecule," as used herein, refers to a compound or molecule having a molecular weight of less than about 1000 daltons.

The term "polymer" or "polymer chain" or "polymeric chain," as used herein interchangeably, refers to a molecule formed by covalent linking of monomeric units.

The term "block copolymer," as used herein, refers to a combination of two or more polymeric chains of constitutionally or configurationally different features linked in a linear fashion. Such distinct polymeric chains of block copolymers are termed "blocks."

The term "amphiphilic block copolymer," as used herein, refers to a block copolymer comprised of at least one hydrophilic polymeric chain and at least one hydrophobic polymeric chain. Examples of hydrophilic polymeric chains include polyethers (e.g., poly(ethylene oxide) (PEO) (or poly(oxyethylene) that is used interchangeably with poly(ethylene glycol) (PEG)), polysaccharides (e.g., dextran), polyglycerol, homopolymers and copolymers of vinyl monomers (e.g., polyacrylamide, polyacrylic esters (e.g., polyacryloyl morpholine), polymethacrylamide, poly(N-(2-hydroxypropyl)methacrylamide, polyvinyl alcohol, polyvinyl pyrrolidone, polyvinyltriazole, N-oxide of polyvinylpyridine, copolymer of vinylpyridine and vinylpyridine N-oxide) polyortho esters, polyaminoacids, polyglycerols, poly(2-oxazolines) (e.g., poly(2-methyl-2-oxazoline), poly(2-ethyl-2-oxazoline) and copolymers), polysarcosine and derivatives thereof. Examples of hydrophobic polymeric chains include poly(propylene oxide) (PPO) (or poly(oxypropylene) that is used interchangeably with PPO), copolymers of poly(ethylene oxide) and PEO, polyalkylene oxide other than PEO and PPO, poly(2-oxazolines) (e.g., poly-(2-propyl-2-oxazoline), poly(2-butyl-2-oxazoline), 2-isobutyl-oxazoline, 2-sec-butyl-2-oxazoline, 2-pentyl-2-oxazoline, 2-heptyl-2-oxazoline, 2-benzyl-2-oxazoline, 2-nonyl-2-oxazoline, and the like), polycaprolactone, poly(D,L-lactide), homopolymers and copolymers of hydrophobic aminoacids and derivatives of amino acids (e.g., alanine, valine, isoleucine, leucine, norleucine, phenylalanine, tyrosine, tryptophan, threonine, proline, cysteine, methionine, serine, glutamine, asparagine), poly(j3-benzyl-L-aspartate) and the like.

The term "not naturally present in the exosome," as used herein, refers to a biological agent that is not present in an exosome as it is found in nature, e.g., exosomes as generated from a cell in a subject or in culture.

The term "functional polynucleotide," as used herein, refers to a polynucleotide that has a biological function without being translated into a polypeptide. Examples include, without limitation, antisense oligonucleotides, recombinant DNAs (rDNAs), plasmid DNAs (pDNAs), ribozymes, messenger RNAs (mRNAs), short (small) interfering RNAs (siRNAs), microRNAs, guide RNAs, and the like.

The term "cancer," as used herein, refers to any benign or malignant abnormal growth of cells. Examples include, without limitation, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma. In some embodiments, the cancer is selected from the group of tumor-forming cancers.

The term "disorder associated with inflammation," as used herein, refers to any disease, disorder, or condition in which inflammation is the cause and/or one of the symptoms.

The term "inflamed tissue," as used herein, refers to a tissue exhibiting one or more signs of inflammation, such as immune cell activation, vasodilation, edema, complement system activation, and leukocyte extravasation.

The present invention is based on the development of compositions useful for delivering biological agents, e.g., therapeutic or protective agents such as small molecules, polypeptides, and polynucleotides, to cells in vitro and in vivo. The compositions provide improved delivery of agents, including crossing the BBB and targeting inflamed tissue, thereby improving therapeutic effects while limiting immune response to the agents. The incorporation of biological agents into exosomes increases the circulation time, preserves therapeutic activity, and improves delivery to the central nervous system, cancer cells, the tumor microenvironment, and inflamed tissue.

Thus, one aspect of the invention relates to a composition for delivery of a biological agent to a cell, the composition comprising an exosome comprising the biological agent, wherein the biological agent is not naturally present in the exosome. The exosomes may be isolated from mammalian cells, for example, cancer cells, immune cells, such as macrophages/monocytes or dendritic cells, or stem cells, such as pluripotent stem cells, and the like. The cells from which the exosomes are isolated may be selected for the characteristics desired in the exosomes, such as targeting specificity. For example, stem cells may be stimulated to particular development pathways such that exosomes derived therefrom will target specific tissues. Monocytes may be stimulated to produce particular macrophages, e.g., M1 or M2 macrophages, prior to isolating exosomes.

Exosomes may be isolated from cells by methods known in the art and as described herein. In some embodiments, the cells are cultured cell lines, e.g., a macrophage cell line such as Raw 264.7. In other embodiments, the cells are primary cells. In some embodiments, the cells are isolated from a subject and cultured to produce exosomes. In particular embodiments, the cells are isolated from the same subject to which the exosomes are to be delivered, e.g., autologous and/or allogeneic cells.

In some embodiments of the instant invention, the cells are treated by a block copolymer or combination of several block copolymers, such as amphiphilic block copolymers, to increase the production of exosomes. In a particular embodiment, the amphiphilic block copolymers comprise at least one block of PEO and at least one block of PPO. In a particular embodiment, the amphiphilic block copolymer is a triblock of PEO-PPO-PEO. Polymers comprising at least one block of PEO and at least one block of PPO are commercially available under such generic trade names as "lipoloxamers", "Pluronic®," "poloxamers," and "synperonics." Examples of poloxamers include, without limitation, Pluronic® L31, L35, F38, L42, L43, L44, L61, L62, L63, L64, P65, F68, L72, P75, F77, L81, P84, P85, F87, F88, L92, F98, L101, P103, P104, P105, F108, L121, L122, L123, F127, 10R5, 10R8, 12R3, 17R1, 17R2, 17R4, 17R8, 22R4, 25R1, 25R2, 25R4, 25R5, 25R8, 31R1, 31R2, and 31R4. Pluronic® block copolymers are designated by a letter prefix followed by a two or a three digit number. The letter prefixes (L, P, or F) refer to the physical form of each polymer, (liquid, paste, or flakeable solid). The numeric code defines the structural parameters of the block copolymer. The last digit of this code approximates the total weight content of PEO blocks in tens of weight percent (for example, 80% weight if the digit is 8, or 10% weight if the digit is 1). The remaining first one or two digits encode the molecular mass of the central PPO block. To decipher the code, one should multiply the corresponding number by 300 to obtain the approximate molecular mass in daltons (Da). Therefore Pluronic® nomenclature provides a convenient approach to estimate the characteristics of the block copolymer in the absence of reference literature. For example, the code 'F127' defines the block copolymer, which is a solid, has a PO block of approximately 3600 Da (12×300) and 70% weight of EO. The precise molecular characteristics of each Pluronic® block copolymer can be obtained from the manufacturer. Amphiphilic block copolymers such as Pluronic® block copolymers may be characterized by different hydrophilic-lipophilic balance (HLB) (Kozlov et al. (2000) Macromolecules, 33:3305-3313). The HLB value, which typically falls in the range of 1 to 31 for Pluronic® block copolymers, reflects the balance of the size and strength of the hydrophilic groups and lipophilic groups of the polymer (see, for example, Attwood and Florence (1983) "Surfactant Systems: Their Chemistry, Pharmacy and Biology," Chapman and Hall, New York) and can be determined experimentally by, for example, the phenol titration method of Marszall (see, for example, "Parfumerie, Kosmetik", Vol. 60, 1979, pp. 444-448; Rompp, Chemistry Lexicon, 8th Edition 1983, p. 1750; U.S. Pat. No. 4,795,643). HLB values for Pluronic® polymers are available from BASF Corp. HLB values can be approximated by the formula:

$$HLB = -36\frac{y}{x+y} + 33,$$

wherein y is the number of hydrophobic propylene oxide units and x is the number of hydrophilic ethylene oxide units, though HLB values provided by BASF are preferred. Notably, as hydrophobicity increases, HLB decreases. In a particular embodiment, the amphiphilic block copolymer of the instant invention has an intermediate HLB or low HLB. For example, the HLB for the amphiphilic block copolymer useful on this invention may be about 20 or less, particularly about 18 or less, particularly about 16 or less. In some embodiments the HLB for the amphiphilic block copolymer is in the range from 12 to 18. In some embodiments, the molecular mass of the PPO block is between about 300 and about 4000, e.g., between about 800 and about 3600, e.g., between about 1000 and about 2900, e.g., between about 1400 and about 2500. The physical and molecular characteristics of Pluronic® polymers are well known in the art and can be found, for example, in Paschalis et al., Colloids and Surfaces A: Physicochemical and Engineering Aspects 96, 1-46 (1995) and Kozlov et al., Macromolecules 33:3305-3313 (2000), incorporated herein by reference. In some embodiments of the instant invention, when block copolymers are used to increase production of the exosomes the block copolymers are added to the donor cells prior to or simultaneously with the isolation of exosomes. In some embodiments, the concentration of block copolymers added to donor cells is in the range from about 0.01% to about 5%, e.g., between about 0.1% and about 1%. In some embodiments, the donor cells are exposed to the block copolymers for the period of from about 1 h to about about 40 h before the exosomes are isolated, e.g., between about 4 and about 20 h before the exosomes are isolated.

The biological agent may be any agent that is desirable to deliver to a cell and/or a subject. The agent may be a therapeutic agent, a prophylactic agent, a marker, a reporter, a research reagent, etc. In some embodiments, the biological agent is a small molecule, e.g., compounds such as synthetic and natural drugs. In other embodiments, the biological agent is a macromolecule, e.g., a polypeptide, polynucleotide, polysaccharide, etc.

In some embodiments of the instant invention, the polypeptide is a therapeutic polypeptide, e.g., it effects amelioration and/or cure of a disease, disorder, pathology, and/or the symptoms associated therewith. The polypeptides may have therapeutic value against neurological disorders (particularly of the CNS) including, without limitation, neurological degenerative disorders and neurodevelopmental disorders, such as Alzheimer's disease (AD), Parkinson's disease (PD), Huntington's disease (HD), Rett syndrome, stroke, trauma, infections, meningitis, encephalitis, gliomas, cancers (including brain metastasis), HIV-1 associated dementia (HAD), HIV associated neurocognitive disorders (HAND), paralysis, amyotrophic lateral sclerosis (ALS or Lou Gehrig's disease), multiple sclerosis (MS), CNS-associated cardiovascular disease, prion disease, obesity, metabolic disorders, inflammatory disease, and lysosomal storage diseases (LSDs; such as, without limitation, Gaucher's disease, Pompe disease, Niemann-Pick, Hunter syndrome (MPS II), Mucopolysaccharidosis I (MPS I), GM2-gangliosidoses, Gaucher disease, Sanfilippo syndrome (MPS IIIA), Tay-Sachs disease, Sandhoffs disease, Krabbe's disease, metachromatic leukodystrophy, and Fabry disease). Therapeutically active polypeptides include, but are not limited to, enzymes, antibodies, hormones, growth factors, other polypeptides, which administration to the brain can effect amelioration and/or cure of a disease, disorder, pathology, and/or the symptoms associated therewith. Neuroactive polypeptides useful in this invention include but are not limited to endocrine factors, growth factors, hypothalamic releasing factors, neurotrophic factors, paracrine factors, neurotransmitter polypeptides, antibodies and antibody fragments which bind to any of the above polypeptides (such neurotrophic factors, growth factors, and others), antibodies and antibody fragments which bind to the receptors of these polypeptides (such as neurotrophic factor receptors), cytokines, endorphins, polypeptide antagonists, agonists for a receptor expressed by a CNS cell, polypeptides involved in lysosomal storage diseases, and the like. In a particular embodiment, the therapeutic protein exerts its effect on the CNS. In another particular embodiment, the therapeutic protein does not cross the BBB by itself.

In certain embodiments, the polypeptide is a neurotrophin, e.g., selected from, without limitation, brain derived neurotrophic factor, nerve growth factor, neurotrophin 3, neurotrophin 4, glial cell derived neurotrophic factor, artemin, neurturin, persephin, ciliary neurotrophic factor, and any combination thereof.

Examples of other polypeptides include, without limitation, enzymes, such as catalase, telomerase, superoxide dismutase (SOD), glutathione peroxidase, glutaminase, cytokines, endorphins (e.g., enkephalin), growth factors (e.g., epidermal growth factor (EGF), acidic and basic fibroblast growth factor (aFGF and bFGF), insulin-like growth factor I (IGF-I), brain-derived neurotrophic factor (BDNF), glial-derived neurotrophic factor (GDNF), platelet derived growth factor (PDGF), vascular growth factor (VGF), nerve growth factor (NGF), insulin-like growth factor-II (IGF-II), tumor necrosis factor-B (TGF-B), leukemia inhibitory factor (LIF), various interleukins, and the like), antiapoptotic proteins (BCL-2, PI3 kinase, and the like), amyloid beta binders (e.g., antibodies), modulators of α-, β-, and/or γ-secretases, vasoactive intestinal peptide, leptin, acid alpha-glucosidase (GAA), acid sphingomyelinase, iduronate-2-sultatase (I2S), α-L-iduronidase (IDU), β-Hexosaminidase A (HexA), Acid β-glucocerebrosidase, N-acetylgalactosamine-4-sulfatase, α-galactosidase A, and neurotransmitters.

In certain embodiments, the biological agent is a polynucleotide encoding a polypeptide or a functional polynucleotide, e.g., a siRNA, microRNA, antisense oligonucleotide, etc.

In certain embodiments, the biological agent is an anticancer agent. Anticancer agents include, without limitation, 1) *vinca* alkaloids (e.g., vinblastine, vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide). In another embodiment, the anticancer agents are anti-angiogenesis agents, such as antibodies to VEGF (e.g., bevacizumab (AVASTIN), ranibizumab (LUCENTIS)) and other promoters of angiogenesis (e.g., bFGF, angiopoietin-1), antibodies to alpha-v/beta-3 vascular integrin (e.g., VITAXIN), angiostatin, endostatin, dalteparin, ABT-510, CNGRC peptide TNF alpha conjugate, cyclophosphamide, combretastatin A4 phosphate, dimethylxanthenone acetic acid, docetaxel, lenalidomide, enzastaurin, paclitaxel, paclitaxel albumin-stabilized nanoparticle formulation (Abraxane), soy isoflavone (Genistein), tamoxifen citrate, thalidomide, ADH-1 (EXHERIN), AG-013736, AMG-706, AZD2171, sorafenib tosylate, BMS-582664, CHIR-265, pazopanib, PI-88, vatalanib, everolimus, suramin, sunitinib malate, XL184, ZD6474, ATN-161, cilenigtide, and celecoxib.

In some embodiments, the exosome further comprises a targeting agent, e.g., an agent that targets the exosome to specific cells or tissues. Examples of targeting agents include, without limitation, receptors, ligands, antibodies, cell surface binding proteins, and substrate binding proteins. Targeting agents may be expressed in cells from which the exosomes are isolated such that the targeting agents are present in the exosomes. Targeting agents may be attached to exosomes (e.g., covalently or non-covalently) after the exosomes are isolated. In some embodiments, the targeting agents are attached to the exosomes through a water soluble polymer linker, for example, PEO (or PEG), poly(2-methyl-2-oxazoline) or poly(2-ethyl-2-oxazoline), polysarcosine, and derivatives thereof. These targeting groups can be attached to the surface of exosomes using such polymeric linker that can be connected to a lipid group.

Work described in the examples below demonstrated that exosomes utilized multiple pathways to enter the cells, including clathrin-mediated endocytosis, caveolae-mediated endocytosis and macropinocytosis. It was additionally shown that the integrin lymphocyte function associated antigen-1 (LFA-1) present on exosomes plays a role in the uptake of exosomes by cells. These pathways can be used advantageously to increase the uptake of exosomes by cells as well as target the exosomes to specific cells or tissues.

The methods of the current invention involve the use of exosomes containing one or several useful biological agents, or use of several exosomes containing different biological agents that can be administered alone or with cells, simultaneously or separately from each other. The exosomes may be in the same composition or may be in separate compositions.

One aspect of the invention relates to methods of loading biological agents into exosomes. The biological agent can be loaded into the isolated exosome by methods known in the art and as described herein. In some embodiments, the invention relates to a method of loading a biological agent into an exosome, comprising a step selected from the group consisting of:

a) incubating the biological agent with the exosome, optionally in the presence of a saponin;

b) combining the biological agent and the exosome and subjecting them to a freeze-thaw cycle;
c) combining the biological agent and the exosome and subjecting them to sonication;
d) combining the biological agent and the exosome and subjecting them to extrusion; and
e) modifying exosomes with a molecule containing multiple charges and optionally purifying the exosomes before adding the biological agent. The optimal loading method will depend at least in part on the characteristics of the biological agent, e.g., the size, charge, hydrophobicity, etc.

In some embodiments, method a) comprises incubating the biological agent with the exosome, e.g., at a temperature of about 20° C. to about 40° C., e.g., at about room temperature, e.g., for at least about 4 h, e.g., at least about 4, 6, 8, 10, 12, 14, 16, 18, 20, 22, or 24 h or any range therein. In some embodiments, agents such as saponins may be added to the mixture, with or without shaking, e.g., at a concentration of about 0.05% to 1%, e.g., about 0.2%, e.g., for about 5 minutes to about 60 minutes e.g., for about 20 minutes.

In some embodiments, method b) comprises combining the biological agent and the exosome and subjecting them to a freeze at about −80° C. and a thaw at about room temperature, which may be repeated 1 or more times, e.g., 1, 2, 3, 4, or 5 or more times.

In some embodiments, method c) comprises sonicating the mixture for 1 or more pulses, e.g., 1, 2, 3, 4, 5, 6, 7, 8, 9, or 10 pulses or more, followed by cooling down on ice and optionally applying further pulses. The pulses may be for about 4 seconds with about a 2 second pause in-between pulses.

In some embodiments, method d) comprises extruding the mixture through an extruder 1 or more times, e.g., 1, 2, 3, 4, 5, 6, 7, 8, 9, or 10 times or more. The pore diameter of the extruder may be about 50 nm to about 1000 nm, e.g., about 100 nm to about 400 nm, e.g., about 200 nm.

In some embodiments, the exosomes are modified with molecules containing multiple charges to increase incorporation of a biological agent into exosomes, and/or stability of the exosomes with the biological agent. In certain embodiments, exosomes may be modified with a polyion or a lipid that can contain multiple charges that can be either positive or negative charges. It is preferred that such polyion or lipid molecule contain at least three charged groups, preferably at least five charged groups, more preferably at least seven charged groups, still more preferably at least nine charged groups. In one preferred embodiment, the exosomes are modified with multivalent cationic molecules. Examples include polycations that can be optionally modified with one or several lipid moieties. Preferred polycations include polyamines (e.g., spermine, polyspermine, polyethyleneimine, polypropyleneimine, polybutileneimine, polypentyleneimine, polyhexyleneimine and copolymers thereof), copolymers of tertiary amines and secondary amines, partially or completely quaternized amines, the quaternary ammonium salts of the polycation fragments, polypeptides such as poly-L-lysine, poly-D-lysine, poly-L-arginine, poly-D-arginine and their copolymers, N-substituted polyaspartamides such as poly[N-(2-aminoethyl)aspartamide] [PAsp (EDA)], poly{N—[N'-(2-aminoethyl)-2-aminoethyl]aspartamide [PAsp(DET)], poly(N—(N'—[N"-(2-aminoethyl)-2-aminoethyl]-2-aminoethyl}aspartamide) [PAsp(TET)], poly-[N—(N'—{N"—[N"'-(2-aminoethyl)-2-aminoethyl]-2-aminoethyl}-2-aminoethyl)aspartamide] [PAsp(TEP)], poly(amidoamine)s and the like. Particularly preferred polycation fragments are those having a plurality of cationic repeating units of the formula —N—$R^0$, wherein $R^0$ is a straight chain aliphatic group of 2 to 6 carbon atoms, which may be substituted. Each —$NHR^0$— repeating unit in a polycation can be the same or different from another —$NHR^0$— repeating unit in the fragment. Examples of polyanions include but are not limited to poly-L-glutamic acid, poly-D-glutamic acid, poly-L-aspartic acid, poly-D-aspartic acid and their copolymers, and the like. The polycations and polyanions of the invention can be randomly branched or have a dendrimer architecture. In some embodiments, the polyion of this invention is covalently linked to a lipid moiety. In some embodiments, the polyions can be covalently linked to lipid moieties or covalently linked to exosomes using conjugation reagents known in the art (see e.g., Hermanson G. T., Bioconjugate Techniques 3d Ed. (Academic Press, NY, 2013). The lipid moieties can be natural or synthetic hydrophobic molecules comprising long chain aliphatic groups that can be saturated or unsaturated or aromatic groups that can be incorporated into the hydrophobic tail of a lipid. The preferred lipid moieties may be long chain alcohols and amines, fatty acids, glycerolipids, glycerophospholipids, sphingolipids, sterol lipids, prenol lipids, saccharolipids, polyketides and their derivatives. Examples of commercially available multivalent lipids include N1-[2-((1S)-1-[(3-aminopropyl)amino]-4-[di(3-aminopropyl)amino]butylcarboxamido)-ethyl]-3,4-di[oleyloxy]-benzamide) (MVL5) available from Avanti Polar Lipids, dioctadecylamidoglycylspermine (DOGS) available as Promega™ Transfectam™, 2,3-dioleyloxy-N-[2-(sperminecarboxamido)ethyl]-N,N-dimethyl-1-propylammonium chloride (DOSPA) available from GOBCO/BRL and the like. Examples of multivalent lipids with dendritic headgroup include MVLBG2 (Evert et al., *J Am Chem Soc.* 128(12): 3998 (2006)). Without wishing to limit this invention to a specific theory it is believed that the lipid moiety incorporates into the membrane of the exosomes. The multivalent lipid head groups partially interact with the negatively charged lipids present in the exosome membranes but due to presence multiple charges retain cationic charges exposed for interaction with the biological agents of this invention. It is preferred that after incorporation of the polyion or a lipid molecule into the exosomes the exosomes are purified from the unincorporated polyion or a lipid molecule. The modified exosomes may be then loaded with a biological agent.

An additional aspect of the invention relates to a method of delivering a biological agent to a cell, comprising contacting the cell with the composition of the invention, thereby delivering the biological agent to the cell.

A further aspect of the invention relates to a method of enhancing delivery of a biological agent to a cancer cell, comprising contacting the cell with the composition of the invention, thereby delivering the biological agent to the cell. The delivery of the biological agent is enhanced relative to the agent without an exosome.

A further aspect of the invention relates to a method of enhancing delivery of a biological agent to a cell in a tumor microenvironment, comprising contacting the cell with the composition of the invention, thereby delivering the biological agent to the cell. The delivery of the biological agent is enhanced relative to the agent without an exosome. The tumor microenvironment is the cellular environment in which the tumor exists, including surrounding blood vessels, immune cells, fibroblasts, bone marrow-derived inflammatory cells, lymphocytes, signaling molecules and the extracellular matrix.

Another aspect of the invention relates to a method of enhancing delivery of a biological agent to a central nervous system cell, comprising contacting the cell with the composition of the invention, thereby delivering the biological agent to the cell. The delivery of the biological agent is enhanced relative to the agent without an exosome. Central nervous system cells include, without limitation, neurons and glial cells, including astrocytes, oligodendrocytes, and microglia.

In some embodiments, the cell is an in vitro cell, e.g., a primary cell or cell line in culture. In other embodiments, the cell is in a subject, e.g., an animal model of a disorder or a subject in need of treatment.

An additional aspect of the invention relates to a method of delivering a biological agent to a subject, comprising delivering the composition of the invention to the subject, thereby delivering the biological agent to the subject.

A further aspect of the invention relates to a method of delivering a biological agent across the BBB of a subject, comprising delivering the composition of the invention to the subject, thereby delivering the biological agent across the BBB of the subject.

Another aspect of the invention relates to a method of delivering a biological agent to inflamed tissue of a subject, comprising delivering the composition of the invention to the subject, thereby delivering the biological agent to inflamed tissue of the subject. In some embodiments, the inflamed tissue is central nervous system tissue. In some embodiments, the inflamed tissue is a tumor microenvironment.

An additional aspect of the invention relates to a method of treating a disorder in a subject in need thereof, comprising delivering a therapeutically effective amount of a composition of the invention to the subject, wherein the biological agent is effective for treating the disorder, thereby treating the disorder in the subject.

In some embodiments, the disorder is associated with inflammation. In certain embodiments, the disorder is cancer or a central nervous system disorder. In any of the methods of the invention, the composition may be delivered by any route effective to deliver the exosomes to the target cells and/or tissues, e.g., intranasally or intravenously. In any of the methods of the invention, the exosomes may be isolated from autologous cells of the subject and administered to the subject.

Another aspect of the invention relates to the use of the exosomes of the invention to deliver polynucleotides to cells. The compositions of the invention provide efficient transfection of polynucleotides into cells compared to transfection techniques known in the art. Thus, one aspect of the invention relates to a method of transfecting a cell with a polynucleotide, comprising contacting the cell with composition comprising an exosome comprising the polynucleotide, wherein the exosome is isolated from a macrophage or a monocyte, and wherein the polynucleotide is not naturally present in the exosome. In some embodiments, the polynucleotide is a plasmid, DNA fragment, mRNA, siRNA, microRNA, tRNA, or rRNA.

The polynucleotide may be loaded into the exosome using methods known in the art and as described herein. In some embodiments, the polynucleotide and the exosome are incubated together, optionally in the presence of a polycation, e.g., polyethyleneimine. In some embodiments, the exosomes are modified with molecules containing multiple positive charges such as polycations, polycations modified with lipid molecules, and/or multivalent cationic lipids before incorporation of a polynucleotide into exosomes. It is preferred that polycation or lipid molecule contain at least three positively charged groups, preferably at least five charged groups, more preferably at least seven charged groups, still more preferably at least nine charged groups. It is preferred that after incorporation of the polycation or a lipid molecule into the exosomes the exosomes are purified from the unincorporated polyion or a lipid molecule. The modified exosomes may be then loaded with a polynucleotide.

In some embodiments, the cell is an in vitro cell, e.g., a primary cell or cell line in culture. In other embodiments, the cell is in a subject, e.g., an animal model of a disorder or a subject in need of treatment. In certain embodiments, the cell is a tumor cell or tumor cell line or a cell in the tumor microenvironment. In certain embodiments, the cell is a central nervous system cell or central nervous system cell line.

In some embodiments, the exosomes may be isolated from autologous macrophages or monocytes of the subject and administered to the subject.

In some embodiments, the invention relates to a method of loading a biological agent into an exosome, comprising:
  a) loading a donor cell with a biological agent that optionally can be incorporated into a nanoparticle comprising a polymer or a lipid, such as polymeric micelle or a polyion complex;
  b) culturing the donor cells to allow for formation of exosomes; and
  c) isolating exosomes loaded with the biological agent from these cells.

It is preferred that a biological agent is incorporated in a nanoparticle and then these nanoparticles are added to the donor cells. The nanoparticles may have a diameter less than about 300 nm, preferably less than about 150 nm, more preferably between about 5 nm and 100 nm, still more preferably between about 10 nm and about 60 nm. The nanoparticles may be comprised of polymer and biological agent. Examples of nanoparticles useful in this invention include but are not limited to polymeric micelles, polyion complexes, polyion complex micelles also known as "block ionomer complexes", nanogels, lipid nanoparticles, liposomes and the like (Kabanov and Vinogradov, *Angew. Chem. Int. Ed Engl.* 48(30):5418-5429 (2009)). In some preferred embodiments biological agents are incorporated in polymeric micelles of block copolymers. In some aspects of the invention hydrophobic and water-insoluble or poorly soluble biological agents are incorporated into polymeric micelles formed by amphiphilic block copolymers. Unexpectedly, exposure of donor cells to polymeric micelles formed by amphiphilic block copolymers increased entrapment of biological agents into exosomes. Without limiting this invention to a specific theory it is believed that water-insoluble or poorly soluble small molecules are solubilized in the core of the micelles formed by the hydrophobic blocks of the block copolymer and the drug-loaded micelles are stabilized in aqueous media due to formation of the shell by the hydrophilic blocks of the block copolymer. Various block copolymers are available in the art for preparation of polymeric micelles (Kabanov and Alakhov, *Crit. Rev. Ther. Drug Carrier Syst.* 19 (1):1-73 (2002)). The amphiphilic block copolymers comprising at least one block of PEO and at least one block of PPO are preferred for incorporation of biological agents. In a particular embodiment, the amphiphilic block copolymer is a triblock of PEO-PPO-PEO. In another embodiment the amphiphilic block copolymers of poly(2-oxazolines) comprising at least one hydrophilic poly (2-oxazoline) block (such as poly(2-methyl-2-oxazoline) or poly(2-ethyl-2-oxazoline) and at least one hydrophobic poly (2-oxazoline) block (such as poly-(2-propyl-2-oxazoline), poly(2-butyl-2-oxazoline), 2-isobutyl-oxazoline, 2-sec-butyl-2-oxazoline, 2-pentyl-2-oxazoline, 2-heptyl-2-oxazoline, 2-benzyl-2-oxazoline, 2-nonyl-2-oxazoline, and the like) are preferred for incorporation of biological agents. Polymeric micelles having high loading capacity of incorporating water-insoluble or poorly soluble small molecules are particularly preferred for the treatment of donor cells. The loading capacity is defined herein as the weight percent of incorporated biological agent relative to the total weight of the biological agent and block copolymer, and can be calculated using the formula $LC=M_{biological\ agent}/(M_{biological\ agent}+M_{block\ copolymer}) \times 100\%$, where $M_{biological\ agent}$ and $M_{block\ copolymer}$ are the weight amounts of the solubilized biological agent and block copolymer in the solution (He et al., *Biomaterials* 101:296-309 (2016)). It is preferred that the LC is at least 5%, more preferred at least 10%, still more preferred at least 15%. In some embodiments the biological agents are incorporated into polyion complexes. In such embodiments coupling biological agents with polyelectrolytes may produce the polyion complexes (see Kabanov and Kabanov, *Bioconjug. Chem.* 6 (1):7-20 (1995)). In some preferred embodiments the block copolymers comprising at least one water-soluble nonionic block and at least one polyion block are used. Particularly preferred nonionic blocks are PEO (or PEG), poly(2-methyl-2-oxazoline) or poly(2-ethyl-2-oxazoline), polysarcosine and derivatives thereof. Polypeptides and polynucleotides can be incorporated into polyion complexes with such block copolymers (see, for example, Vinogradov et al., *Bioconjug. Chem.* 9 (6): 805-812 (1998); Batrakova, et al., *Bioconjug. Chem.* 18(5):1498-1506 (2007); Manickam et al., *J. Control. Release* 162(3):636-645 (2012)). Without wishing to be bound to a specific theory such polyion complexes also known in the art as "polyion complex micelles" or "block ionomer complexes" have a core-shell architecture with the polyion block neutralized biological agent complex forming the core and the nonionic block forming the shell. Upon exposure to cells these complexes may be taken up by the cells and due to their dynamic nature these complexes can release incorporated biological agent inside the cells. Exposure of donor cells to such complexes results in release of the polypeptides in the exosomes, however, the yield of such exosomes loaded with polypeptides is low (Haney et al., *Nanomedicine (Lond)* 6(7):1215-30 (2011)). Unexpectedly, treating the donor cells with polyion complexes combined with concurrent or subsequent treatment with amphiphilic block copolymers results in the increased production of exosomes loaded with polypeptides. Since the trafficking and distribution of the polynucleotides and proteins inside cells is vastly different it is unexpected that exposure of donor cells to polyion complexes of polynucleotides results in loading of exosomes with these polynucleotides. Unexpectedly, treating the donor cells with polyion complexes combined with concurrent or subsequent treatment with amphiphilic block copolymers results in the increased production of exosomes loaded with polynucleotides. The donor cells may be cultured with nanoparticles carrying a biological agent for from about 1 hour to about 96 hours. The cells may be optionally treated with a block copolymer to increase the yield (amount) of exosomes loaded with a biological agent. In a particular embodiment, the amphiphilic block copolymers comprise at least one block of PEO and at least one block of PPO. In a particular embodiment, the amphiphilic block copolymer is a triblock of PEO-PPO-PEO. In these embodiments it is preferred that the concentration of block copolymers added to donor cells is in the range from about 0.01% to 5%, more preferred between 0.1% and 1%. It is also preferred that the donor cells are exposed to the block copolymers for the period of from about 1 h to about 40 h before the exosomes are isolated, more preferred between about 4 and about 20 h before the exosomes are isolated.

In another aspect the invention relates to a method of loading a biological agent into an exosome, comprising:
a) transfecting a donor cell with a polynucleotide that optionally can be incorporated into a nanoparticle comprising a polymer or a lipid, such as a cationic polymer or a cationic lipid;
b) culturing the cells to allow for formation of exosomes;
c) isolating exosomes from the cells.

The isolated exosomes may carry the DNA, RNA and/or protein produced as a result of the transfection of the cells with the polynucleotide. The cells optionally may be treated with a block copolymer to increase the yield (amount) of exosomes loaded with a biological agent. In a particular embodiment, the amphiphilic block copolymers comprise at least one block of PEO and at least one block of PPO. In a particular embodiment, the amphiphilic block copolymer is a triblock of PEO-PPO-PEO. In these embodiments it is preferred that the concentration of block copolymers added to donor cells is in the range from about 0.01% to about 5%, more preferred between 0.1% and about 1%. It is also preferred that the donor cells are exposed to the block copolymers for the period of from about 1 h to about 40 h before the exosomes are isolated, more preferred between about 4 and about 20 h before the exosomes are isolated.

The present invention further provides a composition comprising the exosomes of the invention and a suitable carrier, e.g., a pharmaceutically acceptable carrier.

By "pharmaceutically acceptable" it is meant a material that is not biologically or otherwise undesirable, i.e., the material can be administered to a subject without causing any undesirable biological effects such as toxicity.

The compositions of the invention can optionally comprise medicinal agents, pharmaceutical agents, carriers, adjuvants, dispersing agents, diluents, and the like.

The exosomes of the invention can be formulated for administration in a pharmaceutical carrier in accordance with known techniques. See, e.g., Remington, *The Science And Practice of Pharmacy* ($22^{nd}$ Ed. 2012). In the manufacture of a pharmaceutical formulation according to the invention, the exosomes are typically admixed with, inter alia, an acceptable carrier. The carrier can be a solid or a liquid, or both, and is preferably formulated with the exosomes as a unit-dose formulation, for example, a tablet, which can contain from 0.01 or 0.5% to 95% or 99% by weight of the exosomes. One or more exosomes can be incorporated in the formulations of the invention, which can be prepared by any of the well-known techniques of pharmacy.

A further aspect of the invention is a method of treating subjects in vivo, comprising administering to a subject a pharmaceutical composition comprising the exosomes of the invention in a pharmaceutically acceptable carrier, wherein the pharmaceutical composition is administered in a therapeutically effective amount. Administration of the exosomes of the present invention to a human subject or an animal in need thereof can be by any means known in the art for administering compounds.

Non-limiting examples of formulations of the invention include those suitable for oral, rectal, buccal (e.g., sublingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intracranial, intrathecal, and inhalation administration, administration to the liver by intraportal delivery, as well as direct organ injection (e.g., into the liver, into a limb, into the brain or spinal cord for delivery to the central nervous system, into the pancreas, or into a tumor or the tissue surrounding a tumor). The most suitable route in any given case will depend on the nature and severity of the condition being treated and on the nature of the particular compound which is being used. In some embodiments, it may be desirable to deliver the formulation locally to avoid any side effects associated with systemic administration. For example, local administration can be accomplished by direct injection at the desired treatment site, by introduction intravenously at a site near a desired treatment site (e.g., into a vessel that feeds a treatment site). In some embodiments, the formulation can be delivered locally to ischemic tissue. In certain embodiments, the formulation can be a slow release formulation, e.g., in the form of a slow release depot.

For injection, the carrier will typically be a liquid, such as sterile pyrogen-free water, pyrogen-free phosphate-buffered saline solution, bacteriostatic water, or Cremophor EL[R] (BASF, Parsippany, N.J.). For other methods of administration, the carrier can be either solid or liquid.

Formulations of the present invention suitable for parenteral administration comprise sterile aqueous and non-aqueous injection solutions of the compound, which preparations are preferably isotonic with the blood of the intended recipient. These preparations can contain anti-oxidants, buffers, bacteriostats and solutes which render the formulation isotonic with the blood of the intended recipient. Aqueous and non-aqueous sterile suspensions can include suspending agents and thickening agents. The formulations can be presented in unit/dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, in one aspect of the present invention, there is provided an injectable, stable, sterile composition comprising exosomes of the invention, in a unit dosage form in a sealed container. The exosomes are provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the exosomes. When the compound or salt is substantially water-insoluble, a sufficient amount of emulsifying agent which is pharmaceutically acceptable can be employed in sufficient quantity to emulsify the exosomes in an aqueous carrier. One such useful emulsifying agent is phosphatidyl choline.

The composition can alternatively be formulated for nasal administration or otherwise administered to the lungs of a subject by any suitable means, e.g., administered by an aerosol suspension of respirable particles comprising the exosomes, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn et al., *J. Pharmacol. Toxicol. Meth* 27:143 (1992). Aerosols of liquid particles comprising the exosomes can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the exosomes can likewise be produced with any solid particulate medicament aerosol generator, by techniques known in the pharmaceutical art.

In some embodiments, the compositions are delivered by intranasal-to-brain (INB) delivery. INB delivery may be carried out using techniques known in the art. In particular, the compositions of the invention may be delivered into the upper nasal turbinate area close to the olfactory bulb (e.g., at the cribriform plate). Suitable carriers and formulations for intranasal delivery are known in the art and are described above.

For oral administration, the exosomes can be administered in solid dosage forms, such as capsules, tablets, and powders, or in liquid dosage forms, such as elixirs, syrups, and suspensions. Exosomes can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for buccal (sub-lingual) administration include lozenges comprising the compound in a flavored base, usually sucrose and acacia or tragacanth; and pastilles comprising the exosomes in an inert base such as gelatin and glycerin or sucrose and acacia.

Formulations suitable for rectal administration are preferably presented as unit dose suppositories. These can be prepared by admixing the exosomes with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, Tyle, *Pharm. Res.* 3:318 (1986)) and typically take the form of an optionally buffered aqueous solution of the compound. Suitable formulations comprise citrate or bistris buffer (pH 6) or ethanol/water and contain from 0.1 to 0.2M of the compound.

Alternatively, one can administer the exosomes in a local rather than systemic manner, for example, in a depot or sustained-release formulation.

In the case of water-insoluble compositions, a pharmaceutical composition can be prepared containing the water-insoluble compound, such as for example, in an aqueous base emulsion. In such an instance, the composition will contain a sufficient amount of pharmaceutically acceptable emulsifying agent to emulsify the desired amount of the compound. Particularly useful emulsifying agents include phosphatidyl cholines and lecithin.

In particular embodiments, the composition is administered to the subject in a therapeutically effective amount, as that term is defined above. Dosages of pharmaceutically active compounds can be determined by methods known in the art, see, e.g., *Remington's Pharmaceutical Sciences* (Maack Publishing Co., Easton, Pa.). The therapeutically effective dosage of any specific compound will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the compound, including the cases where a salt is employed. Toxicity concerns at the higher level can restrict intravenous dosages to a lower level such as up to about 10 mg/kg, with all weights being calculated based upon the weight of the compound, including the cases where a salt is employed. A dosage from about 10 mg/kg to about 50 mg/kg can be employed for oral administration. Typically, a dosage from about 0.5 mg/kg to 5 mg/kg can be employed for intramuscular injection. Particular dosages are about 1 µmol/kg to 50 µmol/kg, and more particularly to about 22 µmol/kg and to 33 µmol/kg of the compound for intravenous or oral administration, respectively.

In particular embodiments of the invention, more than one administration (e.g., two, three, four, or more administrations) can be employed over a variety of time intervals (e.g., hourly, daily, weekly, monthly, etc.) to achieve therapeutic effects.

The present invention finds use in veterinary and medical applications. Suitable subjects include both avians and mammals, with mammals being preferred. The term "avian" as used herein includes, but is not limited to, chickens, ducks, geese, quail, turkeys, and pheasants. The term "mammal" as used herein includes, but is not limited to, humans, bovines, ovines, caprines, equines, felines, canines, lagomorphs, etc. Human subjects include neonates, infants, juveniles, and adults. In other embodiments, the subject is an animal model of a disorder, e.g., a CNS disorder or cancer. In certain embodiments, the subject is in need of treatment for a disorder, i.e., a subject that has a disorder or is at increased risk for a disorder relative to the general population.

Having described the present invention, the same will be explained in greater detail in the following examples, which are included herein for illustration purposes only, and which are not intended to be limiting to the invention.

Example 1

Exosomes as Drug Delivery Vehicles for PD Therapy

In this example exosomes are loaded with a protein, catalase, and used for delivery of this protein to the site of inflammation in the brain to treat a neurodegenerative disease. The delivery of catalase to the brain using exosomes as drug delivery vehicles, and therapeutic effect of the catalase-loaded exosomes are demonstrated using an animal model of PD.

Methods

Reagents:

Catalase from bovine liver was purchased from Calbiochem (San Diego, Calif.). A lipophilic fluorescent dyes, 1,1'-dioctadecyl-3,3,3',3'-tetramethylindo-carbocyanine perchlorate (DIL), and 2-(5-(1,3-dihydro-3,3-dimethyl-1-octadecyl-2H-indol-2-ylidene)-1,3-pentadienyl)-3,3-dimethyl-1-octadecyl-perchlorate (DID) were purchased from Invitrogen (Carlsbad, Calif., USA). 6-hydroxydopamine (6-OHDA), lipopolysaccharides (LPS), rhodamine isothiocyanate (RITC), and Triton X-100 were obtained from Sigma-Aldrich (St. Louis, Mo., USA). Interferon gamma (INT-γ) was purchased from Peprotech Inc. (RockyHill, N.J., USA).

Cells:

A mouse macrophage cell line (Raw 264.7) was purchased from American Type Culture Collection (ATCC, Manassas, Va., USA, cat # TIB-71), and cultured in Dulbecco's Modified Eagle's Media (DMEM) (Invitrogen) supplemented with 10%0/(v/v) heat-inactivated fetal bovine serum (FBS). Neuronal PC12 rat adrenal pheochromocytoma cell line was obtained from ATCC, and cultured in Dulbecco's modified Eagle medium (Hyclone, South Logan, Utah, USA) supplemented with 10% FBS, and 1% (v/v) of both penicillin and streptomycin. The cells were grown in an incubator with optimal culture conditions of 37° C. and 5% $CO_2$, and the medium was routinely replaced every 2-3 days.

Bone marrow derived macrophages (BMM) were obtained by differentiation of bone marrow stem cells extracted from murine femurs (C57BL/6, female mice) as described in Dou et al. (*Blood* 108:2827 (2006)). The cells were cultured for 10 days in media supplemented with 1000 U/mL macrophage colony-stimulating factor (MCSF). The purity of monocyte culture was determined by flow cytometry using FACS Calibur (BD Biosciences, San Jose, Calif., USA). Mouse primary cultured cortical neurons and dopaminergic (DA) neurons from substantia nigra pars compacta (SNpc) were isolated from mouse pups cortex and midbrain as described (Pruszak et al., *Curr. Protoc. Stem Cell Biol.* Chapter 2, Unit 2D 5 (2009)).

Isolation of Exosomes:

Concomitant media from Raw 264.7 macrophages grown on 75T flasks ($20 \times 10^6$ cells/flask) was collected, and exosomes were isolated using gradient centrifugation (Thery et al., *Curr. Protoc. Cell Biol.* Chapter 3, Unit 3 22 (2006)). In brief, the culture supernatants were cleared of cell debris and large vesicles by sequential centrifugation at 300 g for 10 min, 1000 g for 20 min, and 10,000 g for 30 min, followed by filtration using 0.2 apm syringe filters. Then, the cleared sample was spun at 100,000 g for one hour to pellet the exosomes, and supernatant was collected. The collected exosomes ($10^{11}$-$10^{12}$ exosomes/flask) were washed twice with phosphate buffer solution (PBS). To avoid contamination by the FBS-derived exosomes, FBS was spun at 100,000 g for 2 hours to remove exosomes before the experiment. The recovery of exosomes was estimated by measuring the protein concentration using the Bradford assay and by Nanoparticle Tracking Analysis (NTA). The obtained exosomal fraction was re-suspended in PBS (500 µl, 1 mg/mL total protein), and characterized for size and polydispersity.

Loading of Exosomes:

Four approaches for catalase incorporation into exosomes were evaluated: the incubation at RT with or without saponin (Method 1), freeze-thaw cycles (Method II), sonication (Method III), and extrusion (Method VI). For Method I, naive exosomes released from Raw 264.7 macrophages were diluted in PBS to a concentration 0.15 mg/mL of total protein, then catalase solution in PBS (0.5 mg/mL) was added to 250 µl of exosomes to the final concentration 0.1 mg/mL total protein, and incubated at RT for 18 hours. In case of a saponin treatment, a mixture of catalase and exosomes was supplemented with 0.2% saponin and placed on shaker for 20 min at RT. For Method II, the catalase solution was added to exosomes as described above, incubated for 30 min, then rapidly frozen at −80° C., and thawed at RT. The freeze-thaw cycle was repeated three times. For Method III, the catalase mixture with exosomes was sonicated (500 v, 2 kHz, 20% power, 6 cycles by 4 sec pulse/2 sec pause), cooled down on ice for 2 min, and then sonicated again using Qsonica Sonicator Q700 (Fisher Scientific, Hampton, N.H., USA). For Method IV, catalase mixture with exosomes was extruded (x10 times) through Avanti Lipids extruder (Avanti Polar lipids Inc., Alabaster, Ala., USA) with 200 nm-pores diameter. Loaded with catalase exosomes were purified from free catalase by gel-filtration chromatography with Sepharose 6 BCL (Sigma-Aldrich).

Characterization of Different exoCAT Formulations by (Dynamic Light Scattering) DLS, (Atomic Force Microscopy) AFM, Nanoparticle Tracking Analysis (NTA), and Hyperspectral Microscopy:

The effective hydrodynamic diameter of empty exosomes, or exosomes loaded with catalase was measured by DLS using the ZetaPlus' Zeta Potential Analyzer (Brookhaven Instruments, Santa Barbara, Calif., USA) equipped with a 35 mW solid state laser (658 nm laser) as described in (Bronich et al., *J. Amer. Chem. Soc.* 122:8339 (2000); Vinogradov et al., *Colloids Surfaces B-Biointerfaces* 16:291 (1999)). The size, distribution, and number of particles for various exosomal formulations were also examined by NTA. For this purpose, exoCAT formulations were prepared at concentration 0.01 mg/mL, and evaluated using NanoSight 500, Version 2.2 (Wiltshire, United Kingdom). The morphology of exoCAT aggregates was investigated by AFM. Different exoCAT formulations were prepared in 50 mM phosphate buffer, pH 7.4 at total protein 10 g/mL. A drop of the sample was placed on a glass slide, and dried under an argon flow. The AFM imaging was operated as described earlier (Zhao et al., *Nanomedicine (Lond)* 6:25 (2011)).

ExoCAT formulations were further characterized by Hyperspectral microscopy (CytoViva Inc., Auburn, Ala., USA). The hyperspectral images and the corresponding hyperspectral data were captured using an Olympus BX43 research grade optical microscope equipped with the patented CytoViva advanced dark field illumination system and diffraction grating hyperspectral imaging system (CytoViva Inc.). A 100× oil iris 0.6-1.30 NA objective was utilized. For the mean spectral comparison, data was captured from multiple pixels within multiple exosome particle areas of each sample. The mean spectrum from each sample was calculated using the CytoViva customized ENVI Hyperspectral Image Analysis software.

Manufacture of Gold Nanoparticles and Imaging of Nanoparticle-Loaded Exosomes by Transmission Electron Microscopy (TEM):

Gold nanoparticles were prepared by mixing of 25 mL HAuCl4 (0.5 mM) TRIS solution (pH 10) with 25 mL Pluronic® block copolymer F127 (10 mM) solution. The mixture was incubated at 55° C. for 2 hours and the obtained nanoparticles were separated by centrifugal filtration at 1500 RPM using a filter with 100 kDa cut off. Effective hydrodynamic diameter and zeta-potential of gold nanoparticles were measured by photon correlation spectroscopy using 'ZetaPlus' Zeta Potential Analyzer (Brookhaven Instruments). The average diameter was 10.3±0.2 nm, the polydispersity index (PDI) value was 0.06±0.002 nm. For TEM evaluations, a drop of isolated exosomal fraction with incorporated by sonication gold nanoparticles was placed on Formvar®-coated copper grid (150 mesh, Ted Pella Inc., Redding, Calif., USA). The dried grid containing exosomes were stained with vanadyl sulfate and visualized using a Philips 201 transmission electron microscope (Philips/FEI Inc., Briarcliff Manor, N.Y., USA).

Poly(Lactic-Co-Glycolic Acid) (PLGA) Particles Preparation:

PLGA nanoparticles were prepared by modification of a w/o/w double emulsion method (Giovagnoli et al., *AAPS PharmSciTech* 5:e51 (2004)). Briefly, 3.2 mL of 5% polyvinyl alcohol (PVA) was added to 100 mL of $dH_2O_2$ to form a w/o emulsion. In parallel, 0.35 g PLGA polymer was dissolved in 3 mL dichloromethane, and 2 µmol DIL was added to the solution. After vigorous stirring, the PLGA emulsion was injected into 50 mL of 5% PVA solution under stirring (1500 rpm, at 4° C.) to form a primary w/o/w double emulsion. Then, the double emulsion was poured into 500 mL of deionized water and maintained at 4° C. In order to evaporate the organic solvent, the temperature was slowly increased up to 20° C. during two hours. The resulting nanoparticles were centrifuged for 30 minutes at 4000 g, washed with deionized water, and lyophilized. The average particle size measured by Malteasizer DLS was 317.5+1.94 nm with PDI of 0.113.

Preparation of Liposomes:

Liposomes were prepared by reverse phase evaporation method. Briefly 2 mg of phospholipids (95 molar % of phosphatidyl choline and 5% of poly(ethylene glycol)-1,2-distearoyl-sn-glycero-3-phosphoethanolamine (PEG-PE)) were dissolved in 6 ml of chloroform: diisopropyl ether 1:1 mixture. Then I ml of 5 mM calcein solution in PBS filtered through 450 nm syringe filter was added to the mixture. Mixture was intensively vortexed and bath sonicated to form stable emulsion. Organic solvents were evaporated on rotary evaporator forming the liposome aqueous dispersion. 200-250 µl of Millipore water can be added at this point to the mixture in case some part of water was also evaporated. Evaporation was continued to get almost clear dispersion. Then volume was adjusted to 1000 µl by addition of small amount of water. Dispersion was vortexed and bath sonicated to get clear solution. Liposomes were sequentially extruded 21 times through 200 nm polycarbonate filters using a hand extruder (Avanti). Liposomes were purified through a Sepharose CL4B column to remove not encapsulated fluorophore. Volume of the sample was doubled after column separation. Calcein loaded liposomes were used within 24 h after column separation.

Western Blot Analysis:

Western blot technique was applied to evaluate loading efficiency for different exoCAT formulations. Protein concentrations were determined using BCA kit (Pierce Biotechnology, Rockford, Ill., USA). The catalase protein bands were detected with primary rabbit polyclonal anti-catalase antibodies (Santa Cruse, Calif., USA; 1:200 dilution), and secondary horseradish peroxidase (HRP)-conjugated goat anti-rabbit Ig-HRP (Santa Cruse; 1:2500 dilution). The protein bands were visualized by chemiluminescent substrate (Pierce Biotechnology) and quantitated using ImageJ software (NIH, Bethesda, Mass., USA) (Batrakova et al., *Bioconjug. Chem.* 18:1498 (2007)). To correct for loading differences, the levels of proteins were normalized to the constitutively expressed in exosomes TSG101 protein. The TSG101 levels were visualized by TSG101 monoclonal antibodies, Abcam (Cambridge, Mass., USA).

Enzymatic Activity of Catalase Loaded into Exosomes:

The loading efficiency for different exoCAT formulations was assessed by catalase enzymatic activity using hydrogen peroxide decomposition assay (Zhao et al., *Nanomedicine (Lond)* 6:25 (2011)). For this purpose, different exoCAT formulations were incubated with pronase (0.1-0.2 mg/mL) for 3 hours at 37° C. Following the incubation, the aliquots were subjected for catalytic activity assessment as described above. The same assay was used to examine the preservation of catalase enzymatic activity in exosomes against proteases degradation. Stability of catalase was expressed in the residual activity vs. initial activity of catalase.

Exosomal Uptake in PC12 Cells:

PC12 neuronal cells is a common model for in vitro evaluation of drug neuroporotective effects (Tan et al., *Neurochem. Res.* 38:512 (2013)). Exosomes (230 µg total protein/mL) were subjected to various procedures (incubation at RT, freeze/thaw cycles, or sonication), and then stained with DIL (2 µmol). PC12 cells were seeded into 96-well plate (50,000 cell/well), cultured for three days, and then incubated with different DIL-labeled exoCAT for various times. Following the incubation, the cells were washed three times with ice-cold PBS, and solubilized in Triton ×100 (1%). Fluorescence in each sample was measured by Shimadzu RF5000 fluorescent spectrophotometer ($\lambda_{ex}$=540 nm, $\lambda_{em}$=565 nm). The amount of exosomes accumulated in neuronal cells was normalized for the total protein content and expressed as a number of exosomes per mg of the protein as means±S.E.M. (n=8). All exoCAT formulations were prepared at the same level of fluorescence, and a separate calibration curve was used for each exoCAT formulation.

In Vitro Confocal Microscopy Studies:

Raw 264.7 macrophages ($20\times10^6$ cells/flask) were cultured for three days in DMEM supplemented with 10%/o FBS, then concomitant media was collected, and exosomes were isolated by gradient centrifugation as described above. The isolated exosomes (100 µg/mL total protein) were sonicated, labeled with DIL (2 µmol), and incubated with PC12 cells grown on chamber slides ($1\times10^5$ cells/chamber) for various time intervals (Batrakova et al., *Bioconjug. Chem.* 16: 793 (2005)). Following the incubation period, the cells were washed, fixed, and stained with rabbit anti-PGP9.5 antibodies (green, Abcam, #10404, 1:500 dilution) for actin micro-filaments, and a fluorescent stain, 4',6-diamidino-2-phenylindole (DAPI) for nuclei prior to the imaging. Accumulation of fluorescently-labeled exosomes was visualized by a confocal fluorescence microscopic system ACAS-570 (Meridian Instruments, Okimos, Mich., USA) with argon ion laser (excitation wavelength, 488 nm) and corresponding filter set. Digital images were obtained using the CCD camera (Photometrics).

Amplex Red Dye Fluorescence Assay:

Raw 264.7 macrophages seeded in 96-well plates ($0.1\times10^6$ cells/well) were stimulated with INF-γ (2 µg/mL) and LPS (200 ng/mL) for 4 hours to induce ROS production. Non-activated cells were used as controls. ExoCAT obtained by sonication in Krebs-Ringer buffer (145 mM NaCl, 4.86 mM KCl, 5.5 mM glucose, 5.7 mM $NaH_2PO_4$, 0.54 mM $CaCl_2$), 1.22 mM $MgCl_2$, pH 7.4) were supplemented with Amplex Red Dye stock solution (10 U/mL HRP and 10 mM Amplex Red), added to the activated macrophages, and the decomposition of ROS was measured by fluorescence at $\lambda_{ex}$=563 nm, $\lambda_{em}$=587 nm as described (Batrakova et al., *Bioconjug. Chem.* 18:1498 (2007)). The effect of the same amount of empty exosomes ($1.4\times10^{11}$/mL exosomes), or catalase alone (3,652 U/mL) on ROS decomposition was evaluated in the control experiments.

Cell Viability Assay:

The protection of PC12 cell by exoCAT prepared by sonication was assessed by MTT assay. For this purpose, PC12 cells ($1\times10^5$ cells/mL) were seeded into a 96-well plate and allowed to attach overnight. Then, the cells were exposed to 200 µM 6-OHDA and different exoCAT formulations, or catalase alone, or empty exosomes for four hours. Following the incubation, the cells were washed 3 times with ice-cold PBS, and incubated with the corresponding exoCAT formulations, or catalase alone, or empty exosomes for another 24 hours. Following the treatment, 20 µL MTT (5 mg/mL) was added into each well. After 3 hours of incubation at 37° C., the medium containing MTT was removed; and 100 µL DMSO was added into each well to dissolve the purple MTT formazan. Absorbances were read at $\lambda$=570 nm by a microplate reader, and cell viability was expressed as a percentage of viable cells in the treated groups compared to the untreated control group.

Animals:

C57BL/6 female mice (Charles River Laboratories, Durham, N.C., USA) eight weeks of age were treated in strict accordance with the recommendations in the Guide for the Care and Use of Laboratory Animals of the National Institutes of Health. The protocol was approved by the Committee on the Ethics of Animal Experiments of the University of North Carolina at Chapel Hill. All surgery was performed under sodium pentobarbital anesthesia, and all efforts were made to minimize suffering. The animals were kept five per cage with an air filter cover under light- (12-hours light/dark cycle) and temperature-controlled (22±1° C.) environment. All manipulations with the animals were performed under a sterilized laminar hood. Food and water were given ad libitum.

Biodistribution of Exosomes in Mouse Brain with Inflammation:

C57BL/6 mice (n=4) were stereotactically injected with 6-OHDA solution (10 µg 6-OHDA in 0.9% NaCl with 0.02% ascorbic acid), flow rate of 0.1 µL/min into the striatum (AP: +0.5; L: −2.0 and DV: −3.0 mm) (Zhao et al., *J. Nanomed. Nanotechnol*. S4 (2011)). Twenty one days later (at the peak of inflammation), mice were intranasally (i.n.) or intravenously (i.v.) injected with fluorescently-labeled exosomes ($2.4\times10^{10}$ exosomes/mouse). Four hours later, mice were sacrificed, perfused, and the brain slides were examined by confocal microscopy. 6-OHDA-intoxicated mice injected with PBS were used as controls. Nuclei were labeled with DAPI. To examine which type of cells accumulates exosomes in the brain, a co-localization study with cell-specific markers was carried out. For this purpose, the brain slides were co-stained with: primary (1) rabbit polyclonal antibodies to neurons, AntiNeuN (ab128886, Abcam, 1:500 dilution), or (2) anti-tyrosine hydroxylase (TH) rabbit antibodies to TH-neurons (Calbiochem, 1:1000 dilution), or (3) rabbit anti CD146 to endothelial cells (ab75769, Abcam, 1:250 dilution), or (4) rabbit anti-GFAP antibodies to astrocyte marker (ab7260, Abcam, 1:500 dilution), and secondary antibodies, donkey anti-rabbit IgG H&L Alexa 555 (abcam ab150074, Abcam, 1:500 dilution). All slides were permeabilized for 60 min in 0.1M citrate buffer pH6.0 and 0.05% Tween 20, washed 3×5 min with 0.05% Tween 20 in PBS, blocked for 30 minutes with PBS and 5% Normal Donkey Serum+0.05% Tween 20, and stained with primary antibody at stated dilution overnight at 4° C. Following the incubation, slides were washed 3×5 minutes/wash in PBS/Tween, and stained with secondary antibodies for one hour at room temperature. Then, the slides were washed 3×PBS/Tween 5 min/wash ddH$_2$O, and covered using Vectashield Hardset mounting media with Dapi. The images were examined by a confocal fluorescence microscopic system ACAS-570 and corresponding filter set.

Immunohistochemical and Stereological Analyses:

6-OHDA-intoxicated mice (n=7) were treated via i.n. administration with PBS, or catalase alone (1.2×10$^9$ exosomes with 408.44 U catalase/mouse×2 in 10 µl PBS, ten times every other day), or exoCAT loaded by sonication or saponin permeabilization with the same amount of catalase (1.2×10$^9$ exosomes/mouse×2 in 10 µl PBS), or the same amount of empty exosomes 48 hours after the intoxication (10 times every other day). Two control groups of healthy non-intoxicated animals were i.c. injected with PBS, and then 48 hours later were i.n. injected with PBS, or empty exosomes. Twenty one days later, animals were sacrificed, perfused; brains were removed, washed, post-fixed, and immunohistochemical analysis was performed in 30 µm thick consecutive coronal brain sections as described (Brynskikh et al., *Nanomedicine* (*Lond*) 5:379 (2010)). For the detection of microglia activation, tissue sections were incubated with primary monoclonal rat anti-mouse anti-CD11b antibodies (1:500 dilution), and secondary biotinylated goat anti-rat antibodies (Vector Laboratories, Burlingame, Calif., 1:200 dilution). Thus, activated microglia within the SNpc will exhibit a more amoeboid morphology with sent out branches, compared to ramified barely visible resting microglia. In addition, levels of astrocytosis were assessed in the ventral midbrain region by fluorescent analysis of glial fibrillary acidic protein (GFAP) expression. For the GFAP staining, tissue sections were permeabilized with 0.01% Triton X-100 in TBS for 30 minutes and blocked for 1 hour with 10% normal goat serum (NGS, Vector Laboratories Inc., Burlingame, Calif.), then incubated with rabbit anti-GFAP primary polyclonal antibodies ab7260 (AbCam, Cambridge, Mass.) 1:100 dilution for 16 hours at 4° C. Tissue slides were incubated with goat anti-rabbit Alexa Fluor 647 secondary antibodies (Invitrogen; 1:200 dilution) for 1 hour, and mounted on slides. Immunoreactivity was evaluated by fluorescent analysis using confocal microscope Zeiss 510 Meta Confocal Laser Scanning Microscope (Jena, Germany), and ImageJ software (NIH, Bethesda, Mass., USA). For the assessment of neuroprotective effects, a TH staining was used to quantitate numbers of DA neurons (Tieu et al., *J Clin. Invest.* 112:892 (2003)). The total number of TH-positive DA neurons was counted by using the optical fractionator module in StereoInvestigator software (MicroBrightField, Inc., Williston, Vt.) (Brynskikh et al., *Nanomedicine* (*Lond*) 5:379 (2010)).

Apomorphine Test:

C57BL/6 mice were i.c. injected with 6-OHDA (n=7). Healthy mice i.c. injected with PBS were used as a control (Keshet et al., *J. Comp. Neurol.* 504:690 (2007)). Starting from 48 hours after intoxication, mice were i.n. injected with PBS, or exoCAT obtained by saponin permeabilization every other day for two weeks. Twenty one days later, the animals were injected with apomorphine (0.05 mg/kg, s.c.) and rotations were scored every 10 min for 90 min as described (Papathanou et al., *Eur. J. Neurosci.* 33:2247 (2011)).

Statistical Analysis:

For all the experiments, data are presented as the mean±S.E.M. Tests for significant differences between the groups were performed using a t-test or one-way ANOVA with multiple comparisons (Fisher's pairwise comparisons) using GraphPad Prism 5.0 (GraphPad software, San Diego, Calif., USA). A minimump value of 0.05 was chosen as the significance level.

Results

Manufacture of Exosomal Formulations of Catalase (exoCAT):

Catalase was incorporated into exosomes using different methods: a) incubation at RT with or without of saponin permeabilization; b) freeze/thaw cycles; c) sonication, and d) extrusion procedures. The last two methods were utilized to cause a reformation/deformation of exosomes in the presence of catalase. The obtained exoCAT formulations were purified from non-incorporated catalase by a gel-filtration chromatography with Sepharose 6BCL as described in Materials and Methods section.

Figure 1A:
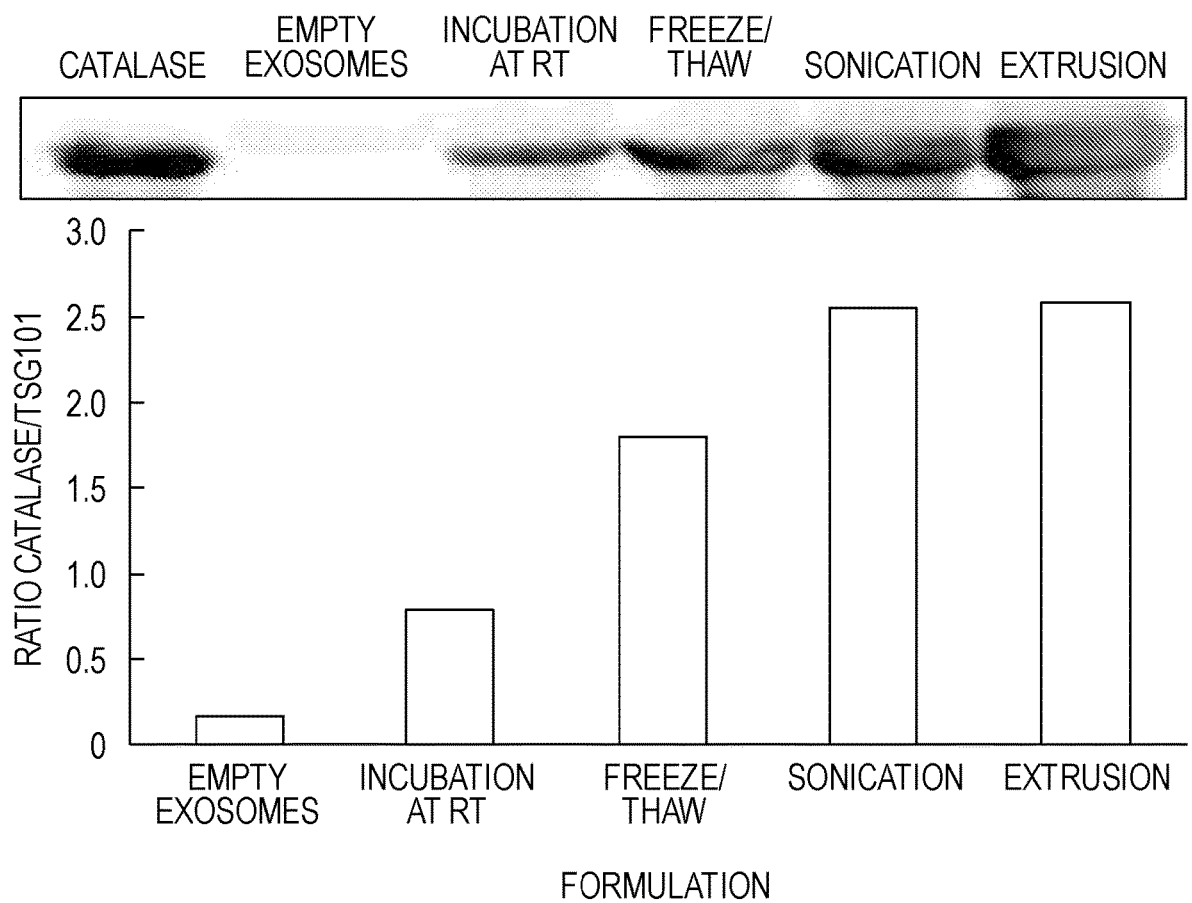
Figure 1B:
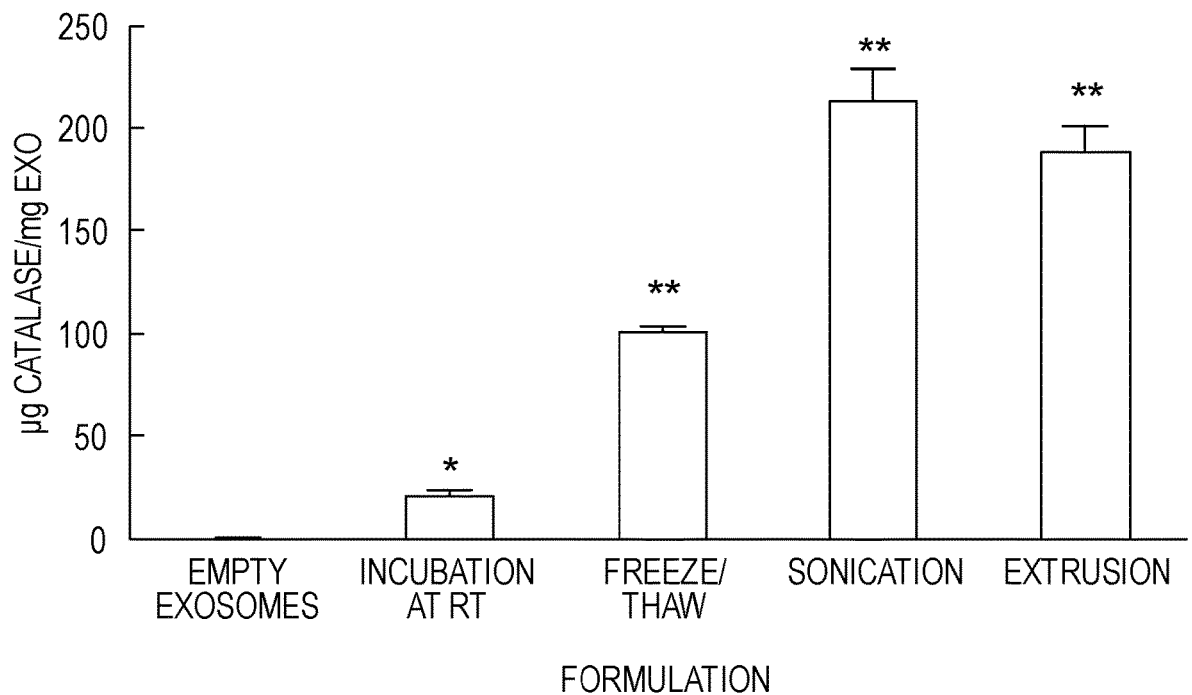

According to the western blot analysis, the amount of catalase loaded into exosomes increased in the row: the incubation at RT<freeze/thaw cycle<sonication extrusion (FIG. 1A). These results were confirmed by catalytic activity of the enzyme (FIG. 1B). ExoCAT obtained by sonication and extrusion showed the highest catalytic activity, followed by exoCAT obtained by freeze/thaw cycles, and then the incubation at RT (without saponin permeabilization). The incubation of catalase with exosomes at RT resulted in the lowest loading efficiency (4.9±0.5%, n=4) among all evaluated methods. Nevertheless, when exosomes were permeabilized with saponin, catalase loading efficiency significantly increased (18.5±1.3%, p<0.05). Furthermore, sonication and extrusion procedures resulted in the most efficient enzinie incorporation (26.1±1.2% and 22.2±3.1%, respectively). We hypothesized that a formation of transient pores or even reformation of exosomes upon sonication and extrusion allowed diffusion of catalase from the surrounding media into exosomes. The freeze/thaw cycles technique gave somewhat intermediate values of loading efficiency (14.7±1.1%). Regarding the yield of the catalase formulations, about 98% of exosomes were recovered upon all loading methods. Noteworthy, catalase structure was stabilized upon incorporation into exosomes. No loss of catalase enzymatic activity was detected in exoCAT upon sonication, while catalase alone was significantly deactivated in the same conditions (down to 14%).

Figure 1C:
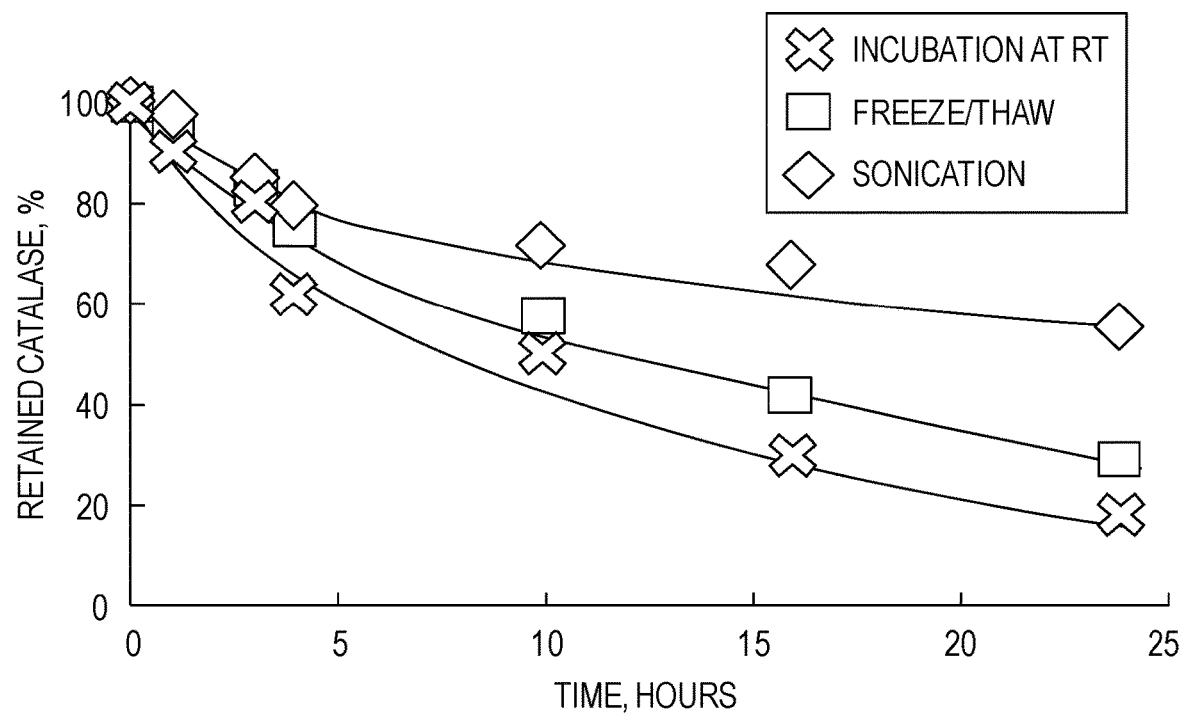

The release of catalase from pre-loaded exosomes was evaluated by enzymatic activity using dialysis membranes with a cut off 2000 KDa (FIG. 1C). The fastest release was observed for the formulation obtained by incubation at RT without saponin (FIG. 1C). In contrast, a prolonged and sustained release was recorded for exoCAT obtained by sonication; less than 40% of catalase was released over 24 hours. Taken together, the sonication of exosomes in the presence of catalase resulted in the high loading efficiency, and sustained release of enzymatically-active catalase. In particular, each mg of exoCAT obtained by sonication contained approximately 1,376±64.1 U of catalase activity in 4×10$^{11}$ exosomes/mL.

Characterization of exoCAT Formulations:

The size of catalase-loaded exosomes was determined by DLS and NTA techniques (Table 1). Particles of naked catalase showed small size (9.5 nm) with low polydispersity index (Pdl), which was close to the theoretical diameter (10.5 nm) of a single protein globule calculated from the molecular mass of the enzyme (Papadopoulos et al., *Bio-* phys. J. 79:2084 (2000)). An average diameter of empty exosomes was around 100 nm with a relatively high polydispersity (Table 1). The incubation of catalase with exosomes at RT (with or without saponin) did not significantly alter their size. However, freeze/thaw cycles, extrusion, and sonication of exosomes resulted in the significant size increases, especially, in the presence of catalase (Table 1). Overall, both DLS and NTA analyses indicate the size of the obtained exoCAT formulations was in the range of 100-200 nm. This suggests that the relatively small catalase-loaded nanoparticles might enter the target cells by endocytosis.

TABLE 1

Size of catalase exosomal formulations obtained by DLS and NTA[a]

| Formulation | DLS | | NTA (nm) |
| --- | --- | --- | --- |
| | $D_{eff}$ (nm) | PdI | |
| Catalase alone | 9.5 ± 0.1 | 0.10 | n/a |
| exosomes alone | 100.5 ± 13.5 | 0.20 | 99.5 ± 11.2 |
| exoCAT, mixture | 108.0 ± 14.3 (ns) | 0.35 | 100 ± 16.3 (ns) |
| exoCAT, mixture & saponin | 110.5 ± 23.1 (ns) | 0.35 | 111 ± 7.8 (ns) |
| exosomes, freeze/thaw | 147.0 ± 10.0 (*) | 0.48 | 125 ± 17 (*) |
| exoCAT, freeze/thaw | 158.0 ± 11.0 (*) | 0.48 | 130 ± 11 (*) |
| exosomes, sonicated | 179.0 ± 10.6 (*) | 0.30 | 150 ± 8.2 (*) |
| exoCAT, sonicated | 183.7 ± 13.8 () | 0.25 | 162.4 ± 6.1 () |
| exosomes, extruded | 134.0 ± 7.5 (*) | 0.25 | 130 ± 7.5 (*) |
| exoCAT, extruded | 154.8 ± 11.0 (*) | 0.29 | 149.4 ± 3.3 (*) |

([a]Statistical significance is compared to the diameter of naïve exosomes alone and shown by symbols: $p < 0.05$ (*), or $p < 0.005$ (**))

Based on the data from NTA experiments and evaluations of catalase activity, about 940±15 catalase molecules per exosome were incorporated by sonication. Noteworthy, exosomal formulations were stable at RT over a week; no changes in size and/or catalase activity were recorded. Furthermore, the restitution of lyophilized exoCAT in water solutions did not alter the size, and activity of exosomal formulations.

Figure 1D:
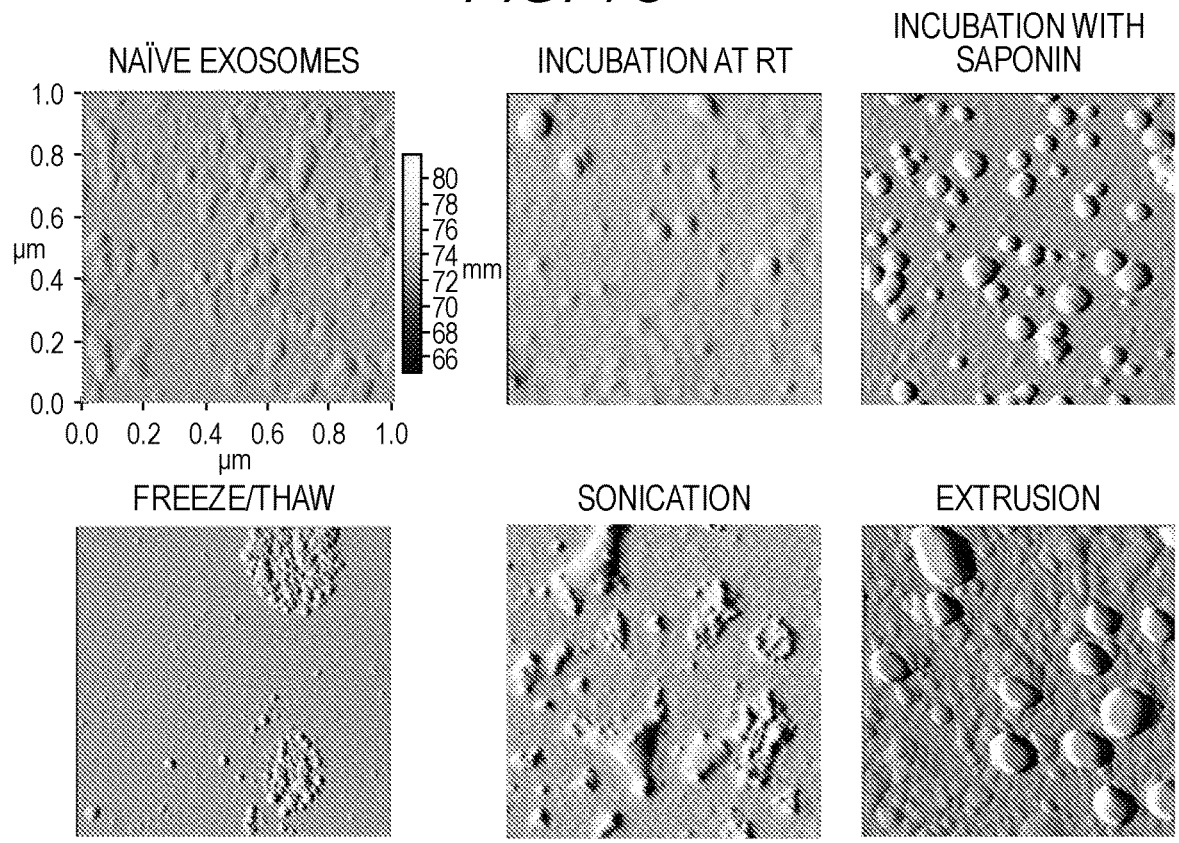

The AFM images revealed considerable differences in the morphology of exoCAT formulations (FIG. 1D). Naïve exosomes isolated from Raw 264.7 macrophages, as well as exosomes incubated with catalase at RT, or obtained by extrusion procedures have a round morphology. Particles of exoCAT formulation manufactured by freeze-thaw cycle were considerably larger in size consisting of several dozen of smaller exosomes, probably due to the aggregation. The AFM images of sonicated exoCAT demonstrated non-spherical associates with a variety of shapes (FIG. 1D).

Figure 2A:
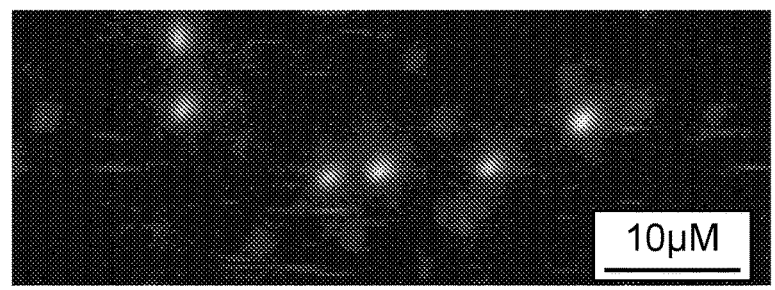
FIGS. 2A-2C show hyperspectral microscopy images of exoCAT formulation. Catalase was loaded into exosomes by sonication as described in Methods section. The obtained exoCAT formulation (FIG. 2A) was examined by CytoViva nanoscale hyperspectral microscopy and compared to empty exosomes (FIG. 2B). The spectral responses of the two samples (FIG. 2C) were quantitatively different showing narrowing of the spectral response of the loaded exosomes versus the unloaded nanoparticles. Images captured at 100× magnification.
Figure 2B:
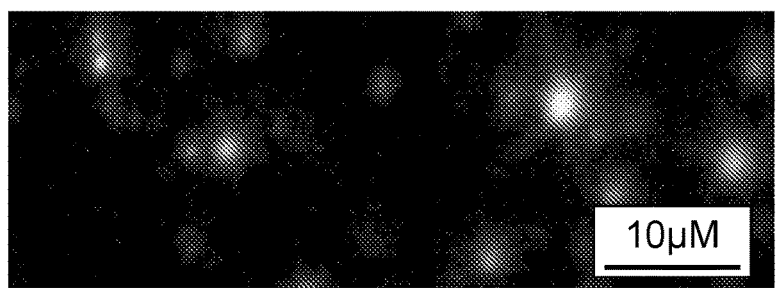
Figure 2C:
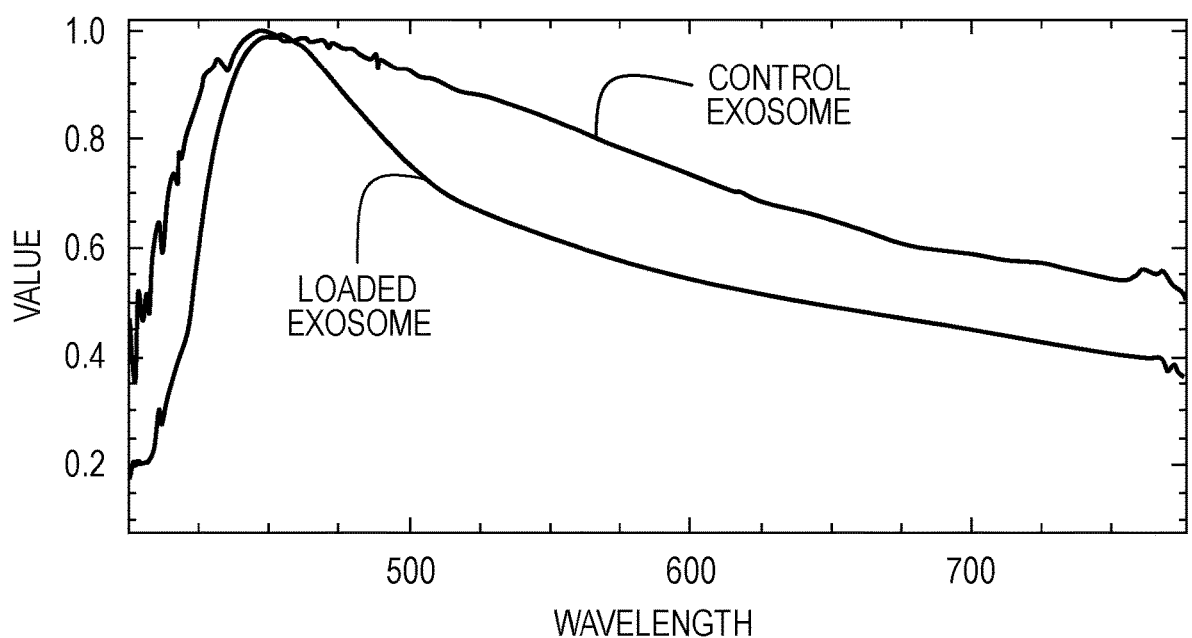
Figure 3:
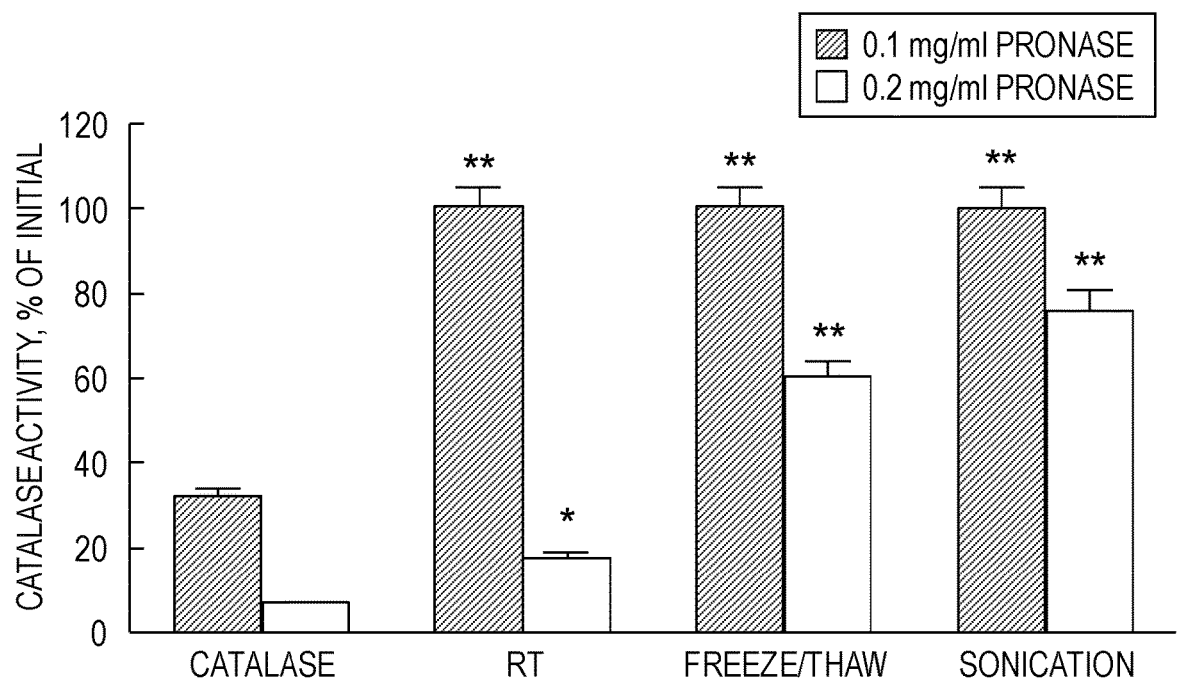
FIG. 3 shows preservation of catalase enzymatic activity in exoCAT. ExoCAT obtained by sonication demonstrated the best protection of catalase.

Next, the loading of catalase into exosomes was confirmed by hyperspectral microscopy. This technique enables optical observation, spectral characterization, and mapping of nanoscale materials in a wide range of biological and material-based environments. FIGS. 2A-2C show representative hyperspectral images of exosomes loaded with catalase by sonication (FIG. 2A), and empty exosomes sonicated at the same conditions (FIG. 2B). The measurements illustrate a narrowing of the spectral response of the loaded versus the unloaded exosomes (FIG. 2C). This suggests that significant alterations/perturbations occur upon catalase incorporation into exosomes. The incorporation of catalase into exosomes significantly improved its enzymatic stability against protease degradation (FIG. 3). In accordance with the loading efficiency (FIG. 1A-1B), and release kinetics (FIG. 1C), the stability of catalase was increased in the row: incubation at RT without saponin<freeze/thaw cycles<sonication (FIG. 3). Altogether, this indicates that catalase was not only associated with the surface of exosome, but was also incorporated into them.

Figure 4A:
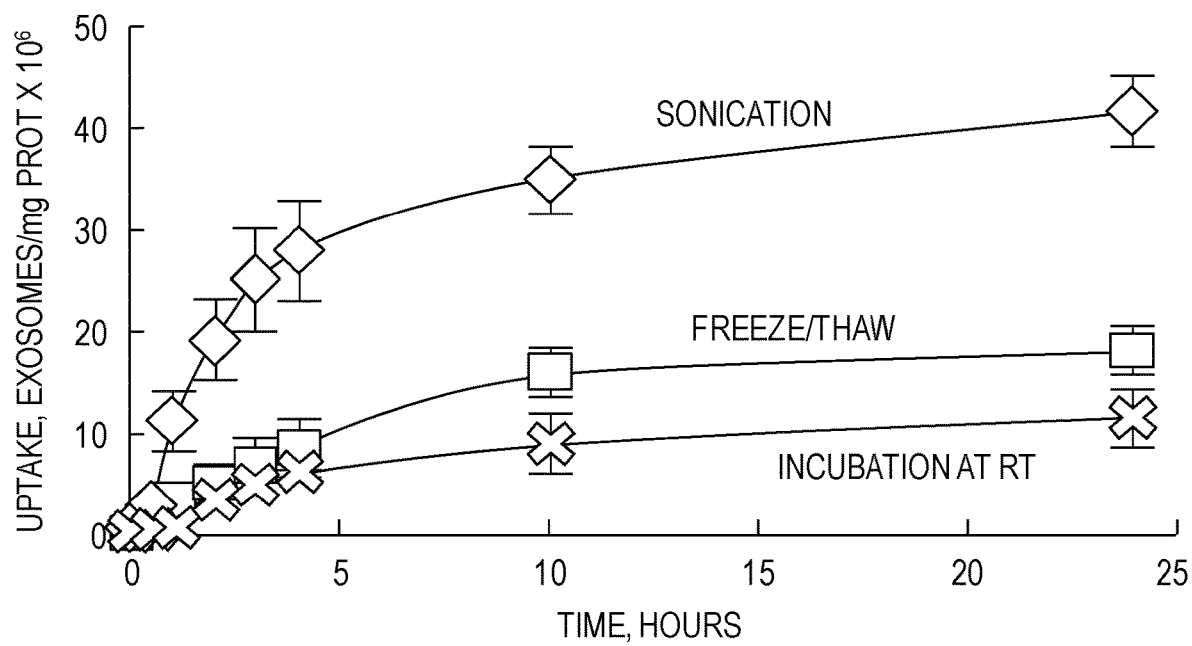
Figure 4B:
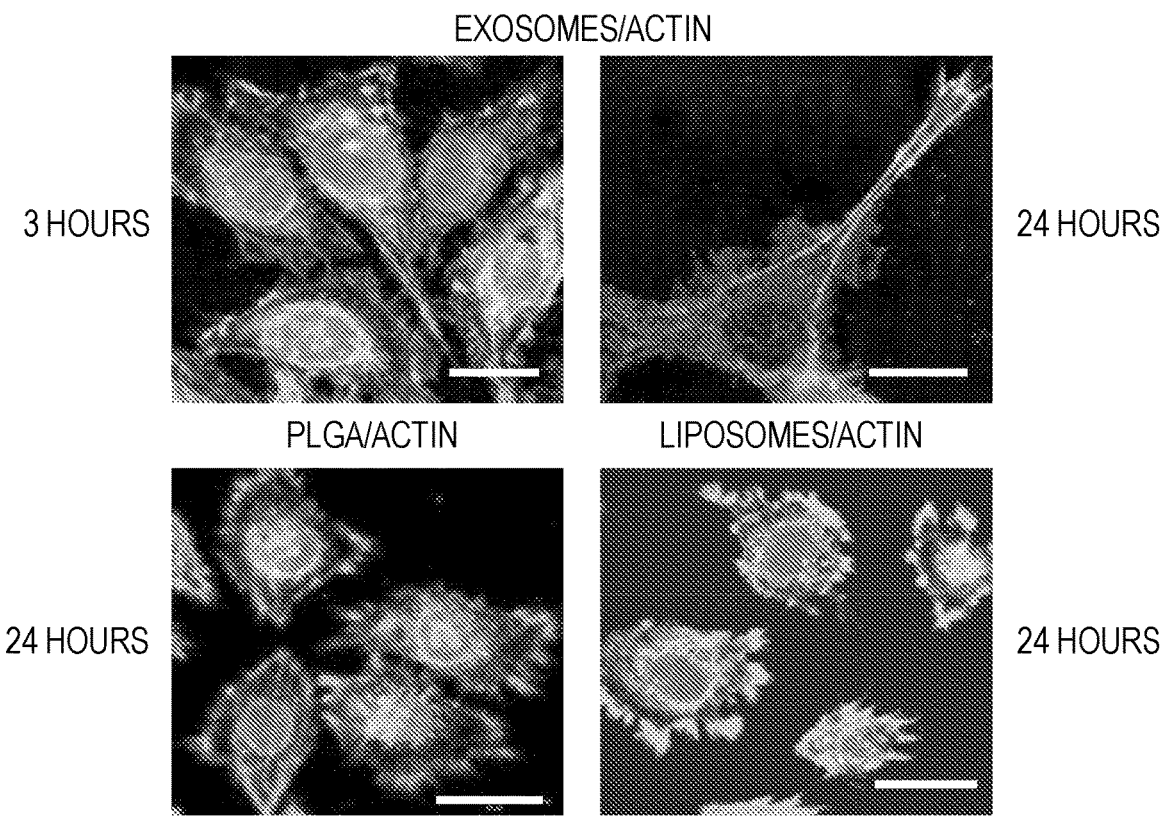

Accumulation and Therapeutic Efficacy of exoCAT in Target Neuronal Cells In Vitro:

The ability of nanocarriers to deliver the drug payload into target cells is crucial for the therapeutic efficiency of exosomal formulations. First, we examined whether manipulations with exosomes affect their transport into target cells in vitro. Exosomes were subjected to various loading procedures (incubation at RT, freeze/thaw cycles, or sonication), labeled with lipophilic fluorescent dye, DIL, and then incubated with PC12 cells. Striking differences in accumulation levels were recorded (FIG. 4A). In spite of their large size, sonicated exosomes were taken up at considerably greater levels than those subjected to freeze/thaw cycles, or incubation at RT. This suggests superior interactions of sonicated exosomes than other exosomal preparations with cellular plasma membranes. We speculate that a reorganization of exosomes upon sonication may result in the exposure of hydrophobic parts of the cellular lipid bilayers or incorporated proteins that improve their interactions with plasma membranes of target cells. Next, confocal images confirmed a profound accumulation of sonicated DIL-labeled exosomes in PC12 cells (FIG. 4B). The exosomes were efficiently internalized into neurons followed 3-hour incubation (FIG. 4B-I), filled the entire neuronal body and build up on the plasma membranes at later time points (FIG. 4B-II). The unparalleled accumulation of exosomes in target cells was even more evident in comparison with the considerably lower uptake of commonly used for the drug delivery polymer-based PLGA nanoparticles (100 nm, FIG. 4B-III), or liposomes (FIG. 4B-IV) that were applied at the same level of fluorescence. These nanocarriers (PLGA nanoparticles and liposomes) were utilized for the brain delivery of L-DOPA to treat PD.

Figure 4C:
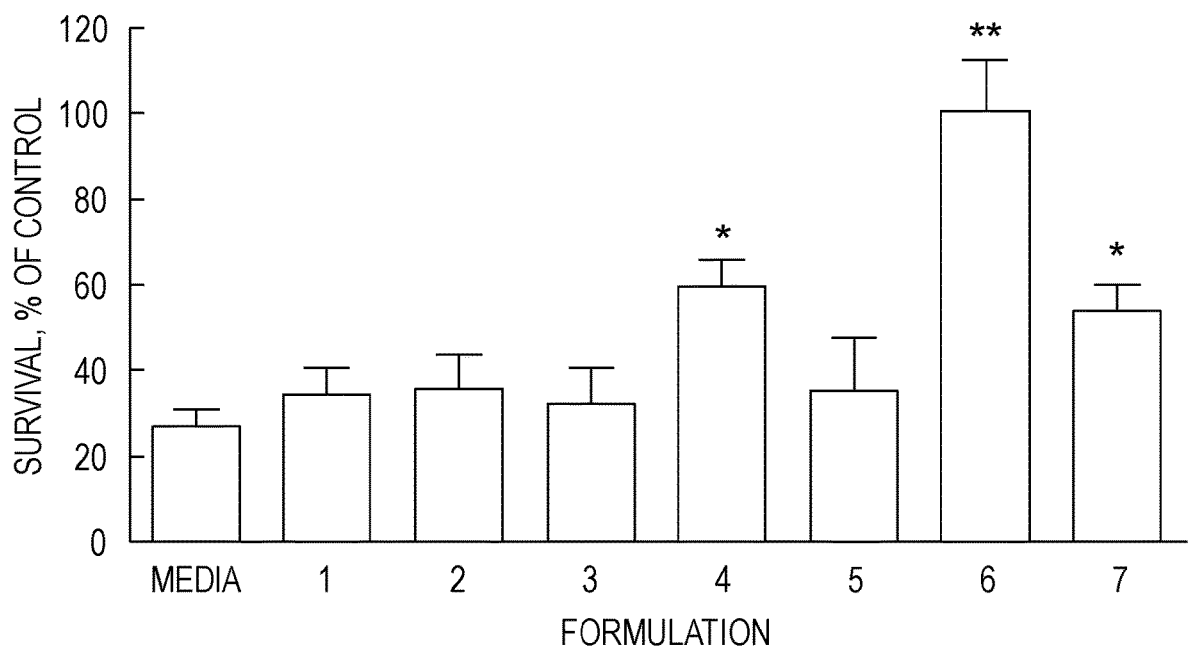

Given the efficient accumulation of exosomes in PC12 neurons, we hypothesized that exosomes with incorporated catalase may deliver a substantial amount of the enzyme into target neuronal cells, and as a result, provide a superior neuro-protective activity against oxidative stress. To test this hypothesis, the effect of exoCAT formulations on neuronal survival was evaluated in PC12 cells pre-treated with 6-OHDA to recapitulate components of PD neurodegeneration in vitro. Following the 6-OHDA pre-treatment, the PC12 cells were supplemented with various exoCAT formulations, and the neuronal survival was evaluated by MTT test (FIG. 4C). As expected, exoCAT prepared by sonication and extrusion demonstrated greater neuroprotective activity than exosomes loaded with catalase by freeze/thaw cycles or incubation at RT, probably, due to the facilitated exoCAT accumulation, and/or protection of catalase against degradation in exosomal carriers. Noteworthy, permeabilization of exosomes by saponin upon loading with catalase significantly increased neuroprotection effect produced by this formulation (FIG. 4C). Catalase alone, as well as empty exosomes did not protect PC12 cells at these experimental conditions.

Next, exoCAT obtained by sonication was evaluated for the ability to eliminate ROS produced by activated macrophages in vitro (FIG. 4D). In this experiment, macrophages pre-incubated with a mixture of LPS (100 ng/mL) and TNF-α (100 ng/mL) were utilized as a model of activated microglia in the PD brain. The activation of macrophages resulted in the significant increase in ROS production, whereas the addition of exoCAT considerably decreased hydrogen peroxide levels (FIG. 4D). Interesting, empty exosomes also decreased ROS levels in activated macrophages down to the levels of the control non-activated cells, although this effect was less significant than the effect of exoCAT. This indicates that exosomes by themselves (probably, their internal content) have a capacity to deactivate free radicals. This result is consistent with the studies demonstrating protection effects of exosomes against myocardial ischemia/reperfusion injury (Lai et al., Stem Cell Res. 4:214 (2010)). Altogether, these data suggests that exoCAT can be a useful tool for ROS deactivation and neuronal protection against oxidative stress.

Transport of Exosomes into Mouse Brain with Inflammation:

To visualize the ability of exosomes to target and deliver their payload to inflamed brain tissues, confocal imaging studies were conducted in a PD mouse model. To induce brain inflammation, C57BL/6 mice were intracranially (i.c.) injected with 6-OHDA into SNpc. Twenty one days later (at the peak of inflammation), mice were injected with DIL-labeled exosomes ($2.4 \times 10^{10}$ exosomes/20 µL/mouse) through intranasal (i.n.) (FIG. 5B), or intravenous (i.v.) (FIG. 5C) routes. Mice i.n. injected with PBS were used as controls (FIG. 5D). Four hours later, mice were euthanized, perfused, and brain slides were examined by confocal microscopy. Nuclei were stained with DAPI (blue). The images revealed a wide distribution of exosomes throughout the brain, in particular, cerebral frontal cortex, central sulcus, and cerebellum (FIG. 5A). The amount of exosomes delivered upon the i.n. administration was greater (FIG. 5B) than those delivered through i.v. injection (FIG. 5C). Confocal images showed diffuse fluorescent staining throughout the brain tissues along with the stained vesicular compartments localized predominantly in perinuclear regions (shown by arrows). No fluorescence was found in control mice with the PBS injection (FIG. 5D). As such, i.n. route of administration was selected for the further evaluations of exoCAT therapeutic effects.

Catalase-Loaded Exosomes Protect SNpc Neurons Against Oxidative Stress in Mice with Acute Brain Inflammation:

The neuropathology of PD includes brain inflammation, microglial activation, and secretion of neurotoxins, such as ROS, all of which contribute to neurodegeneration and degradation of motor function (Stone et al., Antioxid Redox Signal, (2009)). We posit that the successful brain delivery of catalase will reduce neuroinflammation resulting in improved disease outcomes. For this purpose, C57BL/6 mice were stereotactically injected with 6-OHDA into SNpc, and 48 hours later, mice were i.n. injected with exoCAT ($1.2 \times 10^9$ exosomes with catalase activity 408.44 U/10 µL/U mouse into each nostril, 10 times every other day), or the same amount of catalase alone.

Two exoCAT formulations were evaluated; catalase-loaded exosomes by sonication, or permeabilization with saponin at RT (n=7). Mice intoxicated with 6-OHDA, and then i.n. injected with PBS were used as control animals with brain inflammation (PD mice). Non-intoxicated animals i.c. injected with PBS were used as healthy controls. To evaluate the effect of empty exosomes in healthy brain, another control group of healthy animals was i.c. injected with PBS, and then empty exosomes. Twenty-one days following administration of the test formulation, the mice were sacrificed, perfused with paraformaldehyde (PFA), and brains harvested. Brain slides were stained with antibodies to activated microglia (FIGS. 6A-6G), astrocytes (FIGS. 7A-7C), or TH-expressing DA neurons (FIGS. 8A-8G). The quantification of the obtained results for anti-inflammatory and neuroprotective effects is presented on FIGS. 6F and 8F, respectively.

Figure 6A:
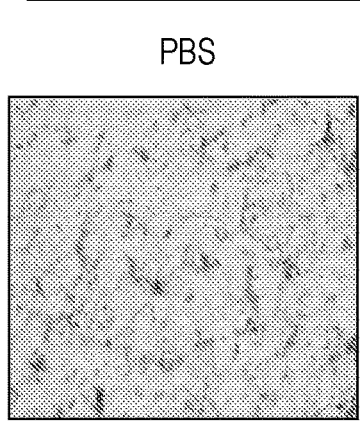
FIGS. 6A-6G show anti-inflammatory effects of exoCAT in PD mouse model. The intranasal administration of exoCAT significantly decreased microglial activation (FIG. 6D, FIG. 6E) in 6-OHDA-intoxicated mice compared to those intoxicated with 6-OHDA and then treated with PBS (FIG. 6C). Catalase alone did not decrease inflammation in PD mice (FIG. 6F). Empty exosomes did not alter the microglial status in healthy animals (FIG. 6B) compared to healthy controls (FIG. 6A). The anti-inflammatory effects of the described exosomal formulations were quantified by the amount of activated microglial cells (FIG. 6G).
Figure 6B:
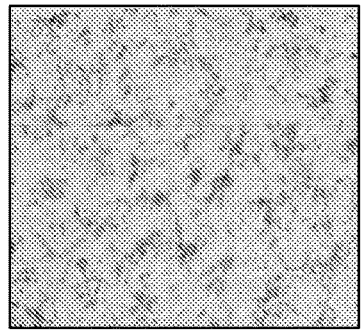
Figure 6C:
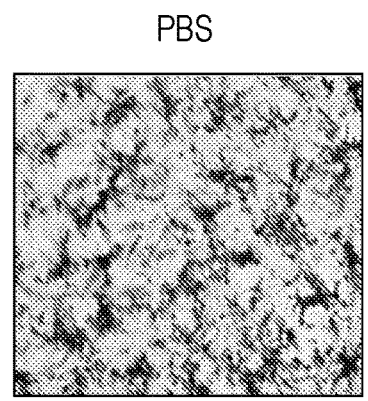
Figure 6D:
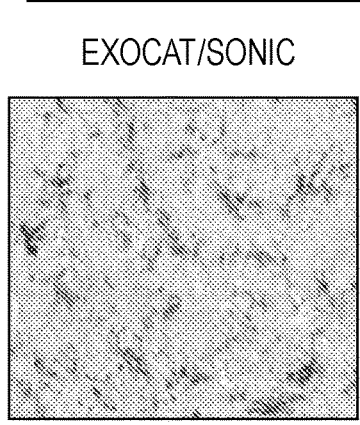
Figure 6E:
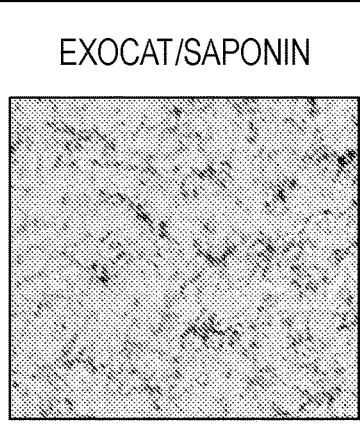
Figure 6F:
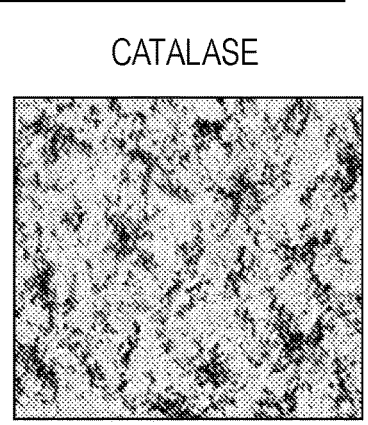
Figure 6G:
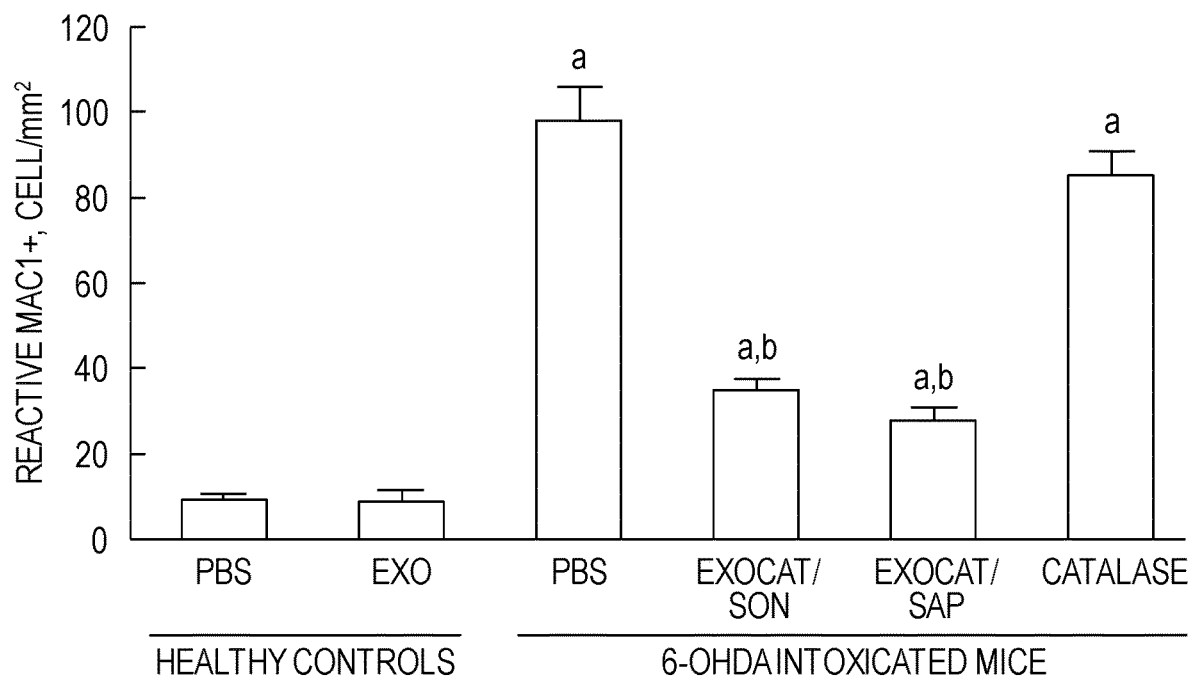
Figures 7A, 7B, 7C:
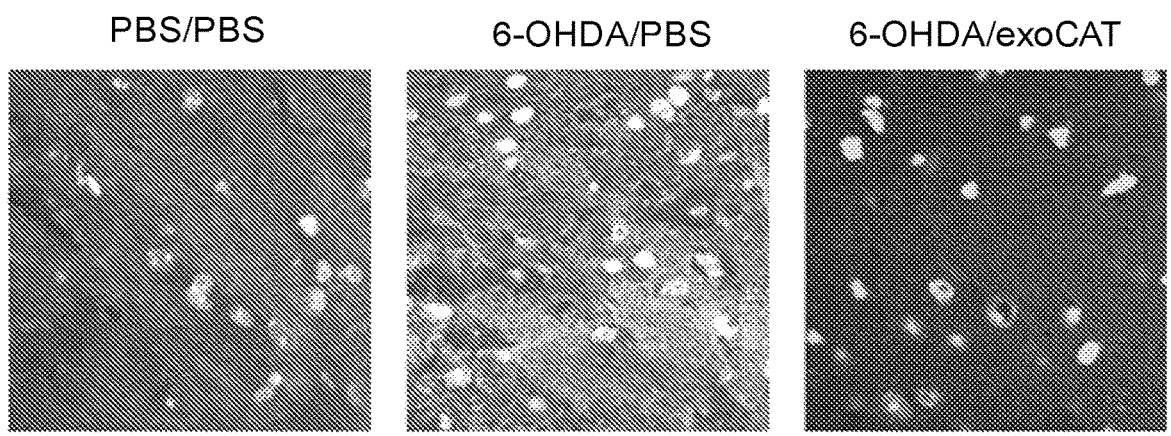
FIGS. 7A-7C show attenuation of astrocytosis in PD mice by exoCAT. 6-OHDA-intoxicated mice were i.v injected with PBS (FIG. 7B), or exoCAT (FIG. 7C). Mice treated with PBS in lieu of 6-OHDA served as non-intoxicated controls (FIG. 7A). 21 days later animals were sacrificed, and brain tissues were subjected for confocal microscopy with staining for glial fibrillary acidic protein (GFAP). Representative images demonstrated decrease of neuroinflammation in animals treated with exoCAT (FIG. 7C) compared to PD mice treated with PBS (FIG. 7B). 63× magnification.
Figure 8G:
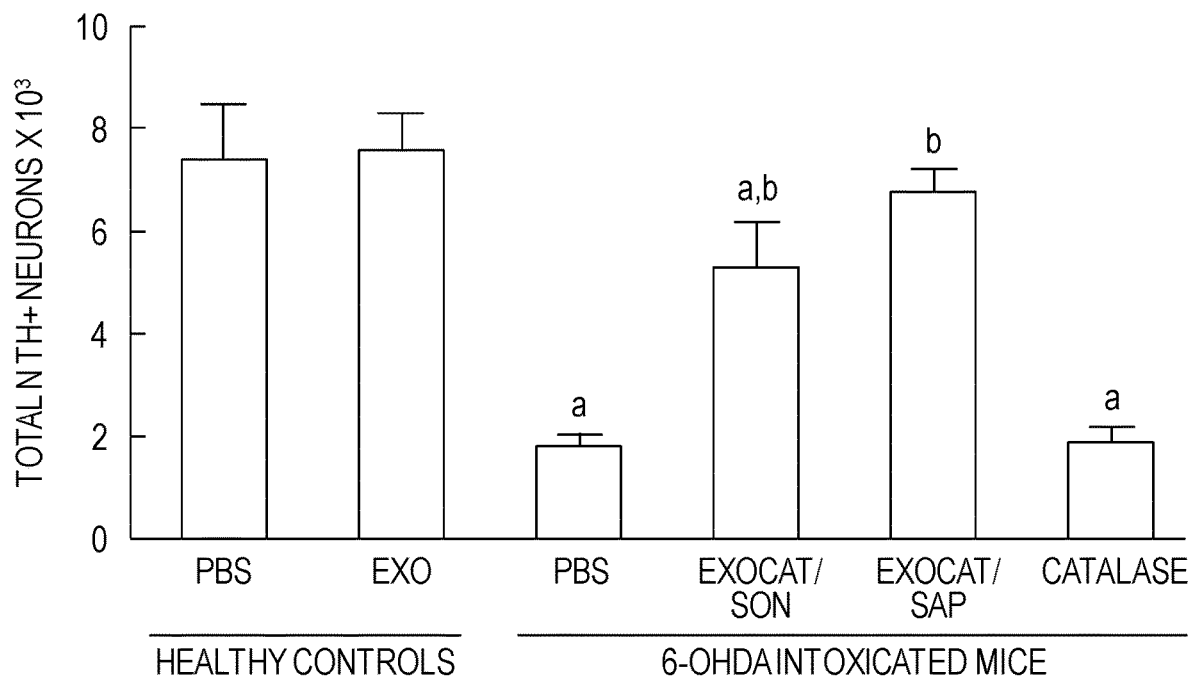

6-OHDA injections produced substantial brain inflammation signified by up-regulated expression of CD11b by microglia within the SNpc that exhibited a more amoeboid morphology (FIG. 6C) than ramified microglia in PBS-treated mice (FIG. 6A). Furthermore, the 6-OHDA-mediated intoxication resulted in the complete degeneration of DA neurons in the ipsilateral hemisphere SNpc (FIG. 5C, arrow). The anti-inflammatory effect of exoCAT was demonstrated by the significant ($p < 0.005$) reduction in microgliosis as measured by CD11b expression (FIGS. 6D, 6E, 6G) and decrease in astrocytosis as demonstrated by GFAP levels (FIGS. 7A-7C). Furthermore, in. administration of exoCAT resulted in a 3-fold increase in survived DA neurons (FIGS. 8D, 8E, 8G) compared to the control 6-OHDA-treated mice injected with PBS (FIGS. 8C, 8G). The neuroprotection was greater in the animal group treated with exoCAT obtained by permeabilization with saponin (FIGS. 8E, 8G) than with exoCAT loaded by sonication (FIGS. 8D, 8G). Not surprisingly, free catalase was not effective in decreasing inflammation or providing neuroprotection in 6-OHDA-intoxicated mice (FIGS. 6E and 6E).

Next, we investigated the effect of exoCAT formulation obtained by saponin permeabilization in apomorphine test. Mice intoxicated with 6-OHDA and treated i.n. with PBS showed 150±11 rotations per minute. In contrast, mice intoxicated with 6-OHDA and then treated i.n. with exoCAT as described above have significantly less rotations (26.1±3.1 per minute). Noteworthy, non-intoxicated healthy controls did not rotate at all.

Figure 9:
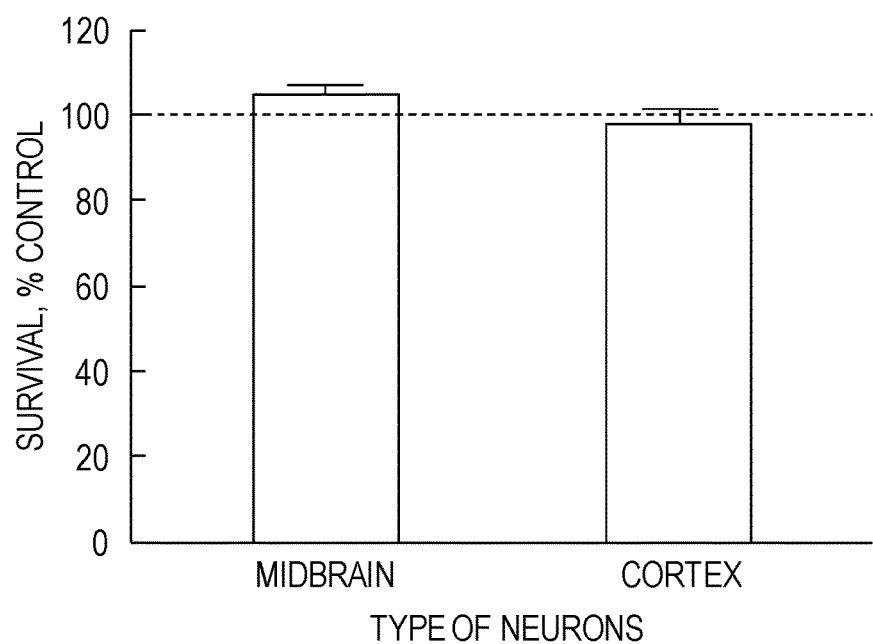
FIG. 9 shows the absence of toxic effect of exosomes released from macrophages in primary neurons. Primary neurons were isolated from mouse pups midbrain and cortex and cultured on 24-well plated for 24 hours. In parallel, exosomes were isolated from BMM concomitant media, and added to the neurons for 48 hours. Neurons incubated in the media without exosomes were used as controls. Following incubation, the cells were collected and their survival was accounted by BSA method. No effect of the neuronal survival upon addition of exosomes was detected.

Finally, we investigated possible toxic effect of exosomal carriers alone. No effect of empty exosomes on the microglial activation or number of DA neurons was found in healthy mice (FIGS. 6B and 8B) compared to the healthy PBS-treated controls (FIGS. 6A and 8A, respectively) suggesting absence of neurotoxic effects of exosomal carriers in the brain. This result was confirmed in in vitro model of primary cortical or DA neurons isolated from mouse pups. Thus, a 48-hour exposure of primary neurons to exosomes released from macrophages did not affect neuronal survival (FIG. 9). Overall, these results demonstrate that exosomal formulations of catalase may be useful for PD therapies.

Figure 10:
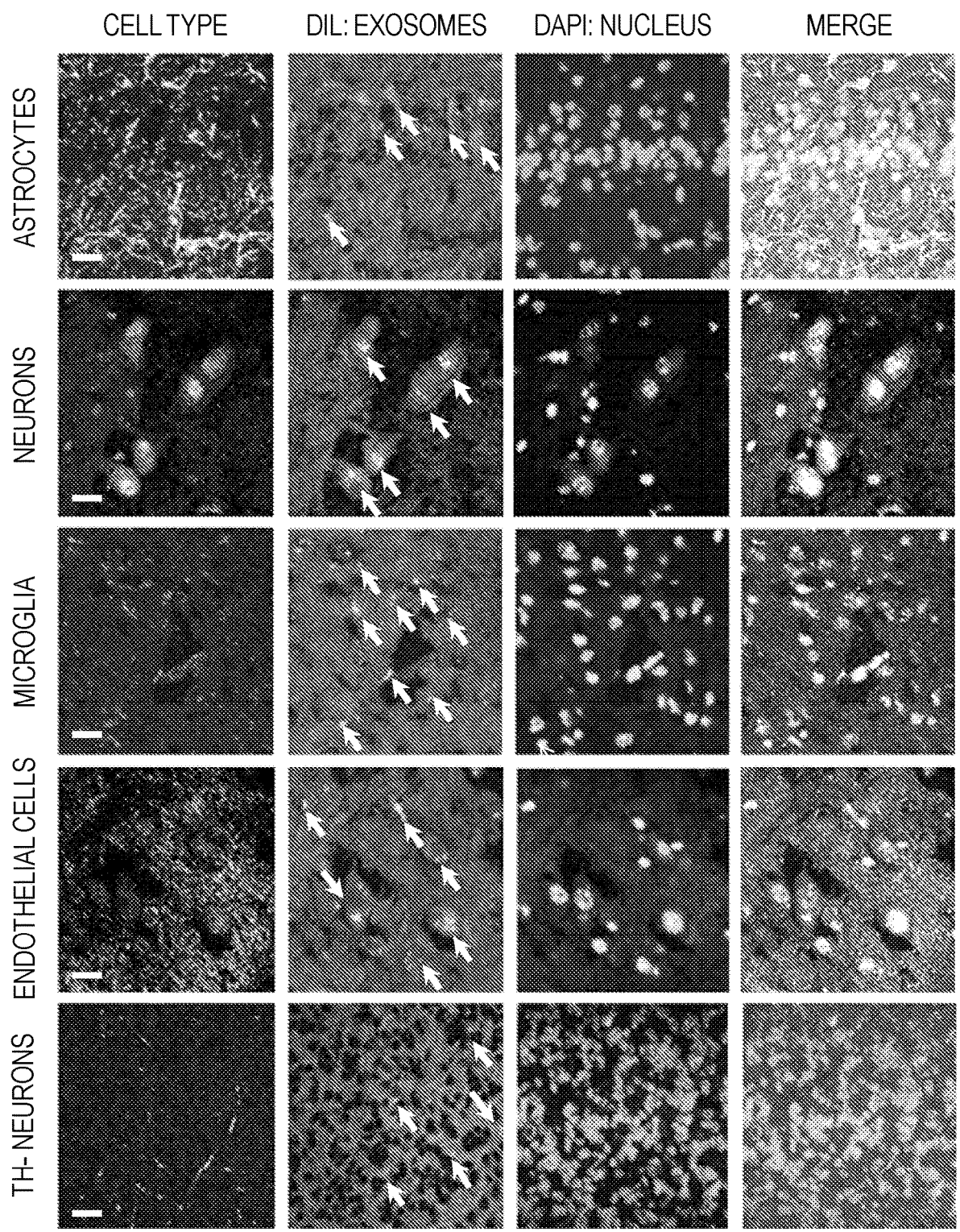
FIG. 10 shows co-localization of exosomes with different cells in the mouse brain with inflammation. Exosomes released by BMM were labeled with DIL (red). C57BL/6 mice were intoxicated with 6-OHDA, and then i.n. injected with fluorescently-labeled exosomes. Four hours later, mice were sacrificed, perfused, and brain slides were subjected for confocal examinations. Brain slides were stained with antibodies to different cell types and then secondary Ab 594. Nucleus was stained with DAPI. Bar: 10 μm.

Co-Localization of Exosomes with Various Types of Cells in the Brain:

To assess which cell type in the brain accumulates exosomes, brain slides were co-stained with different cell markers (FIG. 10). Interesting, exosomes were mostly co-localized with neurons, microglia and partially with endothelial cells (FIG. 10). Noteworthy, along with distinct endosomal compartments filled with exosomes, a diffuse exosomal staining was evident throughout all brain tissues. It is likely the exosome-mediated delivery of catalase to activated microglia, astrocytes, and neurons in the inflamed brain may result in ROS degradation and neuroprotection in PD patients.

Discussion

Currently, there are no treatments that halt or reverse the course of PD, and only palliative therapies, such as replacement strategies for missing neurotransmitters, exist. The inability of most potent therapeutics, and especially therapeutic proteins, to cross the BBB following systemic administration dictates the necessity to develop unconventional, clinically applicable drug delivery systems. In this respect, biocompatible vehicles, such as exosomes, may help to solve this challenging task.

Oxidative stress has long been implicated in the process of neurodegeneration seen in Parkinson's patients. Indeed, the pathogenesis of PD is associated with a lack of the natural antioxidants catalase, glutathione and superoxide dismutase in the midbrain region, specifically, in the SNpc (Jin et al., *Biochim. Biophys. Acta* 1842:1282 (2014)). It was demonstrated that cells of the immune system, and particularly microglia, release pro-inflammatory cytokines in response to different stress conditions (Lucin et al., *Neuron* 64:110 (2009)) leading to neuronal demise (Chan, *J. Cereb. Blood Flow Metab.* 21:2 (2001)). Antioxidants can inhibit inflammatory responses and protect dopaminergic neurons as reported in laboratory and animal models of PD. In particular, catalase, one of the most efficient antioxidants found in nature, has been shown to rescue primary cerebellar granule cells in in vitro models of PD (Prasad et al., *Curr. Opin. Neurol.* 12:761 (1999); Gonzalez-Polo et al., *Cell Biol. Int.* 28:373 (2004)). Several clinical studies have assessed the therapeutic efficacy of low molecular antioxidants for PD therapy. Unfortunately, the results of these investigations have been disappointing due to the drug poor pharmacokinetics and inability to penetrate the BBB (Pappert et al., *Neurology* 47: 1037 (1996)). Thus, the development of novel approaches for brain delivery of antioxidants, and in particular redox enzymes, is of utmost importance.

We report here the development of a new exosomal-based technology for catalase CNS delivery to treat PD. Catalase is a large protein (MW 240 K) that is susceptible to deactivation and rapid degradation. Therefore, different techniques for catalase loading into exosomes were evaluated: incubation at RT with or without saponin permeabilization, freeze/thaw cycles, sonication, or extrusion. Our data indicate the size, morphology, loading efficiency, and stability of exoCAT formulations strongly depended on the method of preparation. Thus, the extensive reformation and reshaping of exosomes upon sonication and extrusion enabled catalase diffusion across relatively tight and highly structured lipid bilayers and resulted in the high loading efficiency of exosomal carriers. Notably, these approaches for incorporation into exosomes are not specific only for proteins, but can be applied to other therapeutic and imaging agents. Thus, TEM studies indicated that a substantial amount of gold nanoparticles with the diameter (10.3±0.2 nm) can be also incorporated/associated with exosomes by sonication (FIG. 11). Interesting, similar to the sonicated exoCAT (FIG. 1D), nanoparticles-loaded exosomes showed non-spherical morphology with a variety of shapes (FIG. 11). Indeed, it should be taken into consideration that the disruption of the exosomes integrity during sonication or extrusion procedures may alter their immune-privileged status, and therefore, make them visible for the MPS.

Noteworthy, saponin treatment also increased loading of catalase into exosomes. Saponin is the efficient permeabilization agent for cellular plasma membranes (Jamur et al., *Meth. Mol. Biol.* 588:63 (2010)). We hypothesized that similar to the whole cells, saponin may selectively remove membrane-bound cholesterol of exosomes, creating holes/pores in the exosomal lipid bilayers and therefore, promoting catalase incorporation. Overall, exoCAT obtained by sonication and extrusion, as well as saponin treatment showed the high loading efficiency, preservation of catalase enzymatic activity against proteases degradation, and prolonged and sustained release.

Regarding the delivery of incorporated therapeutics to the target cells, this study demonstrated the extraordinary ability of exosomes to interact with target cells and deliver their "payload" into neighboring neurons. Confocal images revealed fluorescently-labeled exosomes were adhering and overflow neuronal cells in abundance. Indeed, comprising of cellular membranes exosomes should have an exceptional ability to interact with target cells. Furthermore, exosomal surface is rich with tetraspanins and integrins (Rana et al., *Int. J. Biochem. Cell Biol.* 44:1574 (2012)) that enable the efficient attachment to the plasma membrane of target cells. As a result, exosomes accumulated in considerably greater levels in PC12 cells than PLGA nanoparticles that have been used as common nanocarriers for PD therapy (Danhier et al., *J. Control. Release* 161:505 (2012)) or liposomes (Spuch et al., *J. Drug Delivery* 2011, 469679 (2011)). Interesting, the accumulation levels varied for different exosomal preparations. In particular, sonicated exosomes showed the greatest uptake in neurons compared to exosomes incubated at RT, or aggregates obtained by freeze/thaw cycles. We hypothesized that a reorganization of exosomes upon sonication may alter the content of surface proteins as well as organization of lipid bilayers that resulted in the increased exosomal interactions with cellular membranes of target cells. Obviously, this effect may play a positive role and overpower negative effects of decreased uniformity and increased visibility of exosomal carriers for the cells of immune system mentioned above.

Concerning the antioxidant activity, exoCAT formulations showed the efficient ROS deactivation and significant neuroprotective effects against oxidative stress in vitro. In accordance with the loading efficiency, exoCAT obtained by sonication and extrusion provided the most potent neuroprotection. We reported earlier that exosomes secreted from preloaded with nanoformulated catalase macrophages were accumulated in adjacent cells diffusing broadly throughout the cytoplasm and avoiding degradation in lysosomes (Haney et al., *Nanomedicine* (*Lond*) 7:815 (2012)). This mechanism enabled the drug to reach different intracellular compartments, such as mitochondria, and endoplasmic reticulum, and produce potent therapeutic effects (Haney et al., *Nanomedicine* (*Lond*) 7:815 (2012)). We speculated that the same favorable intracellular localization of exoCAT may support the superior antioxidant and protective activity of exoCAT in neurons.

The intranasal administration provides two main routes for the CNS drug delivery: a) transport across the single epithelial cell layer directly to the systemic blood circulation without first-pass hepatic and intestinal metabolism; and b) transport along the olfactory nerve cells, when drug can bypass the BBB and enter the brain directly. Furthermore, this route is attractive due to the possibility of non-invasive multiple treatments with high patient compliancy. Interesting, some investigators hypothesized that PD have its origin in the bulbs olfactory (Braak et al., *Neurobiol. Aging* 24:197 (2003)). Subsequently, it could spread, ascending cell-by-cell through brainstem, midbrain, and other regions of the brain, and finally result in PD. Therefore, we reasoned that intranasal administration of exoCAT may work the same way delivering therapeutic catalase to the affected brain areas. We report here that intranasally administered exosomes diffused through the mouse brain, localizing predominantly in the cerebral frontal cortex, central sulcus, and cerebellum.

The most important finding of our investigation is that selected exoCAT formulations significantly decreased brain inflammation and increased neuronal survival in a PD mouse model. The mechanism of these effects is yet to be uncovered. We hypothesized the encapsulation of catalase into exosomes may preserve catalase enzymatic activity, prolong the blood circulation time, reduce immunogenicity, and improve its interaction with epithelial cells, thus improving drug transport and therapeutic effects in PD. Here, we investigated two exosomal formulations that were obtained by saponin treatment, and sonication. These formulations were chosen as the most efficient ones that can provide high loading and sustained drug release. In addition, we evaluated whether the reformation of exosomes upon sonication affected their therapeutic efficacy in vivo. We demonstrated that both formulations significantly decreased neuroinflammation and provided potent neuroprotection in 6-OHDA mouse model. Furthermore, catalase-loaded exosomes obtained by permeabilization with saponin have superior therapeutic effects than those obtained by sonication. It is likely that exoCAT obtained by permeabilization with saponin might have better uniformity in their surface morphology presumably with the intact membrane proteins. This may lead to a lower visibility for RES and clearance by macrophages. Overall, successful development of exosome-mediated delivery of catalase could lead to a viable therapy for patients with PD.

In clinical settings, different approaches may be applied to introduce exosomal-based drug delivery systems. First, exosomal carriers harvested from peripheral blood monocytes by apheresis will be loaded with a therapeutic agent and re-administered back into the patient. As an alternative approach, stem cells may be harvested from bone marrow, propagated in culture to obtain specific cell types, or even subtypes, and then released naïve exosomes will be loaded with a therapeutic agent. Although this approach would require a more invasive procedure, a significant amount as well as storage of well-characterized exosomal carriers will be possible (Muller et al., *Nature Rev. Neurosci.* 7:75 (2006)). Noteworthy, exosomes can be concentrated, lyophilized, and reconstituted in water solutions, as this study demonstrated. This will allow scalability, standardization, and consistency of manufacturing different lots of exosomal drug formulations, when a considerable amount and long-turn storage of exosomes might be required. Finally, a library of various types of exosomal carriers for different drug formulations could be developed in future and stored in stock for emergency situations.

Also of note, further tailoring exosomes can provide biologically-active carriers that may be modified in accordance to the disease and produce cytotoxic (for a cancer treatment) or neuroprotective (for the treatment of neurodegenerative disorders) effects enhancing the therapeutic outcomes. Thus, drug-loaded exosomes may well serve as a next generation drug delivery mechanism that combines nanoparticle size with non-cytotoxic effects, a high drug carrying capacity, and a low immunogenic profile.

Conclusion

This work demonstrates that exosomes are exceptionally potent carriers for therapeutic protein, catalase. We developed an efficient method of the drug loading into exosomes without significantly altering their structure, and showed that exosomes loaded with catalase efficiently accumulate in neurons and microglial cells in the brain and produce a potent neuroprotective effect. These findings indicate that an exosomal based formulations could be a valuable tool in the future for the therapy of neurodegenerative disorders. Of course, the complexity of these interventions is challenging, yet they promise an unparalleled efficacy in the treatment of many life-threatening conditions, including those lacking effective pharmacotherapy. Moreover, a positive outcome would also suggest the more general applicability of this innovative approach for delivering therapeutics to the central nervous system (CNS) and beyond.

Example 2

Development of Exosome-Encapsulated Drugs to Treat Multidrug Resistant (MDR) Cancer In this example, anti-cancer drugs, paclitaxel (PTX) and doxorubicin (DOX), are loaded in exosomes, and the obtained exosome-based drug formulations are used for delivery of these drugs to cancer cells. Superior activity of exosome-based drug formulations against MDR cancer compared to commercial drug formulation has been demonstrated. The exosomes are shown to deliver the incorporated drug to pulmonary metastasis and display superior anti-cancer activity against metastatic cancer in a live organism.

Methods

Reagents:

PTX and DOX was purchased from LC Laboratories (Woburn, Mass.). Lipophilic fluorescent dyes, 1,1'-dioctadecyl-3,3,3',3'-tetramethylindo-carbocyanine perchlorate (DIL), and 2-decanoyl-1-(O-(11-(4,4-difluoro-5,7-dimethyl-4-bora-3a,4a-diaza-s-indacene-3-propionyl-amino)undecyl)-sn-glycero-3-phosphocholine (BODIPY-PC), were purchased from Invitrogen (Carlsbad, Calif.) and Molecular Probes (Eugene, Oreg.), respectively. Rhodamine 123 (R123), 4',6-diamidino-2-phenylindole dihydrochloride (DAPI), and Triton X-100 were obtained from Sigma-Aldrich (St. Louis, Mo.). Cell culture medium and fetal bovine serum (FBS) were purchased from Gibco Life Technologies, (Grand Island, N.Y.). Fluorescent polystyrene nanoparticles (Fluoro-Max G100) were obtained from Thermo Fisher Scientific (Waltham, Mass.). ExoQuick-TC™ Exosome Precipitation Solution was obtained from System Biosciences (Mountain View, Calif.).

Cells:

RAW 264.7 macrophages, Madin-Darby canine kidney $MDCK_{WT}$ and $MDCK_{MDR1}$ cells were purchased from ATCC (Manassas, Va.) and cultured in Dulbecco's modified Eagle's medium (DMEM) high glucose (Gibco) supplemented with 10% FBS, 1% penicillin and streptomycin at 37° C. and 5% $CO_2$. Murine Lewis lung carcinoma cell subline (3LL-M27), a highly metastatic lung clone, was a generous gift from Dr. L. Pelletier (CHUL, Laval University, QC, Canada). Pgp protein levels in sensitive and resistant cancer cells were determined by western blot as previously reported (Batrakova et al., *Br. J. Cancer.* 85:1987 (2001)) using monoclonal antibodies to Pgp, C219 (Dako Corp., Carpinteria, Calif.; at dilution 1:100), and secondary horseradish peroxidase donkey anti-mouse IgG antibodies (Amersham Life Sciences, Cleveland, Ohio; at dilution 1:1500). To correct for loading differences, the Pgp levels were normalized to the constitutively expressed β-actin stained with anti-β-1-chicken integrin (Sigma Chemical Co., at dilution 1:200). Specific bands were visualized using a chemiluminescence kit (Pierce, Rockford, Ill.).

Characterization of Exosomes:

Exosomes were harvested from the conditioned media of RAW 264.7 cells cultured in exosome-depleted media using the ExoQuick-TC™ Kit (System BioSciences; Mountain View, Calif.) and characterized by NTA, DLS, AFM and Western Blot Analysis as described previously (Haney et al., *J. Control. Release* (2015) Epub 2015/04/04). BODIPY-PC was used as a probe to examine the fluidic properties of exosomal membranes as described earlier (Laulagnier et al., *Blood Cells Mol. Dis.* 35:116 (2005) Epub 2005/07/19). Briefly, 30 LL exosomes with a concentration of $4\times10^{11}$ particles/mL were mixed with 20 µL BODIPY-PC (0.03 mg/ml) (Boldytev et al., *Bioorganicheskaia khimiia* 32:87 (2006) Epub 2006/03/10) (31) and supplemented with 70 μL deionized water, the mixture was incubated for 45 min at 37° C. in the dark. Unbound label was removed using a Zeba™ column (Life Technologies).

Drug Loading into Exosomes:

For PTX and DOX loading into exosomes, purified exosomes (~$10^{11}$ exosomes) were first mixed with PTX or DOX in 1 mL PBS. Different methods of drug loading were investigated: incubation at room temperature (RT), electroporation, and sonication. For the incubation method, the admixture was incubated at 37° C. for 1 hour with shaking. For the electroporation method, exosomes were mixed with PTX and added to a chilled 4 mm electroporation cuvette. The mixture was then electroporated using an Eppendorf Eporator (Eppendorf AG, Hamburg, Germany) at 1000 kV for 5 ms, and then incubated at 37° C. for 30 min to allow for recovery of the exosomal membrane. For the sonication method, the PTX-exosome or DOX-exosome mixture was sonicated using a Model 505 Sonic Dismembrator with 0.25" tip with the following settings: 20% amplitude, 6 cycles of 30 s on/off for three minutes with a two minute cooling period between each cycle. After sonication, exoPTX or exoDOX solution were incubated at 37° C. for 60 min to allow for recovery of the exosomal membrane. Excess free drug was separated from exoPTX or exoDOX by size exclusion chromatography using a NAP-10 Sephadex G25 column (GE Healthcare, Buckinghamshire, UK).

The amount of PTX loaded into exosomes was measured by a high performance liquid chromatography (HPLC) method. Briefly, exoPTX ($10^{10}$ exosomes/0.1 mL) in a microcentrifuge tube was placed on a heating block set to 75° C. to evaporate solvent. Then, an equal volume of acetonitrile was added and the mixture was vortexed, sonicated and then centrifuged at 13,000 rpm (Thermo Legend Micro 21) for 10 min. Following centrifugation, the supernatant was taken and filtered through a Corning Regenerated Cellulose 0.2 μm syringe filter and transferred into HPLC autosampler vials. 20 μL aliquots were injected into the HPLC system (Agilent 1200, Agilent Technologies, Palo Alto, Calif.). All analyses were performed using a C18 column (Supelco Nucleosil C18, 250 mm×4.6 mm, 5 μm, 100 Å, Sigma-Aldrich) with a mobile phase of $H_2O$:acetonitrile (45:55, v/v) at a flow rate of 1 mL/min at 30° C. Absorbance was measured at 227 nm to monitor the elution of PTX.

To measure PTX release, freshly prepared exoPTX were placed in a 300K MWCO Float-A-Lyzer G2 device (Spectrum Laboratories, Houston, Tex.). The device was then placed in PBS under sink conditions at RT with stirring. Samples were taken at time points from inside the dialysis tube and were analyzed by HPLC as described above. The amount of PTX released from exoPTX was expressed as a percentage of total PTX and plotted as a function of time.

Accumulation of Exosomes and Exosome-Incorporated PTX in Cancer Cells:

To quantify the amount of exosomes taken up by cells, exosomes were stained with a lipophilic fluorescent dye, DIL as described previously (Haney et al., *J. Control. Release* (2015) Epub 2015/04/04). Then, DIL-labeled exosomes, or fluorescently-labeled liposomes, or polystyrene nanoparticles (NPs, Fluoro-Max G100, Thermo Fisher Scientific), were added in equal numbers (~$10^8$ particles/well) and incubated with 3LL-M27 cells at 37° C. and 5% $CO_2$ for various times. After each time point, the media was removed and cells were washed 3× with PBS and fixed by incubating with Formal-Fixx (Thermo Fisher Scientific), and examined by confocal microscopy or using a Shimadzu RF5000 fluorescent spectrophotometer. In case of exoPTX or Taxol, drugs were added in equimolar amounts to the $MDCK_{WT}$, or $MDCK_{MDR1}$ cells and incubated for 72 h. The cell suspension was then lysed and analyzed for PTX content by HPLC as described above.

In Vitro Cytotoxicity Assay:

The in vitro antitumor efficacy of exoPTX was assessed using a standard MTT (3-(4,5-dimethyl-2-thiazolyl)-2,5-diphenyl-2-H-tetrazoliumbromide) assay with three cancer cell lines, and compared to Taxol as described earlier (Batrakova et al., *J. Control. Release* 143:290 (2010) Epub 2010/01/16). Briefly, cancer cells (MDCKMDR1, MDCKwt, and 3LL-M27) were seeded at 5,000 cells/well in 100 μL of media in 96-well plates overnight. Various concentrations of exosomes isolated from macrophages conditioned media and loaded with PTX by sonication, or empty sonicated exosomes, or Taxol, or PTX were added to cancer cells for 48 hours at 37° C., 5% $CO_2$. Following the incubation, the cells were washed and incubated with MTT reagent as described in Batrakova et al., *Mol. Pharm.* 3:113 (2006) Epub 2006/04/04. The cytotoxic activity of PTX was then evaluated using a standard MTT assay (Ferrari et al., *J. Immunol. Meth.* 131:165 (1990)). The absorbance at 570 nm was measured using a Shimadzu RF5000 fluorescent spectrophotometer. The survival values were determined in relation to control cells cultured in drug-free media. All experiments were repeated at least three times. SEM values were less than 10%.

Production of a Lentiviral Vector (LV) and Transduction of Lewis Lung Carcinoma (LLC) Cells:

Lentiviral vector encoding a fusion between the optical reporter mCherry (GBM8FlmC, red) and firefly luciferase (FLuc) were created by PCR amplification of the cDNA sequences for mCherry and FLuc from pEmCherry (Clontech) and pcDNA-Luciferase (Addgene) with restriction enzyme sequences that were engineered into the primers. To create the final constructs, mCherry was digested with BamHI/EcoV and FLuc was digested with EcoV/XhoI. The digested fragments were ligated into the BamHI/XhoI digested pTK402 LV transfer vector (a kind gift from Dr. Tal Kafri, The University of North Carolina at Chapel Hill). LV-mCherryFLuc viral vectors were packaged in 3LL-M27 cells by transient transfection using the psPAX2 and pMD2.G (Addgene) packaging plasmids and following previously described protocols (Sena-Esteves et al., *J. Virol. Meth.* 122:131 (2004) Epub 2004/11/16).

To utilize bioluminescence and fluorescence imaging, 3LL-M27 cells were transduced with lentiviral vectors encoding an mCherry and *Renilla* luciferase (mC-RL) fusion protein. The viral construct also encoded for a puromycin resistance gene downstream of mCherry which was introduced to enable for selection of nearly 100% positively transduced cells. A robust expression of both the fluorescent and bioluminescent markers was observed, and no difference in proliferation was detected between modified and unmodified cells. These cells (8FlmC-FLuc-3LL-M27) were used for biodistribution and therapeutic efficacy studies.

Biodistribution of Exosomes in Mice with Pulmonary Metastases:

The experiments were performed with female C57BL/6 mice (Charles River Laboratories, Durham, N.C.) eight weeks of age in strict accordance with the recommendations in the *Guide for the Care and Use of Laboratory Animals* of the National Institutes of Health. The animals were kept five per cage with an air filter cover under light- (12-hours light/dark cycle) and in a temperature-controlled (22±1° C.)

environment. All manipulations with the animals were performed under a sterilized laminar hood. Food and water were given ad libitum.

C57BU6 mice (n=4) were injected intra tail vein (i.v.) with 8FlmC-FLuc-3LL-M27 cells ($5\times10^6$ cells/mouse in 100 µL saline) and tumor lung metastases were allowed to establish for 10-12 days. Twelve days following cancer cells i.v. injection, DID-labeled exosomes isolated from autologous macrophages were administered intranasally (i.n., $10^7$ particles/10 µl×2) to mice with lung metastases. Four hours later, mice were sacrificed, perfused, lungs were extracted and sectioned on a microtome at a thickness of 20 µm; nuclei were stained with DAPI (300 mM, 5 min). The images of lung sections were examined by a confocal fluorescence microscopic system ACAS-570 and corresponding filter set, and processed using ImageJ software.

In another experiment, mice with established GBM8FlmC-metastases were injected i.n. with non-labeled exosomes loaded with DOX by sonication as described above ($10^7$ particles/10 µL×2). Four hours later mice were sacrificed, perfused; lungs were extracted, sectioned, and co-localization of DOX with pulmonary metastases was visualized by confocal microscopy.

Therapeutic Efficacy of exoPTX Against Pulmonary Metastases:

The antineoplastic effects of exoPTX were evaluated in a mouse model of pulmonary metastases. For this purpose, C57BL/6 mice were i.v. injected with 8FlmC-FLuc-3LL-M27 cancer cells ($5\times10^6$ cells/100 L/J mouse). Forty eight hours later, mice were treated i.n. with exoPTX ($10^7$ particles/10 µl×2), or Taxol (50 mg/kg/mouse), or saline as a control (n=7) every other day with a total of seven treatments. Tumor progression was monitored by luminescence using the IVIS system as described in Brynskikh et al. (*Nanomedicine* (*Lond*). 5:379 (2010) Epub 2010/04/17). The animals were imaged at various time points (1-22 days) post-treatment as described (Brynskikh et al., *Nanomedicine* (*Lond*). 5:379 (2010) Epub 2010/04/17). The chemoluminescent signal was quantified by Living Image® 2.50 software. To assess the amount of cancer metastases at day 22, mice were sacrificed, perfused, and lung slides obtained on microtome (Thermo Scientific) were examined by confocal microscopy.

Statistical Analysis:

For the all experiments, data are presented as the mean±S.E.M. Tests for significant differences between the groups were performed using a t-test or one-way ANOVA with multiple comparisons (Fisher's pairwise comparisons) using GraphPad Prism 5.0 (GraphPad software, San Diego, Calif.). A minimum p value of 0.05 was chosen as the significance level.

Results

Figure 12C:
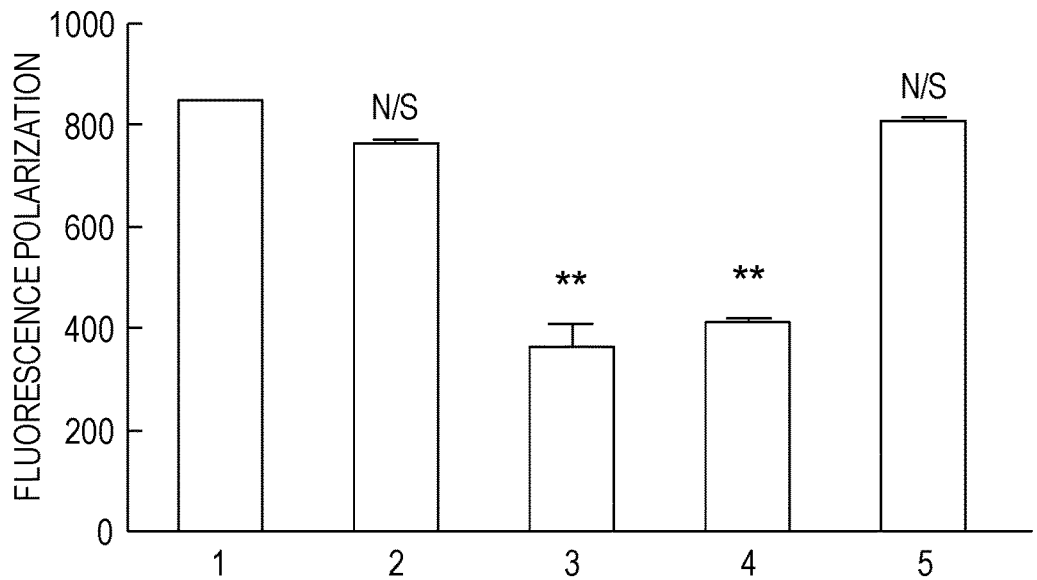
Figure 12D:
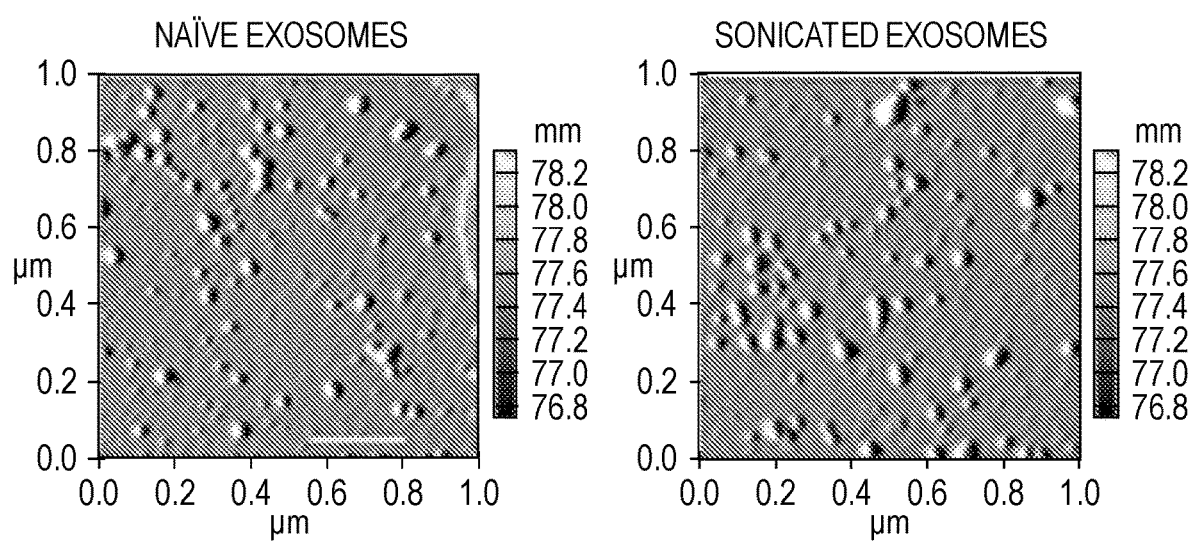

Manufacture and Characterization of Exosomal Formulations of PTX (exoPTX):

Exosomes collected from the conditioned media of RAW 264.7 macrophages were characterized by size, charge, protein content, and morphology (FIGS. 12A, 12B, and 12D). Exosomes showed elevated expression of exosome-associated proteins (Alix, TSG101, and Flotillin) as compared to cell lysate, which displayed greater levels of 3-actin (FIG. 12B). Naïve empty exosomes had a narrow size distribution, with an average particle diameter of 110.4±4.2 nm and 70.8±2.8 nm as revealed by NTA and DLS, respectively (FIG. 12A); and a round morphology as shown by AFM imaging (FIG. 12D).

Figure 13:
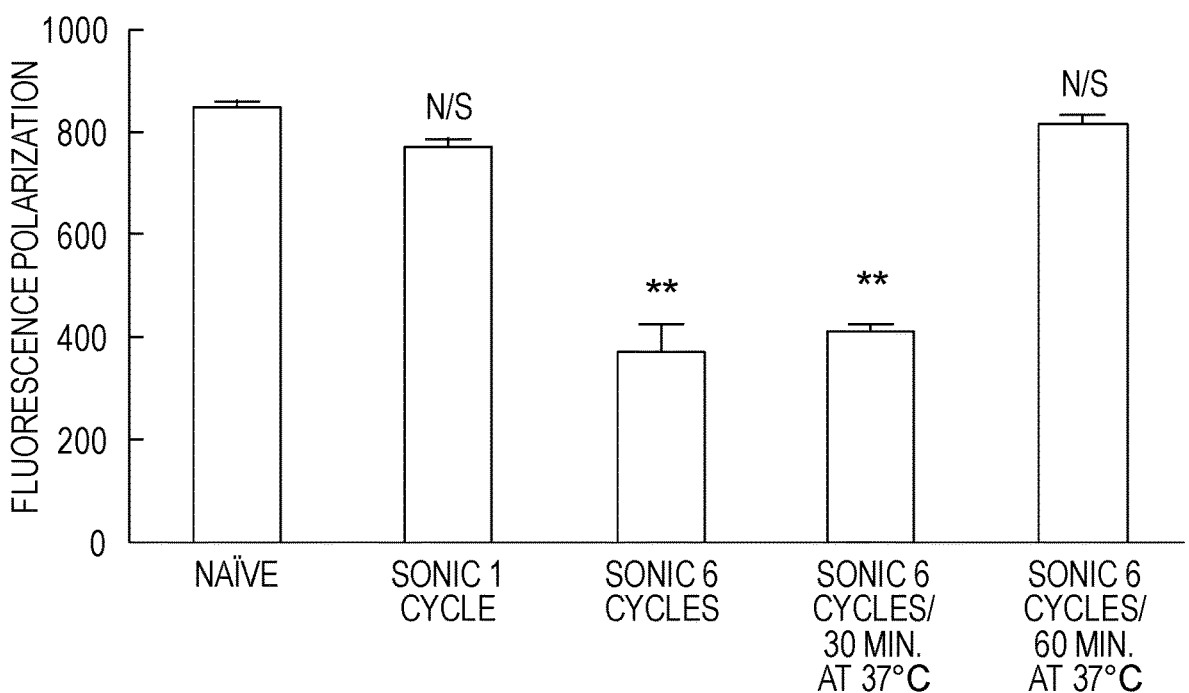
FIG. 13 shows the effect of sonication on fluidity of exosomal membranes. Exosomes isolated from RAW 264.7 macrophages concomitant media were labeled with BODIPY-PC fluorescent dye as described in Methods section, and subjected to one or 6 cycles of ultrasound treatment. The fluorescence polarization was measured right after the sonication, or following 30 min or 1 hour incubation period at 37° C. Values are means±SEM (n=4). Symbols indicate the relative level of significance compared with naive exosomes.

PTX was incorporated into exosomes using three methods: a) incubation at room temperature (RT), b) electroporation, and c) mild sonication. The obtained exoPTX formulations were purified from the non-incorporated drug by size-exclusion chromatography and analyzed by HPLC to determine the loading capacity (LC). The typical HPLC profiles for PTX extracted from exosomes (B) and PTX standards (A) are shown on FIG. 13. The amount of PTX loaded into exosomes increased as follows: incubation at RT<electroporation<<sonication (FIG. 12A). Interestingly, DLS studies revealed that the size of exoPTX nanoformulations increased similarly, with the smaller being exoPTX nanoparticles obtained by electroporation or incubation at RT, and the larger being exosomes loaded with PTX by sonication (FIG. 12A). These data were confirmed by NTA analysis. Exosomes sonicated in the absence of PTX were even larger than those sonicated with PTX (FIG. 12A). We hypothesized this may be due to the stabilization of exosomal membranes by the incorporated drug. We suggested that a reorganization of exosomal membranes under sonication may enable PTX diffusion across relatively tight lipid bilayers. Indeed, fluorescence polarization measurements revealed significant decreases (more than two times) in membrane microviscosity upon sonication (FIG. 12C). To address a concern about possible loosing of exosome-bound proteins, we examined the levels of Alix, TSG101, and Flotillin in exosomes before and after sonication using western blot technique (FIG. 12B). The data indicate that the mild sonication utilized for PTX loading with six cycles, and intermediate time out for cooling down and restoration, did not significantly affect the protein content of exosomes. It is known that the anionic phospholipid phosphatidylserine is abundant on cell membranes and contributes to the surface charge of individual cellular membranes. To this end, all loading procedures did not significantly alter the zeta potential of the nanocarriers (FIG. 12A), suggesting that there were also no major alterations of the lipid content of exosomal membranes. Finally, a complete restoration of membrane microviscosity was observed after a one hour incubation at 37° C. following sonication procedure (FIG. 12C). Retention of shape and round morphology of exosomes (FIG. 12D) confirmed this hypothesis.

Figure 12E:
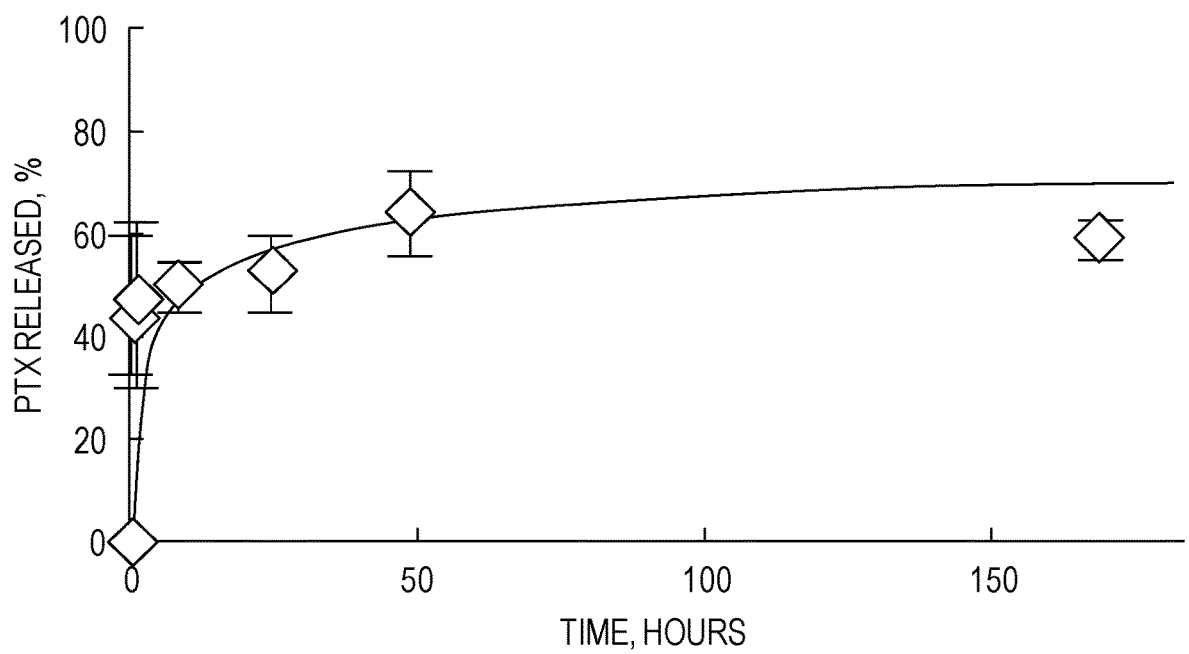
Figure 14:
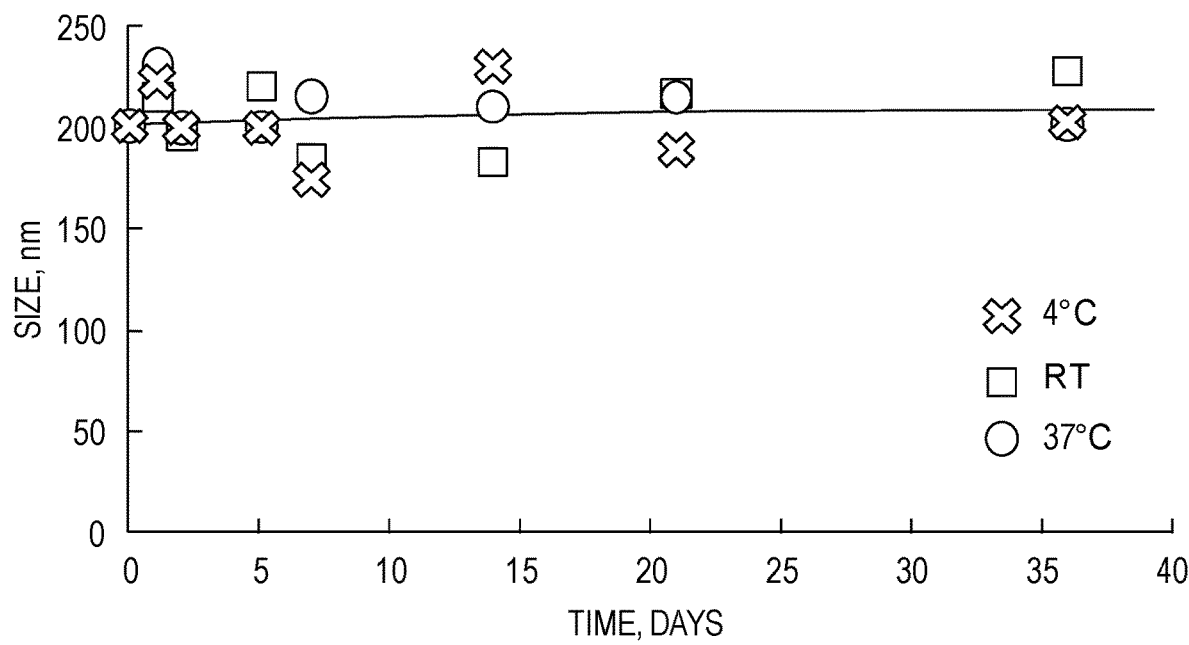
FIG. 14 shows the stability of exoPTX formulations. Exosomes released from Raw 264.7 macrophages were loaded with PTX as described in the methods section, and the size of nanoparticles was measured at 4° C., RT, and 37° C. over the course of a month. No significant changes in size of the exoPTX were registered at all conditions.

Next, exoPTX showed burst release within the first three hours, and then displayed a sustained release profile thereafter (FIG. 12E). The high stability of exosomes in an aqueous solution was demonstrated at three temperatures: 4° C., RT, and 37° C. over a period of one month (FIG. 14). Overall, the mild sonication procedure provided the highest amount of drug loading; the obtained LC of 28.29±1.38% (FIG. 12A) was much higher than the LC of commercially available formulations of PTX, Taxol (~1% LC), or Abraxane (~10% LC). Therefore, exoPTX obtained by sonication was selected for further experiments.

Figure 15A:
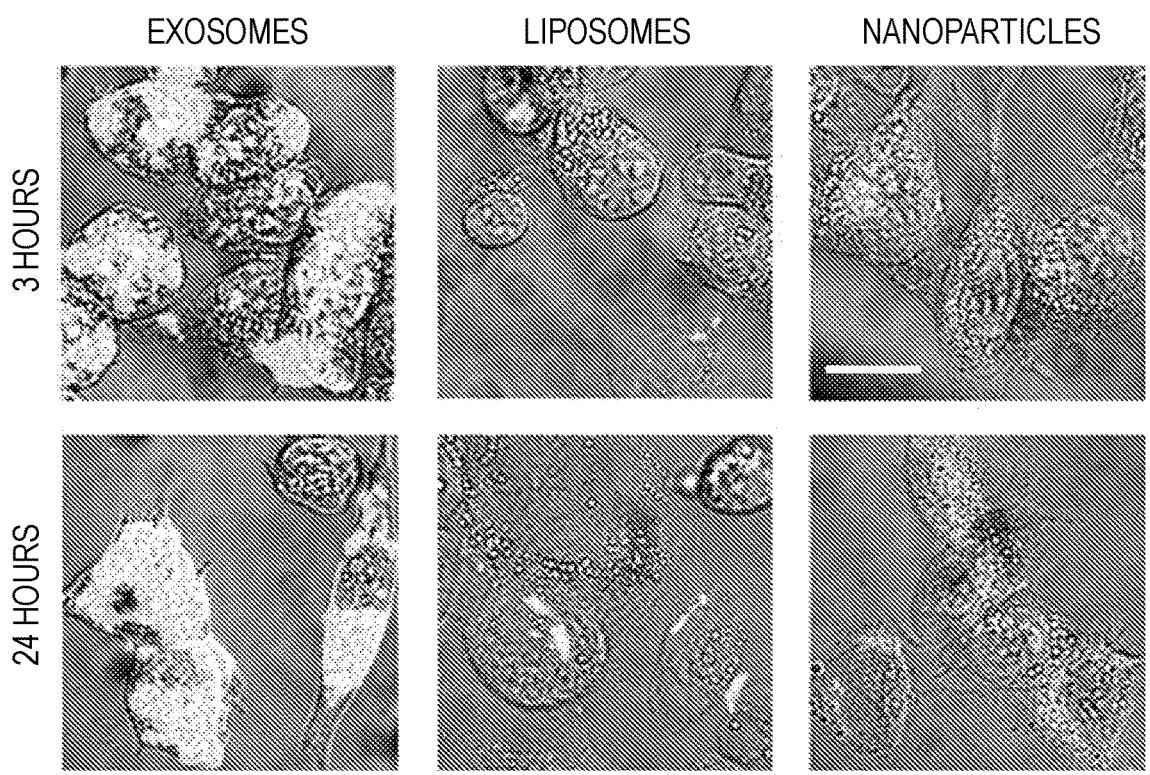
FIGS. 15A-15B show a profound accumulation of exosomes in 3LL-M27 cells in vitro. 3LL-M27 cells were incubated with fluorescently-labeled (red) exosomes, or liposomes, or PS NPs for various times and the amount of accumulated nanocarriers was examined by confocal microscopy (FIG. 15A), and spectrophotometry (FIG. 15B). Bar: 10 μm.
Figure 15B:
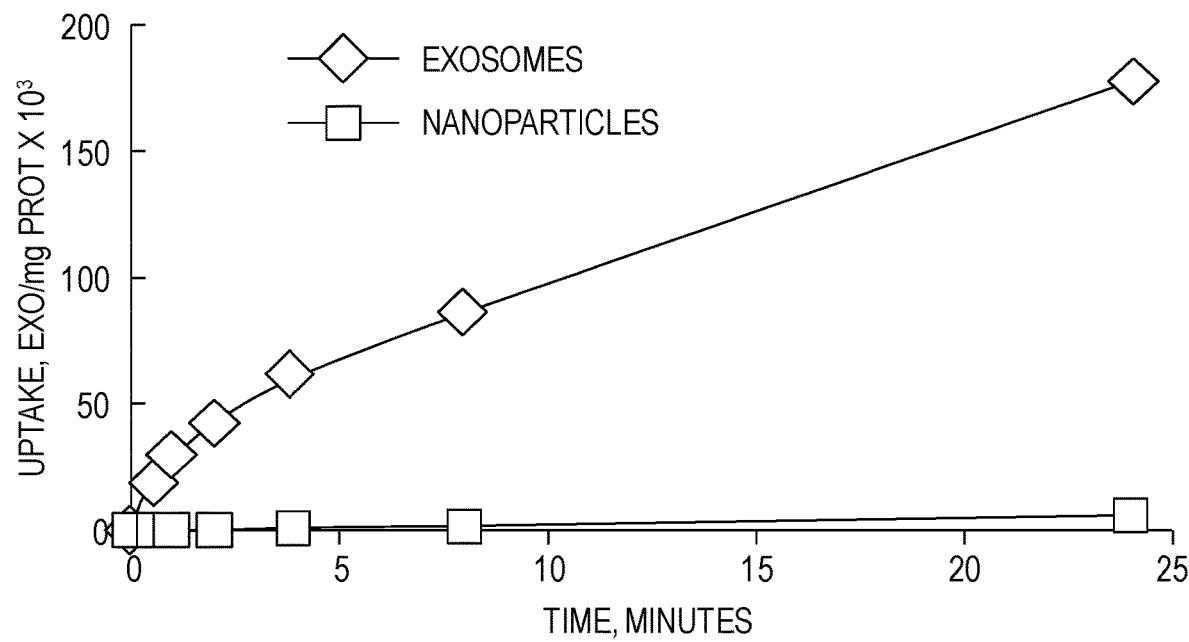

Accumulation and Therapeutic Efficacy of exoPTX in Target Cancer Cells In Vitro:

The ability to deliver the drug payload into target cells was studied with fluorescently-labeled exosomes in 3LL-M27 cells, and compared to the commonly used nanocarriers, liposomes and polystyrene nanoparticles (NPs) (De Jong et al., *Int. J. Nanomedicine*. 3:133 (2008) Epub 2008/08/09) with the same size and level of fluorescence (FIGS. 15A-15B). Liposomes were prepared by a reverse phase evaporation method as described previously (Haney et al., *J. Control. Release* (2015) Epub 2015/04/04). Confocal images revealed a profound accumulation of exosomes in cancer cells and limited uptake of liposomes and NPs (FIG. 15A). This result was further confirmed and quantitated in accumulation studies (FIG. 15B). Exosomes were taken up about 30 times better than the synthetic nanoparticles, suggesting that PTX loaded into exosomes can be efficiently delivered to cancer cells in therapeutically sufficient quantities. These results clearly show the advantages of exosome-based drug delivery systems over common synthetic nanocarriers and confirmed our previous report regarding the profound accumulation of exosomes in neuronal PC12 cells (Haney et al., *J. Control. Release* (2015) Epub 2015/04/04).

Figure 16:
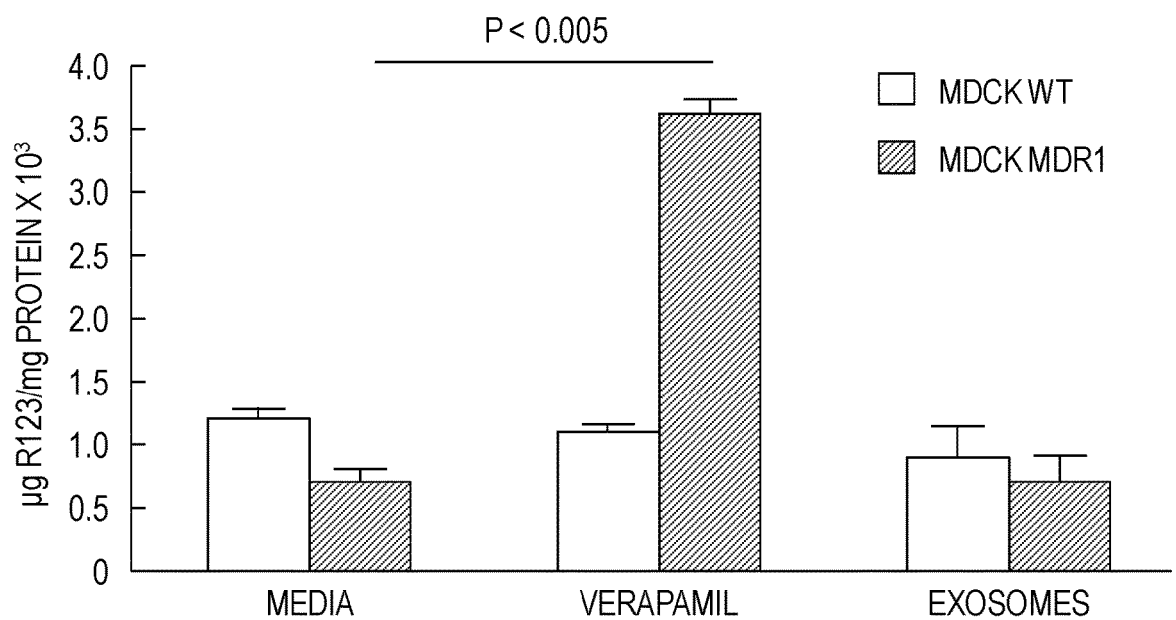
FIG. 16 shows exosomes do not inhibit Pgp-mediated drug efflux in resistant cancer cells. Resistant $MDCK_{MDR1}$ cells and their sensitive counterparts $MDCK_{WT}$ were pre-treated with verapamil, a well-known Pgp inhibitor, or empty exosomes, or media as a control. Then, cells were supplemented with R123 solutions for two hours, washed, and accumulation of a Pgp substrate, R123, was examined by fluorescence. Verapamil significantly increased R123 accumulation in resistant cancer cells and did not alter the R123 uptake in sensitive $MDCK_{WT}$ cells. Contrary to verapamil, exosomes pretreatment did not affect accumulation levels of R123 in resistant $MDCK_{MDR1}$ cells, indicating that exosomes themselves did not inhibit Pgp efflux mechanism. Values are means±SEM (n=6). Symbols indicate the relative level of significance compared with R123 uptake in verapamil or exosome-free media.

The anticancer effects of exoPTX were evaluated in a resistant MDR cells expressing the drug efflux transporter, Pgp (MDCK$_{MDR1}$), and their sensitive counterparts (MDCK$_{WT}$). The loading of PTX into exosomes significantly increased drug cytotoxicity as compared to PTX alone, or Taxol in both sensitive MDCK$_{WT}$ and resistant MDCK$_{MDR1}$ cancer cells (Table 2). These results are consistent with earlier reports regarding increased cytotoxicity of another anticancer agent, DOX in cancer cells (Tian et al., *Biomaterials* 35:2383 (2014) Epub 2013/12/19). The most intriguing observation was made, when the effects of various PTX formulations were compared in sensitive and resistant cancer cells. For this purpose, the increased cytotoxicity of the drug was expressed in the form of a "Resistance Reversion Index" (RRI), i.e. ratio of IC$_{50}$ of PTX alone, and in nanoformulation (e.g. IC$_{50,PTX}$/IC$_{50,exoPTX}$, or IC$_{50,PTX}$/IC$_{50,taxol}$). Both PTX formulations caused significant sensitization of MDR cells with respect to PTX (Table 2). In particular, RRI for exoPTX in MDCK$_{MDR1}$ and MDCK$_{WT}$ was 53.33 and 18.38, respectively. In contrast, RRI for Taxol in both resistant and sensitive cancer cells was c.a. 6 (Table 2). Noteworthy, empty sonicated exosomes did not show any cytotoxicity in all studied cell lines (FIG. 16). Thus, the increase in PTX cytotoxicity afforded by exoPTX was greater in Pgp-overexpressing cells than their sensitive counterparts (Table 2).

TABLE 2

| Drug | Cell line | IC50 (ng/mL) | RRI |
| --- | --- | --- | --- |
| exoPTX | 3LL-M27 | 13.57 ± 1.33 | 9.32 |
|  | MDCK wt | 23.33 ± 3.77 | 18.38 |
|  | MDCK MDR1 | 187.5 ± 38.65 | >53.33 |
| Taxol | 3LL-M27 | 23.16 ± 1.88 | 5.46 |
|  | MDCK wt | 69.54 ± 11.5 | 6.17 |
|  | MDCK MDR1 | 1708.67 ± 299.93 | >5.85 |
| PTX | 3LL-M27 | 126.41 ± 31.31 | 1 |
|  | MDCK wt | 428.77 ± 63.37 | 1 |
|  | MDCK MDR1 | >10,000 | 1 |

Figure 17A:
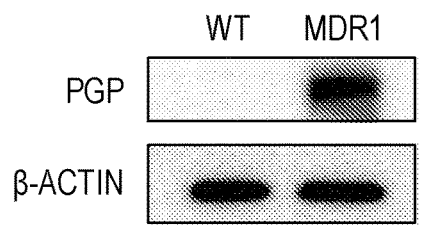
FIGS. 17A-17B show the effect of Pgp inhibition on DOX accumulation in MDR and sensitive cancer cells. The accumulation of free DOX or exoDOX in $MDCK_{MDR1}$ and $MDCK_{WT}$ cells was studied in cell lysates via western blot (FIG. 17A). The DOX incorporation into exosomes significantly increased accumulation in sensitive and resistant cells, while no effect of verapamil on exoDOX accumulation was found in both cell lines (FIG. 17B).
Figure 17B:
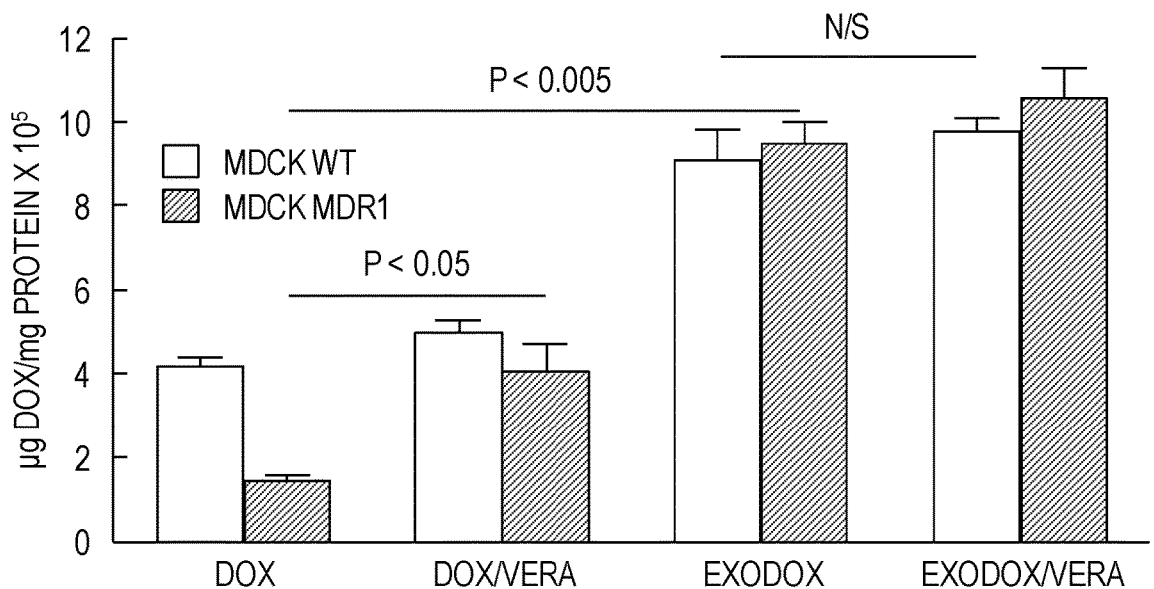

Mechanistic Studies of exoPTX Cytotoxic Effects:

We hypothesized that exoPTX may alter drug intracellular trafficking and bypass the drug efflux system more efficiently than Taxol (in particular, exoPTX may facilitate endosomal release of PTX from exosomes in cancer cells). To prove this hypothesis, we examined the accumulation levels of a fluorescent probe and Pgp substrate, DOX, incorporated into exosomes (exoDOX) in MDCK$_{MDR1}$ and MDCK$_{WT}$ cells. First, elevated Pgp expression levels in MDCK$_{MDR1}$ cells, and low, if any, Pgp levels in MDCK$_{WT}$ cells were confirmed by western blot (FIG. 17A). Next, the uptake of free DOX and exosome-incorporated drug, exoDOX, was compared in the presence/absence of a Pgp inhibitor, verapamil. As expected, the incorporation of Dox into exosomes significantly increased drug accumulation levels in both sensitive and resistant cancer cells (FIG. 17B). Inhibition of Pgp-mediated drug efflux by verapamil increased accumulation of free DOX in resistant MDCKM$_{DR}$I cells, but did not alter drug accumulation in their sensitive counterparts. Remarkably, verapamil treatment did not affect exoDOX accumulation in resistant MDCK$_{MDR1}$ cells, indicating that drug incorporation into exosomes allowed it to bypass this resistance mechanism (FIG. 17B).

Figure 18:
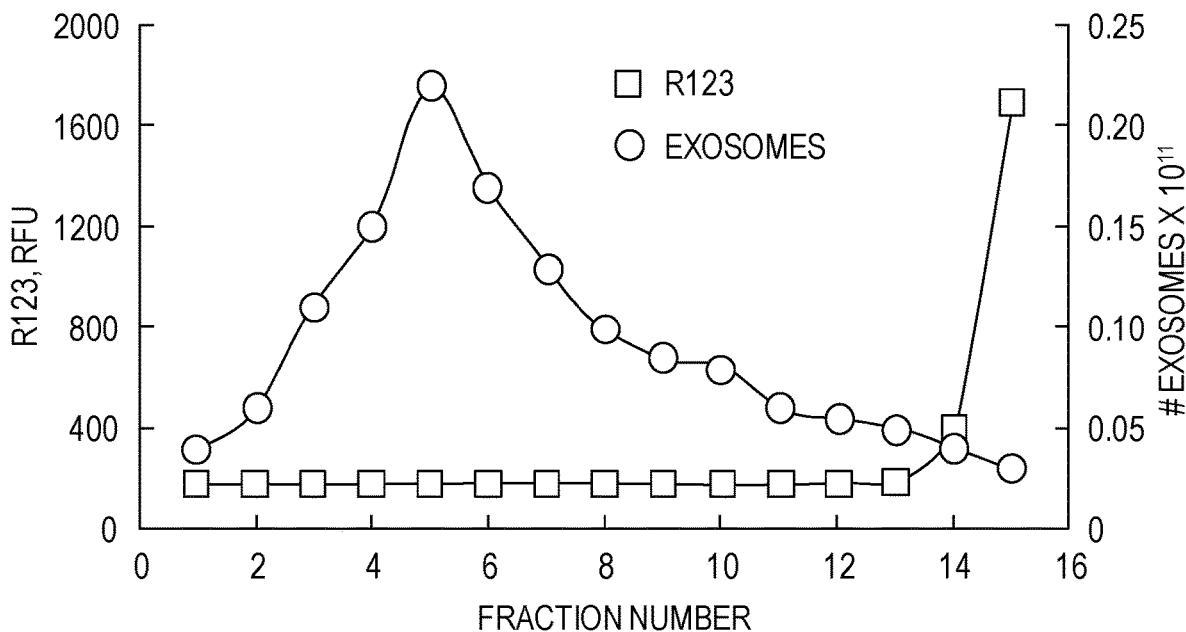
FIG. 18 shows R123 does not incorporate into exosomes upon incubation at RT. Exosomes ($10^{11}$ particles/ml) were supplemented with R123 solution and incubated at RT as described in the methods section. Non-incorporated R123 was separated on from exosomes by size exclusion chromatography using a NAP-10 Sephadex® G25 column. Fractions were collected from a column and analyzed by fluorescence (for R123) and NTA (for exosomes). The chromatography profile showed two separated peaks; the free R123 was expelled from the column at a much later time than the exosomes.

We demonstrated earlier that the incorporation of Pgp substrates, such as R123 or DOX, into block-copolymer-based nanocarriers, i.e. Pluronic® micelles, increased drug accumulation in resistant cancer cells due to the inhibition of Pgp efflux transporter by Pluronic® macromolecules incorporated into the membranes of resistant cancer cells (Batrakova et al., *Br J. Cancer* 85:1987 (2001); Batrakova et al., *Pharm. Res.* 16:1373 (1999); Batrakova et al., *J. Pharmacol. Exp. Ther.* 304:845 (2003); Batrakova et al., *Pharm. Res.* 20:1581 (2003)). To exclude the possibility that exosomes may inhibit Pgp-mediated efflux by their fusion with cellular membranes, accumulation of R123 in both resistant and sensitive MDCK cancer cells was assessed. R123 does not incorporate into exosomes upon incubation at RT, as was confirmed in our preliminary studies (FIG. 18). For this purpose, MDCK$_{WT}$ and MDCK$_{MDR1}$ cell monolayers were pretreated with a Pgp inhibitor, verapamil (positive control), or empty exosomes, or media (negative control), and then were treated with R123 solutions for two hours (FIGS. 19A-19B). R123 accumulation levels in resistant MDCK$_{MDR1}$ cells were increased almost five times in verapamil pre-treated cells. In contrast, treatment with empty exosomes did not affect R123 accumulation in MDCK$_{MDR1}$ cells (FIGS. 19A-19B). As expected, neither treatment with verapamil, nor with empty exosomes, altered R123 accumulation levels in sensitive MDCK$_{WT}$ cells. This indicates that exosomes themselves do not appear to have any inhibitory effect on Pgp-mediated efflux; they allow incorporated drugs to bypass the Pgp efflux protein perhaps, through endocytosis-mediated transport and/or fusion with plasma membranes.

Figure 21A:
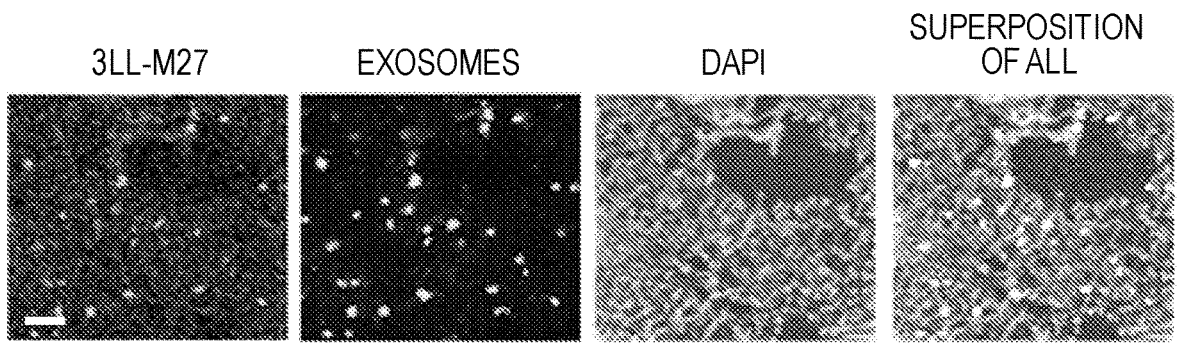
FIGS. 21A-21B show co-localization of airway-delivered exosomes with pulmonary metastases. Exosomes were isolated from macrophages conditioned media, and labeled with fluorescent dye, DID. C57BL/6 mice were i.v. injected with 3LL-M27 cells transduced with lentiviral vectors encoding the optical reporter mCherry (8FlmC) fluorescent protein. 21 days later, the mice with established pulmonary metastases were i.n. injected with DID-labeled exosomes. 4 hours later, mice were euthanized, perfused, lungs were sectioned, and stained with DAPI. The confocal images revealed near complete co-localization of exosomes with metastases. Images were obtained with ×10 (FIG. 21A), and ×60 (FIG. 21B) magnification. Bar: 50 µm.
Figure 21B:
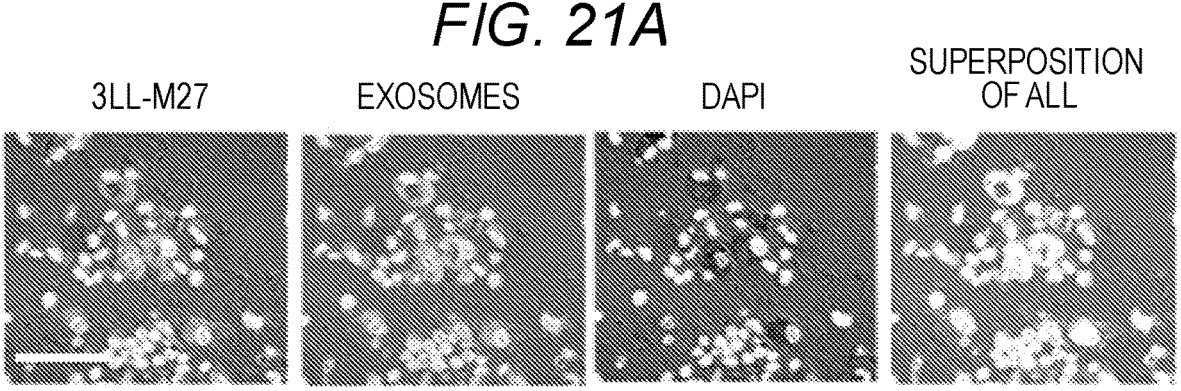

Co-Localization of Airway-Delivered Exosomes with Pulmonary Metastases in LLC Mouse Model:

To establish an in vivo model of pulmonary metastases, C57BL/6 mice were injected intra-tail vein (5×10$^6$ cells/100 μL) with 3LL-M27 cells. Important, this model is particularly relevant to the present investigation, as it was demonstrated that 3LL-M27 tumor cells have high expression levels of the MDR1 gene and Pgp expression in vivo (Batrakova et al., *J. Control. Release.* 143:290 (2010) Epub 2010/01/16). Twenty days later, mice were sacrificed, perfused, and lungs were isolated, sectioned, and stained with Hematoxylin and Eosin (H&E). Multiple metastases were detected in whole lungs (FIGS. 20A-20C). Histological evaluations revealed that the structure of alveoli in tumor-bearing lungs was disrupted by tumor cells (FIG. 20B). Next, mice were injected with 8FlmC-FLuc-3LL-M27 (FIGS. 21A-21B) intra-tail vein as described in Methods section. 22 days later, autologous exosomes stained with a fluorescent dye, DiD (green), were i.n. administered to mice with pulmonary metastases. Four hours later, mice were sacrificed, perfused; lungs were sectioned on microtome and examined by confocal microscopy. Nuclei were stained with DAPI (FIGS. 21A-21B). Confocal images revealed 97.9±2.0% of exosomes were co-localized with lung metastases (FIGS. 21A-21B), indicating efficient targeting of exoPTX in vivo. A similar experiment was performed with exoDOX formulation in order to visualize drug delivery to pulmonary metastases. Non-labeled exosomes loaded with DOX were i.n. administered to mice with established 8FlmC-FLuc-3LL-M27 metastases. Confocal images revealed a substantial amount of DOX in the lungs co-localized with cancer cells (data not shown). These results indicate that airway-administered exosomes reached pulmonary metastases and delivered their drug payload to target cancer cells.

Figure 22A:
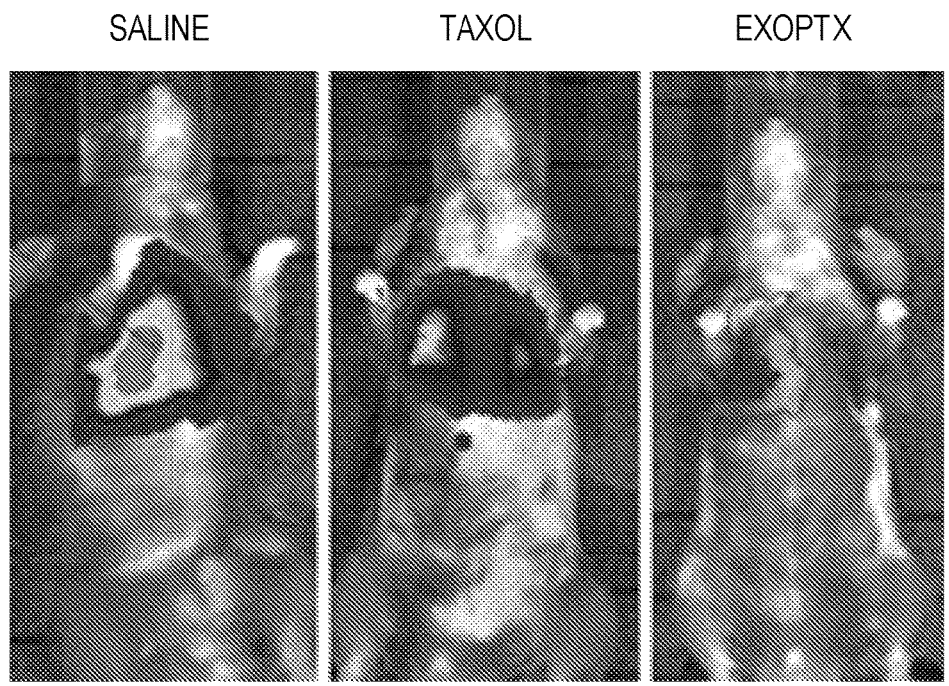
FIGS. 22A-22C show the inhibition of metastases growth in mouse lungs upon exoPTX treatment. C57Bl/6 mice were i.v. injected with 8FlmC-FLuc-3LL-M27 cells to establish pulmonary metastases. 48 hour later mice were treated with exoPTX, or Taxol, or saline, or empty sonicated exosomes as a control, and the treatment was repeated every other day, totally seven times. Representative IVIS images were taken at day 21 (FIG. 22A). Statistical significance of metastases levels from IVIS images in lungs of treated animals compared to control mice is shown by asterisk (*$p<0.05$; **$p<0.005$) (FIG. 22B). At the endpoint, 21 days later, mice were sacrificed, perfused, and lung slides were examined by confocal microscopy (FIG. 22C). The bar: 10 µm.
Figure 22B:
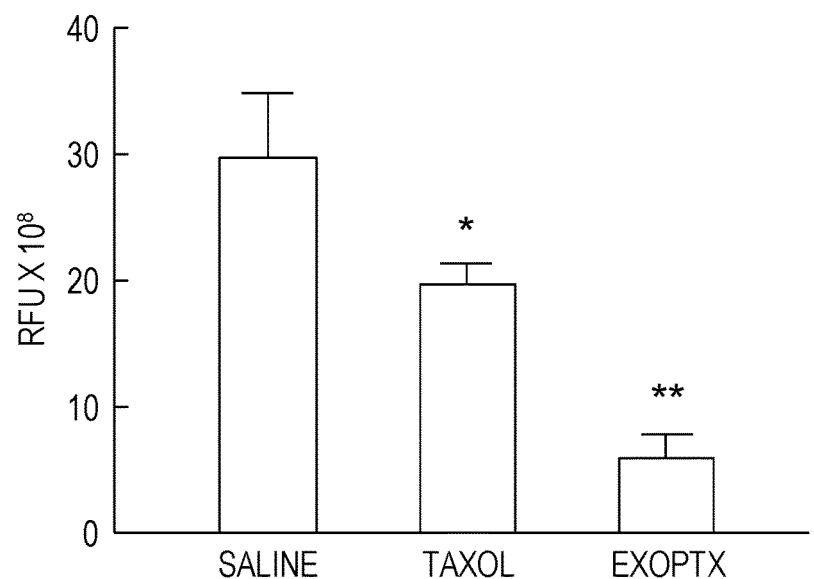
Figure 22C:
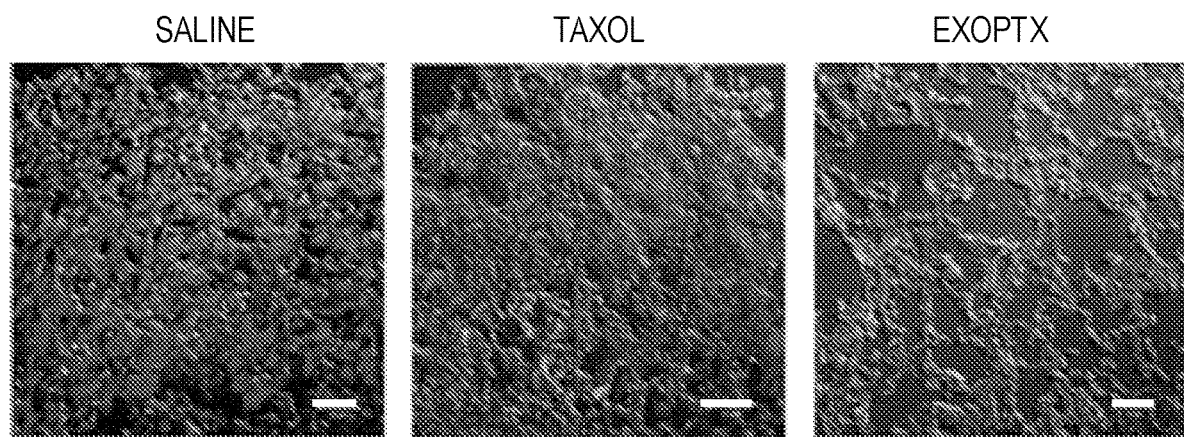

PTX-Loaded Exosomes Produce Strong Antineoplastic Effect in Mice with Lung Metastases:

To provide insight into the potential of exosome-based therapeutic delivery, the antineoplastic effects of exoPTX were evaluated in an LLC mouse model. For this purpose, C57BL/6 mice were i.v. injected with 8FlmC-FLuc-3LL-M27 cells as described above. 48 hours later, mice were i.n. administered exoPTX ($10^7$ particles/10 μl×2), or Taxol, or saline as a control every other day totally, seven times. The progression of pulmonary metastases in treated mice was monitored using IVIS by observing the luminescence of transduced cancer cells in living animals (FIG. 22A). Representative images of dorsal planes of the injected animals at day 22 are shown on (FIG. 22A). A significant ($p<0.05$) inhibition of metastases growth by exoPTX treatment was demonstrated (FIG. 22C). Taxol treatment was shown to inhibit metastases growth as compared to non-treated controls (saline), although to a lesser extent than exoPTX treatment. At the end point of the experiment (day 22), the lung sections were visualized using confocal microscopy (FIG. 22B). A marked number of fluorescent transduced cancer cells were detected in the lungs of animals treated with Taxol (FIG. 22C), while only a few cancer cells were observed in the lungs of exoPTX treated animals. Noteworthy, sonicated empty exosomes showed no significant inhibition on pulmonary metastases growth (FIG. 22A, 22B). This confirms the superior antineoplastic efficacy of exoPTX as compared to Taxol.

Discussion

Exosomal carriers can provide advantages of both cell-based drug delivery and nanotechnology for efficient drug transport capable of overcoming various biological barriers. One difficulty is the efficient loading of exosomes with a therapeutic agent without significant changes in the structure and content of exosomal membranes. In the present study, we utilized various methods for PTX incorporation into exosomes: incubation at RT, electroporation, and mild sonication. The mild sonication of exosomes in the presence of PTX provided the greatest loading capacity. PTX, a highly hydrophobic compound is likely to be incorporated into the hydrophobic inner region of the lipid bilayers of exosomes. We hypothesized that the high rigidity of exosomal membranes may be decreased upon sonication and would thus allow for PTX incorporation into lipid bilayers resulting in a high loading capacity. This hypothesis was confirmed by significant decreases in microviscosity of exosomal membranes upon sonication. Nevertheless, we do not exclude a possibility that a considerable amount of PTX may also be adhered to the surface of exosomes that may account for the burst release from exoPTX observed in the first 3-4 hours. It is worth noting that ~30% of loaded drug was still associated with exosomes after one week in an aqueous solution. Importantly, drug located in the inner bilayer of exosomes may also be available for use: as the exosomal membrane fuses with the cell or endosomal membrane, its intraluminal cargo may be released into the cytosol of a target cell. Next, the aggregation stability of exoPTX formulations is imperative for their use in clinic. We report here that the obtained exoPTX formulation was stable at various conditions for over a month. In addition, exosomes may be lyophilized and reconstituted, while retaining their morphology and other characteristics (Haney et al., *J. Control. Release* (2015) Epub 2015/04/04). This provides a clinical link for exosome-based drug formulations, suggesting that multiple lots of exoPTX may be prepared and stored prior to treatment.

Exosomes possess an extraordinary ability to interact with and accumulate in target cancer cells. The obtained data indicates exosomes are taken up in considerably greater numbers than liposomes or polystyrene NPs. In addition, the incorporation of PTX into exosomes may not only increase its solubility, but also allow for overcoming of Pgp-mediated drug efflux. We demonstrated here that incorporation of a Pgp substrate, DOX, into exosomes significantly increased drug accumulation in MDR cells as compared to free DOX, or even to DOX in the presence of a Pgp-inhibitor, verapamil. Next, the increase in cytotoxicity afforded by the exosomal formulation of PTX was considerably greater in resistant cells (RRI>53.33) than sensitive cells (RRI=18.35), while Taxol showed almost no difference in resistant (RRI>5.85) vs. sensitive cancer cells (RRI=6.17). This effect may be attributed to the difference in route of internalization of exoPTX, as compared to Taxol. Exosomes and micelles, such as those found in Taxol, are taken up by endocytosis, but exosomes have superior uptake due to the presence of adhesion proteins, tetraspanins, integrins, immunoglobulins, proteoglycans, and lectins (Mulcahy et al., *J. Extracellular Vesicles* 3 (2014) Epub 2014/08/22) (42), which are not found on artificial nanoparticles. Furthermore, exosomes consist of cellular membranes that may fuse with the plasma and/or endocytic membranes and deliver their cargo, bypassing Pgp-mediated efflux. Noteworthy, exosomes themselves did not inhibit Pgp, as the pre-treatment with empty exosomes did not increase accumulation of the Pgp substrate, R123, in resistant cancer cells.

Interestingly, it was suggested that the MDR efflux transporters are likely contribute to the production of drug-loaded exosomes during their biogenesis in resistant cancer cells (Safaei et al., *Mol. Cancer Ther* 4:1595 (2005) Epub 2005/10/18). In addition, Pgp may be also involved in the increased drug sequestration in lysosomes and MVB (Yamagishi et al., J. Biol. Chem. 288:31761 (2013) Epub 2013/09/26). Thus, Pgp associated with the endosomal membrane excretes the internalized drug into the endosomal lumen, where newly formed cancer exosomes are literally incubated with the drug and become "drug-loaded" before being released from the cell. The same effect was reported with PTX in Pgp-overexpressing bone marrow mesenchymal stromal cells (SR4987) (Pascucci et al., *J. Control. Release* 192:262 (2014) Epub 2014/08/02). We hypothesized that exoPTX accumulated in the MDR cancer cells may bypass not only efflux by Pgp transporter located on plasma membrane, but also avoid accumulation in lysosomes and MVB of cancer cells, and therefore, reduce drug elimination and increase its therapeutic efficacy in resistant tumors. The investigations regarding this hypothesis are underway in our laboratory.

Finally, the therapeutic efficacy of exoPTX formulation against pulmonary metastases was demonstrated in an LLC mouse model. Intriguingly, airway-delivered exosomes showed near complete co-localization with cancer metastases in this model. The results were confirmed by the significant co-localization of DOX incorporated into exosomes with cancer cells. We speculated that macrophage-released exosomes are likely to have specific proteins on their surface, which might allow for their preferential accumulation in cancer cells. Furthermore, it is known that exosome-mediated cell-to-cell communication is key in the battle between cancer and the immune system (Finn, *Ann. Oncol.* 23 Suppl 8:viii6-9 (2012) Epub 2012/08/29). Thus, Parolini et al. (*J. Biol. Chem.* 284:34211 (2009) Epub 2009/10/06) showed that exosome fusion with target cells occurs more efficiently under acidic conditions, implying that exosomes may be taken up preferentially by tumors (which have an acidic microenvironment) rather than the surrounding healthy tissue. Our results show that exoPTX demonstrated superior inhibition of pulmonary metastases growth in LLC mouse model. All three mechanisms mentioned here are likely to have significant impact on exoPTX anticancer activity, i.e.: (i) preferential accumulation in cancer cells, (ii) efficient delivery of incorporated cargo into target cancer cells, and (iii) by-passing Pgp-mediated drug efflux in resistant cancer cells.

Example 3

Macrophage Exosomes as Natural Nanocarriers for Neurotrophin Delivery to Inflamed Brain In this example exosomes isolated from macrophages and administered intravenously (i.v.) are shown to cross the BBB. The exosomes isolated from macrophages are loaded with neurotrophin, the brain derived neurotrophic factor (BDNF). The BDNF loaded exosomes after i.v. administration are shown to increase delivery of the neurotrophic factor to the brain. This delivery is enhanced in the presence of brain inflammation, a condition often present in those diseases for which brain delivery of the neurotrophic factor beneficial for the therapy or neurodegenerative and neurodevelopmental disorders and stroke.

Methods

Cell Culture.

Raw Mϕs (American Type Culture Collection ATCC® TIB-71TM, Rockville, Md.) between passage 1 and 30 were used. The cells were grown in DMEM medium plus 10% FBS and 1% penicillin-streptomycin, and subcultured by scraping. The conditioned medium for exosome collection was DMEM plus 1% penicillin-streptomycin and 10% FBS pre-centrifuged at 120 kg for 140 min to remove serum exosomes. hCMEC/D3 cells (a kind gift from Dr. Pierre-Olivier Couraud in Cochin Institute, France) between passage 30 and 35 were used. All cell cultureware for hCMEC/D3 cells was coated with 0.15 mg/ml rat collagen I. The cells were grown in EBM-2 endothelial growth basal medium (Lonza) containing 5% FBS, 1% Penicillin-Streptomycin, 1.4 µM hydrocortisone, 5 g/ml acid ascorbic, 100× diluted chemically defined lipid concentrate (Life technologies), 10 mM HEPES and 1 ng/ml human basic fibroblast growth factor (Sigma).

Animals.

All animal experiments were conducted under the approval of the University of North Carolina Institutional Animal Care and Use Committee. Six to eight weeks old male CD-1 mice were purchased from Charles River Laboratories.

Purification of Exosomes.

Exosomes were purified by the common sequential centrifugation method (El-Andaloussi et al., *Nature Protocols* 7:2112 (20012); Thery et al., *Current Protocols in Cell Biology*/editorial board Juan S. Bonifacino . . . [et al.] 2006, Chapter 3, Unit 3 22). Raw Mϕs were grown in 7 T75 flasks to reach 70-80% confluence. Following two phosphate-buffered saline (PBS) washes, the cells were cultured in 10 ml conditioned medium for 2 days. The medium was then collected and centrifuged sequentially at 300 g for 15 min, 3,000 g for 15 min, 20,000 g for 70 min, and filtered through 0.2 µm membrane filters to remove cells and large particles. Exosomes were pelleted at 120,000 g for 70 min, washed by PBS to remove proteins, pelleted again, and then resuspended in 1 ml PBS. The exosome suspension was filtered through 0.22 µm membrane filters and stored in −80° C. for at most 3 weeks. Each batch of exosomes contained around 65 µg exosomal proteins as determined by microBCA and $3 \times 10^{11}$ exosomes as determined by NTA.

Characterization of Exosomes.

Exosomes were characterized by DLS for intensity-weighted z-average diameter, PDI and zeta potential, by NTA for number-weighted diameter and particle concentration, and by TEM for morphology. For DLS, the size was measured in PBS, and the zeta-potential was measured in 10 mM NaCl at 23° C. with a 1730 scattering angle using Zetasizer Nano-ZS instrument (Malvern, UK) in at least triplicates. For NTA, each sample was diluted 500 times in PBS and loaded into Nanosight NS500 (Malvern, UK). Three videos of 60 s with a sample advance in between were recorded with the minimal expected particle size, minimum track length and blur setting all set to automatic. For TEM, exosomes were adsorbed onto Formvar coated copper grid (200 mesh), stained with 2% uranyl acetate and characterized using Zeiss TEM 910 Transmission Electron Microscope (Jena, Germany) at 80 kV accelerating voltage.

Protein Composition and Exosomal Markers.

Mϕs and Mϕ exosomes were lysed with RIPA buffer mixed with proteinase and phosphatase inhibitor cocktail (Thermo Fisher Scientific). Protein composition and exosomal markers were detected by standard SDS-PAGE and western blot under reducing condition (El-Andaloussi et al., *Nature Protocols* 7:2112 (20012)).

Cell Viability.

Cell viability was determined by 3-(4,5-dimethylthiazol-2-yl)-2,5-diphenyltetrazolium bromide (MTT) assay. hCMEC/D3 cells were seeded in 96-well plates at 2000 cells/well in culture medium. After overnight incubation, the cells were treated with test agents in culture medium for time durations indicated in figure legend, and let grown in fresh culture medium (200 µl) for another 72 h. 20 µl of MTT in PBS (5 mg/ml) was added to each well. After 4 h incubation at 37° C., the formed formazan precipitate was dissolved in 150 µl of DMSO. Absorbance at 570 nm (A) was read on a microplate reader SpectraMax M5 (Molecular devices). Blanks (wells without cells) that account for solvent adsorption and controls (wells with cells without test agents) for 100% viability were treated similarly. Cell viability (%) was calculated as $((A_{created} - A_{blank}))/((A_{control} - A_{blank})) \times 100\%$. Data are means±SD of 6 replicate wells.

Flow Cytometry of Cell Uptake.

hCMEC/D3 cells were grown in 24-well plates at $5 \times 10^4$ cells/well for 4-5 days to reach confluence. Exosomes were labeled by adding CM-DiI dyes (2 µg/ml, Life Technologies) to the medium before the first 120 kg pelleting step. In the uptake mechanism studies, the cells were pretreated with endocytosis inhibitors, carbohydrates or EGTA for 0.5 h, and then co-treated with CM-DiI labeled exosomes ($0.6 \times 10^{10}$ exosomes/ml) for 4 h. The inhibition of endocytosis markers uptake was studied similarly. The endocytosis markers used were Alexa Fluor 488-Transferrin (10 µg/ml, Life technologies) for clathrin mediated endocytosis, Alexa Fluor 488-CTB (5 µg/ml, Life technologies) for caveolae mediated endocytosis, and FITC-Dextran (70 kDa, Sigma) (10 mg/ml) for macropinocytosis. The antibody block assays were done by co-incubating exosomes with antibodies or isotype controls at 100 µg/ml for 4 h. The cells were washed trice by PBS, detached by 0.25% trypsin/EDTA, collected by centrifugation at 100 g for 10 min, fixed with 4% paraformaldehyde for 10 min, and then resuspended in 0.35 ml PBS. Viable singlets were gated based on forward scatter and side scatter. 5,000-10,000 viable singlets were recorded for each sample on Becton Dickinson LSRII (BD Biosciences) using 488 nm and 532 nm lasers. Unless otherwise noted in figure legend, data are not normalized and reported as mean fluorescence 1 SD of 3 replicate wells.

LSCM.

hCMEC/D3 cells were cultured in 35 mm glass bottom dishes (MatTek) at $1\times10^5$ cells/well for 5-6 days to reach confluence. In endocytosis pathway studies, the cells were treated with CM-DiI labeled exosomes ($1\times10^{11}$ exosomes/ml) and Alexa Fluor 488-Transferrin (25 µg/ml) or Alexa Fluor 488-CTB (5 µg/ml) for 0.5 h, and then fixed before imaging. In the immunofluorescence studies, the cells were treated with CM-DiI labeled exosomes ($1\times10^{11}$ exosomes/ml) for 0.5 h, fixed by 4% paraformaldehyde, blocked with 10% goat serum/0.3% Triton® X-100 in PBS at room temperature for 1 h, and incubated with anti-clathrin heavy chain or anti-caveolin 1 antibodies (R&D systems) in 1% goat serum/1% BSA/0.3% Triton X-100 in PBS at 4° C. overnight. Followed three washes using 0.1% BSA in PBS, the cells were incubated with Alexa Fluor 488 conjugated secondary antibodies, washed trice and mounted in Slow-Fade® Gold antifade mountant (Life technologies). Images were collected by Zeiss CLSM 700/710 spectral confocal laser scanning microscope (Jena). Mander's colocalization coefficients were calculated using Image J and JACoP plugin (Schneider et al., *Nature Methods* 9:671 (2012); Bolte et al., *J. Microsc.-Oxford* 224:213 (2006)).

Iodine Labeling.

Exosomes and proteins were labeled with iodine by chloramine-T method (Yi et al., *J. Controlled Release* 191:34 (2014)). Briefly, exosomes or proteins were mixed with 1 mCi of Na$^{125}$I or Na$^{131}$I (Perkin Elmer) and 10 µg of chloramine-T in phosphate buffer (0.25 M, pH 7.5) for 60 s. Labeled exosomes and proteins were purified by Illustra Nap-5 columns (Life technologies) and collected in tubes pretreated with 1% BSA in PBS to prevent nonspecific adsorption. The iodine association (iodine in labeled sample/total iodine) was determined by trichloroacetic acid precipitation method (Yi et al., *J. Controlled Release* 191:34 (2014)). Briefly, 1 µl of purified samples was mixed with 0.5 ml of 1% BSA in PBS and 0.5 ml of 30% TCA, and then centrifuged at 5400 g for 10 min. The resulting pellet and supernatant were counted on r-counter (PerkinElmer). The iodine association was calculated as the percentage of pellet radioactivity to total radioactivity. The iodine association for exosomes and BSA/BDNF was higher than 85% and 98%, respectively.

Animal Procedure.

Mice were anesthetized with 40% urethane (4 g/kg) by intraperitoneal injection. Iodine labeled substances ($4\times10^5$ cpm) were injected to the right jugular vein. At each time point, blood was collected from the left carotid artery, allowed to clot and then centrifuged at 5400 g for 10 min to collect serum. The whole brain and peripheral organs were removed and weighed immediately after blood sampling. The radioactivity of serum and tissues were counted and normalized to injected dose (ID) by volume (ml) or weight (g) (% ID/ml or % ID/g). An injection check representing ID was also counted (n=3).

PK Data Analysis.

The noncompartmental PK parameters Vss (ml), Cl (ml/min), MRT$_{last}$ and MRT$_{inf}$ (h) were estimated using Phoenix® WinNonlin® 6.3 (Pharsight). The Ki (slope) and Vi (y-intercept) were calculated from the linear portion of multiple-time regression analysis (Price et al., *J. Pharmacol. Exper. Ther.* 333:253 (2010); Patlak et al., *J. Cerebral Blood Flow Metab.* 3:1 (1983); Patlak et al., *J. Cerebral Blood Flow Metab.* 5:584 (1985)). Brain/serum ratio (Am Cp$_c$, ml/g) of co-injected BSA was used to correct for the vascular space or leakage (Banks et al, *Brain Behav. Immun.* 2010, 24:102 (2010)), and subtracted from that of tested substance to get the delta brain/serum ratio. The delta brain/serum ratio was plotted against exposure time following equation $$Am/Cp_t = Ki\int_0^t Cp_t dt/Cp_t + Vi$$

where the exposure time ($\int_0^t Cp_t dt/Cp_t$) was the trapezoidal integral of serum cpm at time t (Cp$_t$) from time 0 to time t divided by Cp$_t$.

Statistical Analysis.

Statistical analysis was performed using Prism 6.0 (GraphPad Software Inc.) unpaired two-tailed student t-test (# p<0.05, ## p<0.01, and ### p<0.001), or one-way ANOVA with post Newman-Keuls multiple comparison test (* p<0.05,  p<0.01, and * p<0.001) as indicated in the figure legend.

Abbreviations.

Alix, apoptosis-linked-gene-2 interacting protein X; BBB, blood-brain barriers; BDNF, brain derived neurotrophic factor; CTB, cholera toxin subunit B; hCMEC/D3 cells, immortalized human cerebral microvascular endothelial cells; ICAM-1, intercellular adhesion molecule 1; LAMP 2, lysosome-associated membrane protein 2; LFA-1, lymphocyte function-associated antigen 1; LPS, lipopolysaccharide; MPS, mononuclear phagocyte system; PK, pharmacokinetics; Raw Mo., raw 264.7 macrophages; Tsg 101, tumor susceptibility gene 101 protein.

Results and Discussion

Figure 23A:
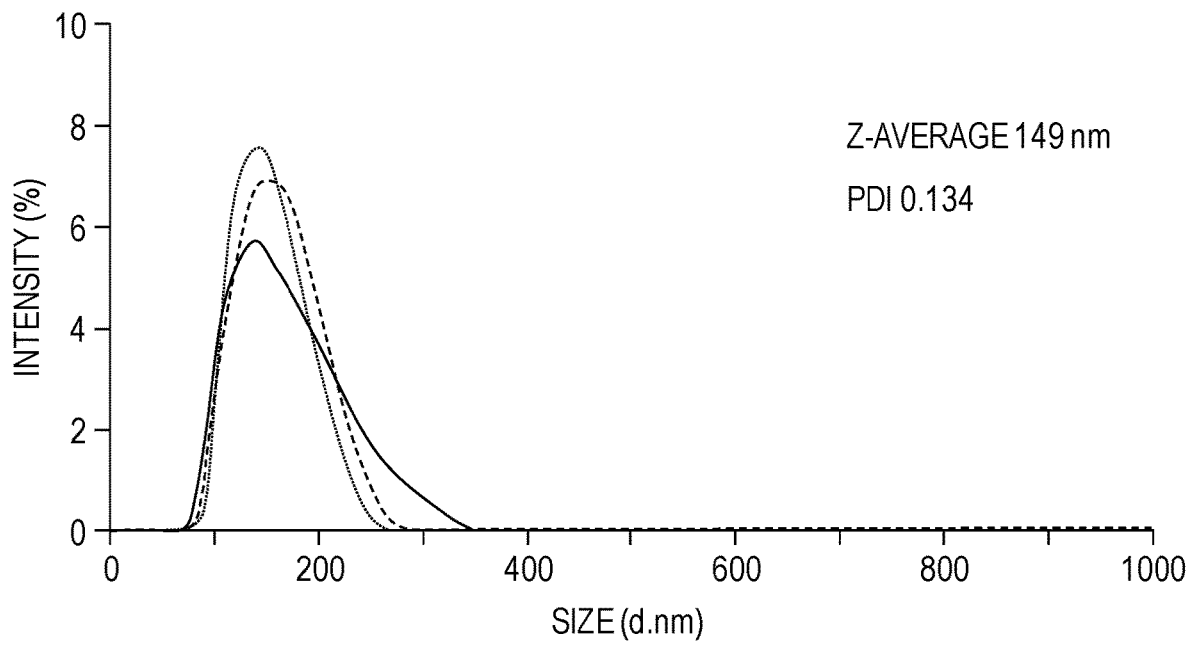
FIGS. 23A-23E show characterization of Mφ exosomes. Exosomes were purified by sequential centrifugation from RAW Mφ s conditioned medium.
Figure 23B:
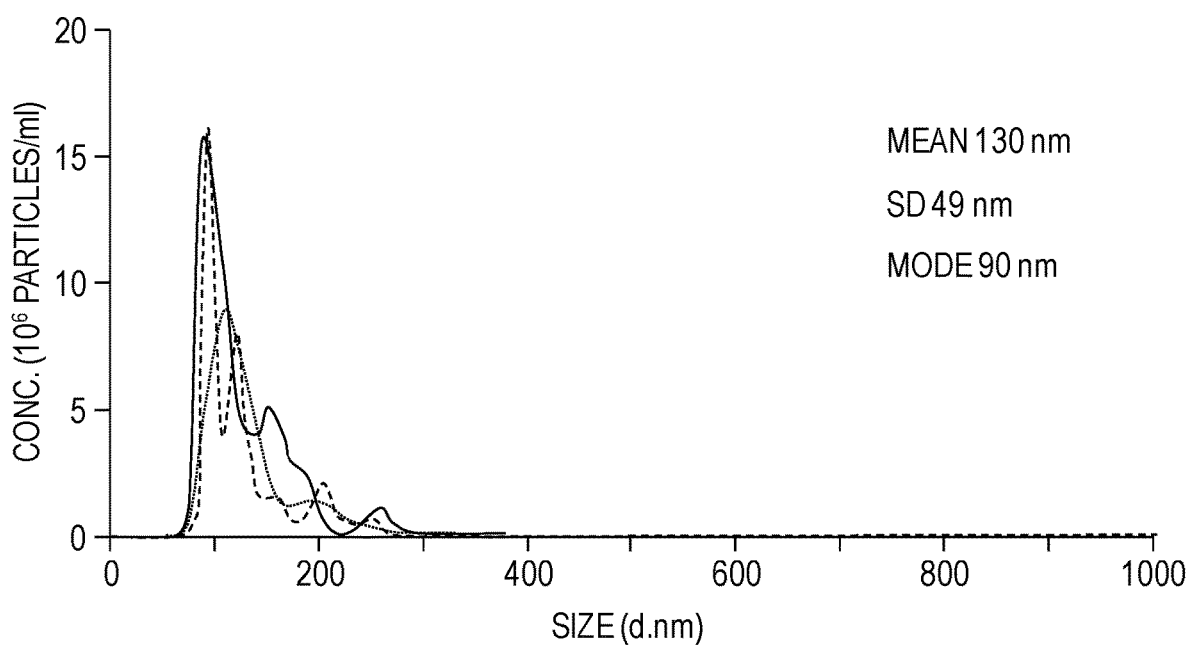
Figure 23C:
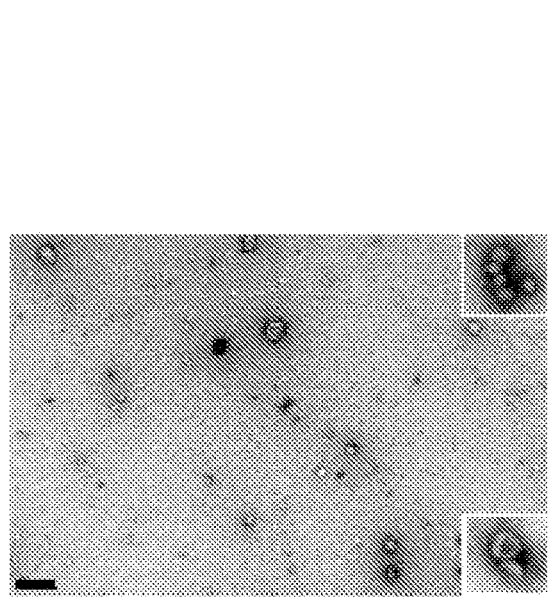
Figure 23D:
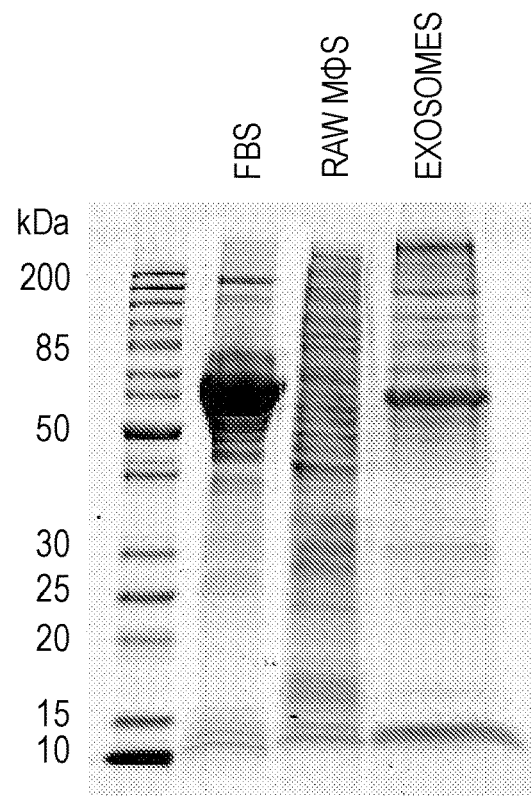
Figure 23E:
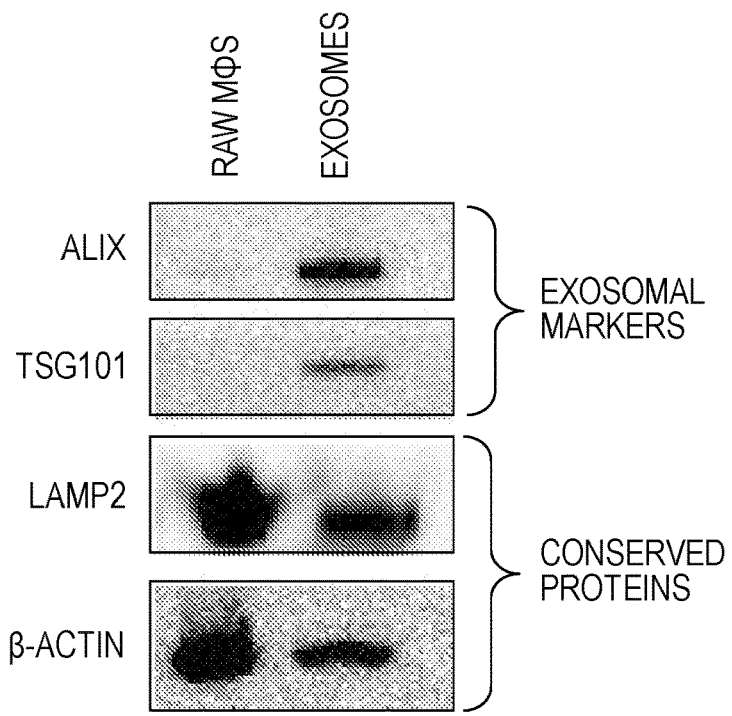
Figure 24A:
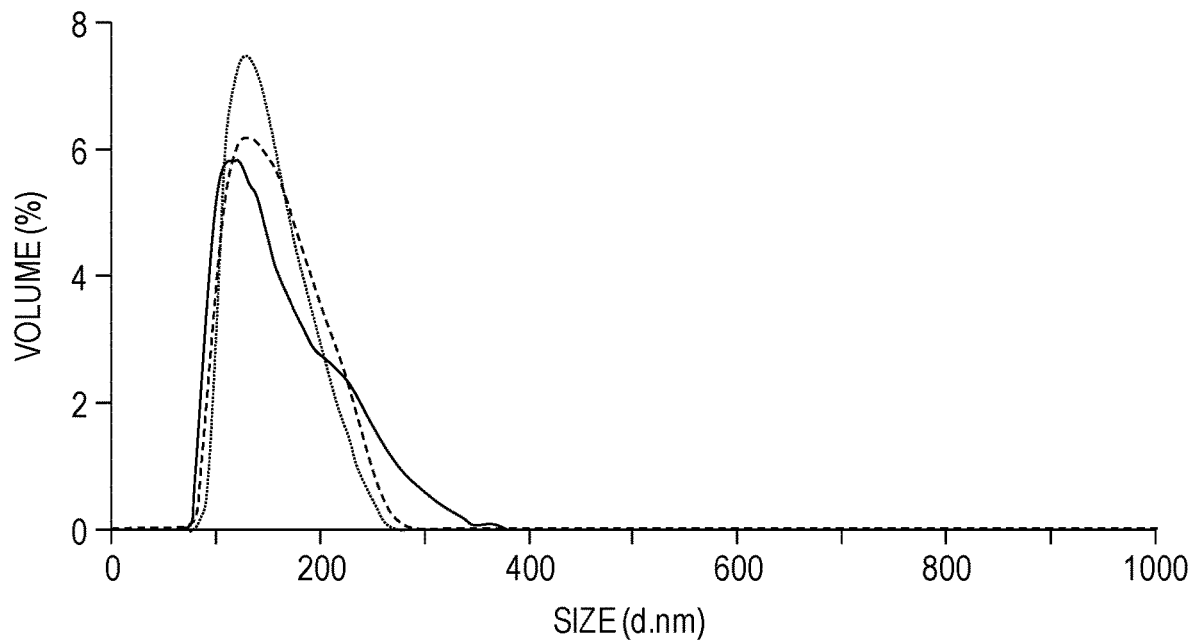
FIGS. 24A-24B show (FIG. 24A) volume-weighted and (FIG. 24B) number-weighted diameter distribution of Mφ exosomes by DLS.
Figure 24B:
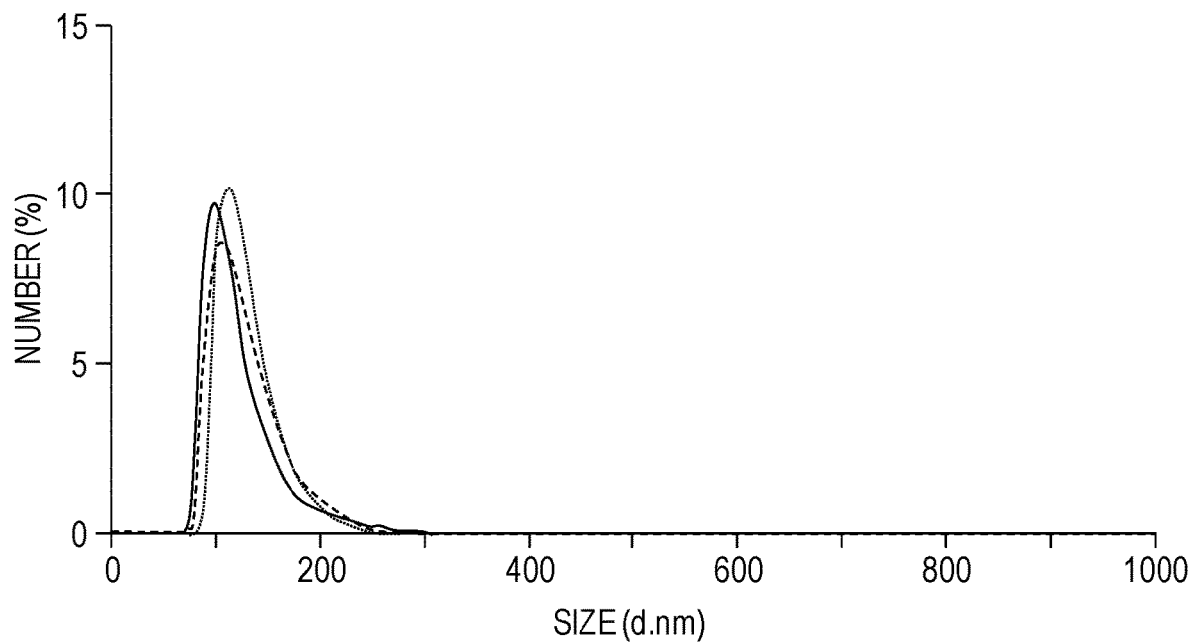

Mϕ exosome is a natural nanomaterial. Exosomes secreted by RAW Mϕs were purified by the sequential centrifugation method (El-Andaloussi et al., *Nature Protocols* 7:2112 (20012); Thery et al., *Curr. Protocols Cell Biol.* 2006, Chapter 3, Unit 3 22). We characterized their size distribution and zeta potential by DLS and NTA, morphology by transmission electron microscopy (TEM), and protein composition by sodium dodecyl sulfate polyacrylamide gel electrophoresis (SDS-PAGE) and western blot (FIGS. 23A-23E). Consistent with published results (El-Andaloussi et al., *Nature Protocols* 7:2112 (20012); Singh et al., *J. Immunol.* 189:777 (2012)), Mϕ exosomes were a heterogeneous population with intensity-weighted z-average diameter of 149 nm, relatively small polydispersity index (PDI) of 0.134 as determined by DLS, and number-weighted mean diameter of 130 nm, mode diameter of 90 nm by NTA. Using instrument software, the intensity-weighted distribution was converted to volume- and number-weighted distributions (FIGS. 24A-24B). The peaks of volume- and number-weighted distributions shifted to slightly smaller diameters. Mϕ exosomes were negatively charged (zeta potential −18 mV) in 10 mM NaCl. TEM showed spherical morphology as published (Thery et al., *Curr. Protocols Cell Biol.* 2006, Chapter 3, Unit 3 22). Occasionally we observed cup-shape as an artifact of sample drying (Thery et al., *Curr. Protocols Cell Biol.* 2006, Chapter 3, Unit 3 22), and aggregation in vitro. Based on SDS-PAGE, the protein composition of exosomes differed from their parent Mϕs and fetal bovine serum (FBS) as published previously (Thery et al., *Curr. Protocols Cell Biol.* 2006, Chapter 3, Unit 3 22). Specifically, as further revealed using western blot, exosomes compared to Mϕs were enriched with apoptosis-linked-gene-2 interacting protein X (Alix) and tumor susceptibility gene 101 protein (Tsg 101), two exosomal markers related to the biogenesis of multivesicular bodies (Urbanelli et al., *Genes* 4:152 (2013)). We also detected in the lysate of Mφ exosomes two conserved proteins that are frequently detected in exosomes: a transmembrane protein lysosome-associated membrane protein 2 (LAMP 2) and a cytosolic protein (-actin (Fais et al., *Biol. Chem.* 394:1 (2013); El-Andaloussi et al., *Nature Protocols* 7:2112 (20012); Li et al., *Nature Immunol.* 14:793 (2013); Graner et al., *FASEB J.* 23:1541 (2009)).

Uptake of Mφ Exosomes in Human Cerebral Microvascular Endothelial Cells.

Figure 25A:
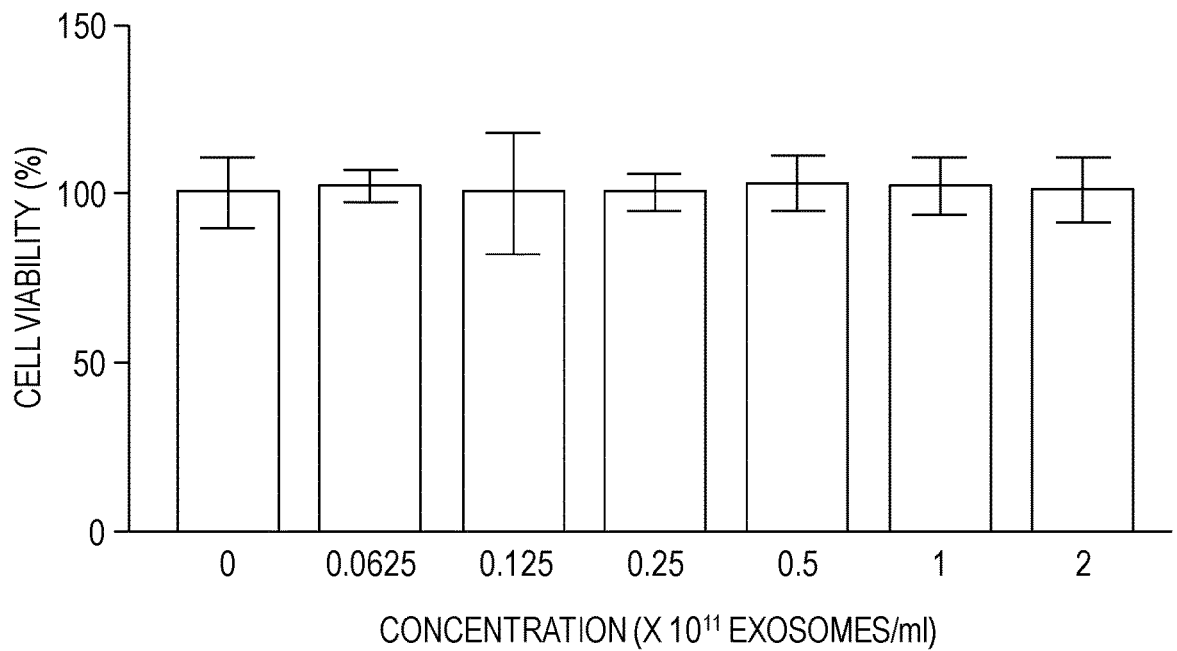
FIGS. 25A-25D show uptake of Mφ exosomes in hCMEC/D3 cells.
Figure 25B:
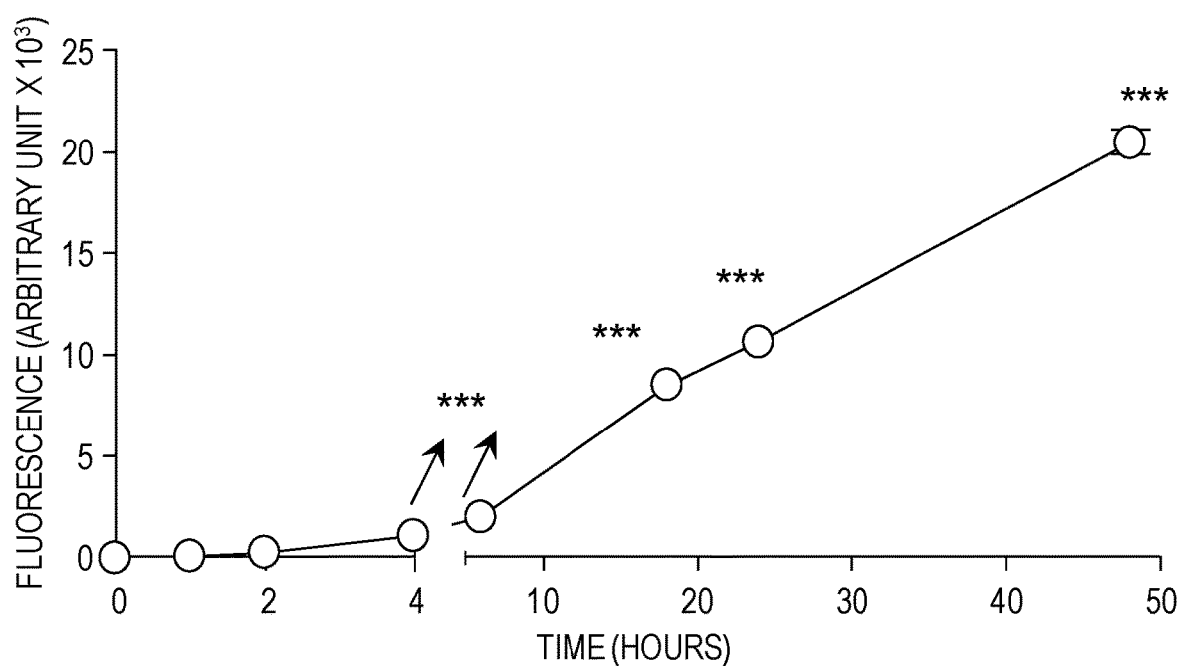
Figure 25C:
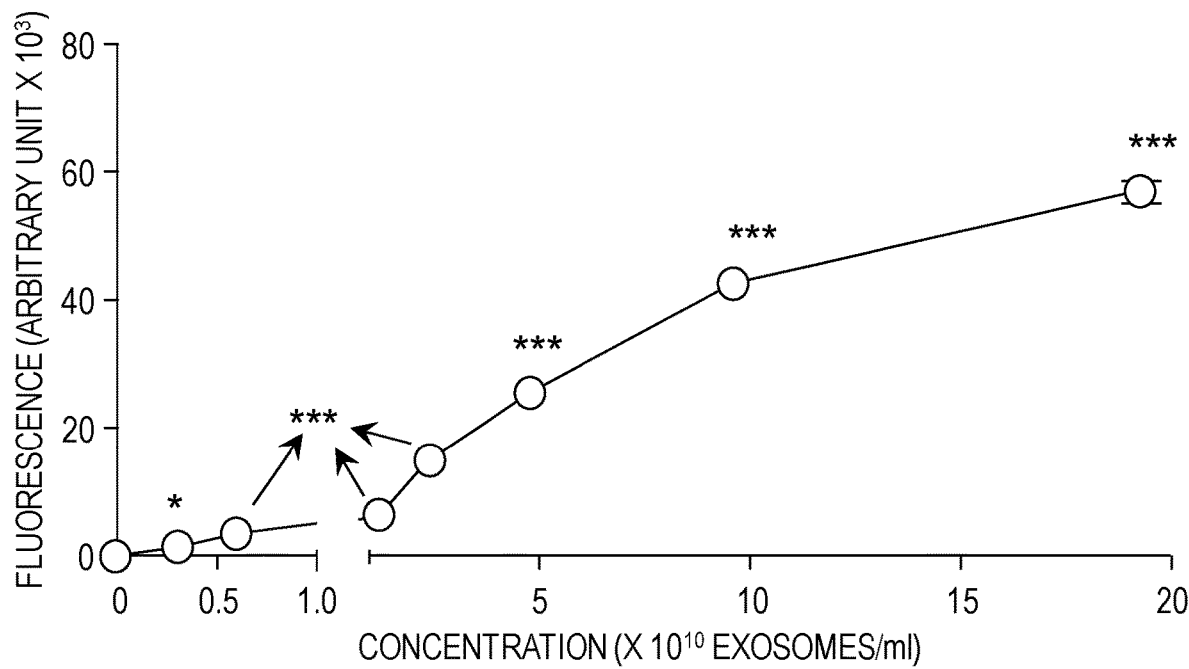
Figure 25D:
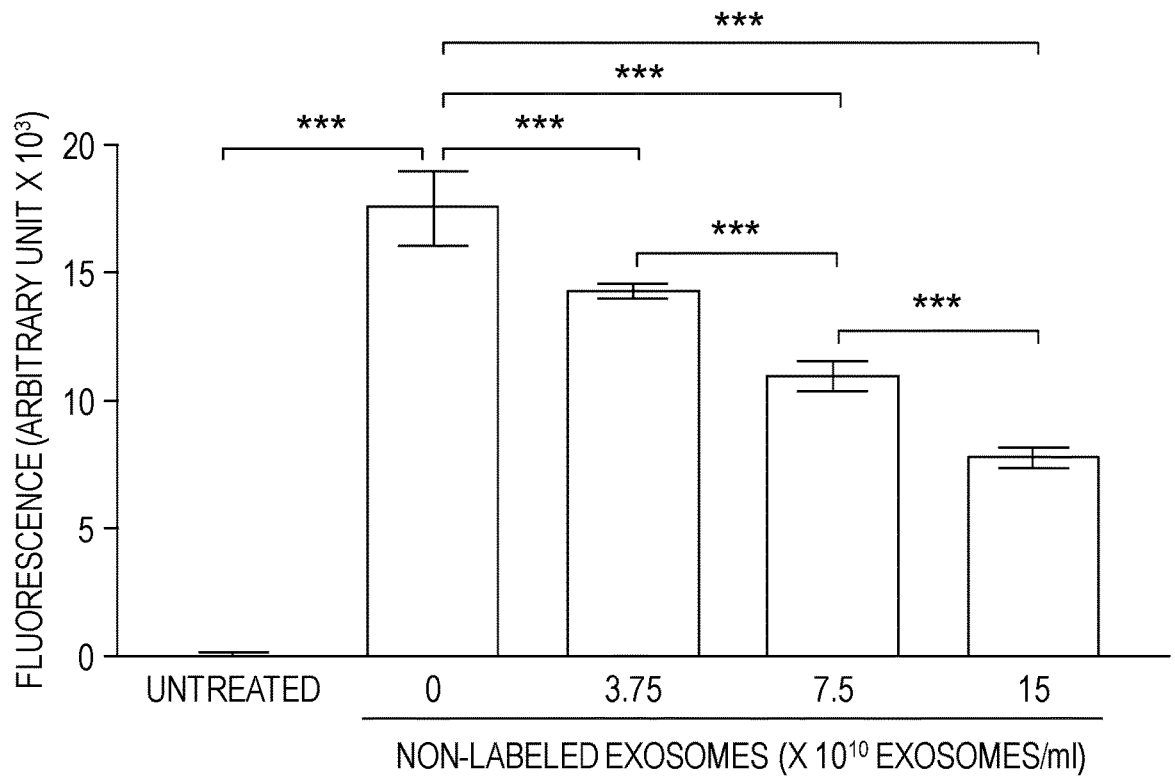

We further characterized the interactions of Mφ exosomes with hCMEC/D3 cells as an in vitro BBB model (FIGS. 25A-25D). The MTT assay showed that the viability of these cells was not affected by their exposure to Mφ exosomes for 24 h up to the highest tested exosome concentration of $2 \times 10^{11}$ exosomes/ml (FIG. 25A). All following studies involving cells used lower concentrations of exosomes. We labeled exosomes with a lipophilic dye CM-DiI to monitor their uptake in cells. The time course of cellular uptake revealed that after an initial lag period of 4 h, the amount of MO exosomes in hCMEC/D3 cells nearly linearly increased over 48 h (FIG. 25B). The concentration dependence of the uptake (at 4 h time point) suggested saturation at high concentration of Mφ exosomes (FIG. 25C), similar to the reported uptake of glioblastoma exosomes in glioblastoma cells (Christianson et al., *Proc. Natl. Acad Sci. USA* 110: 17380 (2013)). Non-labeled exosomes blocked uptake offluorescently labeled exosomes in a concentration-dependent manner, supporting the saturable nature of the uptake of Mφ exosomes in hCMEC/D3 cells (FIG. 25D). This implied a possible receptor-mediated uptake mechanism that was confirmed below.

Endocytosis Pathways of Mφ Exosomes in hCMEC/D3 Cells.

Figure 26A:
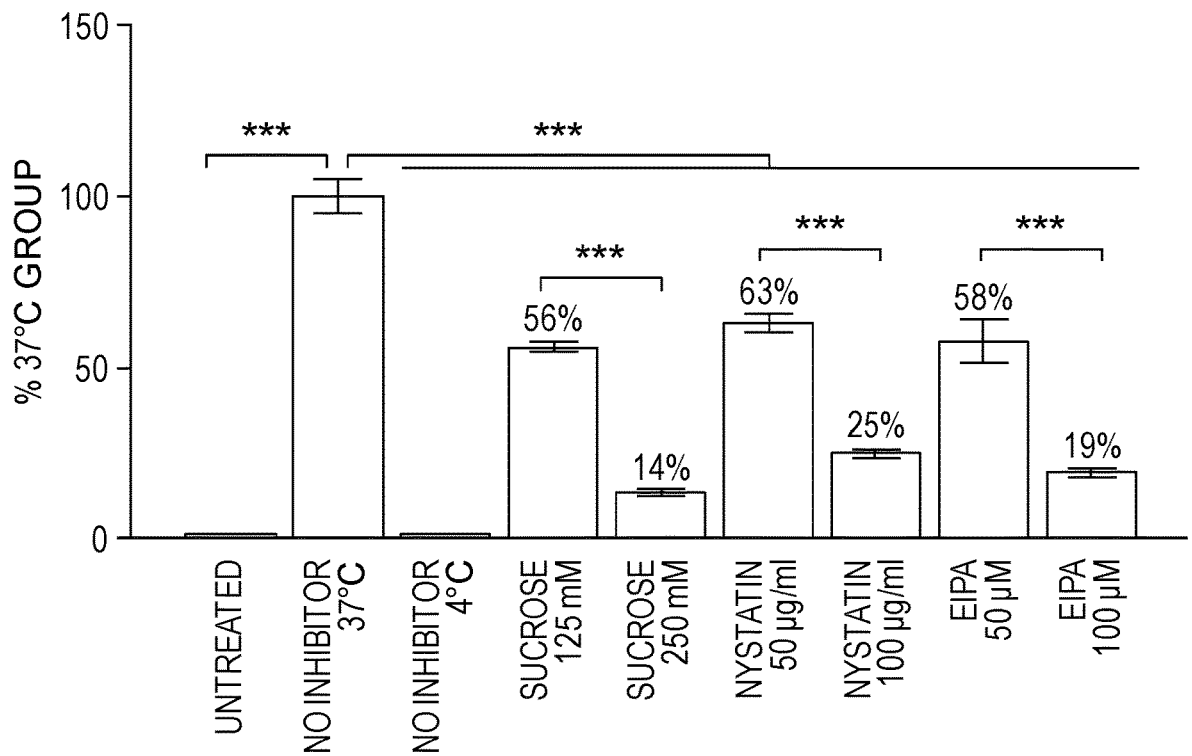
FIGS. 26A-26D show endocytosis pathways of Mφ exosomes in hCMEC/D3 cells. hCMEC/D3 cells were pre-incubated with endocytosis inhibitors for 0.5 h, and then co-incubated with fresh inhibitors and (FIG. 26A) CM-DiI labeled exosomes at $0.6×10^{10}$ exosomes/ml, (FIG. 26B) Alexa Fluor® 488-transferin at 10 µg/ml, (FIG. 26C) Alexa Fluor® 488-CTB at 5 µg/ml, or (FIG. 26D) FITC-dextran (70 kDa) at 10 mg/ml for another 4 h. All inhibitors at selected concentrations (except sucrose at 500 mM) ensured at least 80% cell viability. Cell uptake was determined by flow cytometry. Data are mean fluorescence of 5000-10000 live singlets±SD, n=3. * $p<0.05$,  $p<0.01$, and *$p<0.001$ vs indicated group by one-way ANOVA and post Newman-Keuls multiple comparison test.
Figure 26B:
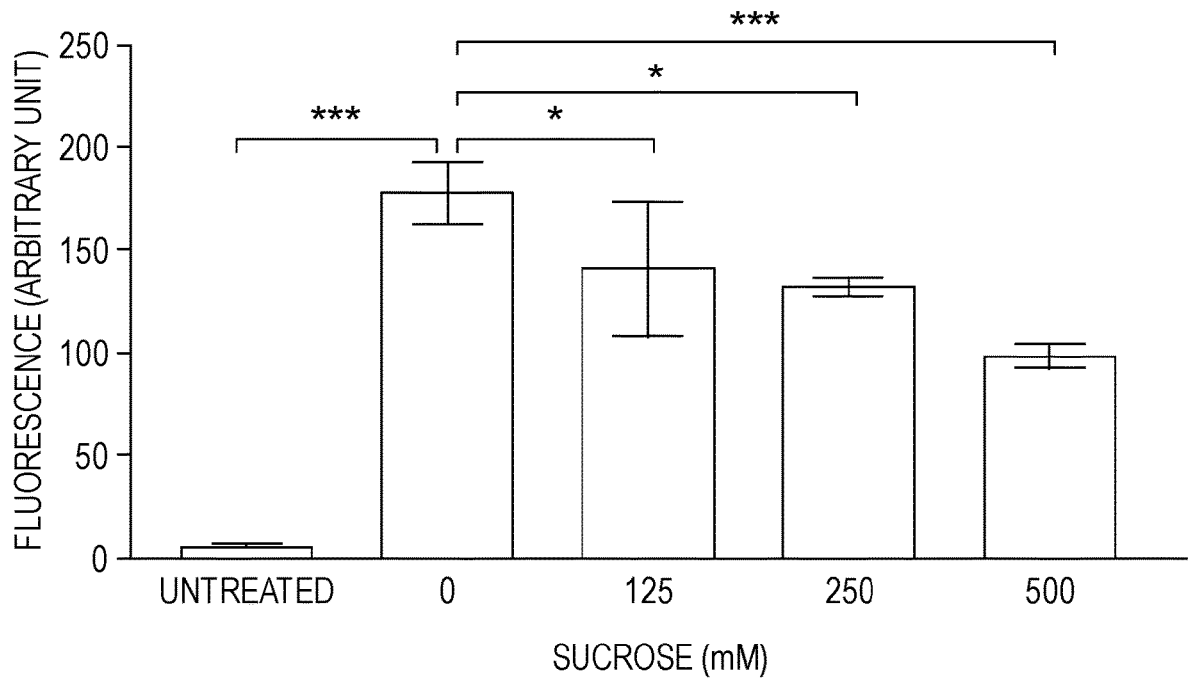
Figure 26C:
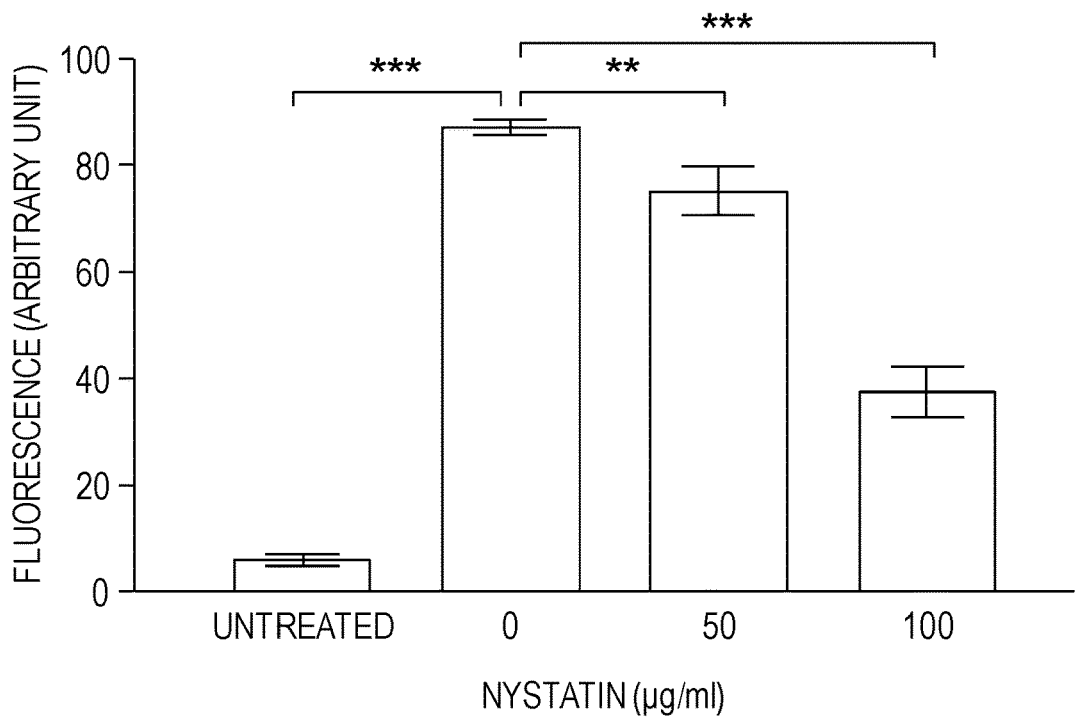
Figure 26D:
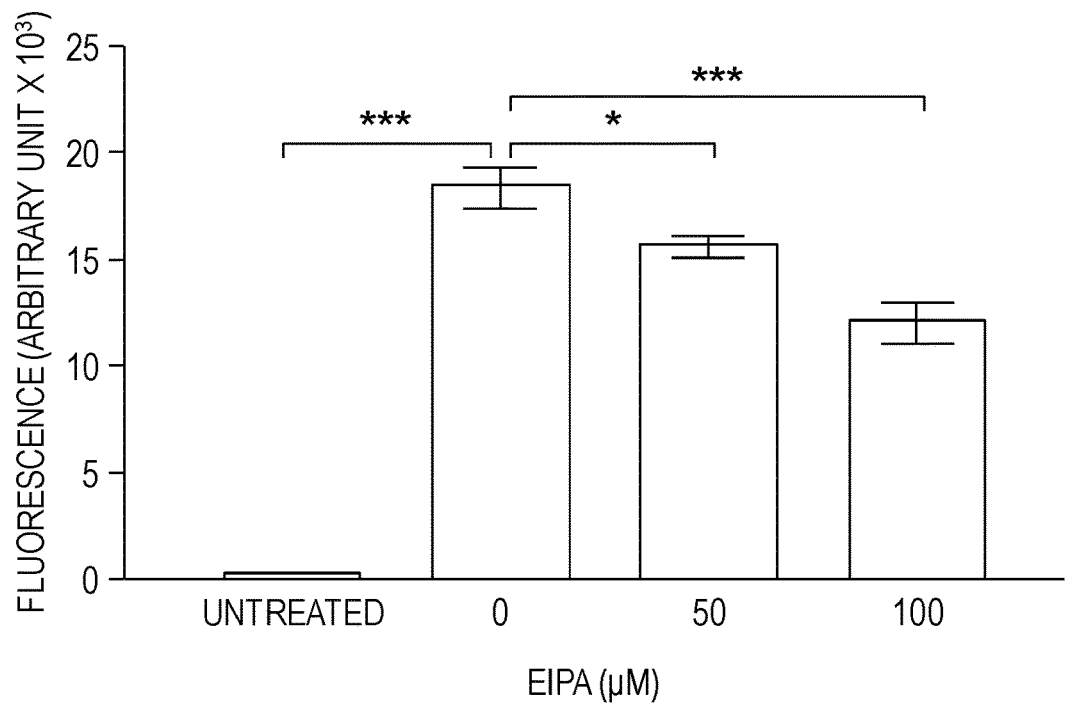
Figure 27:
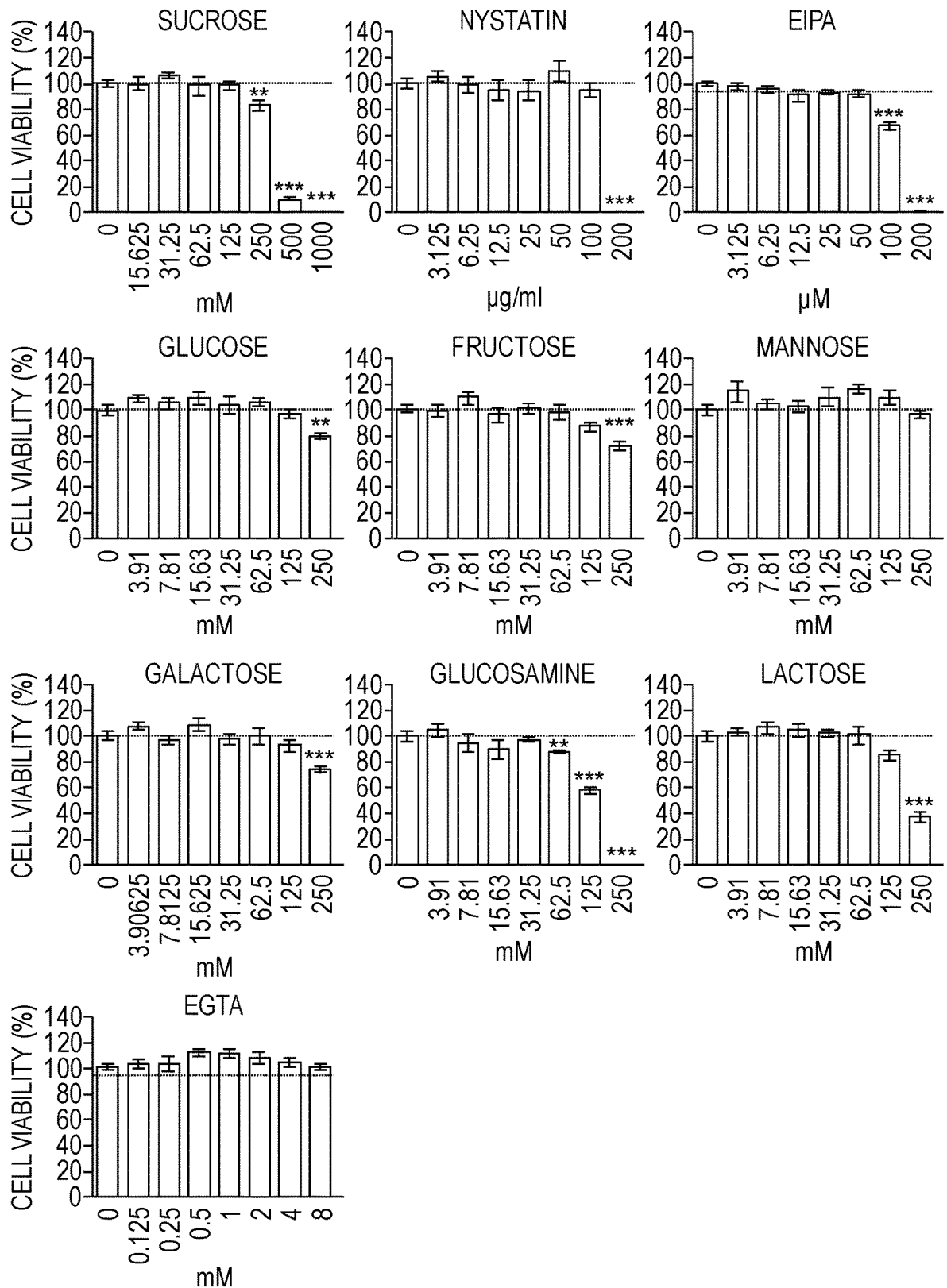
FIG. 27 shows charge saturation analysis by horizontal agarose electrophoresis.
Figure 28A:
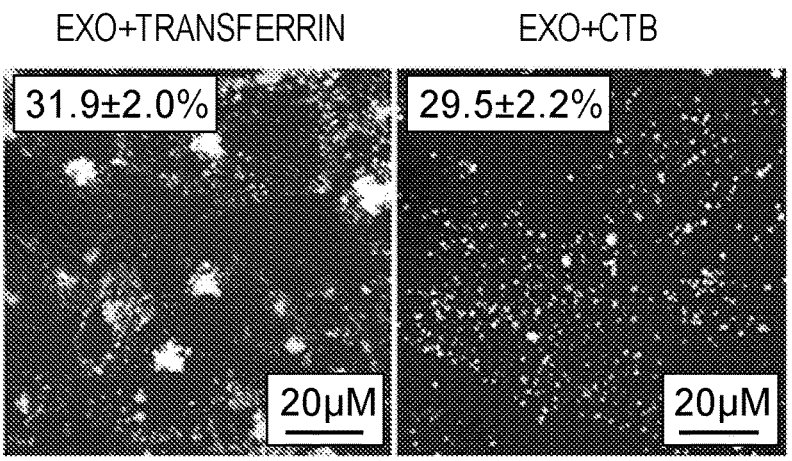
FIGS. 28A-28B show laser scanning confocal microscopy (LSCM) of the uptake of Mφ exosomes in hCMEC/D3 cells.
Figure 28B:
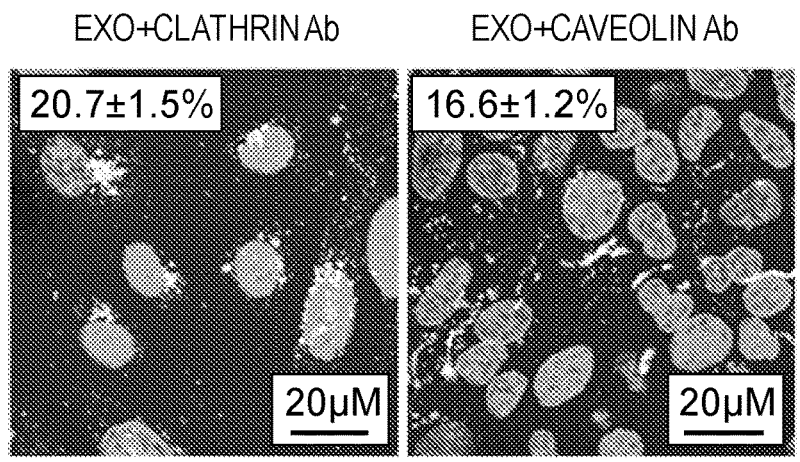

The saturable uptake of Mφ exosomes in hCMEC/D3 cells indicates that these cells internalize Mφ exosomes by some form of receptor-mediated endocytosis, rather than solely by passive fusion or macropinocytosis. Incubation at 4° C. completely blocked the uptake of Mφ exosomes (FIG. 26A), suggesting that their internalization in hCMEC/D3 cells is an energy-dependent process (Morelli et al., *Blood* 104:3257 (2004); Escrevente et al., *BMC Cancer* 11:108 (2011); Tian et al., *J. Cell Biochem.* 111:488 (2010)). To study the endocytosis pathways, we pre-incubated hCMEC/D3 cells with endocytosis inhibitors for 0.5 h, and then co-incubated with fresh inhibitors and Mφ exosomes for another 4 h. We selected sucrose (Chen et al., *J. Cell Sci.* 122:1863 (2009)), nystatin (Chen et al., *J. Cell Sci.* 122:1863 (2009); Hussain et al., *J Biol. Chem.* 286:309 (2011)), and 5-(N-Ethyl-N-isopropyl) amiloride (EIPA) (Feng et al., *Traffic* 11:675 (2010); Commisso et al., *Nature* 497:633 (2013)) as the inhibitors for clathrin-mediated endocytosis, caveolae-mediated endocytosis and macropinocytosis, respectively. Each inhibitor diminished uptake of a respective endocytosis marker at non-toxic concentrations (FIGS. 26A-26D, 27): sucrose of transferrin, nystatin of cholera toxin subunit B (CTB), and EIPA of dextran (70 kDa). Each of these inhibitors significantly decreased the uptake of Mφ exosomes, suggesting that exosomes utilized multiple pathways to enter the cells, similar to the endocytosis of exosomes derived from tumor or immune cells into respective parent cells (Christianson et al., *Proc. Natl. Acad. Sci. USA* 110:17380 (2013); Morelli et al., *Blood* 104:3257 (2004); Escrevente et al., *BMC Cancer* 11:108 (2011); Tian et al., *J. Cell Biochem.* 111:488 (2010); Feng et al., *Traffic* 11:675 (2010); Tian et al., *J. Cell. Physiol.* 228:1487 (2013); Mulcahy et al., *J. Extracellular Vesicles* 3:doi: 10.3402/jev.v3.24641 (2014)). Moreover, M # exosomes colocalized with transferrin, anti-clathrin heavy chain antibodies, CTB and anti-caveolin 1 antibodies at 0.5 h, supporting that both clathrin and caveolae mediated the uptake of Mφ exosomes in hCMEC/D3 cells (FIGS. 28A-28B).

ICAM-1/LFA-1 Mediated Uptake of Mφ Exosomes in hCMEC/D3 Cells.

We anticipated that Mφ exosomes might interact with BBB using similar mechanisms as Mφs, from which these exosomes might inherit some molecular components (Fais et al., *Biol. Chem.* 394:1 (2013)). Interaction between endothelial ICAM-1 and Mφ LFA-1 mediates the lateral migration and paracellular/transcellular diapedesis of Mφs across endothelial barriers (Carman, *J. cell Sci.* 122:3025 (2009)). Previous work also suggested that ICAM-1/LFA-1 mediated the uptake of Mφ exosomes into human umbilical vein endothelial cells (Jang et al., *ACS Nano* 7:7698 (2013). Therefore, we examined the possible involvement of ICAM-1/LFA-1 in the uptake of Mφ exosomes in hCMEC/D3 cells. First, we confirmed the presence of LFA-1 in exosomes and ICAM-1 in hCMEC/D3 cells by western blot (FIGS. 28A-28B). Second, we used LPS to stimulate ICAM-1 expression in hCMEC/D3 cells (Li et al., *J. Neuroinflammation* 9:161 (2012)), essentially mimicking in vitro a process that can take part during inflammation in vivo. Following exposure to LPS, expression level of ICAM-1 in hCMEC/D3 cells increased (FIG. 28B). This was companied by the increase in the cell uptake of exosomes (FIG. 28C). Finally, we demonstrated that each of anti-ICAM-1 or anti-LFA-1 antibodies inhibited exosome uptake (FIG. 28D). Altogether, these experiments suggest that the exosomal integrin LFA-1 and endothelial ICAM-1 play an essential role in the uptake of Mφ exosomes in hCMEC/D3 cells.

C-Type Lectin Receptors Mediated Uptake of Mφ Exosomes in hCMEC/D3 Cells.

During the endocytosis inhibition studies (FIGS. 26A-26D), we noted that sucrose had a more profound inhibitory effect on the cell uptake of Mφ exosomes than that of transferrin. Therefore, we suspected that some carbohydrate binding receptors may be involved in the uptake of exosomes. To evaluate this possibility, we examined the effects of exposure of cells to non-toxic concentrations of various carbohydrates on the cell uptake of Mφ exosomes (FIG. 30A). These effects were observed at the maximal and half-maximal tolerable concentrations that ensure at least 80% cell viability (FIG. 27). The tested carbohydrates inhibited cell uptake of exosomes to different extents. Among them, glucosamine inhibited the uptake at lower concentrations, suggesting that the inhibitory effect differed from hyperosmolarity that is known to block endocytosis (Oka et al., *J. Biol. Chem.* 264:12016 (1989)). Some carbohydrates can inhibit ICAM-1 expression in some cells, such as glucosamine in rat cardiomyocytes (Zou et al., *Am. J. Physiol. Heart Circulatory Physiol.* 296:H515 (2009)) and human retinal pigment epithelial cells (Chen et al., *Invest. Ophthalmol. Visual Sci.* 53:2281 (2012)), and fucose in human keratinocytes (Palacio et al., *Arch Dermatol. Res.* 289:234 (1997)). We selected two carbohydrates that had different level of inhibition. However, even at highest concentration used, glucose and glucosamine did not inhibit the expression of ICAM-1 in our cell model (FIG. 31). Therefore, based on the analysis of different carbohydrates, we conclude that the uptake of Mφ exosomes in hCMEC/D3 cells involves specific carbohydrate binding receptors.

One possible candidate of carbohydrate binding receptors that has been reported for the uptake of exosomes is the C-type lectin receptors (Hao et al., *Immunology* 120:90 (2007)). The carbohydrate recognition domains of C-type lectin receptors require binding of calcium for their carbohydrate-binding activity (Drickamer, *Curr. Opin. Struct. Biol.* 9:585 (1999); Cambi et al., *Cell. Microbiol.* 7:481 (2005)). It is reported that DCs internalized their secreted exosomes partially by mannose/glucosamine-binding C-type lectin receptors (Hao et al., *Immunology* 120:90 (2007)), as demonstrated by blocking assay using DEC205 antibodies, calcium chelator ethylenediaminetetraacetic acid (EDTA) and a panel of monosaccharides, especially mannose and glucosamine. Similarly, cell uptake of Mϕ exosomes in hCMEC/D3 cells was decreased by a panel of carbohydrates, ethylene glycol-bis(2-aminoethylether)-N,N,N',N'-tetraacetic acid (EGTA, an analog to EDTA but has superior selectivity for calcium) (Sanui et al., *J. Cell. Physiol.* 1967, 69:11 (1967)), and especially DEC205 antibodies against 205 kD integral membrane protein homologous to the Mϕ mannose receptor (FIGS. 30A-30C). The selected concentration of EGTA ensured at least 80% cell viability (FIG. 27). Taken together, these experiments confirmed that carbohydrates-, especially glucosamine-binding C-type lectin receptors mediated the uptake of Mϕ exosomes in hCMEC/D3 cells.

PK and Distribution of Mϕ Exosomes in Healthy Mice.

Figure 32A:
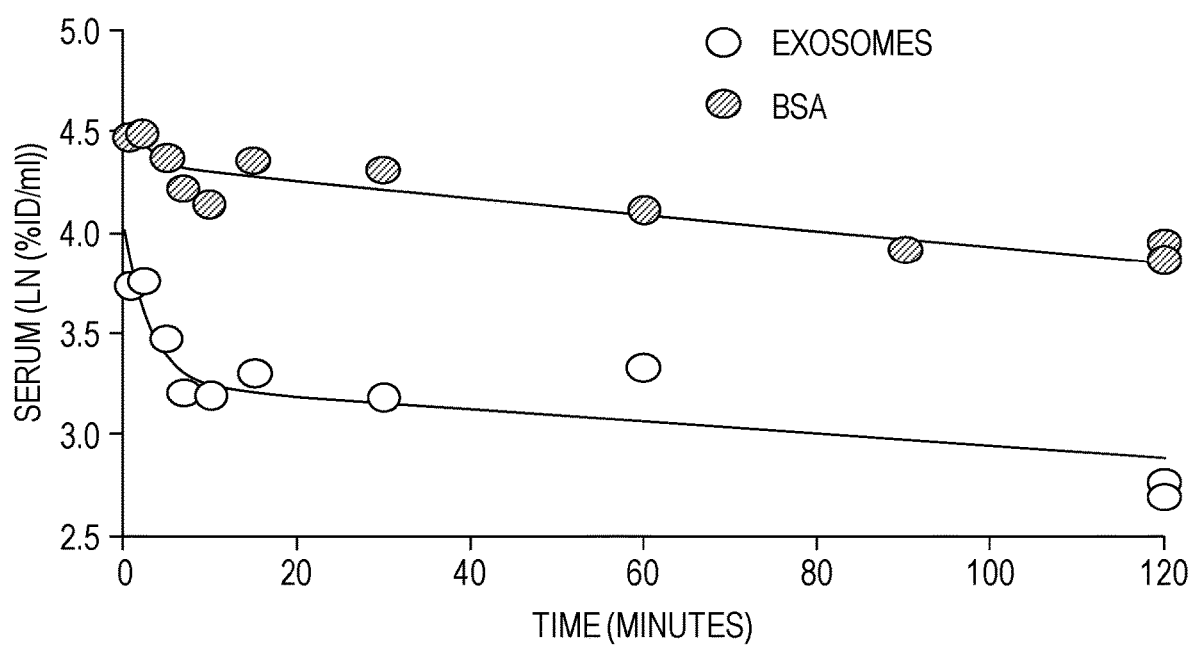
Figure 32B:
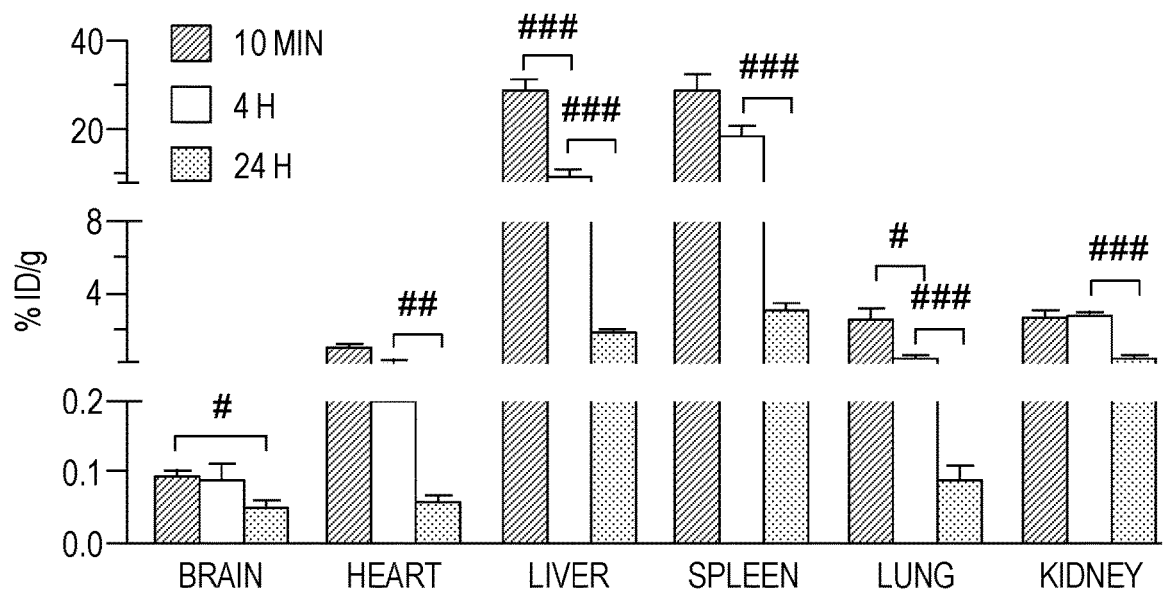
Figure 32C:
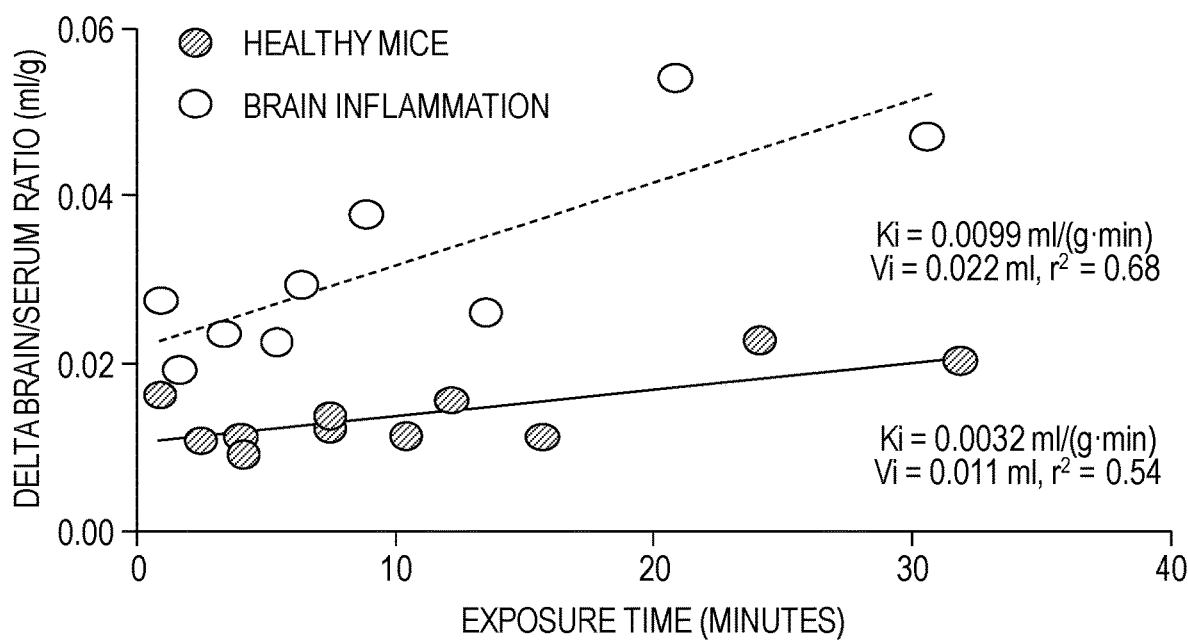

The in vivo distribution of tumor exosomes was previously studied by their radiolabeling with $^{111}$indium (Smyth et al., *J. Controlled Release* 199:145 (2015)), or by incorporating fluorescent dyes (Smyth et al., *J. Controlled Release* 199:145 (2015)) or luciferase (Takahashi et al., *J. Biotechnol.* 165:77 (2013); Imai et al., *J. Extracellular Vesicles* 4:26238 (2015)). In general, tumor exosomes were rapidly cleared by the mononuclear phagocyte system (MPS). We quantitatively characterized the PK and distribution of Mϕ exosomes in healthy CD-1 mice by radiolabeling exosomal proteins with $^{125}$I, a traditional method to track proteins and cells in vivo (Banks et al., *J. Neuroinflammation* 9:231 (2012)). For this study we collected Mϕ exosomes after 12 h incubation of Mϕ in serum-free medium (Dulbecco's modified eagle medium, DMEM) to exclude iodination of serum proteins that could be co-precipitated during isolation of exosomes by ultracentrifugation. $^{131}$I-labeled bovine serum albumin (BSA) was co-injected with $^{125}$I-labeled Mϕ exosomes as a vascular marker. The serum clearance of $^{125}$I-exosomes and $^{131}$I-BSA showed two-phase decay (FIG. 32A). The rate of serum clearance (Cl) and volume of distribution at steady state (Vss) of co-injected BSA (Table 3) were similar to previously published data (0.0035 ml/min and 1.5 ml) (Shinoda et al., *J. Pharm. Sci.* 87:1521 (1998)). It is reported that exosomes from antigen-presenting cells can evade complement-mediated lysis by expression of CD55 and CD59 (Clayton et al., *Eur. J Immunol.* 33:522 (2003)), which are present on monocytes/Mϕs (Christmas et al., *Immunology* 119:522 (2006)). However, the mean residence time from the time of dosing to last detectable concentration ($MRT_{last}$) and from the time of dosing to infinity ($MRT_{inf}$) of Mϕ exosomes was not impressive when compared with the published data for PEGylated liposomes (Qhattal et al., *ACS Nano* 8:5423 (2014); Arndt et al., *Breast Cancer Res. Treat.* 58:71 (1999); Brusa et al., *Anticancer Res.* 27:195 (2007); Gaddy et al., *EJNMMI Res.* 5:24 (2015); Shapiro et al., *Antimicrob. Agents Chemother.* 57:4816 (2013)). Similar to tumor exosomes (Smyth et al., *J. Controlled Release* 199:145 (2015)), Mϕ exosomes mainly accumulated in MPS organs, liver and spleen at 10 min, 4 h and 24 h (FIG. 32B), suggesting insufficient avoidance of MPS. Accumulation of Mϕ exosomes in brain at 10 min and 4 h was 0.1% ID/g and decreased to 0.05% at 24 h, suggesting clearance-limited brain accumulation. Although the limitation of our PK study in CD-1 mice was that the exosomes originated from Raw Mϕs derived from BALB/c mice, we do not believe that the strain difference contributed to the accelerated clearance and poor brain accumulation of the exosomes. It was previously suggested that the homologous tumor exosomes still may not readily evade the immune system (Smyth et al., *J. Controlled Release* 199:145 (2015)). In addition, expression of ICAM-1 (Aoudjit et al., *J. Immunol.* 161:2333 (1998)) and lectin receptors (Vasta et al., *Animal lectins: a functional view.* CRC Press: Boca Raton, 2009; p xxii, 558 p., 16 p. of plates)[6] in liver and spleen might contribute to the distribution of Mϕ exosomes to liver and spleen. Taken together, strategies such as PEGylation can be explored in the future to shield exosomes and extend circulation in order to improve brain accumulation.

TABLE 3

Noncompartmental PK parameters of Mϕ exosomes and BSA in healthy CD-1 mice.

| | Cl (ml/min)* | $V_{SS}$ (ml)* | $MRT_{last}$ (h)* | $MRT_{inf}$ (h)* |
|---|---|---|---|---|
| $^{125}$I-Exosomes | 0.016 | 3.15 | 0.91 | 3.40 |
| $^{131}$I-BSA | 0.0039 | 1.44 | 0.94 | 6.10 |

*Estimated using Phoenix ®WinNonlin® 6.3 (Pharsight).

Inflammation Increased Brain Influx Rate and Brain Accumulation of Mϕ Exosomes.

Figure 29A:
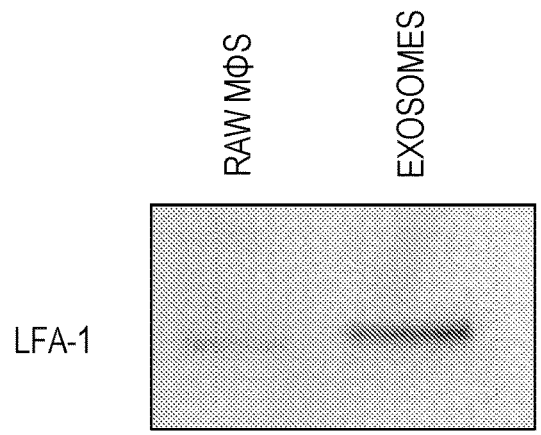
FIGS. 29A-29D show ICAM-1/LFA-1 mediated uptake of Mφ exosomes in hCMEC/D3 cells.
Figure 29B:
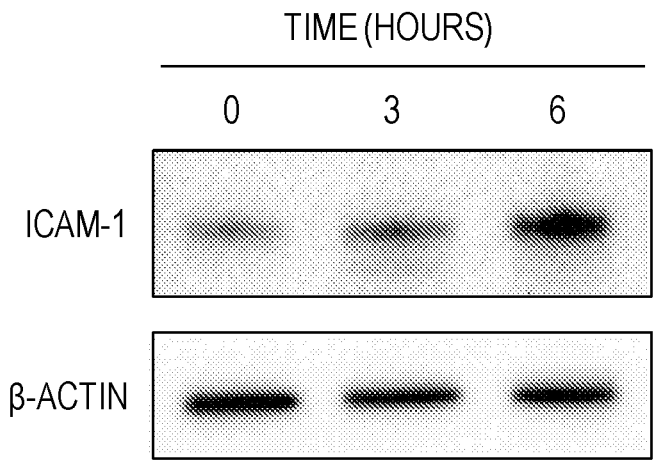
Figure 29C:
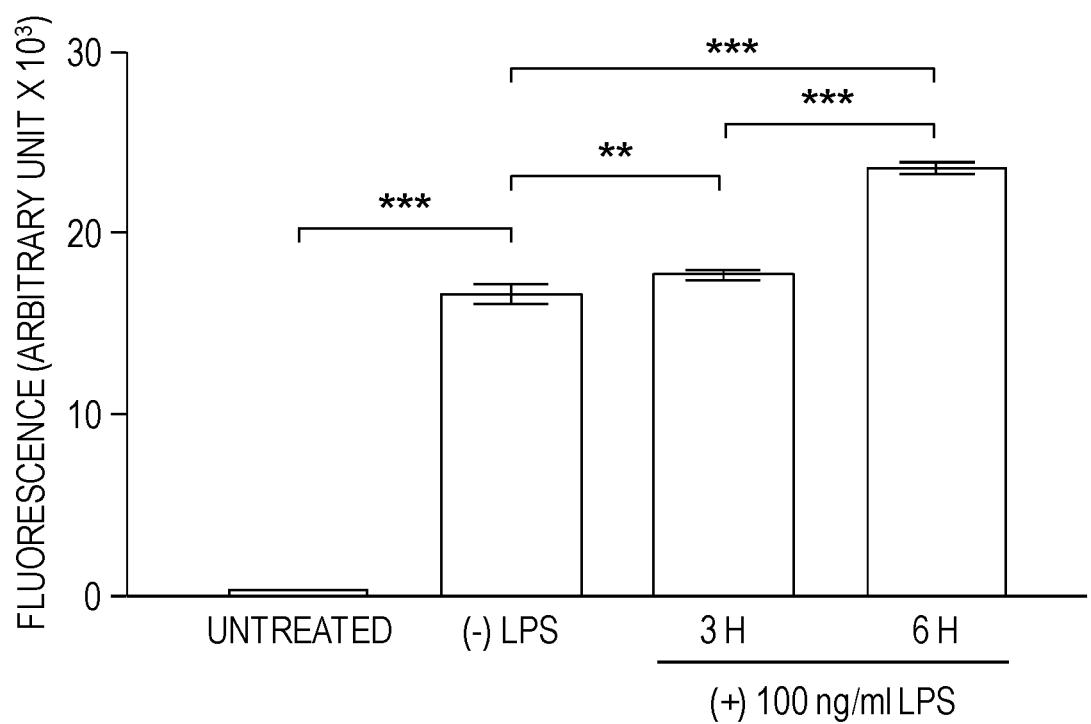
Figure 29D:
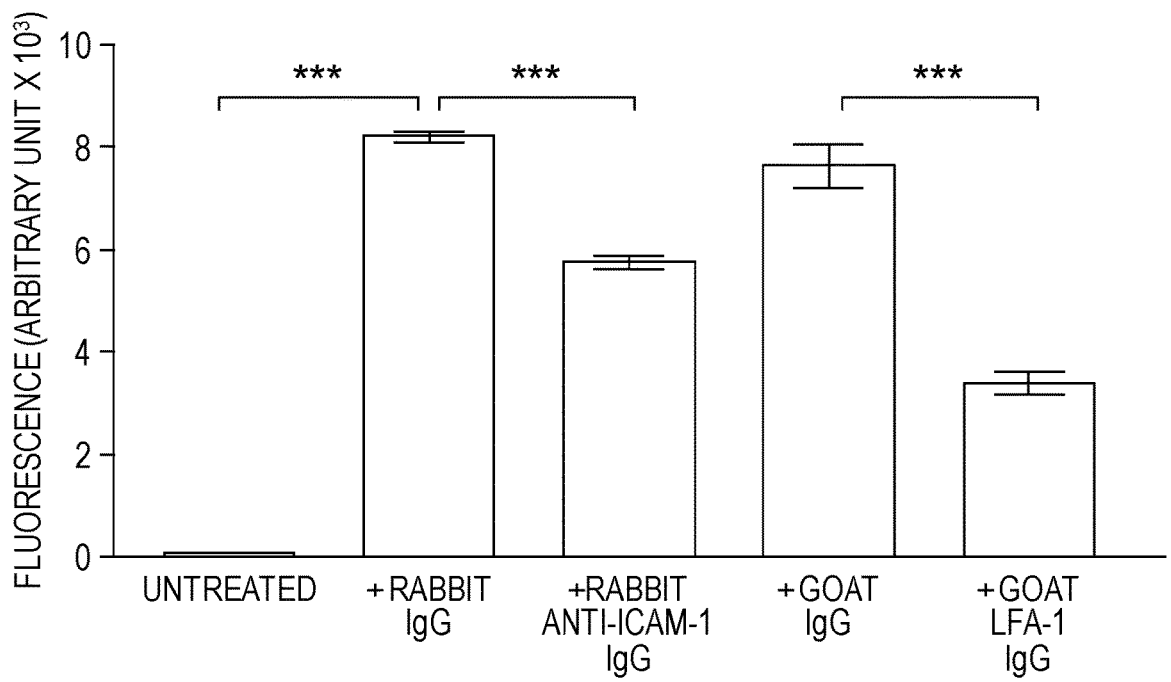
Figure 32D:
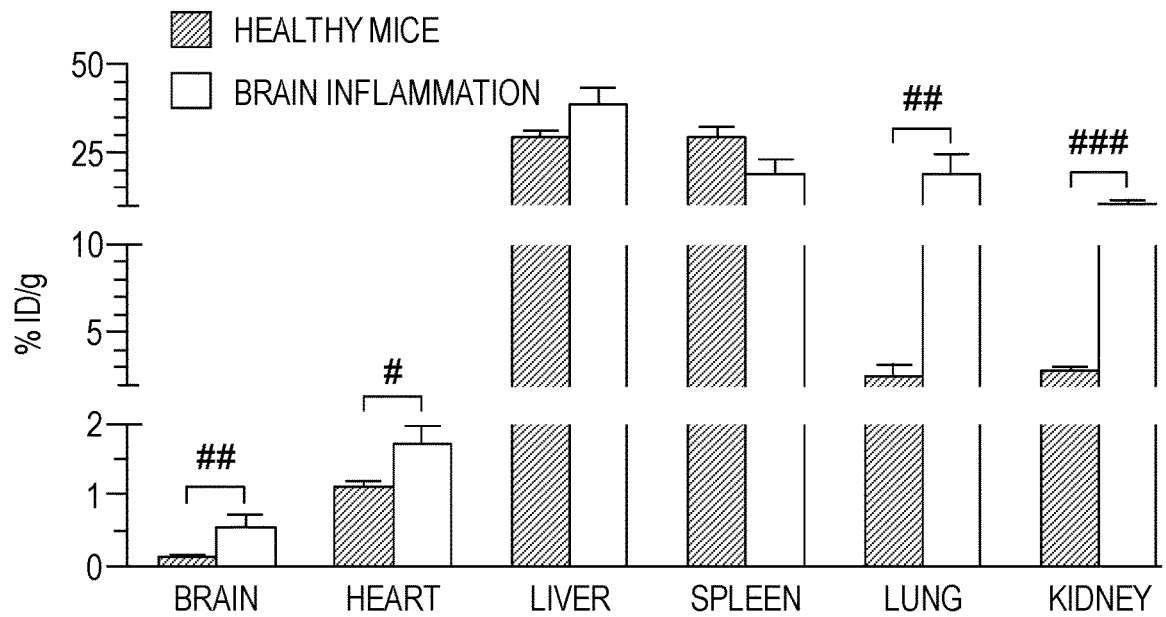

To examine whether the accumulation of Mϕ exosomes in the inflamed brain could increase, we compared the PK of Mϕ exosomes in healthy mice and brain inflammation mouse model. This model was established by intracranial injection of 10 µg of LPS a day before the PK study (Haney et al., *PloS One* 8:e61852 (2013); Zhao et al., *J. Nanomed Nanotechnol.* S4 (2011)). The serum clearances of exosomes and co-injected BSA in the brain-inflamed mice resembled those in the healthy mice (FIG. 33A). Delta brain/serum ratio was calculated by subtracting the brain/serum ratio of BSA from that of exosomes to correct for vascular space (Banks et al., *Brain Behav. Immun.* 24:102 (2010)). Both healthy and brain-inflamed mice showed significant net brain influx of exosomes (FIG. 32C): the slopes (Ki) of delta brain/serum ratio against exposure time significantly deviated from zero (p<0.05 by two-tailed t-test). However, the net brain influx rate (Ki) and volume of brain distribution (Vi) of exosomes in the brain-inflamed mice was 3 and 2 fold higher than those in the healthy mice, respectively. The plot of the delta brain/serum ratio against serum concentration directly demonstrated increased accumulation of Mϕ exosomes in the inflamed brains at similar serum concentrations (FIG. 33B). In addition, the brain influx rates of BSA in the brain-inflamed and healthy mice were comparable (p=0.076, FIG. 33C), suggesting that increase in brain influx of exosomes under inflammation was not due to impaired BBB function. Consistent with the increased brain influx rate, the brain accumulation of Mϕ exosomes in the inflamed brain at 10 min was 5.8 fold higher than that in the healthy brain (FIG. 32D). This data was consistent with the increased accumulation of exosomes in LPS treated hCMEC/D3 cells in vitro (FIG. 29D). As the expression of ICAM-1 in brain endothelium increases during inflammation, the adhesion and potentially brain uptake of exosomes through LFA-1 could also increase. This process may have some commonality with increased brain infiltration of Mϕs upon inflammation (Batrakova et al., *Exp. Opin. Drug Deliv.* 8:415 (2011); Gupta et al., *J. Neuroinflammation* 11:68 (2014); Shi et al., *Nature Rev. Immunol* 11:762 (2011)). The brain-inflamed mouse model also displayed significantly higher accumulation of Mφ exosomes in the heart (1.6 fold), lung (7.1 fold) and kidney (3.9 fold) (FIG. 32D). This could be explained by peripheral inflammation resulting from the absorption of LPS from the brain cerebrospinal fluid to blood (Banks et al., *Brain Behav. Immun.* 24:102 (2010)). The inflammation-responsive brain distribution of Mφ exosomes is remarkable and provides strong rationale for their potential application as natural nanocarriers for inflammation-related brain diseases.

Mφ Exosomes Delivered BDNF to the Inflamed Brain.

To determine whether Mφ exosomes could deliver a therapeutic cargo to the brain, we loaded the exosomes with BDNF by simple mixing in 10 mM phosphate buffer on ice. BDNF can contribute to the neuronal survival and synaptic plasticity by activating the tropomyosin receptor kinase B (TrkB) and is investigated as potential biotherapeutic agent to treat neurodegenerative and neurodevelopmental diseases including AD, PD, Huntington's disease and RETT syndrome as well as stroke (Nagahara et al., *Nature Rev. Drug Discov.* 10:209 (2011)). The complex between exosomes (zeta potential−18 mV) and BDNF (isoelectric point 9.99 (Patterson et al., *Neuron* 16:1137 (1996)) was formed due to electrostatic interactions as well as strong binding of BDNF to polysaccharides (Kanato et al., *Glycobiology* 18:1044 (2008); Kanato et al., *Biosci. Biotechnol. Biochem.* 73:2735 (2009)) that are displayed on the exosomal surface. To confirm the binding of BDNF to exosomes, we used Protein G-magnetic beads coupled with BDNF antibodies to separate BDNF treated exosomes (FIG. 23E). A control experiment without BDNF treatment was used to account for the nonspecific binding. Based on the presence of the exosomal membrane protein LAMP 2 in the magnetic-beads separated fractions the exosomes were captured on the beads only after treatment with BDNF (FIG. 34A). To estimate the amount of BDNF that can be loaded on the exosomes we analyzed various BDNF and exosome mixtures by native gel electrophoresis. In this experiment exosomes prevented the neurotrophin migration in the gel toward the anode up to a BDNF: exosomal proteins weight ratio of 1:5 (FIG. 34B). This further confirmed BDNF and exosomes complex formation and established that Mφ exosomes can capture as much as 20% wt. BDNF relative to its own protein.

We further determined if Mφ exosomes would ferry BDNF to the brain. In this experiment we co-injected $^{131}$I-labeled BSA along with the $^{125}$I-labeled BDNF with or without exosomes into the jugular vein of healthy CD-1 mice. The delta brain/serum ratios of BDNF formulated with exosomes were significantly higher than those of BDNF alone (FIG. 35A). To the contrary, the brain influx rates of co-injected BSA in both groups were comparable and did not differ from 0 (FIG. 35B). This data also indirectly suggested that BDNF remained with exosomes after administration in vivo. We further compared the brain accumulation of native and exosomes formulated BDNF in healthy and brain-inflamed mice (FIG. 35C). The brain accumulation of exosome-formulated BDNF in healthy mice was slightly but not significantly increased compared to BDNF alone (p=0.63). The brain inflammation resulted in a trend to increase the brain accumulation of free BDNF but the difference was not significant when compared to the healthy mice (p=0.11). In contrast, accumulation of exosome-formulated BDNF in the brain-inflamed mice was significantly increased compared to the same formulation in the healthy animals (3.6 fold). Moreover, the brain accumulation of BDNF with this formulation was also superior to that of the naked BDNF in the inflamed brain.

Conclusions

In summary, we demonstrated in vitro and in vivo that exosomes secreted from Raw Mφs have potential as nanocarriers for the delivery of therapeutic payload to the brain for treatment of inflammation-related brain diseases. In vitro Mφ exosomes were endocytosed into human brain endothelial cells in a receptor-dependent manner, which involved ICAM-1/LFA-1 and C-type lectin receptors, was increased in response to stimulation of the cells with LPS along with increased ICAM-1 expression. In vivo Mφ exosomes showed positive influx rate into the brain, which was also increased along with the overall brain uptake in mouse brain inflammation model. Perhaps, even more importantly, we demonstrated that Mφ exosomes can deliver BDNF into the brain in this inflammation model. This finding could provide opportunities for developing of novel therapeutic modalities comprised of neurotrophin-loaded Mφs exosomes for treatment of CNS diseases associated with inflammation, such as AD, PD, and stroke (Batrakova et al., *Exp. Opin. Drug Deliv.* 8:415 (2011)).

Example 4

Exosomes as Carriers for Nucleic Acids

In this example exosomes isolated from macrophages are formulated with polynucleotide pDNA using a cationic polymer as the third component of the formulation exosomes-pDNA-polycation. Without being bound to a specific theory we believe that the polycation 1) condenses polynucleotide and 2) binds with the both the polynucleotide and exosomes (negatively charged) thereby increasing the stability of the exosomes-pDNA-polycation formulation. The resulting formulation is shown to efficiently deliver polynucleotide to the target cell resulting in expression of the gene encoded by this polynucleotide.

Methods

Isolation of Exosomes:

Exosomes were isolated via a PEG method from RAW264.7 cells that were grown until confluent. Briefly, media was harvested from the cells, supplemented with PEG 8000 solution and incubated at 4° C. overnight. Following the incubation, the solution with exosomes was centrifuged at 3200 rpm for 30 minutes. The supernatant was aspirated and spun at 3200 RPM for another 5 min to eliminate residual PEG. The procedure was repeated and all four pellets were combines together and rehydrated in 100 μl phosphate buffered saline (PBS).

Loading of Exosomes with pDNA:

Exosomes suspension in PBS (25 μl) was supplemented with saponin (5 μl stock solution) to the final concentration 0.26%, and incubated 15 min at room temperature (RT). Then, luciferase-encoding pDNA solution (10 μl, 2 μg/ml) was added and all mixture was incubated for another 15 min at RT. Following the incubation, 354.4 μl PBS and 5.6 μl linear polyethyleneimine (PEI) solution in PBS (final concentration 0.378 mg/ml) were added to the exosome suspension and incubated for another 15 min at RT. Obtained exosomes with incorporated pDNA (exoDNA) were used in further experiments.

Results

Transfection of Target Cells with Exosome-Incorporated pDNA:

RAW 264.7 cells were seeded in a 96-well plate. Various formulations of luciferase-encoding pDNA (2 μg/ml): exoDNA, or naked pDNA, or pDNA complexed with PEI, or pDNA mixed with commercially available GenePORTER 3000 transfection reagent (GP3K), were added to cell medium for 4 hours. Then, the cells were cultured for additional 20 hours in 10% serum at 37° C., and the expression of luciferase in cell lysates were assessed by luminescence (FIG. 36). The luciferase expression in the cells was expressed in relative units per mg protein. DNA incorporation into exosomes resulted in the three orders of magnitude increase in the encoded protein expression compared to naked DNA, and significantly greater expression levels than in cells transfected with GP3K, or PEI. Noteworthy, the use of GP3K or PEI in clinic is restricted due to their high toxicity.

Transport of pDNA Formulated in Exosomes to Nuclei of Target Cells: Model pDNA was labeled with a fluorescent dye, YOYO, and then formulated into exosomes as described above. IC21 cells were incubated with exoDNA for 4 hours, then cells were washed, permeabilized, nuclei were labeled with DAPI. Intracellular distribution of exosomes (FIG. 37) was visualized by fluorescent confocal system ACAS-570 (Meridian Instruments, Okimos, Mich.). A considerable co-localization of pDNA and nuclei was evident in the images.

Optimization of exoDNA Formulation:

A relative amount of pDNA and PEI incorporated into exosomes was varied to estimate the best N/P+/−charge ratio resulted in optimal transfection rate. The N/P ratio was calculated by dividing the amount of amino groups of PEI by the total amount of negative phosphate groups of pDNA. Different compositions of exosomes permeabilized with saponin and incubated with luciferase-encoded pDNA and PEI was prepared as described above, and transfection efficacy in RAW 264.7 cells was examined (FIG. 38).

Expression of the Encoded Green Fluorescence Protein (GFP), in Macrophages Transfected with exoDNA:

IC21 macrophages were incubated with optimized exosome-based formulation of GFP-encoding pDNA (2 μg/ml pDNA, N/P ratio—12) for different time points. Then, the cells were washed, fixed and permeabilized. The nuclei were stained with Hoechst reagent. Exosomes were stained with a fluorescent dye, DIL before the loading with pDNA. The intracellular distribution of exosomes and overexpressed GFP in IC21 cells was visualized by fluorescent confocal system ACAS-570 (Meridian Instruments, Okimos, Mich.). Exosomes were readily taken up by IC21 cells in vitro. Considerable amount of the encoded protein, GFP, was detected in the transfected cells (FIG. 39).

Example 5

Cationized Exosomes for Delivery of siRNA to Cancer Cells

In this example, exosomes were modified with a cationic lipid containing multiple positive charges to increase loading of polynucleotide into the exosomes. The exosomes were isolated from IC21 macrophages, then modified with the cationic lipid and then loaded with siRNA. Briefly, exosomes were collected by PEG precipitation from macrophage media ($4.14 \times 10^{12}$ part/ml) and modified with cationic lipid, MVL5, N1-[2-(((1S)-1-[(3-aminopropyl)amino]-4-[di(3-aminopropyl)amino]butylcarboxamido)ethyl]-3,4-di[oleyloxy]-benzamide) (Avanti Polar Lipids, Inc.) having a cationic headgroup that contains five positively charged primary and secondary amines. To incorporate the lipid into the membranes of the exosomes, $1 \times 10^{10}$ exosomes were re-suspended in 1 ml phosphate buffer 10 mM, pH 7.4 and supplemented with 12 μl MVL5 lipid ethanol stock solution (1 mg/200 μl) in one aliquot, or the same volume of this solution in four 3 μl aliquots. The mixture was sonicated in an ultrasound bath for 7-10 min at 40-45° C. every time after the lipid aliquot addition, and then incubated at 37° C. for one more hour to allow for equilibration of the components. One portion of lipid-modified exosomes was permeabilized with 1.6% saponin in PBS.

To load siRNA in exosomes, a dispersion of 0.5 ml lipid-modified exosomes permeabilized with 1.6% saponin was supplemented with three portions of 10 μl CY5-labeled siRNA reconstituted in siRNA buffer (20 μM stock solution of siRNA) and vortexed for 30 sec. The mixture was then incubated for 1 hour at 37° C., and exosomes with incorporated siRNA were purified from non-incorporated siRNA using Sepharose CL4B column (3.7 ml diameter 1 cm). Purified exosomes were collected in 8 fractions (0.5 ml each), and the level of fluorescence (CY5) in exosome fractions was measured at ex 649 nm, em 675 nm using a 96-well-black clear bottom plate. The concentration of the exosomes was determined by the NTA using Nanosight NS500 (Malvern, UK) and the zeta-potential of the exosomes was measured by DLS using Zetasizer Nano-ZS instrument (Malvern, UK).

To evaluate siRNA accumulation in MDA-MB-468 triple negative breast cancer cells, the cells were plated in 8-chamber slides one day prior to the experiment. The cationic lipid-modified exosomes permeabilized with 1.6% saponin and loaded with siRNA (siRNA-MVL5-saponin-exo) and all relevant controls specifically, cationic lipid-modified exosomes loaded with siRNA (siRNA-MVL5-exo); unmodified exosomes loaded with siRNA (siRNA-exo); exosomes modified with cationic lipid (siRNA-MVL5); and naked siRNA were prepared in sterile PBS immediately prior to the experiment Cells were incubated with siRNA formulations for 4 hours, washed thrice with PBS supplemented with 1 mg/mL heparin sulfate to remove unbound exosomes; and fixed for 15 min. at RT in 4.0% paraformaldehyde (PFA). Then, the cells were stained with 1:5000 dilution of Hoechst nucleic acid counterstain, rinsed 3×, supplemented with 200 μL of PBS, and imaged on a Zeiss 710 Confocal Microscope (FIG. 40). The mean intensity of siRNA in the cells was analyzed by Image J software (FIG. 41).

The data demonstrate that the exosomes modified with cationic lipid containing multiple positive charges and loaded with siRNA enhance delivery of the siRNA in cancer cells. The data also demonstrate that in this approach the permeabilization of the exosomes with saponin prior to loading of siRNA is not necessary and in fact results in a decreased delivery of the siRNA in the cancer cells compared to exosomes that were not permeabilized with saponin.

Example 6

Cationized Exosomes for Gene Delivery to Macrophages

In this example, exosomes were modified with a cationic lipid containing multiple positive charges to increase loading of polynucleotide into the exosomes. The exosomes were isolated from IC21 macrophages, modified with the cationic lipid and then loaded with either mRNA or pDNA each encoding a reporter gene, luciferase. Then exosomes loaded with either mRNA or pDNA were used for gene delivery to cells.

To prepare the cationized exosomes the exosomes were collected by PEG precipitation from IC21 macrophages media ($2.9 \times 10^{11}$ part/ml) and modified with cationic lipid, MVL5. To incorporate the lipid into exosomal membranes, $2.9 \times 10^{11}$ exosomes were re-suspended in 1 ml phosphate buffer 10 mM, pH 7.4 and supplemented with 2 µl MVL5 lipid ethanol stock solution (5 mg/ml) four times (total lipid added 8 µl or 40 µg ($7.14 \times 10^4$ molecules lipid/exosome). The mixture was sonicated in an ultrasound bath for 7-10 min at 40-45° C. every time after the lipid addition, and incubated at 37° C. for 30 min. Then, exosomes were supplemented with 40% 8 kDa PEG solution in PBS for 4 hours at 4° C. Following incubation, cationized exosomes were collected by centrifugation for 30 min at 4000 RPM, and the exosomal pellet was reconstituted in 442 µL PBS (to match GP3K control volume).

As the next step the cationized exosomes were loaded with either the firefly luciferase expressing mRNA, Luc-mRNA (TriLink Biotechnologies, San Diego, Calif.) or the pDNA gWIZTMLuc, a gWIZ™ high expression vector encoding the reporter genes luciferase under control of an optimized human cytomegalovirus (CMV) promoter followed by intron A from the CMV immediate-early (IE) gene (Gene Therapy Systems, San Diego, Calif.). To load the cationized exosomes with mRNA or pDNA expressing luciferase, the 0.2 ml of aqueous dispersion containing $1 \times 10^{11}$ of the cationized exosomes modified with MVL5 lipid was supplemented with 2 µl of 2 µg Luc-mRNA or 2 µg pDNA in PBS and incubated for 30 min at 37° C. This results in the formation of the mRNA and pDNA complexes with the cationized exosomes.

The ability of mRNA or pDNA loaded cationized exosomes to transfect cells was examined using Raw 264.7 macrophages. The cells were seeded on 24-well plate one day prior to the experiment. The cationic lipid-modified exosomes loaded with mRNA (EXO+RNA) or pDNA (EXO+DNA) and all relevant controls, including mRNA formulated with GenePorter 3000 (GP3K mRNA); pDNA formulated with GenePorter 3000 (GP3K DNA); or naked mRNA (mRNA Only); and naked pDNA (DNA Only) were prepared in sterile PBS immediately prior to the transfection experiment. Cells were incubated with mRNA and pDNA formulations for 4 hours, washed thrice with PBS, and supplemented with full media for another 24 hours. Then, the cells were lysed and the luciferase levels were determined using a luminometer (FIG. 42).

The data suggest that that both mRNA and pDNA complexes with the cationized exosomes can efficiently transfect Raw 264.7 macrophages resulting in expression of the luciferase reporter gene. The luciferase levels in cells transfected by exosome-based formulations of mRNA and pDNA were significantly greater than in those treated with naked mRNA and pDNA, respectively.

Example 7

Exosomes Expressing GDNF for Treatment of Transgenic Mouse Model of PD

In this example exosomes were isolated from genetically modified macrophages that were transfected with plasmid DNA (pDNA) encoding GDNF. The resulting GDNF-exosomes carried the DNA, RNA and/or protein produced in the genetically modified macrophages as a result of their transfection with the GDNF-encoding pDNA. The exosomes were then used for the delivery of these biological agents and GDNF to the inflammation site in the brain to treat PD.

As the first step IC21 macrophages were transfected with the GDNF-encoding pDNA. To obtain the pDNA the human GDNF cDNA NM_199234 (OriGene Rockville, Md.) was expanded in DH5α *E. coli* and isolated using Qiagen endotoxin-free plasmid Giga-prep kits (Qiagen, Valencia, Calif.) according to the supplier's protocol. Briefly, macrophages grown in T-75 flasks ($20 \times 10^6$ cells/flask) were incubated with a mixture of 13.6 µg GDNF-encoding pDNA formulated with cationic lipid based transfection system GenePorter 3000 (GP3K) in serum free media for 4 hours. Following incubation, an equal volume of full media containing 20% FBS was added bringing the final serum concentration to 10%. Then, macrophages were cultured in FBS-exosome-depleted media for 24 hours; to avoid contamination of the FBS-derived exosomes, FBS was spun at 100,000×g for 2 hours to remove exosomes before use. Following the incubation, exosomes were harvested from genetically modified macrophages media using the ExoQuick-TC™ Kit (System BioSciences; Mountain View, Calif.) and washed twice with PBS. The recovery of exosomes was determined by measuring the protein concentration using the Bradford assay and by NTA ($10^{11}$-$10^{12}$ exosomes/flask). The obtained GDNF-exosomal fraction was re-suspended in PBS (500 µl, 1 mg/mL total protein), and exosome particle size was determined by NTA; the average diameter was 100.9 nm.

Next, GDNF-exosomes were administered in Parkin Q311X(A) transgenic mice (4 months old) through intravenous (i.v.) or intranasal (i.n.) routes at a dose of $1 \times 10^{10}$ GDNF-exosomes per mouse three times every week. After one-month of treatment behavioral studies were performed every month for five months. Healthy non-carriers, as well as PD mice injected with saline were used as control groups. Hanging wire (FIG. 43A), rotarod (FIG. 43B) and escaping activity (FIG. 43C) tests were performed. Parkin Q311X mice treated with GDNF-exosomes demonstrated significant improvements in motor skills compared to the control saline-treated carriers. The performance in Parkin group treated with GDNF-exosomes was similar to healthy controls (FIGS. 43A-43C). The data demonstrate that GDNF-exosomes exhibit therapeutic activity in the transgenic mouse model of PD.

Example 8

Increased Production of Exosomes from Cells Treated by the Block Copolymer

In this example, the production of exosomes by IC21 macrophages was significantly increased as a result of the treatment of the cells with Pluronic® block copolymer. Briefly, cells grown in T25 flasks ($2 \times 10^6$ cells/flask) were incubated with 1% Pluronic® P85 (PEO-PPO-PEO triblock copolymer with average molecular mass 4600, total weight content of PEO blocks 50%, HLB from about 12 to about 18) solution for four hours. Following the incubation, the cells were washed 3×PBS, and cultured in serum-free media for another 20 hours. Macrophages incubated in Pluronic®-free media were used as a control. Exosomes were collected by PEG precipitation from macrophage concomitant media and the number of particles was accessed by NTA. The treatment with Pluronic® P85 significantly increased the amount of exosomes released by IC21 macrophages (FIG. 44).

Example 9

Increased Transfecting Activity of Exosomes from Genetically Modified Cells Treated by Block Copolymer In this example exosomes were isolated from the genetically modified macrophages that were transfected with the plasmid DNA (pDNA) or messenger RNA (mRNA), both encoding luciferase. To increase production of exosomes the genetically modified macrophages prior to isolation of the exosomes were treated with Pluronic® block copolymer.

As the first step, donor Raw 264.7 macrophages were transfected with luciferase-encoding pDNA or mRNA. gWIZ™ Luc, a gWIZ™ high expression vector encoding the luciferase reporter gene under control of an optimized human cytomegalovirus (CMV) promoter followed by intron A from the CMV immediate-early (IE) gene (Gene Therapy Systems, San Diego, Calif.) was used as pDNA, and the firefly luciferase encoding mRNA, Luc-mRNA (TriLink Biotechnologies, San Diego, Calif.) was used as mRNA. Briefly, Raw 264.7 macrophages grown in T75 flasks ($8.0 \times 10^6$ cells/flask) were incubated in 12 mL RPMI 1640 serum-free media (SFM) with six different treatment solutions: flask #1 and #2) SFM (3008 μL RPMI 1640); flask #3 and #4) GP3K prepared as follows: a mixture of 14 μl SFM was added to 2.04 ml GP3K diluent; in parallel 192 μl GP3K reagent was added to 762 μl SFM; serum-free media/reagent mixture was added to diluent mixture and incubated for 15 min at RT before adding to the cells; flask #5) GP3K prepared as follows: a mixture of 14 μg mRNA was added to 2.04 ml GP3K diluent; in parallel 192 μl GP3K reagent was added to 762 μl SFM; serum-free media/reagent mixture was added to diluent mixture and incubated for 15 min at RT before adding to the cells; flask #6) GenePorter 3000 (GP3K) prepared as follows: a mixture of 14 μg pDNA was added to 2.04 ml GP3K diluent; in parallel 192 μl GP3K reagent was added to 762 μl SFM; serum-free media/reagent mixture was added to diluent mixture and incubated for 15 min at RT before adding to the cells. Cells were incubated at 37° C. with these mixtures for 4 hours. Following the incubation, the cells were washed 2× with serum-free media that was supplemented with heparin sulfate (1 mg/ml).

As the second step, each flask containing Raw 264.7 cells was treated as follows: #1) 10 mL SFM, #2) 10 mL SFM supplemented with 0.5% Pluronic® P85, #3) 10 mL SFM, #4) 10 mL SFM supplemented with 0.5% Pluronic® P85, #5) 10 mL SFM supplemented with 0.5% Pluronic® P85, #6) 10 mL SFM supplemented with 0.5% Pluronic® P85. The cells were incubated with these solutions for 18 hours.

After incubation the exosomes were isolated from the treated cells concomitant media by PEG precipitation. For this purpose, media was collected from the cells, and centrifuged at 500 g for 5 min to remove live cells. Next, supernatant was collected and centrifuged again at 4000 g for 15 min to remove cellular debris. Supernatant was then filtered through a 0.22 μm syringe filter, and 8 KDa PEG was added to a final concentration 10%. Then, the mixture was incubated overnight (18 hours) at 4° C., and centrifuged at 4000 g for 1 hour to precipitate exosomes. Supernatant was gently aspirated and the exosome pellet was centrifuged again at 4000 g for 5 min to remove any remaining PEG solution. Then, the exosome pellet was re-suspended in 100 μl PBS. The resulting exosome solutions were #1) exosomes from untreated cells, #2) exosomes from Pluronic® P85-treated cells, #3) exosomes from GP3K-treated cells, #4) exosomes from GP3K and Pluronic® P85-treated cells, #5) exosomes from (GP3K+pDNA) and P85-treated cells, #6) exosomes from (GP3K+mRNA) and Pluronic® P85-treated cells.

As the final step, recipient IC21 macrophages were supplemented with the exosomes isolated from different treatment groups of Raw 264.7 cells. Briefly, IC21 macrophages seeded in 24-well plates (100,000 cells/well) were supplemented with different exosomes ($2.5 \times 10^9$/well) collected from six groups Raw 264.7 macrophages (treated as described above), and incubated at 37° C. for another 18 hours. Next, the cells were lysed and assessed for luciferase. As seen in this example exosomes produced by the donor Raw 264.7 macrophages that were genetically modified with mRNA did not show any detectable level of transfection of the recipient cells (FIG. 45). Only the exosomes released by the Raw 264.7 macrophages that were genetically modified with pDNA and treated with Pluronic® P85 efficiently transfected IC21 macrophages (FIG. 45). This example demonstrates that functionally active exosomes can be produced by first transfecting a donor cell with a polynucleotide that is normally not present in these exosomes and culturing cells with Pluronic® P85.

Example 10

Accumulation of Exosomes from Human Pluripotent Stem Cells in Mouse Lung Metastases In this example exosomes were isolated from human pluripotent stem cells and then used for in vivo delivery to lung metastases in a mouse. Concomitant media from human pluripotent stem cells (hiPSC) grown in 75T flasks ($20 \times 10^6$ cells/flask) was collected, and exosomes were isolated using gradient centrifugation. In brief, the culture supernatants were cleared of cell debris and large vesicles by sequential centrifugation at 300 g for 10 min, 1000 g for 20 min, and 10,000 g for 30 min, followed by filtration using 0.2 μm syringe filters. Then, the cleared sample was spun at 100,000 g for one hour to pellet the exosomes, and supernatant was collected. The collected exosomes ($10^{11}$-$10^{12}$ exosomes/flask) were washed twice with phosphate buffer solution (PBS).

Exosomes were characterized by NTA analysis (FIG. 46) and western blot (FIG. 47). The average size of exosomes was 101 nm. Exosomes from hiPSC showed significant amounts of exosome-associated protein flotilin, as well as LFA-1 as detected by western blot.

To establish lung metastases model in a mouse, 8FlmC-FLuc-3LL-M27 cells ($5 \times 10^6$ cells/mouse in 100 μL saline) were injected i.v. via the tail vein in groups of C57BL/6 mice (n=4). The tumor lung metastases were allowed to establish for 10-12 days. Twelve days after the cancer cells were injected, DID-labeled exosomes isolated from hiPSC were administered intranasally (i.n.) at a dose of $10^7$ particles/10 μl in each nostril (×2) to mice with lung metastases. Four hours later, mice were sacrificed, perfused, lungs were extracted and sectioned on a microtome at a thickness of 20 μm; nuclei were stained with DAPI (300 mM, 5 min). The images of lung sections were examined by a confocal fluorescence microscopic system ACAS-570 and corresponding filter set, and processed using ImageJ software (FIG. 48). Confocal images revealed that 4 h after administration exosomes were co-localized with lung metastases as manifested in yellow color (FIG. 48).

Example 11

Engineered Exosomes for Targeted Delivery of Paclitaxel to Pulmonary Metastases

In this example a formulation of PTX-loaded exosomes with incorporated anisamide-polyethylene glycol (AA-PEG) vector moiety to target the sigma receptor, which is overexpressed by lung cancer cells, was developed and optimized. The AA-PEG-vectorized exosomes loaded with PTX (AA-PEG-exoPTX) possessed a high loading capacity, profound ability to accumulate in cancer cells upon systemic administration, and improved therapeutic outcomes.
Methods
Reagents.
1,2-distearoryl-sn-glycero-3-phosphoethanolamine-N-[methoxy(polyethyleneglycol-2000) ammonium salt (DSPE-PEG) and DSPE-PE-anisamide (DSPE-PEG-AA) were a generous gift from Dr. L. Huang (University of North Carolina at Chapel Hill, N.C., USA). DSPE-PEG-NH2 was purchased from NOF America Corporation (White Plains, N.Y., USA). 4-Methoxybenzoyl chloride, 2-Bromoethylamine hydrobromide, benzene, sodium hydroxide, acetonitrile, N,N-Diisopropylethylamine (DIPEA), ether, and methanol were all purchased from Sigma-Aldrich (St. Louis, Mo., USA). A lipophilic fluorescent dye, 1,1'-dioctadecyl-3,3,3', 3'-tetramethylindo-carbocyanine perchlorate (DiL), was purchased from Invitrogen (Carlsbad, Calif., USA). A sigma receptor ligand, anisamide (AA), and Triton X-100 were obtained from Sigma-Aldrich (St. Louis, Mo., USA). Cell culture medium and fetal bovine serum (FBS) were purchased from Gibco Life Technologies, Inc. (Grand Island, N.Y., USA). Culture flasks and dishes were from Corning Inc. (Corning, N.Y., USA). ExoQuick-TC™ Exosome Precipitation Solution was obtained from System Biosciences (Mountain View, Calif., USA). LysoTracker Green DND-26, ER-Tracker Blue-White DPX, and MitoTracker Deep Red were purchased from Invitrogen (Waltham, Mass., USA).
Cell Culture.
RAW 264.7 macrophages (purchased from ATCC, Manassas, Va., USA) were cultured in Dulbecco's modified Eagle's medium (DMEM) high glucose (Gibco, Grand Island, N.Y., USA) supplemented with 10% fetal bovine serum (FBS; Thermo Fisher Scientific), 1% penicillin and streptomycin at 37° C. and 5% $CO_2$. Murine Lewis Lung Carcinoma cell subline (3LL-M27), a highly metastatic lung clone, a generous gift from Dr. L. Pelletier (CHUL, Laval University, QC, Canada), murine lung adenocarcinoma cells (344SQ), a generous gift from Dr. Pecot (UNC at Chapel Hill; USA), as well as human small-cell lung carcinoma cells (H69/AR), human non-small cell lung carcinoma cells (A549), and normal human lung fibroblasts (Hel 299) were cultured in DMEM high glucose supplemented with 10% FBS, 10 mM HEPES, 1% penicillin and streptomycin at 37° C. and 5% $CO_2$.
Animals.
The experiments were performed with female C57BL/6 mice (Charles River Laboratories, Durham, N.C., USA) eight weeks of age in strict accordance with the recommendations in the *Guide for the Care and Use of Laboratory Animals* of the National Institutes of Health. The protocol was approved by the Committee on the Ethics of Animal Experiments of the University of North Carolina at Chapel Hill. The animals were kept five per cage with an air filter cover under light- (12-hours light/dark cycle) and temperature-controlled (22±1° C.) environment. All manipulations with the animals were performed under a sterilized laminar hood. Food and water were given ad libitum.
Exosome Isolation.
For all studies, exosome-depleted media was prepared by ultracentrifugation of fetal bovine serum (FBS) at 120,000×g for 110 min to remove all vesicular content, prior to addition to culture media. Exosomes were harvested from the supernatants of RAW 264.7 cells cultured in exosome-depleted media using the ExoQuick-TC™ Kit (System BioSciences; Mountain View, Calif., USA). Briefly, >90% confluent RAW 264.7 cells were cultured in exosome-depleted media for 2 days. 50 mL conditioned cell culture media were centrifuged at 300×g for 10 min (Thermo CL-10 centrifuge with O-G26/1 rotor, Thermo Fisher Scientific, Waltham, Mass., USA) in order to remove cells and cellular debris. The supernatant was then taken, filtered with a 0.22 μm PES filter, and ExoQuick-TC™ Exosome Precipitation Solution (System Biosciences, Mountain View, Calif., USA) was added to the filtered supernatant and the mixture was vortexed and incubated overnight at 4° C. After overnight incubation, the mixture was vortexed and subsequently centrifuged at 1500×g for 30 min. and 5 min. to pellet exosomes. The supernatant was discarded and the exosome pellet was re-suspended in PBS. Freshly prepared exosomes or exosomes stored at −20° C. were used for all experiments.
Preparation of AA-Vectorized Exosomes Targeted to the Sigma Receptor.
Exosomes targeted to sigma receptor with DSPE-PEG-AA (AA-PEG-exo) and non-vectorized control exosomes with DSPE-PEG (PEG-exo) were prepared as follows: exosomes were isolated from macrophage media as described above and then DSPE-PEG or DSPE-PEG-AA (50 μg/ml) were added to the exosome mixture (for PEG-exo and AA-PEGexo, respectively). 100 μL of 10 mg/mL PTX in EtOH was also added to the mixture to load into exosomes. The mixtures were then sonicated by the same method described previously (Kim et al., *Nanomedicine* 12: 655-664 (2016)). Briefly, the mixture was sonicated using a Model 505 Sonic Dismembrator with 0.25" tip (Thermo Fisher Scientific, USA) with the following settings: 20% amplitude, 6 cycles of 30 s on/off. After sonication, the AA-PEGexo or PEGexo or AA-exoPTX solutions were incubated at 37° C. for 60 min to allow for recovery of the exosomal membrane.
Exosomes were purified from the excess of free DSPE-PEG or DSPE-PEG-AA by size exclusion chromatography using a NAP-10 Sephadex G25 column (GE Healthcare, Buckinghamshire, UK) according to the manufacturer's recommended protocol. Briefly, 750 μL of AA-PEGexo or AA-exo were added to the NAP-10 column and the void volume was discarded. 250 μL of PBS was then added to the column and allowed to enter the gel bed completely. 1.2 mL of PBS was then added to the column and the eluate containing purified exosomal formulations was collected and stored at −20° C.
Characterization of AA-Vectorized Exosomes. Nanoparticle Tracking Analysis (NTA).
Exosomes were identified and characterized using a NanoSight LM 10 instrument (NanoSight Ltd., Amesbury, UK). The settings were optimized and kept constant between samples, and each video was analyzed using the Nanosight system to obtain the size and concentration of exosomes. The stability of exosomes was monitored by measuring size over a period of time under various conditions (4° C., room temperature, or 37° C.). Prior to measurement, exosomes were diluted 1:1000 to yield a particle concentration in the region of 108 particles/mL, in accordance with the manufacturer's recommendations. All samples were analyzed in triplicate.

Dynamic Light Scattering (DLS).

The average hydrodynamic diameter and zeta potential of exosomes was measured by DLS using a Malvern Zetasizer Nano ZS system (Malvern, Worcestershire, UK) equipped with He—Ne laser (5 mW, 633 nm) as the light source at 22° C. All samples were analyzed in triplicate.

Western Blot Analysis.

The levels of proteins constitutively expressed in exosomes, Alix and flotillin 1, as well as the lymphocyte function associated antigen-1 (LFA-1, subunit CD11a), were examined by western blot analysis. Protein concentrations were determined using a BCA kit (Pierce Biotechnology, Rockford, Ill.). The protein bands were detected with Alix, flotillin 1, and CD11a primary monoclonal antibodies, (Abcam, Cambridge, UK; 1:1000 dilution), and secondary HRP-conjugated rabbit anti-goat IgG-HRP (Santa Cruse, Calif., USA; 1:5000 dilution). The TSG101 levels were visualized by TSG101 monoclonal antibodies, Abcam (Cambridge, Mass., USA). The protein bands were visualized by chemiluminescent substrate (Pierce Biotechnology, Rockford, Ill., USA) and quantified using ImageJ software (National Institute of Health, Bethesda, Md., USA). To correct for loading differences in cellular lysates and exosomal fractions, the levels of proteins were normalized to constitutively expressed β-actin in cells with goat polyclonal antibodies to β-actin (Abcam, ab8229; 1:500 dilution); and TSG101 in exosomes with goat polyclonal antibodies to TSG101 (Santa Cruz, S.C.6037; 1:200 dilution).

Membrane Fluidity Measurements.

BODIPY-PC, a fluorescent dye, was used as a probe to examine the effect of incorporation DSPE-PEG-AA on the fluidity properties of exosomal membranes as described earlier (Thery et al., *Curr Protoc Cell Biol*, Chapter 3: Unit 3 22C, (2006)). Briefly, 30 μl exosomes with a concentration of $4 \times 10^{11}$ particles/ml were mixed with 20 μl BODIPY-PC (0.03 mg/ml) and supplemented with 70 μl deionized water; the mixture was incubated for 45 min 37 C in darkness. Unbound label was removed by Zeba™ column (Life Technologies). The obtained exosomal mixture was sonicated by one or six cycles US in the presence of various amounts of DSPE-PEG-AA with or without PTX, and the membrane fluidity was accessed by fluorescence of incorporated BODIPY-PC. Fluorescence intensities were measured with a Spectramax M5 plate reader. An excitation wavelength of 495 nm and an emission wavelength of 502 nm were used for both probes.

Drug Loading and Optimization AA-PEG-exoPTX.

For PTX loading into vectorized exosomes, lmL of purified exosomes (~$10^{11}$ exosomes) in PBS was mixed with PTX and DSPE-PEG-AA. For this purpose, first PTX (10 mg/mL drug in EtOH stock solution) was added to 1 mL exosomes in PBS. Then, different amounts of AA-PEG-DSPE (0.05-0.50 mg/ml) in PBS were added to the mixture of exosomes with PTX. The obtained mixture was sonicated using a Model 505 Sonic Dismembrator using a 0.25" tip (Thermo Fisher Scientific, USA) with the following settings: 20% amplitude, 6 cycles of 30 s on/off for three minutes with a two-minute cooling period between each cycle. After the sonication, solutions of AA-vectorized exosomes loaded with PTX (AA-PEG-exoPTX) were incubated at 37° C. for 60 minutes to allow for recovery of the exosomal membrane. Excess free PTX and AA-PEG-DSPE was separated from AA-PEG-exoPTX by size exclusion chromatography using a NAP-10 Sephadex G25 column (GE Healthcare, Buckinghamshire, UK) according to the manufacturer's protocol. Briefly, 750 μL of AA-PEG-exoPTX were added to the NAP-10 column and the void volume was discarded. 250 μL of PBS was then added to the column and allowed to enter the gel bed completely and the eluate was discarded. 1.2 mL of PBS was then added to the column and the eluate containing purified AA-PEG-exoPTX was collected and stored at −20° C.

Quantification of Drug Loading by High Performance Liquid Chromatography (HPLC).

The amount of PTX loaded into exosomes was measured by HPLC method as described earlier (Kim et al., *Nanomedicine* 12: 655-664 (2016)). Briefly, AA-PEG-exoPTX or exoPTX (~$10^{10}$ exosomes/0.1 mL) in a microcentrifuge tube was placed on a heating block set to 75° C. to evaporate solvent. After all solvent had evaporated, an equal volume of acetonitrile was added to the tube and the mixture was vortexed, sonicated, and vortexed again. The sample was then centrifuged at 13,000 rpm (Thermo Legend Micro 21, Thermo Fisher Scientific, Waltham, Mass., USA) for 10 min. Following centrifugation, the supernatant was taken and filtered through a Corning Regenerated Cellulose 0.2 μm syringe filter and transferred into HPLC autosampler vials. 20 μL aliquots were injected into the HPLC system (Agilent 1200, Agilent Technologies, Palo Alto, Calif., USA). All analyses were performed using a C18 column (Supelco Nucleosil C18, 250 mm×4.6 mm, 5 μm, 100 Å, Sigma-Aldrich) with a mobile phase of $H_2O$:acetonitrile (45:55, v/v) at a flow rate of 1 mL/min at 30° C. Absorbance was measured at 227 nm to monitor the elution of PTX. The area under the PTX peak was measured for each sample and compared with known concentration of standard. A calibration curve was constructed by plotting peak area versus concentrations of PTX and was found to be linear within the tested concentration range ($r2=0.997$). Exosome protein content was measured using the Pierce BCA Protein Assay Kit (Thermo Fisher Scientific, Waltham, Mass., USA) according to the manufacturer's recommended protocol. Loading capacity is expressed by μg protein of exosomes.

Accumulation of AA-Vectorized Exosomes in 3LL-M27 Cancer Cells In Vitro.

To determine the uptake of AA-vectorized exosomes (AA-PEG-exo) as compared to empty exosomes (exo) and control PEGylated exosomes without anisamide (PEG-exo), 3LL-M27 cells were seeded overnight at 50,000 cells/well in a 96-well plate. Exosomes (exo, PEG-exo, AA-PEG-exo) were labeled with DiL dye. Briefly, exosomes were incubated with DiL (2 μM) at 37° C. for 20-30 min. Afterwards, excess free dye was separated from labeled exosomes by size exclusion chromatography using a NAP-10 Sephadex G25 column (GE Healthcare, Buckinghamshire, UK) according to the manufacturer's recommended protocol as described above. An equivalent number of DiL-labeled exosomes (~$10^8$ particles/well) were added to 3LL-M27 cells and incubated for varying lengths of time. Afterwards, the treatment solutions were removed and cells were washed 3× with PBS. 1% Triton X-100 was then added to each well and the 96-well plate was placed at −80° C. for 5 min and then shaken at 37° C. for 1 h. The fluorescence in cell suspensions was measured by a Shimadzu RF5000 fluorescent spectrophotometer. The suspensions were also analyzed for protein content by BCA Assay using the Pierce BCA Protein Assay Kit (Thermo Fisher Scientific, Waltham, Mass., USA) according to the manufacturer's recommended protocol. Results were given as number of exosomes per μg protein vs. time.

Receptor Competitive Inhibition.

To determine whether AA-vectorized exosomes to sigma receptor were accumulated in cancer cells via receptor-mediated endocytosis, a receptor competitive inhibition study was carried out. For this purpose, first a lipophilic fluorescent dye, DiL, was incorporated into exosome membranes. Briefly, the supernatant of RAW 264.7 macrophage conditioned media free of cells and cellular debris was filtered with a 0.22 μm PES filter and incubated with DiL dye (4 μM) at 37° C. for 20 min. Following a 20-minute incubation, ExoQuick-TC™ exosome precipitation solution was added to the filtered supernatant, the mixture was vortexed, and incubated overnight at 4° C. Then, the mixture was vortexed again and subsequently centrifuged at 1500×g for 30 minute to pellet exosomes. The supernatant was discarded and the exosome pellet was re-suspended in PBS. Freshly-prepared fluorescently labeled exosomes or exosomes stored at −20° C. were used for all experiments.

Next, 3LL-M27 cells were seeded overnight at 50,000 cells/well in a 96-well plate. Anisamide (AA) stock solution was prepared using DMSO and diluted to working concentration in cell culture media. Cells were pre-treated with AA in media at varying concentrations for 30 min. Afterwards, media was removed from wells, and solutions of DiL-labeled AA-PEG-exo supplemented with free AA at varying concentrations were added to the cells and incubated for one hour. Cells were washed 3× with PBS, and supplemented with 1% Triton X-100. The fluorescence levels in cell suspensions were measured by a Shimadzu RF5000 fluorescent spectrophotometer, and adjusted for protein content analyzed by BCA Assay using the Pierce BCA Protein Assay Kit (Thermo Fisher Scientific, Waltham, Mass., USA). Results were plotted as number of accumulated exosomes/μg protein vs. concentration of free AA.

Effect of Proteinase K Treatment on Exosome Uptake in 3LL-M27 Cancer Cells In Vitro.

Exosomes possess a variety of surface proteins which are believed to play a significant role in cell uptake and adhesion, such as tetraspanins (CD63, CD81, CD9), heat shock proteins (Hsc70), lysosomal proteins (Lamp2b) and fusion proteins (CD9, flotillin, Annexin) (Lotvall et al., *J Extracell Vesicles* 3: p. 26913 (2014)). In order to explore the role of surface proteins on the exosome-based formulations uptake, samples of non-vectorized exosomes (exo), or AA-vectorized exosomes (AA-PEG-exo) were prepared at the same concentration (~$10^{11}$ exosomes/mL) and treated with Proteinase K. Briefly, 10 μL of 10 mg/mL proteinase K or PBS (as a control) were added to 1 mL DiL-labeled exo or AA-PEG-exo and incubated at 37° C. for 30 min. Excess free enzyme and dye was separated from digested exosomes by size exclusion chromatography using a NAP10 column packed with Sepharose CL-6B. Briefly, 750 μL exosomes were added to the column and the void volume was discarded. 250 μL of PBS was then added to the column and allowed to enter the gel bed completely and the eluate was discarded. 1.2 mL of PBS was then added to the column and the eluate containing purified exosomes was collected and stored at −20° C.

Next, 3LL-M27 cells were seeded overnight in a black/clear bottom 96-well plate (Corning Costar, Corning, N.Y., USA) at 50,000 cells/well. Proteinase K-treated DiL-labeled exosomes and non-treated exosomes as a control were diluted to the same concentration and added to wells for varying lengths of time. After two hours, media was removed, cells were washed 3× with PBS, and supplemented with 1% Triton X-100 (Sigma-Aldrich, St. Louis, Mo., USA). The fluorescence levels in cell suspensions were measured using a Spectramax M5 microplate reader (Molecular Devices, Sunnyvale, Calif., USA) at λex=540 nm and λem=570 nm, and compared against a known concentration of standard. A calibration curve constructed by plotting peak area versus concentrations of DiL labeled exosomes was found to be linear within the tested concentration range ($r^2$=0.999). Exosomal protein content was measured using the Pierce BCA Protein Assay Kit (Thermo Fisher Scientific, Waltham, Mass., USA). Results were expressed as number of accumulated exosomes per μg protein vs time.

Intracellular Trafficking of Exosomes.

In order to assess the intracellular trafficking of exosomes, 3LL-M27 cells were seeded at 500,000 cells/well in chamber slides and incubated overnight AA-vectorized (AA-exo) and non-vectorized exosomes (exo) were labeled with DiL as described above, and added to cells for varying times. Media was then removed, and pre-warmed staining solutions (ER Tracker Blue-White DPX, or LysoTracker Green DND-26, or MitoTracker Deep Red) were added to the cells according to the manufacturer's recommended instructions. Then, cells were washed 3× with PBS, and fixed by the addition of Formal-Fixx for 20 min at 37° C. Exosomes and organelles were visualized by confocal fluorescence microscopic system ACAS-570 (Meridian Instruments, Okimos, Mich., USA) with argon ion laser and corresponding filter set. Excitation/emission were set and measured at 540 nm/570 nm for DiL-labeled exo and AA-exo, and 358 nm/461 nm, or 490 nm/520 nm, or 640 nm/670 nm for ER Tracker Blue-White DPX, LysoTracker Green DND-26, and MitoTracker Deep Red, respectively.

Biodistribution of Intravenously Injected Exosomes in Mice with Pulmonary Metastases.

To utilize fluorescence imaging, 3LL-M27 cells were transduced with lentiviral vectors encoding the optical reporter FITC (FITCFlmC, green) fluorescent protein as reported earlier (Sena-Esteves et al., *Journal of Virological Methods;* 122(2):131-9 (2004)). The viral construct also encoded for a puromycin resistance gene downstream of FITC, which was introduced to enable for the selection of positively transduced cells. C57BL/6 mice (n=4) were injected intra tail vein (i.v.) with FITC-FLmC-3LL-M27 cells (5×$10^6$ cells/mouse in 100 μl saline) and tumor lung metastases were allowed to establish for 10-12 days. In parallel, exosomes isolated from autologous macrophages conditioned media were stained with a fluorescent lipophilic dye DiD (red) and vectorized to the sigma receptor with DSPE-PEG-AA. Twelve days following cancer cells i.v. injection, DiD-labeled AA-PEG-exo formulation was administered intravenously (i.v., $10^8$ particles/100 μl) through intra-tail vein to mice with lung metastases. Four hours later, mice were sacrificed and perfused according to a standard protocol. Lungs were extracted and sectioned on a microtome at a thickness of 20 μm; nuclei were stained with DAPI (300 mM, 5 min). The images of lung sections were examined by a confocal fluorescence microscopic system ACAS-570 and corresponding filter set, and processed using ImageJ software.

Therapeutic Efficacy of AA-exoPTX Against Pulmonary Metastases.

The antineoplastic effects of PTX exosome formulation were evaluated in a mouse model of pulmonary metastases. To utilize fluorescence imaging, 3LL-M27 cells were transduced with lentiviral vectors encoding the optical reporter mCherry (GBM8FlmC, red) as described earlier (Kim et al., *Nanomedicine* 12: 655-664 (2016)). To establish pulmonary metastases, C57BL/6 mice were i.v. injected with 8FlmC-3LL-M27 cancer cells (5×$10^6$ cells/100 μl/mouse). Forty-eight hours later, mice were treated i.v. with AA-PEG-exoPTX, or exoPTX, or empty exosomes (exo) ($4 \times 10^{11}$ particles/100 µl, three times on day 1, 4, and 7; 0.5 mg/kg totally), or Taxol (same regiment as exosome-based formulations), or saline as a control (n=7). To assess amount of cancer metastases, two mice from each group were sacrificed on day 16, perfused, and lung slides obtained on microtome (Thermo Scientific) were examined by confocal microscopy. The rest of the mice (five in each group) were monitored daily for the signs of the reduced physical activity and the progression of the tumor. The survive time of each mouse was recorded.

Statistical Analysis.

For the all experiments, data are presented as the mean±S.E.M. Tests for significant differences between the groups were performed using a t-test or one-way ANOVA with multiple comparisons (Fisher's pairwise comparisons) using GraphPad Prism 5.0 (GraphPad software, San Diego, Calif.). A minimum p value of 0.05 was chosen as the significance level.

Results

Manufacture and Characterization of AA-PEG-exoPTX.

As shown in Example 2, efficient loading of PTX can be achieved when exosomes are subjected to ultrasound treatment in the presence of the drug (Kim et al., *Nanomedicine* 12: 655-664 (2016)). It is likely that the reorganization/reshuffling of the exosome membranes upon sonication enabled PTX diffusion across highly impermeable lipid bilayers. Based on these findings, we applied the same approach for simultaneous loading of PTX to exosomes along with vectorization to sigma receptor using an anisamide moiety. For this purpose, exosomes were isolated from macrophages conditioned media, supplemented with varying amounts of AA-PEG-DSPE lipid and PTX in ethanol solution, and subjected to ultrasound treatment as described above. Obtained formulations were purified from non-incorporated drug on Sepharose 6BCL columns and characterized by size, charge, as well as by PTX and protein content.

First, the effect of lipid incorporation on the loading capacity for PTX into exosomes was evaluated. The amount of PTX loaded into exosomes was determined by HPLC on a Nucleosil C18 reverse phase column, and the loading capacity (LC) was expressed as the amount of the drug vs. the amount of exosomal protein. HPLC analysis revealed that incorporation of high amounts of AA-PEG-DSPE (0.5 mg/ml) into exosomes significantly decreased their loading capacity (LC) for PTX (FIG. 49A). In contrast, lower amounts of the lipid (0.25-0.05 mg/ml) did not affect LC for PTX. It is likely that excess of hydrophobic chains of the lipid incorporated into exosomal membranes diminished available for PTX space. Based on these findings, the highest amount of the incorporated vector moiety (0.25 mg/ml) that did not significantly reduce PTX loading in exosomes was selected for all further evaluations. LC for the optimal AA-PEG-exoPTX formulation was ~33%, comparable to the LC achieved for non-vectorised exoPTX (FIG. 49A). Noteworthy, ultrasound treatment significantly increased amount of PTX incorporated into exosomes; the LC in exosomes without sonication was as low as 1.4%.

Next, to address a concern about possible alterations in the exosomal membranes upon sonication, the levels of exosome-specific proteins, TSG101 and flotillin, in different exosomal formulations were examined by western blot technique (FIG. 49B). The data indicated that the mild sonication utilized for PIX loading with six cycles, and intermediate time out for cooling down and membrane restoration, did not affect the protein content of exosomes. In particular, naïve exosomes, as well as both vectorized and non-vectorized exosomal formulations showed elevated expression of exosome-associated proteins (TSG101, and flotillin) as compared to cell lysate, which displayed greater levels of j-actin (FIG. 49B). Noteworthy, all exosomal formulations, as well as parental macrophages, were also found to express the lymphocyte function associated antigen-1 (LFA-1, subunit CD11a) (FIG. 49B), which assists in cell uptake and may bind to endothelial cell adhesion molecules (in particular, ICAM1) which are overexpressed on activated endothelial cells such as those found in tumors (Maruo et al., *International journal of cancer* 100: 486-490 (2002)). This is important, since the presence of LFA-1 on the surface may improve specific targeting of exosome-based PTX formulations to tumors.

Finally, the hydrodynamic size was determined by DLS and NTA (FIG. 49C). Naïve empty exosomes had a narrow size distribution, with an average particle diameter of 110.8±4.1 nm and 75.9±2.6 nm as revealed by NTA and DLS, respectively. The sonication procedure significantly increased size of exosomes (FIG. 49C). Noteworthy, exosomes sonicated in the presence of PTX were smaller than those sonicated in the absence of the drug. We hypothesized that this effect may be due to the stabilization of exosomal membranes by the incorporated drug. Furthermore, it is known that the anionic phospholipid phosphatidylserine is abundant on cell membranes and contributes to the surface charge of individual cellular membranes. In this regard, loading of exosomes with PTX did not significantly alter the slightly negative change of the nanocarriers (FIG. 49C), suggesting that there were also no major alterations of the lipid content of exosomal membranes. However, the vectorized AA-PEG-exoPTX formulation was found to have a less negative surface charge than exoPTX, probably due to the shielding of the exosomal membrane by the long PEG chains of the lipid.

Effect of AA-PEG-DSPE Incorporation on Membrane Fluidity in Exosomes.

Fluidity of exosomal membrane upon AA-PEG-DSPE incorporation was examined using BODIPY-PC. This is a hydrophobic fluorescent compound, which incorporates in the hydrocarbon regions of lipid membranes. Transfer of BODIPY-PC from the aqueous environment into lipid bilayers results in a drastic increase of the fluorescence emission for this probe. Once the probe is incorporated into lipid membranes, its fluorescence polarization is strongly dependent on the microenvironment, with decreases in membrane microviscosity resulting in increased fluorescent polarization.

Exosomes labeled with BODIPY-PC were sonicated in the presence of AA-PEG-DSPE lipid, and fluorescence polarization measurements were recorded (FIG. 50). Co-incubation of PTX with exosomes in the absence of sonication did not alter membrane microviscosity, although small but statistically significant fluidization of exosomal membranes was recorded when a high amount of lipid (0.5 µg/ml) was added to the solution. Next, significant decreases (more than two times) in membrane microviscosity were recorded upon sonication, consistent with our previous observations (Haney at al., *J Control Release* 31; 207:18-30 (2015)). The fluidity of exosomal membranes was partially restored when PTX was added to the solution. Furthermore, sonication of exoPTX in the presence of the lipid further increased membrane microviscosity up to naïve non-sonicated exosomes (FIG. 50). Noteworthy, the greater amount of lipid was added to the solution; the higher the microviscosity levels obtained. We hypothesize that sonication leads to dysregulation of exosomal membranes and the creation of additional space for PTX molecules. This resulted in an increased LC for PTX. The incorporation of high amounts of lipid molecules upon sonication allowed sealing membrane bilayers that may impede PTX loading, and as a result, diminish LC (FIG. 49A).

Accumulation of AA-PEGexoPTX in Target Cancer Cells In Vitro.

The ability to deliver the drug payload into target cells is crucial for the therapeutic efficacy of exosomal formulations. Although the molecular function of sigma receptors is not yet fully defined, there is increasing evidence that these receptors are overexpressed in many cancer cells (Maruo et al., *International journal of cancer* 100: 486-490 (2002)).

Previously, we demonstrated that accumulation levels of fluorescently-labeled exosomes in 3LL-M27 cells was considerably greater (about 30 times) than accumulation of liposomes or polystyrene nanoparticles (Kim et al., *Nanomedicine* 12: 655-664 (2016)). Here, we compared the uptake of AA-vectorized exosomes against control non-vectorized exosomes. The receptor-mediated accumulation of DiL-labeled vectorized exosomes (AA-PEG-exo) was studied in target 3LL-M27 cells in vitro, and compared to non-vectorized sonicated exosomes (exo), as well as exosomes with incorporated PEG-DSPE lipid without anisamide targeting moiety (PEG-exo) (FIG. 51A). The obtained data indicated that vectorized AA-PEG-exo nanocarriers were taken up in much higher quantities than non-vectorized sonicated exosomes. The PEGylated exosomes without AA-targeting moiety were taken up less than parental exosomes, probably due to the PEG chains blocking interaction of exosomal surface proteins, which assist in cell accumulation.

To further assess the capability of incorporated AA to target exosomes to the sigma receptor, a receptor competitive inhibition study was carried out in 3LL-M27 cells (FIG. 51B). In this experiment, 3LL-M27 cells were pre-treated with free AA at varying concentrations, washed with PBS, and then equal amounts of vectorized AA-PEG-exo along with free AA were added to the cells and incubated for one hour. Fluorescence levels were measured; the amount of exosomes/µg protein was quantified and graphed against the concentration of AA (FIG. 51B). Results showed a dose-dependent response of AA-PEG-exo to competitive inhibition by increasing concentrations of free AA, indicating that AA-PEG-exo were targeted to the sigma receptor and taken up by receptor-mediated endocytosis. Noteworthy, even a large amount of free AA added to the AA-vectorized exosomes was not able completely inhibit exosome uptake in target cells, suggesting the involvement of other exosomal surface proteins in this process, for example LFA-1 as demonstrated by western blot.

The importance of exosomal surface proteins in assisting in exosome take-up was confirmed in accumulation studies using proteinase K treatment to strip exosomes of surface proteins (FIG. 52). In this experiment, sonicated AA-vectorized (AA-PEG-exo) and non-vectorized sonicated exosomes (exo/sonic), as well as non-sonicated naïve exosomes (exo/naïve) were labeled with the fluorescent dye DiL, and incubated with 3LL-M27 cancer cells for various times. The obtained data indicate that accumulation levels in target cells increased in order: exo/naïve<exo/sonic<AA-PEG-exo (FIG. 52). This confirmed our previous reports that treatment with ultrasound improved exosome accumulation in cancer cells (Kim et al., *Nanomedicine* 12: 655-664 (2016)), as well as neuronal PC12 cells (Haney at al., *J Control Release* 31; 207:18-30 (2015)). In parallel, the same exosomal formulations were treated with proteinase K, and added to the cells. The digestion of the exosomal surface proteins significantly decreased uptake by target cells in all formulations. These results clearly show the advantages of exosome-based drug delivery systems over common synthetic nanocarriers related to the facilitated uptake of exosome carriers by means of surface adhesive proteins. Noteworthy, stripping of surface proteins from vectorized exosomes (AA-PEG-exo) decreased their transport at significantly lesser extent than non-vectorized exosomes (FIG. 52), probably due to the assisted AA-mediated accumulation in cancer cells.

Effect of AA-Vectorization on Intracellular Distribution of Exosomes in Cancer Cells.

Exosomes are known to function as intracellular messengers, delivering proteins and nucleic acids (Gyorgy et al., *Cell Mol Life Sci*, 68:2667-2688 2011)) from cell to cell. The intracellular fate of exosomes is of the utmost importance if drugs are to be delivered effectively into target cells. However, the effect of vectorization with AA on intracellular fate of exosomes and their cargo remains unknown. To assess the intracellular trafficking of exosomes, 3LL-M27 cells were incubated with DiL-labeled AA-PEG-exo and exo as a control for one hour, and then stained with MitoTracker, or LysoTracker, or ER Tracker dye to visualize mitochondria, lysosomes, or endoplasmic reticulum (ER), respectively (FIG. 53). Results showed that exosomes preferentially distribute in order: lysosomes>ER>mitochondria. Confocal images revealed that the intracellular fate of exosomes was not altered by the addition of a vector to the sigma receptor.

Co-Localization of Systemically-Administered Exosomes with Pulmonary Metastases in LLC.

To assess the ability of AA-vectorized exosomes to target sigma receptor expressing pulmonary metastases, confocal images were conducted in an LLC mouse model. For this purpose, 3LL-M27 cells were transduced with a lentiviral vector encoding the optical reporter GFP fluorescent protein. To induce metastases, C57BL/6 mice were injected with GFP/3LL-M27 ($5 \times 10^6$ cells/100 CtL) intra-tail vein as described above. 21 days later, autologous non-vectorized (exo) and AA-vectorized (AA-PEG-exo) exosomes were stained with a fluorescent dye, DiD, and administered intravenously (i.v., $10^8$ particles/100l) to C57BL/6 mice. Four hours later, mice were sacrificed, perfused; lungs were sectioned on a microtome and examined by confocal microscopy. Nuclei were stained with DAPI.

Confocal images revealed 98.9±0.8% of AA-exosomes (FIG. 54D-54F) were co-localized with lung metastases indicating efficient targeting of AA-exoPTX in vivo. In contrast, only 21.8±0.2% of systemically-injected non-vectorized exosomes were co-localized with cancer metastases (FIG. 54A-54C). Noteworthy, no AA-exosomes were found in the lungs of healthy animals (FIG. 54G-54J). These results suggest that systemically-administered exosomes can efficiently reach pulmonary metastases and deliver their drug payload to target cancer cells.

Therapeutic Efficacy of AA-PEG-exoPTX Against Lung Metastases.

C57BL/6 mice were i.v. injected with mCherry-3LL-M27 cells transduced with lentiviral vectors encoding the optical reporter mCherry (GBM8FlmC). When metastases were established, mice were systemically injected with AA-PEG-exoPTX or exoPTX ($4 \times 10^{11}$ particles/100 µl, 3 times on day 1, 4, and 7; 0.5 mg/kg totally), or Taxol (same regimen as AA-PEG-exoPTX), or saline as a control. 18 days later mice were sacrificed, perfused, and lung slides were examined by confocal microscopy (FIG. 55A). The images revealed a superior antineoplastic efficacy of AA-exoPTX compared to non-vectorized exoPTX, or Taxol resulting in potent eradication of pulmonary metastases. The survival studies confirmed these results (FIG. 55B). The administration of AA-exoPTX formulation resulted in a significantly stronger suppression of metastases growth and greater survival time in mice with pulmonary metastases. This confirms the superior antineoplastic efficacy of AA-PEG-exoPTX upon systemic administration as compared to Taxol and non-vectorized exoPTX formulation.

Conclusions.

The efficient targeted delivery of anticancer agents to pulmonary metastases remains one of the greatest challenges for therapy. A common approach for building a drug delivery system is to incorporate the drug within a nanocarrier that allows higher solubility, metabolic stability, and improved circulation time. Several formulations are being studied in clinical trials, or have already been approved by the FDA for use in humans (Peer et al., Nat Nanotechnol 2:751-760 (2007); Davis et al., Nature, 464:1067-1070 (2010)). However, conventional nanoparticles have limited biocompatibility, and normally are cleared rapidly from the circulation by the MPS (Peng et al., Biomaterials 34(33):8521-30 (2013)). This example presents a new drug delivery system that is based on natural vectors, exosomes, released by autologous macrophages for the delivery of a biological agent exemplified here by PTX. Exosomes play a significant and diverse role in intercellular communication that is an essential process for the development and function of multicellular organisms. In this regard, we utilize macrophage-derived exosomes that exert unique biological activity reflective of their origin and can provide advantages of both cell-mediated drug delivery that based on innate functions of immune cells and nanotechnology.

Using exosomes as drug delivery vehicles offers a number of benefits over common drug administration regimens; however, there are some limitations and challenges that need to be addressed. One of the major challenges is the efficient loading of exosomes without significant changes in the structure and content of exosomal membranes. PTX is a highly hydrophobic compound that is likely to be incorporated into the hydrophobic inner region of the relatively tight and highly structured lipid bilayers of exosomes. Therefore, we developed a specific procedure when lipid bilayers were reshuffled upon mild sonication without significant alterations of protein and lipid content. To target exosomal carriers to cancer cells, we also incorporated a vector moiety with anisamide that is known to specifically bind sigma receptor overexpressed on many cancer cells using the same sonication procedure. Using mild sonication of exosomes in the presence of PTX and anisamide vector we optimized the amount of incorporated vector moiety to the levels which allow high loading capacity for the drug. The obtained AA-PEG-exoPTX formulation showed an extraordinary ability to accumulate in target cancer cells; these exosomes were taken up via receptor-mediated endocytosis in considerably greater numbers than non-vectorized exosomes in vitro. Noteworthy, vectorization with anisamide did not alter intracellular trafficking of exosomal formulations in cancer cells.

The most interesting results were obtained in the mouse LLC model. Our data demonstrate a robust accumulation and nearly complete co-localization of systemically administered AA-vectorized exosomes with cancer cells. We hypothesized that both AA-vector along with LFA-1 protein expressed on exosomal membranes were responsible for this preferential accumulation in pulmonary metastases upon systemic administration. Significantly, exosomes were targeted to liver metastases as well; a complete co-localization of AA-vectorized exosomes with cancer cells was demonstrated in this work.

It is likely that the efficient targeted delivery of PTX incorporated into AA-vectorized exosomes resulted in superior inhibition of pulmonary metastases growth in the LLC mouse model compared to exoPTX or Taxol. Significantly, LLC cells are known to express Pgp drug efflux transporter in vivo (Batrakova et al., J Control Release 143: 290-301 (2010)). We demonstrated earlier that the incorporation of PTX into exosomes may not only increase its solubility, but also allow for overcoming Pgp-mediated drug efflux in the resistant cancer cells. This effect may be attributed to the difference in route of internalization of exoPTX, as compared to Taxol. Exosomes and micelles, such as those found in Taxol, are taken up by endocytosis, but exosomes have superior uptake due to the presence of adhesion proteins, tetraspanins, integrins, immunoglobulins, proteoglycans, and lectins (Mulcahy et al., J Extracell Vesicles 4; 3 (2014)), which are not found on artificial nanoparticles. Furthermore, exosomes consist of cellular membranes that may fuse with the plasma and/or endocytic membranes and deliver their cargo, bypassing Pgp-mediated efflux.

Moreover, it is known that exosome-mediated cell-to-cell communication is key in the battle between cancer and the immune system (Finn et al., Ann Oncol 23 Suppl 8: viii6-9 (2012)). Thus, Parolini et al. (Parolini et al., J Biol Chem 284: 34211-34222 (2009)) showed that exosome fusion with target cells occurs more efficiently under acidic conditions, implying that exosomes may be taken up preferentially by tumors (which have an acidic microenvironment) rather than the surrounding healthy tissue. Finally, decoration of exosomes with PEG chains may significantly increase their circulation in the blood as was demonstrated earlier (Kooijmans et al., J Control Release 224: 77-85 (2016)). Without limiting our invention to a specific theory, all four mechanisms mentioned here are likely to have significant impact on AA-PEG-exoPTX anticancer activity, i.e.: (i) vector-mediated preferential accumulation in cancer cells, (ii) efficient delivery of incorporated cargo into target cancer cells, (iii) by-passing Pgp-mediated drug efflux in resistant cancer cells, and (iv) prolonged circulation time in the blood. Indeed, further investigations are necessary to uncover this mechanism. Overall, macrophage-derived exosomes allow harnessing the innate biology of immune cells and combining these advantages with nanotechnology. Thus, exosomes promise an unparalleled efficacy in the treatment of many life-threatening conditions, including those lacking effective pharmacotherapy.

Example 12

Preparation of Exosomes Loaded with Small Molecule Biological Agents Using Poly(2-oxazoline) Polymeric Micelles Poly(2-oxazoline) micelles loaded with single drug or multiple drugs were prepared via the thin film hydration method (Luxenhofer et al., Biomaterials 31(18):4972 (2010)). Briefly, predetermined amounts of polymer and drugs were solubilized in an organic solvent (e.g., acetone, acetonitrile, and ethanol) and mixed together. The organic solvent was then removed under a stream of nitrogen gas or air (40° C.) to produce a thin film of intrinsically mixed drug-polymer blend. In order to completely remove the residual solvents and obtain dry film, the films were deposited in the vacuum chamber (approx. 0.2 mbar) overnight. Subsequently, the formed thin films were rehydrated with the desired amounts of aqueous saline or bi-distilled water and then solubilized at either room temperature or upon heating at 50-60° C. for 5-20 minutes to produce drug loaded polymeric micelle solutions. The rehydration time was dependent on either the drug concentration or the composition of the drugs or the multi-drug mixtures. The polymeric micelles loaded with the single drug were prepared accordingly with the final polymer concentration of 10 g/L and each drug feed concentration of 2 g/L, 4 g/L, 8 g/L, 10 g/L and 12 g/L. The polymeric micelles co-loaded with multiple drugs were prepared using the same final polymer concentration (10 g/L) and predetermined concentrations of each drug component of multiple drug mixtures. The aqueous polymeric micelle formulation was centrifuged at 10,000 rpm for 3 minutes to precipitate non-dissolved drugs or drug-polymer aggregates. A triblock copolymer of poly(2-butyl-2-oxazoline) (PBuOx) as the hydrophobic block and poly(2-methyl-2-oxazoline) (PMeOx) as the hydrophilic block having PMeOx-b-PBuOx-b-PMeOx structure was used as the polymer. The length of the PBuOx block ranged from about 10 to 30 repeating units (r.u.) while the length of each PMeOx block ranged from about 30 to about 50 r.u. and this variation did not affect the solubilization results.

The following small molecule biological agents were used to prepare single drug micelles or multiple drug micelles: an ATM (Ataxia telangiectasia mutated) kinase inhibitor KU55933, cytoskeletal drugs that target tubulin-paclitaxel (PTX) and docetaxel (DTX), ATM/ATR (ataxia telangiectasia and Rad3-related protein) inhibitor VE-822, Bcl-2 family protein inhibitors ABT-263 (Navitoclax), PI3K/AKT (Protein kinase B) inhibitors AZD5363 and LY294002 and LY294002 hydrochloride, a check point inhibitor AZD7762, an Mtor (mechanistic target of rapamycin) inhibitor AZD8055, a topoisomerase II inhibitor etoposide (ETO) or VP-16, a proteasome inhibitor LDN-57444, topoisomerase II inhibitors podophyllotoxin (PPT), otherwise known as podofilox and teniposide, a bioflavonoid rutin, a synthetic retinoic acid receptor a (RARa) agonist, tamibarotene, an antagonist of aldosterone spironolactone, a 3-hydroxy-3-methylglutaryl (HMG) coenzyme A reductase inhibitor simvastatin, third generation taxoids SB-T-1213, SB-T-121302, SB-T-121303, SB-T-1214, SB-T-121402, SB-T-1216 and SB-T-121602 (He et al., *J. Control. Release* 208:67 (2015)), a vitamin D2 ergocalciferol, a third generation retinoid bexarotene (Schulz et al., *Polymer Preprints* 53(1): 354 (2012)), a proteasome inhibitor bortezomib (BTZ) and Hsp90 inhibitor 17-N-allylamino-17-demethoxygeldanamycin (17-AAG) (Han et al., *Mol. Pharm* 9(8): 2302 (2012)). All of these APIs have very low (less than about 0.1 µg/mL) or low (from about 0.1 to about 1 µg/mL) solubility.

As the next step the IC21 macrophages are treated with the obtained polymeric micelle solutions. Briefly, macrophages grown in T-75 flasks ($15 \times 10^6$ cells/flask) are incubated with the polymeric micelles containing biological agents obtained as described above in serum free media for 2 hours to 96 hours. In each case the duration of exposure of the cells with the polymeric micelle solutions is adjusted to ensure that the cytotoxic effect on the donor cells is minimal. In selected cases the donor cells are additionally incubated with 0.5% Pluronic® P85 solution for four hours. Following the incubation, the cells are washed 3×PBS, and cultured in serum-free media for another 20 hours. Following the incubation, exosomes are harvested from the macrophages media using the ExoQuick-TC™ Kit (System BioSciences; Mountain View, Calif.) and washed twice with PBS. The recovery of exosomes is determined by measuring the protein concentration using the Bradford assay and by NTA. The amount of biological agents incorporated in exosomes is quantified via reverse-phase high performance liquid chromatography (HPLC).

Example 13

Preparation of Exosomes Loaded with Small Molecule Biological Agents Using Pluronic® Polymeric Micelles Pluronic® polymeric micelles loaded with drugs were prepared via the thin film hydration method as described in Example 12. A triblock copolymer of PEO-PPO-PEO Pluronic® F127 was used as the polymer. The following small molecule biological agents were used to prepare single drug-containing polymeric micelles: doxorubicin, epirubicin, daunorubicin, vinblastine, mitoxantrone, camptothecin, and SN-38. As the next step the IC21 macrophages are treated with the obtained polymeric micelle solutions as described in Example 12. In selected cases the donor cells are additionally incubated with 0.5% Pluronic® P85 solution for four hours. Following the incubation, the cells are washed 3×PBS, and cultured in serum-free media for another 20 hours. Exosomes were collected by PEG precipitation from macrophage concomitant media and the number of particles was accessed by NTA. The amount of biological agents incorporated in exosomes is quantified by HPLC.

The foregoing is illustrative of the present invention, and is not to be construed as limiting thereof. The invention is defined by the following claims, with equivalents of the claims to be included therein.

We claim:

1. A composition for delivery of a biological agent to a cell, the composition comprising an exosome comprising the biological agent, wherein the biological agent is not naturally present in the exosome and is a neurotrophin, wherein the exosome is isolated from a macrophage/monocyte.

2. The composition of claim 1, wherein the exosome further comprises a targeting agent.

3. The composition of claim 2, wherein the targeting agent is attached to the surface of the exosome.

4. The composition of claim 3, wherein the targeting agent is attached using a polymeric linker.

5. The composition of claim 4, wherein the polymer linker is a water soluble polymer liker.

6. The composition of claim 2, wherein the targeting agent or polymeric linker is connected to a lipid group in or on the exosome.

7. The composition of claim 1, wherein the exosome is modified with a molecule containing multiple charges.

8. The composition of claim 7, wherein the molecule containing multiple charges is a polyion or a lipid.

9. The composition of claim 1, further comprising a pharmaceutically acceptable carrier.

10. A method of delivering a biological agent to a cell, comprising contacting the cell with the composition of claim 1, thereby delivering the biological agent to the cell.

11. A method of enhancing delivery of a biological agent to a cell in a tumor microenvironment, to a cancer cell, or to a central nervous system cell, comprising contacting the cell with the composition of claim 1, thereby enhancing delivery of the biological agent to the cell relative to the delivery of the biological agent in the absence of an exosome.

12. A method of delivering a biological agent to a subject, across the blood brain barrier of a subject, or to inflamed tissue of a subject, comprising delivering the composition of claim 1 to the subject, thereby delivering the biological agent to the subject.

13. A method of treating a disorder in a subject in need thereof, comprising delivering a therapeutically effective amount of the composition of claim 1 to the subject, wherein the biological agent is effective for treating the disorder, thereby treating the disorder in the subject.

14. The composition of claim 1, wherein the neurotrophin is brain derived neurotrophic factor, nerve growth factor, neurotrophin 3, neurotrophin 4, glial cell derived neurotrophic factor, artemin, neurturin, persephin, or ciliary neurotrophic factor.

* * * * *

UNITED STATES PATENT AND TRADEMARK OFFICE
CERTIFICATE OF CORRECTION

PATENT NO. : 11,458,097 B2
APPLICATION NO. : 16/089833
DATED : October 4, 2022
INVENTOR(S) : Batrakova et al.

It is certified that error appears in the above-identified patent and that said Letters Patent is hereby corrected as shown below:

In the Specification

Column 9, Line 4: Please correct "MO" to read --Mϕ--

Column 9, Line 46: Please correct "10 jpg" to read --10 μg--

Column 9, Line 63: Please correct "MO" to read --Mϕ--

Column 11, Line 59: Please correct "C57B/U6" to read --C57BL/6--

Column 12, Line 36: Please correct "exosomes/g" to read --exosomes/μg--

Column 13, Line 6: Please correct "C57BU6" to read --C57BL/6--

Column 14, Line 20: Please correct "of 20%" to read --of ±20%--

Column 16, Line 5: Please correct "poly(j3-benzyl-L-aspartate)" to read --poly(β-benzyl-L-aspartate)--

Column 30, Line 26: Please correct "10%0/(v/v)" to read --10% (v/v)--

Column 30, Line 55: Please correct "0.2 apm" to read --0.2 μm--

Column 33, Line 42: Please correct "10%/o" to read --10%--

Column 33, Line 67: Please correct "CaCl$_2$)," to read --CaCl$_2$,--

Column 39, Line 4: Please correct "ofexoCAT." to read --of exoCAT.--

Signed and Sealed this
Seventh Day of February, 2023

Katherine Kelly Vidal
*Director of the United States Patent and Trademark Office*

CERTIFICATE OF CORRECTION (continued)
U.S. Pat. No. 11,458,097 B2

Column 39, Line 51-52: Please correct "408.44 U/10 µL/U mouse" to read --408.44 U/10 µL/mouse--

Column 40, Line 10: Please correct "FIG. 5C" to read --FIG.8C--

Column 40, Line 24: Please correct "(FIGS. 6E and 6E)" to read --(FIGS. 6E and 8E)--

Column 44, Line 66: Please correct "30 LL" to read --30 µL--

Column 47, Line 29: Please correct "100 L/J mouse" to read --100 µL/mouse--

Column 47, Line 60: Please correct "3-actin" to read --β-actin--

Column 49, Line 64: Please correct "MDCKM$_{DR}$I cells" to read --MDCK$_{MDR1}$ cells--

Column 53, Line 46: Please correct "5 g/ml" to read --5 µg/ml--

Column 54, Line 7: Please correct "$3x10^1$" to read --$3x10^{11}$--

Column 54, Line 14: Please correct "1730" to read --173°--

Column 56, Line 4: Please correct "Am Cp$_c$," to read --Am/Cp$_t$,--

Column 56, Line 20: Please correct "* $p<0.0^5$" to read --* $p<0.05$--

Column 56, Line 31: Please correct "Raw Mo.," to read --Raw Mϕ,--

Column 57, Line 6: Please correct "(-actin" to read --β-actin--

Column 57, Line 22: Please correct "MO" to read --Mϕ--

Column 58, Line 2: Please correct "M #" to read --Mϕ--

Column 65, Line 25: Please correct "gWIZTMLuc" to read --gWIZ™Luc--

Column 71, Line 52: Please correct "ImL" to read --1 mL--

Column 75, Line 66: Please correct "PIX" to read --PTX--

Column 76, Line 6: Please correct "j -actin" to read --β-actin--

Column 78, Line 40: Please correct "100 CtL" to read --100 µL--

Column 78, Line 44: Please correct "100l" to read --100 µl--

Column 81, Line 41: Please correct "receptor a (RARa)" to read --receptor α (RARa)--